(12) United States Patent
Devine et al.

(10) Patent No.: US 10,570,405 B2
(45) Date of Patent: *Feb. 25, 2020

(54) ELITE EVENT CANOLA NS-B50027-4

(71) Applicant: Nuseed Pty Ltd.

(72) Inventors: Malcolm Devine, Calgary (CA); Antonio Leonforte, Horsham (AU); Nelson Gororo, Horsham (AU); Greg Buzza, Horsham (AU); Shunxue Tang, Woodland, CA (US); Wenxiang Gao, Woodland, CA (US); James Petrie, Canberra (AU); Surinder Singh, Canberra (AU)

(73) Assignee: NUSEED PTY LTD., Laverton (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/626,064

(22) Filed: Jun. 16, 2017

(65) Prior Publication Data

US 2018/0016591 A1    Jan. 18, 2018

Related U.S. Application Data

(60) Provisional application No. 62/351,246, filed on Jun. 16, 2016.

(51) Int. Cl.
*C12N 15/82* (2006.01)
*C12Q 1/6895* (2018.01)

(52) U.S. Cl.
CPC ....... *C12N 15/8247* (2013.01); *C12Q 1/6895* (2013.01); *C12N 15/8274* (2013.01); *C12N 15/8281* (2013.01); *C12N 15/8282* (2013.01); *C12N 15/8283* (2013.01); *C12N 15/8286* (2013.01); *C12N 15/8289* (2013.01); *C12Q 2600/13* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,769,061 A | 9/1988 | Comai |
| 4,810,648 A | 3/1989 | Stalker |
| 4,940,835 A | 7/1990 | Shah et al. |
| 5,266,317 A | 11/1993 | Tomalski et al. |
| 5,478,369 A | 12/1995 | Albertsen et al. |
| 5,591,616 A | 1/1997 | Hiei et al. |
| 5,767,373 A | 6/1998 | Ward et al. |
| 5,824,524 A | 10/1998 | Albertsen et al. |
| 5,850,014 A | 12/1998 | Albertsen et al. |
| 5,859,341 A | 1/1999 | Albertsen et al. |
| 5,959,185 A | 9/1999 | Streit et al. |
| 5,969,212 A | 10/1999 | Getschman |
| 5,973,234 A | 10/1999 | Mueller et al. |
| 5,977,445 A | 11/1999 | Soper et al. |
| 6,225,529 B1 | 5/2001 | Lappegard et al. |
| 6,265,640 B1 | 7/2001 | Albertsen et al. |
| 6,282,837 B1 | 9/2001 | Ward et al. |
| 6,288,306 B1 | 9/2001 | Ward et al. |
| 6,297,426 B1 | 10/2001 | Albertsen et al. |
| 7,164,059 B2 | 1/2007 | Barham |
| 8,816,111 B2 | 8/2014 | Petrie et al. |
| 8,946,460 B2 | 2/2015 | Petrie et al. |
| 8,975,374 B2 | 3/2015 | Kimura |
| 9,550,718 B2* | 1/2017 | Petrie .................. C11B 1/00 |
| 9,932,541 B2 | 4/2018 | Petrie et al. |
| 9,969,954 B2 | 5/2018 | Petrie et al. |
| 10,125,084 B2 | 11/2018 | Petrie et al. |
| 2006/0225158 A1 | 10/2006 | Jonsson |
| 2010/0092640 A1 | 4/2010 | Ursin et al. |
| 2011/0321187 A1 | 12/2011 | Malcuit et al. |
| 2015/0045569 A1 | 2/2015 | Petrie et al. |
| 2015/0166928 A1 | 6/2015 | Petrie et al. |
| 2015/0374654 A1 | 12/2015 | Petrie et al. |
| 2016/0002566 A1 | 1/2016 | Vanhercke et al. |
| 2018/0016590 A1* | 1/2018 | Devine .............. C12N 15/8247 |

FOREIGN PATENT DOCUMENTS

| | | |
|---|---|---|
| EP | 0242246 A1 | 10/1987 |
| EP | 0333033 A1 | 9/1989 |
| EP | 3472281 A1 | 4/2019 |
| WO | 199213956 A1 | 8/1992 |
| WO | 199213957 A1 | 8/1992 |
| WO | 199302197 A1 | 2/1993 |
| WO | 199516776 A1 | 6/1995 |
| WO | 199518855 A2 | 7/1995 |
| WO | 199630530 A1 | 10/1996 |
| WO | 200011177 A1 | 3/2000 |
| WO | 200112825 A1 | 2/2001 |

(Continued)

OTHER PUBLICATIONS

Petrie et al, Plos One, online, Nov. 2012, vol. 7, Issue 11, pp. 1-7 (Year: 2012).*

International Search Report and Written Opinion dated Nov. 3, 2017, in related International Patent Application No. PCT/US2017/038047, filed Jun. 16, 2017.

"International Preliminary Report on Patentability received for PCT Patent Application No. PCTUS2017038047, dated Dec. 27, 2018", 10 pages.

NCBI, "Predicted: *Brassica rapa* Uncharacterized LOC103853728 (LOC103853728), mRNA", NCBI Reference Sequence: XM_009130638.2, Oct. 13, 2016, pp. 1-2.

Atanassova, et al., "A 126 bp Fragment of a Plant Histone Gene Promoter Confers Preferential Expression in Meristems of Transgenic *Arabidopsis*", The Plant Journal, vol. 02, No. 03, 1992, pp. 291-300.

Bernardo, et al., "North American Study on Essential Derivation in Maize: Inbreds Developed without and with Selection from F2 Populations", Theor Appl Genet, vol. 102, 2001, pp. 986-992.

(Continued)

*Primary Examiner* — Eileen B O Hara
(74) *Attorney, Agent, or Firm* — Wiley Rein, LLP

(57) ABSTRACT

The present embodiments relate to elite event NS-B50027-4, seeds and oils obtained from NS-B50027-4, progeny derived from NS-B50027-4, the genetic and phenotypic characteristics of NS-B50027-4, and compositions and methods for the identification of elite event NS-B50027-4. In particular, NS-B50027-4 is a transgenic canola line capable of producing at least 5% DHA in its seed oil.

9 Claims, 18 Drawing Sheets

Specification includes a Sequence Listing.

(56) References Cited

FOREIGN PATENT DOCUMENTS

| WO | 2001016342 A1 | 3/2001 |
|---|---|---|
| WO | 200129237 A2 | 4/2001 |
| WO | 2013185184 A2 | 12/2013 |
| WO | 2015089587 A1 | 6/2015 |
| WO | 2017/219006 A1 | 12/2017 |

OTHER PUBLICATIONS

Betancor, et al., "A Nutritionally-Enhanced Oil from Transgenic Camelina Sativa Effectively Replaces Fish Oil as a Source of Eicosapentaenoic Acid for Fish", Scientific Reports, vol. 5, Article No. 8104, 2014, 10 pages.

Bevan, "Binary Agrobacterium Vectors for Plant Transformation", Nucleic Acids Research, vol. 12, No. 22, 1984, pp. 8711-8721.

Chalhoub, et al., "Early Allopolyploid Evolution in the Post-Neolithic Brassica napus Oilseed Genome", Science, vol. 345, No. 6199, Aug. 22, 2014, pp. 950-953.

Christensen, et al., "Maize Polyubiquitin Genes: Structure, Thermal Perturbation of Expression and Transcript Splicing, and Promoter Activity Following Transfer to Protoplasts by Electroporation", Plant Molecular Biology, vol. 18, 1992, pp. 675-689.

Christensen, et al., "Sequence Analysis and Transcriptional Regulation by Heat Shock of Polyubiquitin Transcripts from Maize", Plant Molecular Biology, vol. 12, 1989, pp. 619-632.

Coutu, et al., "pORE: A Modular Binary Vector Series Suited for Both Monocot and Dicot Plant Transformation", Transgenic Res, vol. 16, 2007, pp. 771-781.

Creissen, et al., "Molecular Characterization of Glutathione Reductase cDNAs from pea (Pisum sativum L.)", The Plant Journal, vol. 2, No. 1, 1991, pp. 129-131.

Cullis, et al., "Spatial Analysis of Field Experiments—An Extension to Two Dimensions", Biometrics, vol. 47, No. 4, 1991, pp. 1449-1460.

Diwan, et al., "Automated Sizing of Fluorescent-Labeled Simple Sequence Repeat (SSR) Markers to Assay Genetic Variation in Soybean", Theor Appl Genet, vol. 95, 1997, pp. 723-733.

Fehr, "Principles of Cultivar Development: Theory and Technique (vol. 1)", 1993, 551 pages.

Fontes, et al., "Characterization of an Immunoglobulin Binding Protein Homolog in the Maize floury-2 Endosperm Mutant", The Plant Cell, vol. 3, May 1991, pp. 483-496.

Fraley, et al., "Expression of Bacterial Genes in Plant Cells", Proc. NatL. Acad. Sci., vol. 80, Aug. 1983, pp. 4803-4807.

Gatz, et al., "Regulation of a Modified CaMV 35S Promoter by the TnI0-encoded Tet Repressor in Transgenic Tobacco", Mol Gen Genet, vol. 227, 1991, pp. 229-237.

Gilmour, et al., "ASReml User Guide—Release 3.0", 2009, 398 pages.

Kalderon, et al., "A Short Amino Acid Sequence Able to Specify Nuclear Location", Cell, vol. 39, 1984, pp. 499-509.

Kay, et al., "Duplication of CaMV 35S Promoter Sequences Creates a Strong Enhancer for Plant Genes", Science, vol. 236, 1987, pp. 1299-1302.

Knox, et al., "Structure and Organization of Two Divergent α-Amylase Genes from Barley", Plant Molecular Biology, vol. 9, 1987, pp. 3-17.

Last, et al., "pEmu: An Improved Promoter for Gene Expression in Cereal Cells", Theor Appl Genet, vol. 81, 1991, pp. 581-588.

Lepetit, et al., "A Plant Histone Gene Promoter Can Direct Both Replication-Dependent and -Independent Gene Expression in Transgenic Plants", Moi Gen Genet, vol. 231, 1992, pp. 276-285.

Lerner, et al., "Cloning and Characterization of Root-Specific Barley Lectin", Plant Physiol., vol. 91, 1989, pp. 124-129.

Marcroft, et al., "Blackleg of Canola", Agriculture Victoria, Note No. AG1352, May 2008, 2 pages.

Matsuoka, et al., "Propeptide of a Precursor to a Plant Vacuolar Protein Required for Vacuolar Targeting", Proc. Nati. Acad. Sci., vol. 88, Feb. 1991, pp. 834-838.

Mcelroy, et al., "Isolation of an Efficient Actin Promoter for Use in Rice Transformation", The Plant Cell, vol. 2, Feb. 1990, pp. 163-171.

Mett, et al., "Copper-controllable Gene Expression System for Whole Plants", Proc. Natl. Acad. Sci., vol. 90, May 1993, pp. 4567-4571.

Napoli, et al., "Introduction of a Chimeric Chalcone Synthase Gene into Petunia Results in Reversible Co-Suppression of Homologous Genes in trans", The Plant Cell, vol. 2, Apr. 1990, pp. 279-289.

Odell, et al., "Identification of DNA Sequences Required for Activity of the Cauliflower Mosaic Virus 35S Promoter", Nature, vol. 313, 1985, pp. 810-812.

Patterson, et al., "Health Implications of High Dietary Omega-6 Polyunsaturated Fatty Acids", Journal of Nutrition and Metabolism, 2012, 16 pages.

Petrie, et al., "Metabolic Engineering Camelina sativa with Fish Oil-Like Levels of DHA", PLOS One, vol. 9, No. 1, Jan. 2014, e85061, 8 pages.

Petrie, et al., "Metabolic Engineering of Omega-3 long-Chain Polyunsaturated Fatty Acids in Plants using an Acyl-CoA Δ6-Desaturase with ω3-Preference from the Marine Microalga Micromonas pusilla", Metabolic Engineering, vol. 12, 2010, pp. 233-240.

Petrie, et al., "Rapid Expression of Transgenes Driven by Seed-Specific Constructs in Leaf Tissue: DHA Production", Plant Methods, vol. 6, 2010, 6 pages.

Petrie, et al., "Transgenic Production of Arachidonic Acid in Oilseeds", Transgenic Res, vol. 21, 2012, pp. 139-147.

Poehlman, et al., "Bredding Field Crops", 1994, 495 pages.

Roder, et al., "Efficiency of the Tetracycline-Dependent Gene Expression System: Complete Suppression and Efficient Induction of the rolB Phenotype in Transgenic Plants", Mol Gen Genet, vol. 243, 1994, pp. 32-38.

Rossak, et al., "Expression of the FAE1 Gene and FAE1 Promoter Activity in Developing Seeds of Arabidopsis thaliana", Plant Molecular Biology, vol. 46, 2001, pp. 717-725.

Schena, et al., "A Steroid-Inducible Gene Expression System for Plant Cells", Proc. Natl. Acad. Sci., vol. 88, Dec. 1991, pp. 10421-10425.

Seberry, et al., "Quality of Australian Canola", Department of Primary Industries, Australian Oilseeds Federation, vol. 18, 2011/12, 34 pages.

Smith, et al., "Analyzing Variety by Environment Data Using Multiplicative Mixed Models and Adjustments for Spatial Field Trend", Biometrics, vol. 57, 2001, pp. 1138-1147.

Sosnowski, et al., "Infection of Australian Canola Cultivars (Brassica napus) by Leptosphaeria Maculans is Influenced by Cultivar and Environmental Conditions", Australasian Plant Pathology, vol. 33, 2004, pp. 401-411.

Stalberg, et al., "Deletion Analysis of a 2S Seed Storage Protein Promoter of Brassica napus in Transgenic Tobacco", Plant Molecular Biology, vol. 23, 1993, pp. 671-683.

Steifel, et al., "Expression of a Maize Cell Wall Hydroxyproline-Rich Glycoprotein Gene in Early Leaf and Root Vascular Differentiation", The Plant Cell, vol. 2, Aug. 1990, pp. 785-793.

Strobel, et al., "Survey of n-3 and n-6 Polyunsaturated Fatty Acids in Fish and Fish Products", Lipids in Health and Disease, vol. 11, 2012, 10 pages.

Thompson, et al., "Structural Elements Regulating Zein Gene Expression", BioEssays, vol. 10, 1989, pp. 108-113.

Tinoco, et al., "Analysis of Fatty Acid Mixtures: Comparison of Two "Absolute" Methods of Determination", Analytical Biochemistry, vol. 3, 1962, pp. 514-518.

Tocher, "Omega-3 Long-Chain Polyunsaturated Fatty Acids and Aquaculture in Perspective", Aquaculture, vol. 449, 2015, pp. 94-107.

Van Bokland, et al., "Transgene-Mediated Suppression of Chalcone Synthase Expression in Petunia Hybrida Results from an Increase in RNA Turnover", The Plant Journal, vol. 6, 1994, pp. 861-877.

Van De Wouw, et al., "Blackleg Disease of Canola in Australia", Crop and Pasture Science, vol. 67, 2016, pp. 273-283.

Velten, et al., "Isolation of a Dual Plant Promoter Fragment from the Ti Plasmid of Agrobacterium Tumefaciens", The EMBO Journal, vol. 3, No. 12, 1984, pp. 2723-2730.

(56) References Cited

OTHER PUBLICATIONS

Wang, et al., "*Brassica rapa* Cultivar Chiifu-401-42 Chromosome A2, Brapa_1.0, Whole Genome Shotgun Sequence", NCBI Reference Sequence: NC_024796.1, Oct. 13, 2016, pp. 1-2.
Ward, et al., "Chemical Regulation of Transgene Expression in Plants", Plant Molecular Biology, vol. 22, 1993, pp. 361-366.
Who Technical Report Series 916, "Diet, Nutrition and the Prevention of Chronic Diseases", Report of a Joint WHO/FAO Expert Consultation, 2003, 160 pages.
*Brassica rapa* cultivar Chiifu-401-42 chromosome A2, Brapa_1.0, whole genome shotgun sequence, NCBI Reference Sequence: NC_024796.1.

\* cited by examiner

FIG. 5

GAGCCTTGAGTGCTACTTTGGGAACAAAAACTTGGTTTGATGCTATCCTAGTCTTTTTCTCTTTTATAAACTATTATTAG
ATAAAAACTAAAAAATAGTATTTATGAGATTTGTCTTTTTTTCACAATATAAATTATTTTAGGTATAAAAATAAATAATA
GAATTAGTATTATTAGATATATAAAATACATTTAATTTAATTAATAATATAACTGTAAAGTATAATTAAGTTATACAATA
TCTAATAAATATAAAAATTGTATTAAAATATGGGAAAACAATATTATATTTTAAAGCGATCTTACTCGATCTCTCTTTGA
TCCCAAAGTTTTCATTCCTTTTAATTATATTTGTTGCAGAATATTAAAACCAGTGATTTCTGGGGTTTGATAGGATTAAG
ACACGATCGCAGAGAAAGTAGAATCAATCGTGGAAGGGAAGGGATATTCGAAACCCTAATTTCGATCGTATCCCCATCTT
CTACGAAAGCATCGATCGACTTTTTTCTGATTCAGTGAGAGTTTGAAATCAAAGTTTGATTTTTTCGACCTGATGGGTTT
CTTAAAGAAGTTAACGGGGATTTTCGGGTTCGGGCACAACGATGGTGGGCACGGAGCTGCTGCGAGAGACGAAGATGGTG
AAGGGGATAACACTGGATCAGTCTCTGAGGACGGAGATAAACGCCGGGAGGGTAATCAGGCAAGGTTCCGTGAAACCGGA
CTTCCAAGGAGGGGTTTTGGAGTTCCGGTTCAAGTAGCCGTCGAACGGTCTAGTCCTGGTCCTATTCTTCAGCCTTGTGC
TGCTTCTGACGGTGGAGTTCAGGTTTGTCTTTCTTTCATGGTTGTGATTTTAACTGTGTAGAAGTCTAGGGACTGAAGAA
ATTAATGAGAATTTGAGGGTTGCTAGTTTTGATTCTGATCTTGTAATGTGGCTACAGTGTTGTACTTGTCTTGTTGCAGG
ATCGTTAAATCCATTTGTTTGGTTCCGATCATCCTATGTTAGTTGGTAAAATTGGTCTTGTGAGTTTGTTTAAGTTGTTT
TTGTGTCTTCATTCATTTTCTAAGCTTAGCATTGATGAACAGTTGAATTTAGAATCTTTGTTCTAAGCTTAACATTAATG
AATATCGAATCTTTGTTCTACTCAGTCCTTTCTTTGTTTTTGGTTGTGATATGTTCTCGTTTCAACGTAGTTTATGTTCT
TCTTGTGATTGGCTTTACATTCTGCACGGTTTCCGCTTTAGTTAGGTGTCTGCATTATAGTTAGTTCATTGCTATCTTAA
ATTCTCTGTTCATTCATCTCTATATATCAAATTAAAGAGTGGCAGTGAAGTTTATGACAGGACACGATATATGTTTAGC
TTGATTAGTTGCGGTTAAAGCAAAAAGTTTTGTTTCACTCTGTCTGCTACAGAACCTGTAATTTAGAAATGATGATGGA
TCTCATGTCTTAACGGTTTCGTATTCATCATGAGTCACGAGGCTGCTATAGAGTTTGAATCTTAATTGGTTCTGTTGTTG
GGGAAAGACAATAATCCAGTCTTTAAGAAGCTAGTGGGGTTGATTCATCCCCAAGACTATTCGATTGTCCAAACGCATTG
ATATGTTTTTTTAATCAAGTTTTTGTTGATGGCAATAAACTAACATCCCAGCATAGTTATTGACTCGACTTAGTTTTAC
CATTAGGGACTACGATGGTACTCAATGCGGCTAAGGATTGATGAAGATGGAGATGTTGCAGATGAGTTCTTGGAAGATGA
TAACTGTAAGACTTTGCCCAGAAAATGCAAAACAAAAGCTGCAAAAGTGAGAGGTTTAGTGATATCTTCTGATGGGAAAC
TTCAGCCATTAATGCATTGAGCAGTGAACACCAAGGATAAATATTTACTGATTAGTGTGTGATTGAATCAAAGAAAGGTT
AGAATCTGGTTTTCATTTAGCCATTCAATCTCGATGTAAAATCGGTTAGATTCTGGTTGTTGATACTTGAGAACTTGAAA
TGTTTTGTAACTGTGAATTTTGTTTTGAAAATAGACAAGTGAATCTGTTTGGGGTTGTGTGAAAACGTGTGAGCAATTGT
TGGAGGTGTTCAAACACTGATAGTTTAAACTGAAGGCGGGAAACGACAATCTGCTAGTGGATCTCCCAGTCACGACGTTG
TAAAACGGGCGCCCGCGGAAAGCTTGCGGCCGCGGTACCGCCCGTTCGACTCAGATCTTCCAAGGCCTCGTCTCCGAGT
CCGCTGCTTCTCGCCGCGCCGATCACTTCTCCGCCGCCAACAAGGCTTGTAGTTAATAGGAATCATTCAGGGATTGTGAT
TCCGGGCAGTAGTAATTAATAATATAGTATTAGTATAGATAATATGTTTCGTTTGGGATCTTTGGAACGTTGCTCTGTTC
CTTGTTGTTCATTTTAAAGCTTTTGAGGGATAGTTGCAGAACTGTTCGGTGATGCTTCATCCTCTCAAGAACTAGATTTG
GGTAAAGAAACATCCATGCATGGATATGGAATGTTGTTCTTCCGATTGGAGATTATTTTATAAAATTTAAAATTCATGAT
TTAAAAAAACACATAAAAACCACAAAATTCATGATTTATTGACAATACGATACAAAATTAGCACCACCGGCTACTGGCTC
ATTACACATTTCCCCTTCCCCTCATTCTCACTTTGTGGCTTTATTATTATTATTATTACATATATTTACCGTTATTATT
TCACGTCACATAAGCTTGTTAATTAATCATTAGTGAGCCTTCTCAGCCTTTCCGTTAACGTAGTAGTGCTGTCCCACCTT
ATCAAGGTTAGAGAAAGTAGCCTTCCAAGCACCGTAGTAGAGAGGACACCTTGTAGTTGAGTCCCCACTTCTTAGCGAAAG
GAACGAATCTTCTGCTAACCTCAGGCTGTCTGAATTGAGGCATATCGGGGAAGAGGTGGTGGATAACCTGACAGTTAAGG
TATCCCATAAGCCAGTTCACGTATCCTCTAGAAGGATCGATATCAACGGTGTGATCAACAGCGTAGTTAACCCAAGAAAG
GTGCTTATCAGATGGAACAACAGGGAGGTGAGTATGAGAAGTAGAGAAGTGAGCGAAAAGGTACATGTAAGCGATCCAGT
TTCCGAAAGTGAACCACCAGTAAGCAACAGGCCAAGAGTATCCAGTAGCAAGCTTGATAACAGCGGTTCTAACAACATGA
GAAACGAGCATCCAAGAAGCCTCTTCGTAGTTCTTCTTACGGAGAACTTGTCTAGGGTGGAGAACGTAGATCCAGAAAGC
TTGAACAAGAAGTCCAGAGGTAACAGGAACGAAAGTCCAAGCTTGAAGTCTAGCCCAAGCTCTAGAGAATCCTCTAGGTC
TGTTATCCTCAACAGCAGTGTTGAAGAAAGCCACAGCAGGAGTGGTATCAAGATCCATATCGTGTCTAACCTTTTGAGGG
GTAGCATGGTGCTTGTTATGCATCTGGTTCCACATCTCACCAGAAGTAGAAAGTCCGAATCCACAAGTCATAGCCTGAAG
TCTCTTGTCCACGTAAACAGATCCGGTAAGAGAGTTATGTCCACCCTCATGTTGAACCCATCCACATCTAGCTCCGAAGA
AAGCACCGTAAACAACAGAAGCAATGATAGGGTATCCAGCGTACATAAGAGCAGTTCCAAGAGCGAATGTAGCAAGAAGC
TCGAGAAGTCTGTAAGCCACATGGGTGATAGAAGGCTTGAAGAATCCATCTCTCTCAAGCTCAGCACGCCATCTAGCGAA
ATCCTCAAGCATAGGAGCATCCTCAGACTCAGATCTCTTGATCTCAGCAGGTCTAGAAGGCAAAGCTCTAAGCATCTTCC
AAGCCTTGAGAGAACGCATGTGGAATTCTTTGAAAGCCTCAGTAGCATCAGCACCAGTGTTAGCAAGCATGTAGAAGATC
ACAGATCCACCAGGGTGCTTGAAGTTAGTCACATCGTACTCAACGTCCTCAACTCTAACCCATCTAGTCTCGAAAGTAGC
AGCAAGCTCATGAGGCTCAAGAGTCTTAAGATCAACAGGAGCAGTAGAAGCATCCTTAGCATCAAGAGCCTCAGCAGAAG
ATTTAGACCTGGTAAGTGGAGATCTAGGAGAAGATCTTCCATCAGTCTTAGGAGGGCACATGGTATGGTAATTGTAAATG
TAATTGTAATGTTGTTTGTTGTTTGTTGTTGGTAATTGTTGTAAAATTAATTAAGTGGGTATCTTTTGGATGGATAA
GCAAGTAGTGATGATGTTCTAGGTGAAGTGATGGGGGTGTTTTATAGCGGGACATGGTGAAATGGATGGTCGCCACATAA
GAAATGGAGGGGAAGGGTTCTTGCGCCATTCTTCAGTTTGCATGGATGCATGGGTTTCATTTGTAACACGTAATAAGGA
CAATGAAGTGCAGGTGTCTCTCAAGTTTCAGAGGGGATATGTGGACAGAAGAAGAACGGCGATGATATTGATGGAAATGG

FIG. 5 (con't)

```
CCATCTAGTGTGAATCTATTCGGTTGATAATACTAGTGCATTTTGGCCGTTAATCCCTTCAATTAACTGCACAAACTTCA
GTTGAGTATTGATTATTTGATTATAGGTTCTGTAAACACAATACCAAGTTTATTTAGAGGGGAGACATACAAATAGTTTC
GATATAAATAATAGAGTGGTTAAACTTAGTTATTAAAACTATATATAAAGTCTAAAAGTTAAATTATTTTTTTAATTGCA
AATATATAAAGTCTAAAGGGGTTACATTATTTCTTAAGAGATGTAACTCTGTTGGAATCTGACTTAATCCGTCTCATCAC
TCTGGTTTCCAGTTCTAATCTAATGAATTGTTTCTGCCAAAGAATTTGAAGCAAGAAGTAAATTGATCAATGCCGTCAA
CCCACACCAAACCGTCAACCCACTACCATCGCCGCGGAGACCCCAAACTCAACCTCCACCCATCGGTAAGAAGCACAGG
GCAGCCCGCACCACCACCAATTTGGCGTGCATGACACCTAGGGACTTGGCACGGGAGGCGGCGCACGTGGATGCAAATGA
CGGGATATCAGATGACAGGAAACGACGTTGAGAGACCATACGATGTAGAATATGAGCTCACCATCAACGAGAAACTAGGA
AAATCACAAAAAAACAACTCTCGTAATTGTACGAGTGGCACAGATGGGTCTGCCTCAACATATCTCTAATACGGCGAAG
CCTGCCCAACACGTAGTTGCCGGAATCCGGTGTGGAGCTCACGACTCTGAAAGATAGGCGCTTCCTGTTCGTTCGCTC
ACCCACTGGACGTCCGTCATGTGATGGATTTCGGTCATTGGTTTGCTGACAACCACATTCTGAAGCTCCATGAGATGAGT
CTTCACAATAGGTCCTGCTCAATACCGTGGAGTTATGGTTGCAAGTCCATAACTTGCCGTTCGAATATTTTGCGGAGCCA
GTCGGACGGGAATTGGCGAGCTCGGCTGACACCTATAAAGGCCATGACAAGAAGAACCAAAAGTTCTTCCCTAATGCTTT
CATGAGGCTTCGGGTCGTTATGGATGTCGGAAAACCCCTCTTGAAGGAACGAGACGTTATTATGCATGACGGTAAGACTA
TTACTTGTCAGTATAAGTATGAAAGATTACCTGTCTTCTGCTTTGTTTGTGGATTGATTGGACACGTTGAAAAAAAATGT
GCACTTCGATTTCAATACTCAGAGATCGACTTCCCTTTTCTCTAGGAGTATTCGATCAAGGCATTAACATGGAAGGAAGC
TCAAGCTCTAAAGGCTTCACAATGGAACCTGAAAAATTTCAACAAGCCTAAACTGAAATCGAAGTCAAATCACCCAACCG
GGAGCTCTAAATCAGCAAACACTCCTCCTCCACAGTATCCAATCATCGTGCACGATGCTCCAGGTATTGCAAGCCAGGTA
TTGCAAGCTAGGAGTAGGATAGAGACCTTAAACGTCGTTGGTGTGAAGAGTCATCTTCAGACCTAATGGAGATAGATGTA
GACGGCGGCACGAAGACTCTGAAACACCAGAAAGGCTAGTCCAGGATAAGGATCTGCTATCCCAACTGACCTCTCGTTAG
TCCCAAGGCCTCTCAACTAGAGCAGGAGGAAGGATGGTCACAAGACTAGGATAATGATGTTTCCAATATGAACCTGAATG
TCCATAGCTAATTTTTTAGTCTTGCTTCTGCACTTTTTGTTTATTATGTTCTGGTGACTATGTTATTTACCCTTGTCCG
TATGCTTGAGGGTACCCTAGTAGATTGGTTGGTTGGTTTCCATGTACCAGAAGGCTTACCCTATTAGTTGAAAGTTGAAA
CTTTGTTCCCTACTCAATTCCTAGTTGTGTAAATGTATGTATATGTAATGTGTATAAAACGTAGTACTTAAATGACTAGG
AGTGGTTCTTGAGACCGATGAGAGATGGGAGCAGAACTAAAGATGATGACATAATTAAGAACGAATTTGAAAGGCTCTTA
GGTTTGAATCCTATTCGAGAATGTTTTTGTCAAAGATAGTGGCGATTTGAACCAAAGAAAACATTTAAAAAATCAGTAT
CCGGTTACGTTCATGCAAATAGAAAGTGGTCTAGGATCTGATTGTAATTTTAGACTTAAAGAGTCTCTTAAGATTCAATC
CTGGCTGTGTACAAAACTACAAATAATATATTTTAGACTATTTGGCCTTAACTAAACTTCCACTCATTATTTACTGAGGT
TAGAGAATAGACTTGCGAATAAACACATTCCCGAGAAATACTCATGATCCCATAATTAGTCAGAGGGTATGCCAATCAGA
TCTAAGAACACACATTCCCTCAAATTTTAATGCACATGTAATCATAGTTTAGCACAATTCAAAAATAATGTAGTATTAAA
GACAGAAATTTGTAGACTTTTTTTGGCGTTAAAAGAAGACTAAGTTTATACGTACATTTTATTTTAAGTGGAAAACCGA
AATTTTCCATCGAAATATATGAATTTAGTATATATATTTCTGCAATGTACTATTTTGCTATTTTGGCAACTTTCAGTGGA
CTACTACTTTATTACAATGTGTATGGATGCATGAGTTTGAGTATACACATGTCTAAATGCATGCTTTGTAAAACGTAACG
GACCACAAAAGAGGATCCATACAAATACATCTCATAGCTTCCTCCATTATTTTCCGACACAAACAGAGCATTTTACAACA
ATTACCAACAACAACAAACAACAAACAACATTACAATTACATTTACAATTACCATACCATGGCCTCTATCGCTATCCCTG
CTGCTCTTGCTGGAACTCTTGGATACGTTACCTACAATGTGGCTAACCCTGATATCCCAGCTTCTGAGAAAGTTCCTGCT
TACTTCATGCAGGTTGAGTACTGGGGACCTACTATCGGAACTATTGGATACCTCCTCTTCATCTACTTCGGAAAGCGTAT
CATGCAGAACAGATCTCAACCTTTCGGACTCAAGAACGCTATGCTCGTTTACAACTTCTACCAGACCTTCTTCAACAGCT
ACTGCATCTACCTTTTCGTTACTTCTCATAGGGCTCAGGGACTTAAGGTTTGGGGAAACATCCCTGATATGACTGCTAAC
TCTTGGGGAATCTCTCAGGTTATCTGGCTTCACTACAACAACAAGTACGTTGAGCTTCTCGACACCTTCTTCATGGTGAT
GAGGAAGAAGTTCGACCAGCTTTCTTTCCTTCACATCTACCACCACACTCTTCTCATCTGGTCATGGTTCGTTGTTATGA
AGCTTGAGCCTGTTGGAGATTGCTACTTCGGATCTTCTGTTAACACCTTCGTGCACGTGATCATGTACTCTTACTACGGA
CTTGCTGCTCTTGGAGTTAACTGTTTCTGGAAGAAGTACATCACCCAGATCCAGATGCTTCAGTTCTGTATCTGTGCTTC
TCACTCTATCTACACCGCTTACGTTCAGAATACCGCTTTCTGGCTTCCTTACCTTCAACTCTGGGTTATGGTGAACATGT
TCGTTCTCTTCGCCAACTTCTACCGTAAGAGGTACAAGTCTAAGGGTGCTAAGAAGCAGTGATAAGGCGCGCGGCGCGCC
GGGCCGCCGCCATGTGACAGATCGAAGGAAGAAAGTGTAATAAGACGACTCTCACTACTCGATCGCTAGTGATTGTCATT
GTTATATATAATAATGTTATCTTTCACAACTTATCGTAATGCATGTGAAACTATAACACATTAATCCTACTTGTCATATG
ATAACACTCTCCCCATTTAAAACTCTTGTCAATTTAAAGATATAAGATTCTTTAAATGATTAAAAAAATATATTATAAA
TTCAATCACTCCTACTAATAAATTATTAATTATTATTTATTGATTAAAAAATACTTATACTAATTTAGTCTGAATAGAA
TAATTAGATTCTAGTCTCATCCCCTTTTAAACCAACTTAGTAAACGTTTTTTTTTTAATTTTATGAAGTTAAGTTTTTA
CCTTGTTTTTAAAAGAATCGTTCATAAGATGCCATGCCAGAACATTAGCTACACGTTACACATAGCATGCAGCCGCGGA
GAATTGTTTTCTTCGCCACTTGTCACTCCCTTCAAACACCTAAGAGCTTCTCTCTCACAGCACACATACAATCACAT
GCGTGCATGCATTATTACACGTGATCGCCATGCAAATCTCCTTTATAGCCTATAAATTAACTCATCCGCTTCACTCTTTA
CTCAAACCAAAACTCATCGATACAAACAAGATTAAAAACATACACGAGGATCTTTTACAACAATTACCAACAACAACAAA
CAACAAACAACATTACAATTACATTTACAATTACCATACCATGCCTCCAAGGGACTCTTACTCTTATGCTGCTCCTCCTT
CTGCTCAACTTCACGAAGTTGATACTCCTCAAGAGCACGACAAGAAAGAGCTTGTTATCGGAGATAGGGCTTACGATGTT
```

FIG. 5 (con't)

```
ACCAACTTCGTTAAGAGACACCCTGGTGGAAAGATCATTGCTTACCAAGTTGGAACTGATGCTACCGATGCTTACAAGCA
GTTCCATGTTAGATCTGCTAAGGCTGACAAGATGCTTAAGTCTCTTCCTTCTCGTCCTGTTCACAAGGGATACTCTCCAA
GAAGGGCTGATCTTATCGCTGATTTCCAAGAGTTCACCAAGCAACTTGAGGCTGAGGGAATGTTCGAGCCTTCTCTTCCT
CATGTTGCTTACAGACTTGCTGAGGTTATCGCTATGCATGTTGCTGGTGCTGCTCTTATCTGGCATGGATACACTTTCGC
TGGAATCGCTATGCTTGGAGTTGTTCAGGGAAGATGTGGATGGCTTATGCATGAGGGTGGACATTACTCTCTCACTGGAA
ACATTGCTTTCGACAGAGCTATCCAAGTTGCTTGTTACGGACTTGGATGTGGAATGTCTGGTGCTTGGTGGCGTAACCAG
CATAACAAGCACCATGCTACTCCTCAAAAGCTTCAGCACGATGTTGATCTTGATACCCTTCCTCTCGTTGCTTTCCATGA
GAGAATCGCTGCTAAGGTTAAGTCTCCTGCTATGAAGGCTTGGCTTTCTATGCAAGCTAAGCTTTTCGCTCCTGTTACCA
CTCTTCTTGTTGCTCTTGGATGGCAGCTTTACCTTCATCCTAGACACATGCTCAGGACTAAGCACTACGATGAGCTTGCT
ATGCTCGGAATCAGATACGGACTTGTTGGATACCTTGCTGCTAACTACGGTGCTGGATACGTTCTCGCTTGTTACCTTCT
TTACGTTCAGCTTGGAGCTATGTACATCTTCTGCAACTTCGCTGTTTCTCATACTCACCTCCCTGTTGTTGAGCCTAACG
AGCATGCTACTTGGGTTGAGTACGCTGCTAACCACACTACTAACTGTTCTCCATCTTGGTGGTGTGATTGGTGGATGTCT
TACCTTAACTACCAGATCGAGCACCACCTTTACCCTTCTATGCCTCAATTCAGACACCCTAAGATCGCTCCTAGAGTTAA
GCAGCTTTTCGAGAAGCACGGACTTCACTACGATGTTAGAGGATACTTCGAGGCTATGGCTGATACTTTCGCTAACCTTG
ATAACGTTGCCCATGCTCCTGAGAAGAAAATGCAGTAATGAGATCGTTCAAACATTTGGCAATAAAGTTTCTTAAGATTG
AATCCTGTTGCCGGTCTTGCGATGATTATCATATAATTTCTGTTGAATTACGTTAAGCACGTAATAATTAACATGTAATG
CATGACGTTATTTATGAGATGGGTTTTTATGATTAGAGTCCCGCAATTATACATTTAATACGCGATAGAAAACAAAATAT
AGCGCGCAAACTAGGATAAATTATCGCGCGGTGTCATCTATGTTACTAGATCGGTCGATTAAAAATCCCAATTATATT
TGGTCTAATTTAGTTTGGTATTGAGTAAAACAAATTCGAACCAAACCAAAATATAAATATATAGTTTTTATATATATGCC
TTTAAGACTTTTTATAGAATTTTCTTTAAAAAATATCTAGAAATATTTGCGACTCTTCTGGCATGTAATATTTCGTTAAA
TATGAAGTGCTCCATTTTTATTAACTTTAAATAATTGGTTGTACGATCACTTTCTTATCAAGTGTTACTAAAATGCGTCA
ATCTCTTTGTTCTTCCATATTCATATGTCAAAATCTATCAAAATTCTTATATATCTTTTTCGAATTTGAAGTGAAATTTC
GATAATTTAAAATTAAATAGAACATATCATTATTTAGGTATCATATTGATTTTTATACTTAATTACTAAATTTGGTTAAC
TTTGAAAGTGTACATCAACGAAAAATTAGTCAAACGACTAAAATAAATAAATATCATGTGTTATTAAGAAAATTCTCCTA
TAAGAATATTTTAATAGATCATATGTTTGTAAAAAAAATTAATTTTTACTAACACATATATTTACTTATCAAAAATTTGA
CAAAGTAAGATTAAAATAATATTCATCTAACAAAAAAAAACCAGAAAATGCTGAAAACCCGGCAAAACCGAACCAATCC
AAACCGATATAGTTGGTTTGGTTTGATTTTGATATAAACCGAACCAACTCGGTCCATTTGCACCCCTAATCATAATAGCT
TTAATATTTCAAGATATTATTAAGTTAACGTTGTCAATATCCTGGAAATTTTGCAAAATGAATCAAGCCTATATGCTGT
AATATGAATTTAAAAGCAGCTCGATGTGGTGGTAATATGTAATTTACTTGATTCTAAAAAAATATCCCAAGTATTAATAA
TTTCTGCTAGGAAGAAGGTTAGCTACGATTTACAGCAAAGCCAGAATACAAAGAACCATAAAGTGATTGAAGCTCGAAAT
ATACGAAGGAACAAATATTTTTAAAAAAATACGCAATGACTTGGAACAAAAGAAAGTGATATATTTTTTGTTCTTAAACA
AGCATCCCCTCTAAAGAATGGCAGTTTTCCTTTGCATGTAACTATTATGCTCCCTTCGTTACAAAAATTTTGGACTACTA
TTGGGAACTTCTTCTGAAAATAGTGATAGAACCCACACGAGCATGTGCTTTCCATTTAATTTTAAAAACCAAGAAACATA
CATACATAACATTCCATCAGCCTCTCTCTCTTTTTATTACGGTTAATGACTTAAAACACATCTTATTATCCCATCCTTAA
CACCTAGCAGTGTCTTTATACGATCTCATCGATCACCACTTCAAAACCATGCAGACTGCTGCTGCCCCTGGAGCTGGCAT
CGGCTAGGCTGGGTGCCGCACTGTCCCGGAAGGTCCCTAGCGACTTGTTTAGATTGATGGGACCACCTCTCAACTTCCTG
CTGCTGTCCCTGCTGCTGGATGTCCTGCCTCATCTGGCCGATTGCACGCTCCAGTCCCCTGCATGTGCACTCGCTCCTCA
ATTGCTTAAGATCATCGCAGCAGCTATCGAAGTGCTGGCTCTGTTGCCCTCCTCCACGGCCTTGGTTGTAGTAGTAGCTG
CCGCCGCCCTTCTGGACTTTTTCCCACAGGAACCGCCGAATAATTCGATAGAACCACACGAGCATGTGCTTTCATTTATT
TTAAAAACCAAGAAACATACATAACATTTCATCAGCCTCTCTCTCTCTCTCTCTCTCTCTCTCTCTCTCTCTCTCT
CTCTCTCTTTATTACAGCTGTTACACTAACTTAAAACACATTCATCTCATTATTATTATTATTATCCATCCTTAACACCT
AGCAGTGTCTTTGTACGATCTCATAATCGATCACCCCTTCATCAGGTATCCTTAGGCTTCACTCCAACGTTGTTGCAGTT
ACGGAACATGTACACACCATCATGGTTCTCAACGAACTGGCAAGATCTCCAAGTTTTCCAAAGGCTAACCCACATGTTCT
CATCGGTGTGTCTGTAGTGCTCTCCCATAACTTTCTTGATGCACTCGGTAGCTTCTCTAGCATGGTAGAATGGGATCCTT
GAAACGTAGTGATGGAGCACATGAGTCTCGATGATGTCATGGAAGATGATTCCGAGGATTCCGAACTCTCTATCGATAGT
AGCAGCAGCACCCTTAGCGAAAGTCCACTCTTGAGCATCGTAATGAGGCATAGAAGAATCGGTGTGCTGAAGGAAGGTAA
CGAAAACAAGCCAGTGGTTAACAAGGATCCAAGGACAGAACCATGTGATGAAAGTAGGCCAGAATCCGAAAACCTTGTAA
GCGGTGTAAACAGAAGTGAGGGTAGCAAGGATTCCAAGATCAGAAAGAACGATGTACCAGTAGTCCTTCTTATCGAAAAC
AGGGCTAGAAGGCCAGTAGTGAGACTTGAAGAACTTAGAAACACCAGGGTAAGGTTGTCCAGTAGCGTTAGTAGCAAGGT
AAAGAGAAAGTCCTCCAAGCTGTTGGAACAAGAGAGCGAAAACAGAGTAGATAGGAGTTTCCTCAGCGATATCGTGAAGG
CTGGTAACTTGGTGCTTCTCTTTGAATTCCTCGGCGGTGTAAGGAACGAAAACCATATCTCTGGTCATGTGTCCAGTAGC
CTTATGGTGCTTAGCATGAGGAACTTCCAGCTGAAGTAAGGAACCATAACAAGAGAGTGGAGAACCCATCCAACGGTAT
CGTTAACCCATCCGTAGTTAGAGAAAGCAGAATGTCCACACTCATGTCCAAGGATCCAGATTCCGAATCCGAAACAAGAG
ATAGAGAACACGTAAGCAGACCAAGCAGCGAATCTAAGGAATTCGTTAGGGAGAAGAGGGATGTAGGTAAGTCCAACGTA
AGCGATAGCAGAGATAGCCACGATATCTCTCACCACGTAAGACATAGACTTCACGAGAGATCTCTCGTAACAGTGCTTAG
GGATAGCGTCAAGGATATCCTTGATGGTGTAATCTGGCACCTTGAAAACGTTTCCGAAGGTATCGATAGCGGTCTTTTGC
```

FIG. 5 (con't)

```
TGCTTGAAAGATGCAACGTTTCCAGAACGCCTAACGGTCTTAGTAGATCCCTCAAGGATCTCAGATCCAGACACGGTAAC
CTTAGACATGGTATGGTAATTGTAAATGTAATTGTAATGTTGTTTGTTGTTTGTTGTTGTTGGTAATTGTTGTAAAATTT
TTGGTGGTGATTGGTTCTTTAAGGTGTGAGAGTGAGTTGTGAGTTGTGTGGTGGGTTTGGTGAGATTGGGGATGGTGGGT
TTATATAGTGGAGACTGAGGAATGGGGTCGTGAGTGTTAACTTTGCATGGGCTACACGTGGGTTCTTTTGGGCTTACACG
TAGTATTATTCATGCAAATGCAGCCAATACATATACGGTATTTTAATAATGTGTGGGAATACAATATGCCGAGTATTTTA
CTAATTTTGGCAATGACAAGTGTACATTTGGATTATCTTACTTGGCCTCTCTTGCTTTAATTTGGATTATTTTTATTCTC
TTACCTTGGCCGTTCATATTCACATCCCTAAAGGCAAGACAGAATTGAATGGTGGCCAAAAATTAAAACGATGGATATGA
CCTACATAGTGTAGGATCAATTAACGTCGAAGGAAAATACTGATTCTGCCCGTTCGACTCAGATCTTCCAAGGCCTCGTC
TCCGAGTCCGCTGCTTCTCGCCGCGCCGATCACTTCTCCGCCGCCAACAAGGCTTGTAGTTAATAGGAATCATTCAGGGA
TTGTGATTCCGGGCAGTAGTAATTAATAATATAGTATTAGTATACAGAACCTCTTATTTAGCTAAAAGATTATGTTCTTA
ATGTTGATAAGAAGTTTGAGAAACAAATATAATTGAGCTTCTGATTAGTTGATCGTAATTGGTCATTAATAATTGTATCT
AACCAGTGCAGTATAAGAGCGTATAAGAGCATCTTCAAAAAGACTTTATTTTAGAGTTAATCAGTGCAGTATAAGAGCAT
CTCTAAAAAAACTCTAATTATAGAGTTTTGCAAACTCTATATTTGAAGTTTTAAGGTGTTTTTTTTTCAAAAGCAAAACT
TCAAATTTAACTTCAAAATTATTTGTAATTTACACTATGCTCTTTATATTTATCATAATTAATATAAGGGGTGTTAGTG
GGACTTAGATTTCTATAGAGTTTGTTGATTTTAAAAGTTGAGAGATTTGTTAAATTTAGAAAGAGATGTAGAGAATTTTG
TCTATTGTGAAAATCTATGAAAATAGAGTAATGTAATGATTCTAAGAATTCAAAGTAAACATGTAGTATTCTCAAAATCT
AAATTTGTGAAACAGTGGTCCCAGATTTTCAAGACTCAGACTAAAGGCTATGGAGGAAGCTAGGGTTTTGGCGATTGGCG
ACACTAGGGTTTCGAGTACGGCAGATTTGGATGAAACTATGATGGATGTGGGGAGAGAGGGAGACCGCCAGGAGATCCG
CCAGATAAGTTAACCTCATGGGTAGCGAAGGTGGTGGAGACGGCTGAGGGAGGGATGCCAGTACCGGAGGTTTTGATTGC
AGATTCTTTTGTGTCGGAGAGGGTACGGGTAGAATTTCCGAATG
(SEQ ID NO:40)
```

FIG.6

```
AAAAAATACAACCAAAGAAAAATATACCAGAAGGTTGTGATTTGGTCCATTATATAAAAATTACGAAATGAATTTCTTTA
TCCTTTTATCTCAAATTTTATTGAAGACTTTTGTAGGATTATAGTTGACTTTATGCTCACATATATATACACTGATCAAA
ACTTTTTAAAAACATAAAGAAATTGTGAAACAATAAAAATAAAATGAAATGAGTAATTAATGAGTAGATTAAGACATTGG
ACCCTCCACAGGCGATAAAGTAAAATAATCAGAAGTTGCAGGAGGCAAAGGAGGACTACTACTAATACTTGGAACTTGGA
AGTAGCTATCGTGCGCATCTGCCTCCAAGTCCAACACCTTATAACAAATTTCCGCCGGGAAGAAAGAAAAGTCTCTCTGC
CCTCTCTTCTTTAGCCTCCAGCTTCTGCAAACCATACGTACAAACAAGATAGACACAATCCTCCCTACCTCCTTCTTCTA
TCTTCATCGAAAGATTCAACCACCACTCAAGTCTTCTCTCTCTTTTTTGGAAAGAAAAAAGGTAAAAGCTTTCTTCTTTC
TGAGCAAACTCCCATGAATTTCCCTTTTGGGGGTTTAGGGTCTTTCCTTTTATGTTCCTACTTCGGTATAATTCGATTTC
ATGCGAACTTAGATTATAAAAATTTGATCTTTTTTTTGTGGGGTTTGAAATTGAAATCCATTTTAGGGGTTACCATCGTT
GACCAAATGTCTCGACTTTGTTCGAATCATGATGTTACTTAATCATGGAGGAGAAGAAGGATTTTTATAACCATGTCTCT
GTTGCTTGCTGCTTAAACCCTATATAATTGGAAACTTTTTGTTTTAGTCTGTGTCTGAAAGTTTCTATATTCGTATTGTC
TATTTTGTAAAGACTAAAACAAAAATGCCTATTTTAGTTTGTTCTTGTTCCGCAACACCGTTACTGAACTCTTCGTTCA
CTTAAACAGTTTGTGTGTGTGAGAAACAGCGTAATGAGCTGCTTTGGTTGTTGTGGTGGTGACGATTTTCGTCGAGTTGC
TGAAACTGGACCCAAGCCAGTGTACGGCGCAGGAGGTACTTTAAGCTTATAACCCTTTGTCTATCCTTTGGCTAGCGGCT
AATGTTGATGAACTTTTTATTCAACCGTTGGCTAAGGTAACACTGATAGTTTAAACTGAAGGCGGGAAACGACAATCTG
CTAGTGGATCTCCCAGTCACGACGTTGTAAAACGGCGCCCCGCGGAAAGCTTGCGGCCGCGGTACCGCCCGTTCGACTC
AGATCTTCCAAGGCCTCGTCTCCGAGTCCGCTGCTTCTCGCCGCGCCGATCACTTCTCCGCCGCCAACAAGGCTTGTAGT
TAATAGGAATCATTCAGGGATTGTGATTCCGGGCAGTAGTAATTAATAATATAGTATTAGTATAGATAATATGTTTCGTT
TGGGATCTTTGGAACGTTGCTCTGTTCCTTGTTGTTCATTTTAAAGCTTTTGAGGGATAGTTGCAGAACTGTTCGGTGAT
GCTTCATCCTCTCAAGAACTAGATTTGGGTAAAGAAACATCCATGCATGGATATGGAATGTTGTTCTTCCGATTGGAGAT
TATTTTATAAAATTTAAAATTCATGATTTAAAAAAACACATAAAAACCACAAAATTCATGATTTATTGACAATACGATAC
AAAATTAGCACCACCGGCTACTGGCTCATTACACATTTCCCCTTCCCCTCATTCTCACTTTGTGGCTTTATTATTATTAT
TATTACATATATTTTACCGTTATTATTTCACGTCACATAAGCTTGTTAATTAATCATTAGTGAGCCTTCTCAGCCTTTCC
GTTAACGTAGTAGTGCTGTCCCACCTTATCAAGGTTAGAGAAAGTAGCCTTCCAAGCACCGTAGTAAGAGAGCACCTTGT
AGTTGAGTCCCCACTTCTTAGCGAAAGGAACGAATCTTCTGCTAACCTCAGGCTGTCTGAATTGAGGCATATCAGGGAAG
AGGTGGTGGATAACCTGACAGTTAAGGTATCCCATAAGCCAGTTCACGTATCCTCTAGAAGGATCGATATCAACGGTGTG
ATCAACAGCGTAGTTAACCCAAGAAAGGTGCTTATCAGATGGAACAACAGGGAGGTGAGTATGAGAAGTAGAGAAGTGAG
CGAAAGGTACATGTAAGCGATCCAGTTTCCGAAAGTGAACCACCAGTAAGCAACAGGCCAAGAGTATCCAGTAGCAAGC
TTGATAACAGCGGTTCTAACAACATGAGAAACGAGCATCCAAGAAGCCTCTTCGTAGTTCTTCTTACGGAGAACTTGTCT
AGGGTGGAGAACGTAGATCCAGAAAGCTTGAACAAGAAGTCCAGAGGTAACAGGAACGAAAGTCCAAGCTTGAAGTCTAG
CCCAAGCTCTAGAGAATCCTCTAGGTCTGTTATCCTCAACAGCAGTGTTGAAGAAAGCCACAGCAGGAGTGGTATCAAGA
TCCATATCGTGTCTAACCTTTTGAGGGGTAGCATGGTGCTTGTTATGCATCTGGTTCCACATCTCACCAGAAGTAGAAAG
TCCGAATCCACAAGTCATAGCCTGAAGTCTCTTGTCCACGTAAACAGATCCGGTAAGAGAGTTATGTCCACCCTCATGTT
GAACCCATCCACATCTAGCTCCGAAGAAAGCACCGTAAACAACAGAAGCAATGATAGGGTATCCAGCGTACATAAGAGCA
GTTCCAAGAGCGAATGTAGCAAGAAGCTCGAGAAGTCTGTAAGCCACATGGGTGATAGAAGGCTTGAAGAATCCATCTCT
CTCAAGCTCAGCACGCCATCTAGCGAAATCCTCAAGCATAGGAGCATCCTCAGACTCAGATCTCTTGATCTCAGCAGGTC
TAGAAGGCAAAGCTCTAAGCATCTTCCAAGCCTTGAGAGAACGCATGTGGAATTCTTTGAAAGCCTCAGTAGCATCAGCA
CCAGTGTTAGCAAGCATGTAGAAGATCACAGATCCACCAGGGTGCTTGAAGTTAGTCACATCGTACTCAACGTCCTCAAC
TCTAACCCATCTAGTCTCGAAAGTAGCAGCAAGCTCATGAGGCTCAAGAGTCTTAAGATCAACAGGAGCAGTAGAAGCAT
CCTTAGCATCAAGAGCCTCAGCAGAAGATTTAGACCTGGTAAGTGGAGATCTAGGAGAAGATCTTCCATCAGTCTTAGGA
GGGCACATGGTATGGTAATTGTAAATGTAATTGTAATGTTGTTTGTTGTTGTTGTTGGTAATTGTTGTAAAATTAA
TTAAGTGGGTATCTTTTGGATGGATAAGCAAGTAGTGATGATGTTCTAGGTGAAGTGATGGGGGTGTTTTATAGCGGGAG
ATGGTGAAATGGATGGTCGCCACATAAGAAATGGAGGGGAAGGGTTCTTGCGCCATTCTTCAGTTTGCATGGATGCATGG
GTTTCATTTTGTAACACGTAATAAGGACAATGAAGTGCAGGTGTCTCTCAAGTTTCAGAGGGGATATGTGGACAGAAGAA
GAACGGCGATGATATTGATGGAAATGGCCATCTAGTGTGAATCTATTCGGTTGATAATACTAGTGCATTTTGGCCGTTAA
TCCCTTCAATTAACTGCACAAACTTCAGTTGAGTATTGATTATTTGATTATAGGTTCTGTAAACACAATACCAAGTTTAT
TTAGAGGGGAGACATACAAATAGTTTCGATATAAATAATAGAGTGGTTAAACTTAGTTATTAAAACTATATATAAAGTCT
AAAAGTTAAATTATTTTTTAATTGCAAATATATAAAGTCTAAAGGGGTTACATTATTTCTTAAGAGATGTAACTCTGTT
GGAATCTGACTTAATCCGTCTCATCACTCTGGTTTCCAGTTCTAATCTAATGAATTGTTTCTGCCAAAGAATTTGAAGC
AAGAAGTAAATTGATCAATGCCGTCAACCCACACCAAACCGTCAACCCACTACCATCGCCGCGGAGACCCCAAACTCAA
CCTCCACCCATCGGTAAGAAGCACAGGGCAGCCCGCACCACCACCAATTTGGCGTGCATGACACCTAGGGACTTGGCACG
GGAGGCGGCGCACGTGGATGCAAATGACGGGATATCAGATGACAGGAAACGACGTTGAGAGACCATACGATGTAGAATAT
GAGCTCACCATCAACGAGAAACTAGGAAAATCACAAAAAAAACAACTCTCGTAATTGTACGAGTGGCACAGATGGGTCTG
CCTCAACATATCTCTAATACGGCGAAGCCTGCCCAACACGTAGTTGCCGGAATCCGGTGTGGAGCTCACGACTCTGAAAG
ATAGGCGCTTCCTGTTTCGTTTCGCTCACCCACTGGACGTCCGTCATGTGATGGATTTCGGTCATTGGTTTGCTGACAAC
CACATTCTGAAGCTCCATGAGATGAGTCTTCACAATAGGTCCTGCTCAATACCGTGGAGTTATGGTTGCAAGTCCATAAC
```

FIG. 6 (con't)

```
TTGCCGTTCGAATATTTTGCGGAGCCAGTCGGACGGGAATTGGCGAGCTCGGCTGACACCTATAAAGGCCATGACAAGAA
GAACCAAAAGTTCTTCCCTAATGCTTTCATGAGGCTTCGGGTCGTTATGGATGTCGGAAAACCCCTCTTGAAGGAACGAG
ACGTTATTATGCATGACGGTAAGACTATTACTTGTCAGTATAAGTATGAAAGATTACCTGTCTTCTGCTTTGTTTGTGGA
TTGATTGGACACGTTGAAAAAAAATGTGCACTTCGATTTCAATACTCAGAGATCGACTTCCCTTTTCTCTAGGAGTATTC
GATCAAGGCATTAACATGGAAGGAAGCTCAAGCTCTAAAGGCTTCACAATGGAACCTGAAAAATTTCAACAAGCCTAAAC
TGAAATCGAAGTCAAATCACCCAACCGGGAGCTCTAAATCAGCAAACACTCCTCCTCCACAGTATCCAATCATCGTGCAC
GATGCTCCAGGTATTGCAAGCCAGGTATTGCAAGCTAGGAGTAGGATAGAGACCTTAAACGTCGTTGGTGTGAAGAGTCA
TCTTCAGACCTAATGGAGATAGATGTAGACGGCGGCACGAAGACTCTGAAACACCAGAAAGGCTAGTCCAGGATAAGGAT
CTGCTATCCCAACTGACCTCTCGTTAGTCCCAAGGCCTCTCAACTAGAGCAGGAGGAAGGATGGTCACAAGACTAGGATA
ATGATGTTCCAATATGAACCTGAATGTCCATAGCTAATTTTTTAGTCTTGCTTCTGCACTTTTTGTTTATTATGTTCT
GGTGACTATGTTATTTACCCTTGTCCGTATGCTTGAGGGTACCCTAGTAGATTGGTTGGTTGGTTTCCATGTACCAGAAG
GCTTACCCTATTAGTTGAAAGTTGAAACTTTGTTCCCTACTCAATTCCTAGTTGTGTAAATGTATGTATATGTAATGTGT
ATAAAACGTAGTACTTAAATGACTAGGAGTGGTTCTTGAGACCGATGAGAGATGGGAGCAGAACTAAAGATGATGACATA
ATTAAGAACGAATTTGAAAGGCTCTTAGGTTTGAATCCTATTCGAGAATGTTTTGTCAAAGATAGTGGCGATTTTGAAC
CAAAGAAAACATTTAAAAAATCAGTATCCGGTTACGTTCATGCAAATAGAAAGTGGTCTAGGATCTGATTGTAATTTTAG
ACTTAAAGAGTCTCTTAAGATTCAATCCTGGCTGTGTACAAAACTACAAATAATATATTTTAGACTATTTGGCCTTAACT
AAACTTCCACTCATTATTTACTGAGGTTAGAGAATAGACTTGCGAATAAACACATTCCCGAGAAATACTCATGATCCCAT
AATTAGTCAGAGGGTATGCCAATCAGATCTAAGAACACACATTCCCTCAAATTTTAATGCACATGTAATCATAGTTTAGC
ACAATTCAAAAATAATGTAGTATTAAAGACAGAAATTTGTAGACTTTTTTTGGCGTTAAAAGAAGACTAAGTTTATACG
TACATTTTATTTTAAGTGGAAAACCGAAATTTTCCATCGAAATATATGAATTTAGTATATATATTTCTGCAATGTACTAT
TTTGCTATTTTGGCAACTTTCAGTGGACTACTACTTTATTACAATGTGTATGGATGCATGAGTTTGAGTATACACATGTC
TAAATGCATGCTTTGTAAAACGTAACGGACCACAAAAGAGGATCCATACAAATACATCTCATAGCTTCCTCCATTATTTT
CCGACACAAACAGAGCATTTTACAACAATTACCAACAACAACAAACAACAAACAACATTACAATTACATTTACAATTACC
ATACCATGGCCTCTATCGCTATCCCTGCTGCTCTTGCTGGAACTCTTGGATACGTTACCTACAATGTGGCTAACCCTGAT
ATCCCAGCTTCTGAGAAAGTTCCTGCTTACTTCATGCAGGTTGAGTACTGGGGACCTACTATCGGAACTATTGGATACCT
CCTCTTCATCTACTTCGGAAAGCGTATCATGCAGAACAGATCTCAACCTTTCGGACTCAAGAACGCTATGCTCGTTTACA
ACTTCTACCAGACCTTCTTCAACAGCTACTGCATCTACCTTTTCGTTACTTCTCATAGGGCTCAGGGACTTAAGGTTTGG
GGAAACATCCCTGATATGACTGCTAACTCTTGGGGAATCTCTCAGGTTATCTGGCTTCACTACAACAACAAGTACGTTGA
GCTTCTCGACACCTTCTTCATGGTGATGAGGAAGAAGTTCGACCAGCTTTCTTTCCTTCACATCTACCACCACACTCTTC
TCATCTGGTCATGGTTCGTTGTTATGAAGCTTGAGCCTGTTGGAGATTGCTACTTCGGATCTTCTGTTAACACCTTCGTG
CACGTGATCATGTACTCTTACTACGGACTTGCTGCTCTTGGAGTTAACTGTTTCTGGAAGAAGTACATCACCCAGATCCA
GATGCTTCAGTTCTGTATCTGTGCTTCTCACTCTATCTACACCGCTTACGTTCAGAATACCGCTTTCTGGCTTCCTTACC
TTCAACTCTGGGTTATGGTGAACATGTTCGTTCTCTTCGCCAACTTCTACCGTAAGAGGTACAAGTCTAAGGGTGCTAAG
AAGCAGTGATAAGGCGCGCGGCGCGCCGGGCCGCCGCCATGTGACAGATCGAAGGAAGAAAGTGTAATAAGACGACTCTC
ACTACTCGATCGCTAGTGATTGTCATTGTTATATATAATAATGTTATCTTTCACAACTTATCGTAATGCATGTGAAACTA
TAACACATTAATCCTACTTGTCATATGATAACACTCTCCCCATTTAAAACTCTTGTCAATTTAAAGATATAAGATTCTTT
AAATGATTAAAAAAAATATATTATAAATTCAATCACTCCTACTAATAAATTATTAATTATTATTTATTGATTAAAAAAT
ACTTATACTAATTTAGTCTGAATAGAATAATTAGATTCTAGTCTCATCCCCTTTTAAACCAACTTAGTAAACGTTTTTT
TTTTAATTTTATGAAGTTAAGTTTTTACCTTGTTTTTAAAAAGAATCGTTCATAAGATGCCATGCCAGAACATTAGCTAC
ACGTTACACATAGCATGCAGCCGCGGAGAATTGTTTTTCTTCGCCACTTGTCACTCCCTTCAAACACCTAAGAGCTTCTC
TCTCACAGCACACACATACAATCACATGCGTGCATGCATTATTACACGTGATCGCCATGCAAATCTCCTTTATAGCCTAT
AAATTAACTCATCCGCTTCACTCTTTACTCAAACCAAAACTCATCGATACAAACAAGATTAAAAACATACACGAGGATCT
TTTACAACAATTACCAACAACAACAAACAACAAACAACATTACAATTACATTTACAATTACCATACCATGCCTCCAAGGG
ACTCTTACTCTTATGCTGCTCCTCCTTCTGCTCAACTTCACGAAGTTGATACTCCTCAAGAGCACGACAAGAAAGAGCTT
GTTATCGGAGATAGGGCTTACGATGTTACCAACTTCGTTAAGAGACACCCTGGTGGAAAGATCATTGCTTACCAAGTTGG
AACTGATGCTACCGATGCTTACAAGCAGTTCCATGTTAGATCTGCTAAGGCTGACAAGATGCTTAAGTCTCTTCCTTCTC
GTCCTGTTCACAAGGGATACTCTCCAAGAAGGGCTGATCTTATCGCTGATTTCCAAGAGTTCACCAAGCAACTTGAGGCT
GAGGGAATGTTCGAGCCTTCTCTTCCTCATGTTGCTTACAGACTTGCTGAGGTTATCGCTATGCATGTTGCTGGTGCTGC
TCTTATCTGGCATGGATACACTTTCGCTGGAATCGCTATGCTTGGAGTTGTTCAGGGAAGATGTGGATGGCTTATGCATG
AGGGTGGACATTACTCTCTCACTGGAAACATTGCTTTCGACAGAGCTATCCAAGTTGCTTGTTACGGACTTGGATGTGGA
ATGTCTGGTGCTTGGTGGCGTAACCAGCATAACAAGCACCATGCTACTCCTCAAAAGCTTCAGCACGATGTTGATCTTGA
TACCCTTCCTCTCGTTGCTTTCCATGAGAGAATCGCTGCTAAGGTTAAGTCTCCTGCTATGAAGGCTTGGCTTTCTATGC
AAGCTAAGCTTTTCGCTCCTGTTACCACTCTTCTTGTTGCTCTTGGATGGCAGCTTTACCTTCATCCTAGACACATGCTC
AGGACTAAGCACTACGATGAGCTTGCTATGCTCGGAATCAGATACGGACTTGTTGGATACCTTGCTGCTAACTACGGTGC
TGGATACGTTCTCGCTTGTTACCTTCTTTACGTTCAGCTTGGAGCTATGTACATCTTCTGCAACTTCGCTGTTTCTCATA
CTCACCTCCCTGTTGTTGAGCCTAACGAGCATGCTACTTGGGTTGAGTACGCTGCTAACCACACTACTAACTGTTCTCCA
```

FIG. 6 (con't)

```
TCTTGGTGGTGTGATTGGTGGATGTCTTACCTTAACTACCAGATCGAGCACCACCTTTACCCTTCTATGCCTCAATTCAG
ACACCCTAAGATCGCTCCTAGAGTTAAGCAGCTTTTCGAGAAGCACGGACTTCACTACGATGTTAGAGGATACTTCGAGG
CTATGGCTGATACTTTCGCTAACCTTGATAACGTTGCCCATGCTCCTGAGAAGAAAATGCAGTAATGAGATCGTTCAAAC
ATTTGGCAATAAAGTTTCTTAAGATTGAATCCTGTTGCCGGTCTTGCGATGATTATCATATAATTTCTGTTGAATTACGT
TAAGCACGTAATAATTAACATGTAATGCATGACGTTATTTATGAGATGGGTTTTTATGATTAGAGTCCCGCAATTATACA
TTTAATACGCGATAGAAAACAAAATATAGCGCGCAAACTAGGATAAATTATCGCGCGCGGTGTCATCTATGTTACTAGAT
CGGTCGATTAAAAATCCCAATTATATTTGGTCTAATTTAGTTTGGTATTGAGTAAAACAAATTCGAACCAAACCAAAATA
TAAATATATAGTTTTTATATATATGCCTTTAAGACTTTTTATAGAATTTTCTTTAAAAAATATCTAGAAATATTTGCGAC
TCTTCTGGCATGTAATATTTCGTTAAATATGAAGTGCTCCATTTTTATTAACTTTAAATAATTGGTTGTACGATCACTTT
CTTATCAAGTGTTACTAAAATGCGTCAATCTCTTTGTTCTTCCATATTCATATGTCAAAATCTATCAAAATTCTTATATA
TCTTTTTCGAATTTGAAGTGAAATTTCGATAATTTAAAATTAAATAGAACATATCATTATTTAGGTATCATATTGATTTT
TATACTTAATTACTAAATTTGGTTAACTTTGAAAGTGTACATCAACGAAAAATTAGTCAAACGACTAAAATAAATAAATA
TCATGTGTTATTAAGAAAATTCTCCTATAAGAATATTTTAATAGATCATATGTTTGTAAAAAAAATTAATTTTTACTAAC
ACATATATTTACTTATCAAAAATTTGACAAAGTAAGATTAAAATAATATTCATCTAACAAAAAAAAACCAGAAAATGCT
GAAAACCCGGCAAAACGAACCAATCCAAACGATATAGTTGGTTTGGTTTGATTTGATATAAACCGAACCAACTCGGT
CCATTTGCACCCTAATCATAATAGCTTTAATATTTCAAGATATTATTAAGTTAACGTTGTCAATATCCTGGAAATTTTG
CAAAATGAATCAAGCCTATATGGCTGTAATATGAATTTAAAAGCAGCTCGATGTGGTGGTAATATGTAATTTACTTGATT
CTAAAAAAATATCCCAAGTATTAATAATTTCTGCTAGGAAGAAGGTTAGCTACGATTTACAGCAAAGCCAGAATACAAAG
AACCATAAAGTGATTGAAGCTCGAAATATACGAAGGAACAAATATTTTAAAAAAATACGCAATGACTTGGAACAAAAGA
AAGTGATATATTTTTGTTCTTAAACAAGCATCCCTCTAAAGAATGGCAGTTTTCCTTTGCATGTAACTATTATGCTCC
CTTCGTTACAAAAATTTTGGACTACTATTGGGAACTTCTTCTGAAAATAGTGATAGAACCCACACGAGCATGTGCTTTCC
ATTTAATTTTAAAAACCAAGAAACATACATACATAACATTCCATCAGCCTCTCTCTCTTTTTATTACGGTTAATGACTTA
AAACACATCTTATTATCCCATCCTTAACACCTAGCAGTGTCTTTATACGATCTCATCGATCACCACTTCAAAACCATGCA
GACTGCTGCTGCCCCTGGAGCTGGCATCGGCTAGGCTGGGTGCCGCACTGTCCCGGAAGGTCCCTAGCGACTTGTTTAGA
TTGATGGGACCACCTCTCAACTTCCTGCTGCTGTCCCTGCTGCTGGATGTCCTGCCTCATCTGGCCGATTGCACGCTCCA
GTCCCCTGCATGTGCACTCGCTCCTCAATTGCTTAAGATCATCGCAGCAGCTATCGAAGTGCTGGCTCTGTTGCCCTCCT
CCACGGCCTTGGTTGTAGTAGTAGCTGCCGCCGCCCTTCTGGACTTTTTCCCACAGGAACCGCCGAATAATTCGATAGAA
CCACACGAGCATGTGCTTTCATTTATTTTAAAAACCAAGAAACATACATAACATTTCATCAGCCTCTCTCTCTCTCTCTC
TCTCTCTCTCTCTCTCTCTCTCTCTCTCTCTTTATTACAGCTGTTACACTAACTTAAAACACATTCATCTCATTAT
TATTATTATTATCCATCCTTAACACCTAGCAGTGTCTTTGTACGATCTCATAATCGATCACCCCTTCATCAGGTATCCTT
AGGCTTCACTCCAACGTTGTTGCAGTTACGGAACATGTACACACCATCATGGTTCTCAACGAACTGGCAAGATCTCCAAG
TTTTCCAAAGGCTAACCCACATGTTCTCATCGGTGTGTCTGTAGTGCTCTCCCATAACTTTCTTGATGCACTCGGTAGCT
TCTCTAGCATGGTAGAATGGGATCCTTGAAACGTAGTGATGGAGCACATGAGTCTCGATGATGTCATGGAAGATGATTCC
GAGGATTCCGAACTCTCTATCGATAGTAGCAGCAGCACCCTTAGCGAAAGTCCACTCTTGAGCATCGTAATGAGGCATAG
AAGAATCGGTGTGCTGAAGGAAGGTAACGAAAACAAGCCAGTGGTTAACAAGGATCCAAGGACAGAACCATGTGATGAAA
GTAGGCCAGAATCCGAAAACCTTGTAAGCGGTGTAAACAGAAGTGAGGGTAGCAAGGATTCCAAGATCAGAAAGAACGAT
GTACCAGTAGTCCTTCTTATCGAAAACAGGGCTAGAAGGCCAGTAGTGAGACTTGAAGAACTTAGAAACACCAGGGTAAG
GTTGTCCAGTAGCGTTAGTAGCAAGGTAAAGAGAAAGTCCTCCAAGCTGTTGGAACAAGAGAGCGAAAACAGAGTAGATA
GGAGTTTCCTCAGCGATATCGTGAAGGCTGGTAACTTGGTGCTTCTCTTTGAATTCCTCGGCGGTGTAAGGAACGAAAAC
CATATCTCTGGTCATGTGTCCAGTAGCCTTATGGTGCTTAGCATGAGAGAACTTCCAGCTGAAGTAAGGAACCATAACAA
GAGAGTGGAGAACCCATCCAACGGTATCGTTAACCCATCCGTAGTTAGAGAAAGCAGAATGTCCACACTCATGTCCAAGG
ATCCAGATTCCGAATCCGAAACAAGAGATAGAGAACACGTAAGCAGACCAAGCAGCGAATCAAGGAATTCGTTAGGGAG
AAGAGGGATGTAGGTAAGTCCAACGTAAGCGATAGCAGAGATAGCCACGATATCTCTCACCACGTAAGACATAGACTTCA
CGAGAGATCTCTCGTAACAGTGCTTAGGGATAGCGTCAAGGATATCCTTGATGGTGTAATCTGGCACCTTGAAAACGTTT
CCGAAGGTATCGATAGCGGTCTTTTGCTGCTTGAAAGATGCAACGTTTCCAGAACGCCTAACGGTCTTAGTAGATCCCTC
AAGGATCTCAGATCCAGACACGGTAACCTTAGACATGGTATGGTAATTGTAAATGTAATTGTAATGTTGTTTGTTTG
TTGTTGTTGGTAATTGTTGTAAAATTTTGGTGGTGATTGGTTCTTTAAGGTGTGAGAGTGAGTTGTGAGTTGTGTGGTG
GGTTTGGTGAGATTGGGGATGGTGGGTTTATATAGTGGAGACTGAGGAATGGGGTCGTGAGTGTTAACTTGCATGGGCT
ACACGTGGGTTCTTTTGGGCTTACACGTAGTATTATTCATGCAAATGCAGCCAATACATATACGGTATTTTAATAATGTG
TGGGAATACAATATGCCGAGTATTTTACTAATTTTGGCAATGACAAGTGTACATTTGGATTATCTTACTTGGCCTCTCTT
GCTTTAATTTGGATTATTTTTATTCTCTTACCTTGGCCGTTCATATTCACATCCCTAAAGGCAAGACAGAATTGAATGGT
GGCCAAAAATTAAAACGATGGATATGACCTACATAGTGTAGGATCAATTAACGTCGAAGGAAAATACTGATTCTCTCAAG
CATACGGACAAGGGTAAATAACATAGTCACCAGAACATAATAAACAAAAGTGCAGAAGCAAGACTAAAAAAATTAGCTA
TGGACATTCAGGTTCATATTGGAAACATCATTATCCTAGTCTTGTGACCATCCTTCCTCCTGCTCTAGTTGAGAGGCCTT
GGGACTAACGAGAGGTCAGTTGGGATAGCAGATCCTTATCCTGGACTAGCCTTTCTGGTGTTTCAGAGTCTTCGTGCCGC
CGTCTACATCTATCTCCATTAGGTCTGAAGATGACTCTTCACACCAACGACGTTTAAGGTCTCTATCCTACTCCTAGCTT
```

FIG. 6 (con't)

```
GCAATACCTGGCTTGCAATACCTGGAGCATCGTGCACGATGATTGGATACTGTGGAGGAGGAGTGTTTGCTGATTTAGAG
CTCCCGGTTGGGTGATTTGACTTCGATTTCAGTTTAGGCTTGTTGAAATTTTTCAGGTTCCATTGTGAAGCCTTTAGAGC
TTGAGCTTCCTTCCATGTTAATGCCTTGATCGAATACTCCTAGAGAAAAGGGAAGTCGATCTCTGAGTATTGAAATCGAA
GTGCACATTTTTTTCAACGTGTCCAATCAATCCACAAACAAAGCAGAAGACAGGTAATCTTTCATACTTATACTGACAA
GTAATAGTCTTACCGTCATGCATAATAACGTCTCGTTCCTTCAAGAGGGGTTTTCCGACATCCATAACGACCCGAAGCCT
CATGAAAGCATTAGGGAAGAACTTTTGGTTCTTCTTGTCATGGCCTTTATAGGTGTCAGCCGAGCTCGCCAATTCCCGTC
CGACTGGCTCCGCAAAATATTCGAACGGCAAGTTATGGACTTGCAACCATAACTCCACGGTATTGAGCAGGACCTATTGT
GAAGACTCATCTCATGGAGCTTCAGAATGTGGTTGTCAGCAAACCAATGACCGAAATCCATCACATGACGGACGTCCAGT
GGGTGAGCGAAACGAAACAGGAAGCGCCTATCTTTCAGAGTCGTGAGCTCCACACCGGATTCCGGCAACTACGTGTTGGG
CAGGCTTCGCCGTATTAGAGATATGTTGAGGCAGACCCATCTGTGCCACTCGTACAATTACGAGAGTTGTTTTTTTGTG
ATTTTCCTAGTTTCTCGTTGATGGTGAGCTCATATTCTACATCGTATGGTCTCTCAACGTCGTTTCCTGTCATCTGATAT
CCCGTCATTTGCATCCACGTGCGCCGCCTCCCGTGCCAAGTCCCTAGGTGTCATGCACGCCAAATTGGTGGTGGTGCGGG
CTGCCCTGTGCTTCTTACCGATGGGTGGAGGTTGAGTTTGGGGGTCTCCGCGGCGATGGTAGTGGGTTGACGGTTTGGTG
TGGGTTGACGGCATTGATCAATTTACTTCTTGCTTCAAATTCTTTGGCAGAAAACAATTCATTAGATTAGAACTGGAAAC
CAGAGTGATGAGACGGATTAAGTCAGATTCCAACAGAGTTACATCTCTTAAGAAATAATGTAACCCCTTTAGACTTTATA
TATTTGCAATTAAAAAAATAATTTAACTTTTAGACTTTATATATAGTTTTAATAACTAAGTTTAACCACTCTATTATTTA
TATCGAAACTATTTGTATGTCTCCCCTCTAAATAAACTTGGTATTGTGTTTACAGAACCTATAATCAAATAATCAATACT
CAACTGAAGTTTGTGCAGTTAATTGAAGGGATTAACGGCCAAAATGCACTAGTATTATCAACCGAATAGATTCACACTAG
ATGGCCATTTCCATCAATATCATCGCCGTTCTTCTTCTGTCCACATATCCCTCTGAAACTTGAGAGACACCTGCACTTC
ATTGTCCTTATTACGTGTTACAAAATGAAACCCATGCATCCATGCAAACTGAAGAATGGCGCAAGAACCCTTCCCCTCCA
TTTCTTATGTGGCGACCATCCATTTCACCATCTCCCGCTATAAAACACCCCATCACTTCACCTAGAACATCATCACTAC
TTGCTTATCCATCCAAAAGATACCCACTTTTACAACAATTACCAACAACAACAAACAACAAACAACATTACAATTACATT
TACAATTACCATACCATGCCACCTAGCGCTGCTAAGCAAATGGGAGCTTCTACTGGTGTTCATGCTGGTGTTACTGACTC
TTCTGCTTTCACCAGAAAGGATGTTGCTGATAGACCTGATCTCACCATCGTTGGAGATTCTGTTTACGATGCTAAGGCTT
TCAGATCTGAGCATCCTGGTGGTGCTCATTTCGTTTCTTTGTTCGGAGGAAGAGATGCTACTGAGGCTTTCATGGAATAC
CATAGAAGGGCTTGGCCTAAGTCTAGAATGTCTAGATTCCACGTTGGATCTCTTGCTTCTACTGAGGAACCTGTTGCTGC
TGATGAGGGATACCTTCAACTTTGTGCTAGGATCGCTAAGATGGTGCCTTCTGTTTCTTCTGGATTCGCTCCTGCTTCTT
ACTGGGTTAAGGCTGGACTTATCCTTGGATCTGCTATCGCTCTTGAGGCTTACATGCTTTACGCTGGAAAGAGACTTCTC
CCTTCTATCGTTCTTGGATGGCTTTTCGCTCTTATCGGTCTTAACATCCAGCATGATGCTAACCATGGTGCTTTGTCTAA
GTCTGCTTCTGTTAACCTTGCTCTTGGACTTTGTCAGGATTGGATCGGAGGATCTATGATCCTTTGGCTTCAAGAGCATG
TTGTTATGCACCACCTCCACACTAACGATGTTGATAAGGATCCTGATCAAAAGGCTCACGGTGCTCTTAGACTCAAGCCT
ACTGATGCTTGGTCACCTATGCATTGGCTTCAGCATCTTTACCTTTTGCCTGGTGAGACTATGTACGCTTTCAAGCTTTT
GTTCCTCGACATCTCTGAGCTTGTTATGTGGCGTTGGGAGGGTGAGCCTATCTCTAAGCTTGCTGGATACCTCTTTATGC
CTTCTTTGCTTCTCAAGCTTACCTTCTGGGCTAGATTCGTTGCTTTGCCTCTTTACCTTGCTCCTTCTGTTCATACTGCT
GTGTGTATCGCTGCTACTGTTATGACTGGATCTTTCTACCTCGCTTTCTTCTTCTTCATCTCCCACAACTTCGAGGGTGT
TGCTTCTGTTGGACCTGATGGATCTATCACTTCTATGACTAGAGGTGCTAGCTTCCTTAAGAGACAAGCTGAGACTTCTT
CTAACGTTGGAGGACCTCTTCTTGCTACTCTTAACGGTGGACTCAACTACCAAATTGAGCATCACTTGTTCCCTAGAGTT
CACCATGGATTCTACCCTAGACTTGCTCCTCTTGTTAAGGCTGAGCTTGAGGCTAGAGGAATCGAGTACAAGCACTACCC
TACTATCTGGTCTAACCTTGCTTCTACCCTCAGACATATGTACGCTCTTGGAAGAAGGCCTAGATCTAAGGCTGAGTAAT
GACAAGCTTATGTGACGTGAAATAATAACGGTAAAATATATGTAATAATAATAATAATAAAGCCACAAAGTGAGAATGAG
GGGAAGGGGAAATGTGTAATGAGCCAGTAGCCGGTGGTGCTAATTTTGTATCGTATTGTCAATAAATCATGAATTTTGTG
GTTTTTATGTGTTTTTTTAAATCATGAATTTTAAATTTTATAAAATAATCTCCAATCGGAAGAACAACATTCCATATCCA
TGCATGGATGTTTCTTTACCCAAATCTAGTTCTTGAGAGGATGAAGCATCACCGAACAGTTCTGCAACTATCCCTCAAAA
GCTTTAAAATGAACAACAAGGAACAGAGCAACGTTCCAAAGATCCCAAACGAAACATATTATCTATACTAATACTATATT
ATTAATTACTACTGCCCGGAATCACAATCCCTGAATGATTCCTATTAACTACAAGCCTTGTTGGCGGCGGAGAAGTGATC
GGCGCGGCGAGAAGCAGCGGACTCGGAGACGAGGCCTTGGAAGATCTGAGTCGAACGGGCAGAATCAGTATTTTCCTTCG
ACGTTAATTGATCCTACACTATGTAGGTCATATCCATCGTTTAATTTTTGGCCACCATTCAATTCTGTCTTGCCTTTAG
GGATGTGAATATGAACGGCCAAGGTAAGAGAATAAAAATAATCCAAATTAAAGCAAGAGAGGCCAAGTAAGATAATCCAA
ATGTACACTTGTCATTGCCAAAATTAGTAAAATACTCGGCATATTGTATTCCCACACATTATTAAAATACCGTATATGTA
TTGGCTGCATTTGCATGAATAATACTACGTGTAAGCCCAAAAGAACCCACGTGTAGCCCATGCAAAGTTAACACTCACGA
CCCCATTCCTCAGTCTCCACTATATAAACCCACCATCCCCAATCTCACCAAACCCACCACACAACTCACAACTCACTCTC
ACACCTTAAAGAACCAATCACCACCAAAAATTTTACAACAATTACCAACAACAACAAACAACAAACAACATTACAATTAC
ATTTACAATTACCATACCATGAGCGCTGTTACCGTTACTGGATCTGATCCTAAGAACAGAGGATCTTCTAGCAACACCGA
GCAAGAGGTTCCAAAAGTTGCTATCGATACCAACGGAAACGTGTTCTCTGTTCCTGATTTCACCATCAAGGACATCCTTG
GAGCTATCCCTCATGAGTGTTACGAGAGAAGATTGGCTACCTCTCTCTACTACGTGTTCAGAGATATCTTCTGCATGCTT
ACCACCGGATACCTTACCCATAAGATCCTTTACCCTCTCCTCATCTCTTACACCTCTAACAGCATCATCAAGTTCACTTT
```

FIG. 6 (con't)

```
CTGGGCCCTTTACACTTACGTTCAAGGACTTTTCGGAACCGGAATCTGGGTTCTCGCTCATGAGTGTGGACATCAAGCTT
TCTCTGATTACGGAATCGTGAACGATTTCGTTGGATGGACCCTTCACTCTTACCTTATGGTTCCTTACTTCAGCTGGAAG
TACTCTCATGGAAAGCACCATAAGGCTACTGGACACATGACCAGAGATATGGTTTTCGTTCCTGCCACCAAAGAGGAATT
CAAGAAGTCTAGGAACTTCTTCGGTAACCTCGCTGAGTACTCTGAGGATTCTCCACTTAGAACCCTTTACGAGCTTCTTG
TTCAACAACTTGGAGGATGGATCGCTTACCTCTTCGTTAACGTTACAGGACAACCTTACCCTGATGTTCCTTCTTGGAAA
TGGAACCACTTCTGGCTTACCTCTCCACTTTTCGAGCAAGAGATGCTCTCTACATCTTCCTTTCTGATCTTGGAATCCT
CACCCAGGGAATCGTTCTTACTCTTTGGTACAAGAAATTCGGAGGATGGTCCCTTTTCATCAACTGGTTCGTTCCTTACA
TCTGGGTTAACCACTGGCTCGTTTTCATCACATTCCTTCAGCACACTGATCCTACTATGCCTCATTACAACGCTGAGGAA
TGGACTTTCGCTAAGGGTGCTGCTGCTACTATCGATAGAAAGTTCGGATTCATCGGACCTCACATCTTCCATGATATCAT
CGAGACTCATGTGCTTCACCACTACTGTTCTAGGATCCCATTCTACAACGCTAGACCTGCTTCTGAGGCTATCAAGAAAG
TTATGGGAAAGCACTACAGGTCTAGCGACGAGAACATGTGGAAGTCACTTTGGAAGTCTTTCAGGTCTTGCCAATACGTT
GACGGTGATAACGGTGTTCTCATGTTCCGTAACATCAACAACTGCGGAGTTGGAGCTGCTGAGAAGTAATGAAGGGGTGA
TCGATTATGAGATCGTACAAAGACACTGCTAGGTGTTAAGGATGGATAATAATAATAATGAGATGAATGTGTTTTAA
GTTAGTGTAACAGCTGTAATAAAGAGAGAGAGAGAGAGAGAGAGAGAGAGAGAGAGAGAGAGAGAGAGAGAGAGGCTGAT
GAAATGTTATGTATGTTCTTGGTTTTAAAATAAATGAAAGCACATGCTCGTGTGGTTCTATCGAATTATTCGGCGGTT
CCTGTGGGAAAAAGTCCAGAAGGGCCGCCGCAGCTACTACTACAACCAAGGCCGTGGAGGAGGGCAACAGAGCCAGCACT
TCGATAGCTGCTGCGATGATCTTAAGCAATTGAGGAGCGAGTGCACATGCAGGGGACTGGAGCGTGCAATCGGCCAGATG
AGGCAGGACATCCAGCAGCAGGGACAGCAGCAGGAAGTTGAGAGGTGGTCCCATCAATCTAAACAAGTCGCTAGGGACCT
TCCGGGACAGTGCGGCACCCAGCCTAGCCGATGCCAGCTCCAGGGGCAGCAGCAGTCTGCATGGTTTTGAAGTGGTGATC
GATGAGATCGTATAAAGACACTGCTAGGTGTTAAGGATGGGATAATAAGATGTGTTTTAAGTCATTAACCGTAATAAAAA
GAGAGAGAGGCTGATGGAATGTTATGTATGTATGTTTCTTGGTTTTAAAATTAAATGGAAAGCACATGCTCGTGTGGGT
TCTATCTCGATTAAAAATCCCAATTATATTTGGTCTAATTTAGTTTGGTATTGAGTAAAACAAATTCGAACCAAACCAAA
ATATAAATATATAGTTTTTATATATATGCCTTTAAGACTTTTTATAGAATTTTCTTTAAAAAATATCTAGAAATATTTGC
GACTCTTCTGGCATGTAATATTTCGTTAAATATGAAGTGCTCCATTTTTATTAACTTTAAATAATTGGTTGTACGATCAC
TTTCTTATCAAGTGTTACTAAAATGCGTCAATCTCTTTGTTCTTCCATATTCATATGTCAAAATCTATCAAAATTCTTAT
ATATCTTTTTCGAATTTGAAGTGAAATTTCGATAATTTAAAATTAAATAGAACATATCATTATTTAGGTATCATATTGAT
TTTTATACTTAATTACTAAATTTGGTTAACTTTGAAAGTGTACATCAACGAAAAATTAGTCAAACGACTAAAATAAATAA
ATATCATGTGTTATTAAGAAAATTCTCCTATAAGAATATTTTAAGATCATATGTTTGTAAAAAAATTAATTTTTACT
AACACATATATTTACTTATCAAAAATTTGACAAAGTAAGATTAAAATAATATTCATCTAACAAAAAAAAAACCAGAAAAT
GCTGAAAACCCGGCAAAACCGAACCAATCCAAACCGATATAGTTGGTTTGGTTTGATTTTGATATAAACCGAACCAACTC
GGTCCATTTGCACCCCTAATCATAATAGCTTTAATATTTCAAGATATTATTAAGTTAACGTTGTCAATATCCTGGAAATT
TTGCAAAATGAATCAAGCCTATATGGCTGTAATATGAATTTAAAAGCAGCTCGATGTGGTGGTAATATGTAATTTACTTG
ATTCTAAAAAATATCCCAAGTATTAATAATTTCTGCTAGGAAGAAGGTTAGCTACGATTTACAGCAAAGCCAGAATACA
AAGAACCATAAAGTGATTGAAGCTCGAAATATACGAAGGAACAAATATTTTTAAAAAAATACGCAATGACTTGGAACAAA
AGAAAGTGATATATTTTTTGTTCTTAAACAAGCATCCCCTCTAAAGAATGGCAGTTTTCCTTTGCATGTAACTATTATGC
TCCCTTCGTTACAAAAATTTTGGACTACTATTGGGAACTTCTTCTGAAAATAGTCCTGCAGGCTAGTAGATTGGTTGGTT
GGTTTCCATGTACCAGAAGGCTTACCCTATTAGTTGAAAGTTGAAACTTTGTTCCCTACTCAATTCCTAGTTGTGTAAAT
GTATGTATATGTAATGTGTATAAAACGTAGTACTTAAATGACTAGGAGTGGTTCTTGAGACCGATGAGAGATGGGAGCAG
AACTAAAGATGATGACATAATTAAGAACGAATTTGAAAGGCTCTTAGGGTTTGAATCCTATTCGAGAATGTTTTTGTCAAA
GATAGTGGCGATTTTGAACCAAAGAAAACATTTAAAAAATCAGTATCCGGTTACGTTCATGCAAATAGAAAGTGGTCTAG
GATCTGATTGTAATTTTAGACTTAAAGAGTCTCTTAAGATTCAATCCTGGCTGTGTACAAAACTACAAATAATATATTTT
AGACTATTTGGCCTTAACTAAACTTCCACTCATTATTTACTGAGGTTAGAGAATAGACTTGCGAATAAACACATTCCCGA
GAAATACTCATGATCCCATAATTAGTCAGAGGGTATGCCAATCAGATCTAAGAACACACATTCCCTCAAATTTTAATGCA
CATGTAATCATAGTTTAGCACAATTCAAAAATAATGTAGTATTAAAGACAGAAATTTGTAGACTTTTTTTGGCGTTAAA
AGAAGACTAAGTTTATACGTACATTTTATTTTAAGTGGAAAACCGAAATTTTCCATCGAAATATATGAATTTAGTATATA
TATTTCTGCAATGTACTATTTTGCTATTTTGGCAACTTTCAGTGGACTACTACTTTATTACAATGTGTATGGATGCATGA
GTTTGAGTATACACATGTCTAAATGCATGCTTTGTAAAACGTAACGGACCACAAAAGAGGATCCATACAAATACATCTCA
TAGCTTCCTCCATTATTTTCCGACACAAACAGAGCATTTTACAACAATTACCAACAACAACAAACAACAAACAACATTAC
AATTACATTTACAATTACCATACCATGGAATTTGCTCAACCTCTCGTTGCTATGGCTCAAGAGCAGTACGCTGCTATCGA
TGCTGTTGTTGCTCCTGCTATCTTCTCTGCTACCGACTCTATTGGATGGGGACTCAAGCCTATCTCTTCTGCTACTAAGG
ATCTCCCTCTCGTTGAATCTCCTACCCCTCTTATCCTTTCTCCTCGCTTACTTCGCTATCGTTGGTTCTGGACTCGTT
TACCGTAAAGTGTTCCCTAGAACCGTTAAGGGACAGGATCCTTTCCTTCTCAAGGCTCTTATGCTCGCTCACAACGTTTT
CCTTATCGGACTCAGCCTTTACATGTGCCTCAAGCTCGTTTACGAGGCTTACGTGAACAAGTACTCCTTCTGGGGAAACG
CTTACAACCCTGCTCAAACCGAGATGGCTAAGGTGATCTGGATCTTCTACGTGTCCAAGATCTACGAGTTCATGGACACC
TTCATCATGCTTCTCAAGGGAAACGTTAACCAGGTTTCCTTCCTCCATGTTTACCACCACGGATCTATCTCTGGAATCTG
GTGGATGATCACTTATGCTGCTCCAGGTGGAGATGCTTACTTCTCTGCTGCTCTCAACTCTTGGGTTCATGTGTGCATGT
```

FIG. 6 (con't)

```
ACACCTACTACTTCATGGCTGCTGTTCTTCCTAAGGACGAAAAGACCAAGAGAAAGTACCTTTGGTGGGGAAGATACCTT
ACCCAGATGCAAATGTTCCAGTTCTTCATGAACCTTCTCCAGGCTGTTTACCTCCTCTACTCTTCTTCTCCTTACCCTAA
GTTCATTGCTCAACTCCTCGTTGTTTACATGGTTACCCTCCTCATGCTTTTCGGAAACTTCTACTACATGAAGCACCACG
CTTCTAAGTGATAAGGGCCGCCGCCATGTGACAGATCGAAGGAAGAAAGTGTAATAAGACGACTCTCACTACTCGATCGC
TAGTGATTGTCATTGTTATATATAATAATGTTATCTTTCACAACTTATCGTAATGCATGTGAAACTATAACACATTAATC
CTACTTGTCATATGATAACACTCTCCCCATTTAAAACTCTTGTCAATTTAAAGATATAAGATTCTTTAAATGATTAAAAA
AAATATATTATAAATTCAATCACTCCTACTAATAAATTATTAATTATTATTTATTGATTAAAAAAATACTTATACTAATT
TAGTCTGAATAGAATAATTAGATTCTAGCCTGCAGGGCGGCCGCGGATCCCATGGAGTCAAAGATTCAAATAGAGGACCT
AACAGAACTCGCCGTAAAGACTGGCGAACAGTTCATACAGAGTCTCTTACGACTCAATGACAAGAAGAAAATCTTCGTCA
ACATGGTGGAGCACGACACACTTGTCTACTCCAAAAATATCAAAGATACAGTCTCAGAAGACCAAAGGGCAATTGAGACT
TTTCAACAAAGGGTAATATCCGGAAACCTCCTCGGATTCCATTGCCCAGCTATCTGTCACTTTATTGTGAAGATAGTGGA
AAAGGAAGGTGGCTCCTACAAATGCCATCATTGCGATAAAGGAAAGGCCATCGTTGAAGATGCCTCTGCCGACAGTGGTC
CCAAAGATGGACCCCCACCCACGAGGAGCATCGTGGAAAAAGAAGACGTTCCAACCACGTCTTCAAAGCAAGTGGATTGA
TGTGATATCTCCACTGACGTAAGGGATGACGCACAATCCCACTATCCTTCGCAAGACCCTTCCTCTATATAAGGAAGTTC
ATTTCATTTGGAGAGAACACGGGGGACTGAATTAAATATGAGCCCTGAGAGGCGTCCTGTTGAAATCAGACCTGCTACTG
CTGCTGATATGGCTGCTGTTTGTGATATCGTGAACCACTACATCGAGACTTCTACCGTTAACTTCAGAACTGAGCCTCAA
ACTCCTCAAGAGTGGATCGATGATCTTGAGAGACTCCAAGATAGATACCCTTGGCTTGTTGCTGAGGTTGAGGGTGTTGT
TGCTGGAATCGCTTACGCTGGACCTTGGAAGGCTAGAAACGCTTACGATTGGACTGTTGAGTCTACCGTTTACGTTTCAC
ACAGACATCAGAGACTTGGACTTGGATCTACCCTTTACACTCACCTTCTCAAGTCTATGGAAGCTCAGGGATTCAAGTCT
GTTGTTGCTGTTATCGGACTCCCTAACGATCCTTCTGTTAGACTTCATGAGGCTCTTGGATACACTGCTAGAGGAACTCT
TAGAGCTGCTGGATACAAGCACGGTGGATGGCATGATGTTGGATTCTGGCAAAGAGATTTCGAGCTTCCTGCTCCTCCTA
GACCTGTTAGACCAGTTACTCAGATCTGAATTTGCGTGATCGTTCAAACATTTGGCAATAAAGTTTCTTAAGATTGAATC
CTGTTGCCGGTCTTGCGATGATTATCATATAATTTCTGTTGAATTACGTTAAGCATGTAATAATTAACATGTAATGCATG
ACGTTATTTATGAGATGGGTTTTTATGATTAGAGTCCCGCAATTATACATTTAATACGCGATAGAAAACAAAATATAGCG
CGCAAACTAGGATAAATTATCGCGCGCGGTGTCATCTATGTTACTAGATCACTAGTGATGTACGGTTAAAACCACCCCAG
TACATTAAAAACGTCCGCAATGTGTTATTAAGTTGTCTAAGCGTCAATTTGTTTACACCACAATATATTGTGGTGTAAAC
AAATTGACGCTTAGACAACTTAATAACACATTGCGGACGTTTTAATGTACTGGGGTGGTTTAACCGTACATCACTAGT
GATCTAGTAACATAGATGACACCGCGCGATAATTTATCCTAGTTTGCGCGCTATATTTGTTTCTATCGCGTATTAA
ATGTATAATTGCGGGACTCTAATCATAAAAACCCATCTCATAAATAACGTCATGCATTACATGTTAATTATTACATGCTT
AACGTAATTCAACAGAAATTATATGATAATCATCGCAAGACCGGCAACAGGATTCAATCTTAAGAAACTTTATTGCCAAA
TGTTTGAACGATCACGCAAATTCAGATCTGAGTAACTGGTCTAACAGGTCTAGGAGGAGCAGGAAGCTCGAAATCTCTTT
GCCAGAATCCAACATCATGCCATCCACCGTGCTTGTATCCAGCAGCTCTAAGAGTTCCTCTAGCAGTGTATCCAAGAGCC
TCATGAAGTCTAACAGAAGGATCGTTAGGGAGTCCGATAACAGCAACAACAGACTTGAATCCCTGAGCTTCCATAGACTT
GAGAAGGTGAGTGTAAAGGGTAGATCCAAGTCCAAGTCTCTGATGTCTGTGTGAAACGTAAACGGTAGACTCAACAGTCC
AATCGTAAGCGTTTCTAGCCTTCCAAGGTCCAGCGTAAGCGATTCCAGCAACAACACCCTCAACCTCAGCAACAAGCCAA
GGGTATCTATCTTGGAGTCTCTCAAGATCATCGATCCACTCTTGAGGAGTTTGAGGCTCAGTTCTGAAGTTAACGGTAGA
AGTCTCGATGTAGTGGTTCACGATATCACAAACAGCAGCCATATCAGCAGCAGTAGCAGGTCTGATTTCAACAGGACGCC
TCTCAGGGCTCATATTTAATTCAGTCCCCGTGTTCTCTCCAAATGAAATGAACTTCCTTATATAGAGGAAGGGTCTTGC
GAAGGATAGTGGGATTGTGCGTCATCCCTTACGTCAGTGGAGATATCACATCAATCCACTTGCTTTGAAGACGTGGTTGG
AACGTCTTCTTTTTCCACGATGCTCCTCGTGGGTGGGGGTCCATCTTTGGGACCACTGTCGGCAGAGGCATCTTCAACGA
TGGCCTTTCCTTTATCGCAATGATGGCATTTGTAGGAGCCACCTTCCTTTTCCACTATCTTCACAATAAAGTGACAGATA
GCTGGGCAATGGAATCCGAGGAGGTTTCCGGATATTACCCTTTGTTGAAAAGTCTCAATTGCCCTTTGGTCTTCTGAGAC
TGTATCTTTGATATTTTGGAGTAGACAAGTGTGTCGTGCTCCACCATGTTGACGAAGATTTTCTTCTTGTCATTGAGTC
GTAAGAGACTCTGTATGAACTGTTCGCCAGTCTTTACGGCGAGTTCTGTTAGGTCCTCTATTTGAATCTTTGACTCCATG
GGATCCGCGGCCGCCCTGCAGGCTAGAATCTAATTATTCTATTCAGACTAAATTAGTATAAGTATTTTTTAATCAATAA
ATAATAATTAATAATTTATTAGTAGGAGTGATTGAATTTATAATATATTTTTTTAATCATTTAAAGAATCTTATATCTT
TAAATTGACAAGAGTTTTAAATGGGGAGAGTGTTATCATATGACAAGTAGGATTAATGTGTTATAGTTTCACATGCATTA
CGATAAGTTGTGAAAGATAACATTATTATATATAACAATGACAATCACTAGCGATCGAGTAGTGAGAGTCGTCTTATTAC
ACTTTCTTCCTTCGATCTGTCACATGGCGGCGGCCCTTATCACTTAGAAGCGTGGTGCTTCATGTAGTAGAAGTTTCCGA
AAAGCATGAGGAGGGTAACCATGTAAACAACGAGGAGTTGAGCAATGAACTTAGGGTAAGGAGAAGAAGAGTAGAGGAGG
TAAACAGCCTGGAGAAGGTTCATGAAGAACTGGAACATTTGCATCTGGGTAAGGTATCTTCCCCACCAAAGGTACTTTCT
CTTGGTCTTTTCGTCCTTAGGAAGAACAGCAGCCATGAAGTAGTAGGTGTACATGCACACATGAACCCAAGAGTTGAGAG
CAGCAGAGAAGTAAGCATCTCCACCTGGAGCAGCATAAGTGATCATCCACCAGATTCCAGAGATAGATCCGTGGTGGTAA
ACATGGAGGAAGGAAACCTGGTTAACGTTTCCCTTGAGAAGCATGATGAAGGTGTCCATGAACTCGTAGATCTTGGACAC
GTAGAAGATCCAGATCACCTTAGCCATCTCGGTTTGAGCAGGGTTGTAAGCGTTTCCCCAGAAGGAGTACTTGTTCACGT
```

FIG. 6 (con't)

```
AAGCCTCGTAAACGAGCTTGAGGCACATGTAAAGGCTGAGTCCGATAAGGAAAACGTTGTGAGCGAGCATAAGAGCCTTG
AGAAGGAAAGGATCCTGTCCCTTAACGGTTCTAGGGAACACTTTACGGTAAACGAGTCCAGAACCAACGATAGCGAAGTA
AGCGAGGAGAGAAAGGATAAGAGGGGTAGGAGATTCAACGAGAGGGAGATCCTTAGTAGCAGAAGAGATAGGCTTGAGTC
CCCATCCAATAGAGTCGGTAGCAGAGAAGATAGCAGGAGCAACAACAGCATCGATAGCAGCGTACTGCTCTTGAGCCATA
GCAACGAGAGGTTGAGCAAATTCCATGGTATGGTAATTGTAAATGTAATTGTAATGTTGTTTGTTGTTTGTTGTTGTTGG
TAATTGTTGTAAAATGCTCTGTTTGTGTCGGAAAATAATGGAGGAAGCTATGAGATGTATTTGTATGGATCCTCTTTTGT
GGTCCGTTACGTTTTACAAAGCATGCATTTAGACATGTGTATACTCAAACTCATGCATCCATACACATTGTAATAAAGTA
GTAGTCCACTGAAAGTTGCCAAAATAGCAAAATAGTACATTGCAGAAATATATATACTAAATTCATATATTTCGATGGAA
AATTTCGGTTTTCCACTTAAAATAAAATGTACGTATAAACTTAGTCTTCTTTTAACGCCAAAAAAAGTCTACAAATTTC
TGTCTTTAATACTACATTATTTTTGAATTGTGCTAAACTATGATTACATGTGCATTAAAATTTGAGGGAATGTGTGTTCT
TAGATCTGATTGGCATACCCTCTGACTAATTATGGGATCATGAGTATTTCTCGGGAATGTGTTTATTCGCAAGTCTATTC
TCTAACCTCAGTAAATAATGAGTGGAAGTTTAGTTAAGGCCAAATAGTCTAAAATATATTATTTGTAGTTTTGTACACAG
CCAGGATTGAATCTTAAGAGACTCTTTAAGTCTAAAATTACAATCAGATCCTAGACCACTTTCTATTTGCATGAACGTAA
CCGGATACTGATTTTTTAAATGTTTTCTTTGGTTCAAAATCGCCACTATCTTTGACAAAAACATTCTCGAATAGGATTCA
AACCTAAGAGCCTTTCAAATTCGTTCTTAATTATGTCATCATCTTTAGTTCTGCTCCCATCTCTCATCGGTCTCAAGAAC
CACTCCTAGTCATTTAAGTACTACGTTTTATACACATTACATATACATACATTTACACAACTAGGAATTGAGTAGGGAAC
AAAGTTTCAACTTTCAACTAATAGGGTAAGCCTTCTGGTACATGGAAACCAACCAACCAATCTACTAGCCTGCAGGACTA
TTTTCAGAAGAAGTTCCCAATAGTAGTCCAAAATTTTTGTAACGAAGGGAGCATAATAGTTACATGCAAAGGAAAACTGC
CATTCTTTAGAGGGGATGCTTGTTTAAGAACAAAAAATATATCACTTTCTTTTGTTCCAAGTCATTGCGTATTTTTTAA
AAATATTTGTTCCTTCGTATATTTCGAGCTTCAATCACTTTATGGTTCTTTGTATTCTGGCTTTGCTGTAAATCGTAGCT
AACCTTCTTCCTAGCAGAAATTATTAATACTTGGGATATTTTTTAGAATCAAGTAAATTACATATTACCACCACATCGA
GCTGCTTTTAAATTCATATTACAGCCATATAGGCTTGATTCATTTTGCAAAATTTCCAGGATATTGACAACGTTAACTTA
ATAATATCTTGAAATATTAAAGCTATTATGATTAGGGGTGCAAATGGACCGAGTTGGTTCGGTTTATATCAAAATCAAAC
CAAACCAACTATATCGGTTTGGATTGGTTCGGTTTTGCCGGGTTTTCAGCATTTTCTGGTTTTTTTTTGTTAGATGAAT
ATTATTTTAATCTTACTTTGTCAAATTTTTGATAAGTAAATATATGTGTTAGTAAAAATTAATTTTTTTACAAACATAT
GATCTATTAAAATATTCTTATAGGAGAATTTTCTTAATAACACATGATATTTATTTATTTTAGTCGTTTGACTAATTTTT
CGTTGATGTACACTTTCAAAGTTAACCAAATTTAGTAATTAAGTATAAAAATCAATATGATACCTAAATAATGATATGTT
CTATTTAATTTTAAATTATCGAAATTTCACTTCAAATTCGAAAAAGATATATAAGAATTTTGATAGATTTTGACATATGA
ATATGGAAGAACAAAGAGATTGACGCATTTTAGTAACACTTGATAAGAAAGTGATCGTACAACCAATTATTTAAAGTTAA
TAAAAATGGAGCACTTCATATTTAACGAAATATTACATGCCAGAAGAGTCGCAAATATTTCTAGATATTTTTTAAAGAAA
ATTCTATAAAAAGTCTTAAAGGCATATATATAAAAACTATATATTTATATTTTGGTTTGGTTCGAATTTGTTTTACTCAA
TACCAAACTAAATTAGACCAAATATAATTGGGATTTTTAATCGAGATAGAACCCACACGAGCATGTGCTTTCCATTTAAT
TTTAAAAACCAAGAAACATACATACATAACATTCCATCAGCCTCTCTCTCTTTTTATTACGGTTAATGACTTAAAACACA
TCTTATTATCCCATCCTTAACACCTAGCAGTGTCTTTATACGATCTCATCGATCACCACTTCAAAACCATGCAGACTGCT
GCTGCCCCTGGAGCTGGCATCGGCTAGGCTGGGTGCCGCACTGTCCCGGAAGGTCCCTAGCGACTTGTTTAGATTGATGG
GACCACCTCTCAACTTCCTGCTGCTGTCCCTGCTGCTGGATGTCCTGCCTCATCTGGCCGATTGCACGCTCCAGTCCCCT
GCATGTGCACTCGCTCCTCAATTGCTTAAGATCATCGCAGCAGCTATCGAAGTGCTGGCTCTGTTGCCCTCCTCCACGGC
CTTGGTTGTAGTAGTAGCTGCGGCGGCCCTTCTGGACTTTTTCCCACAGGAACCGCCGAATAATTCGATAGAACCACACG
AGCATGTGCTTTCATTTATTTTAAAAACCAAGAAACATACATAACATTTCATCAGCCTCTCTCTCTCTCTCTCTCTCT
CTCTCTCTCTCTCTCTCTCTCTCTCTTTATTACAGCTGTTACACTAACTTAAAACACATTCATCTCATTATTATTATT
ATTATCCATCCTTAACACCTAGCAGTGTCTTTGTACGATCTCATAATCGATCACCCCTTCATTACTTCTCAGCAGCTCCA
ACTCCGCAGTTGTTGATGTTACGGAACATGAGAACACCGTTATCACCGTCAACGTATTGGCAAGACCTGAAAGACTTCCA
AAGTGACTTCCACATGTTCTCGTCGCTAGACCTGTAGTGCTTTCCCATAACTTTCTTGATAGCCTCAGAAGCAGGTCTAG
CGTTGTAGAATGGGATCCTAGAACAGTAGTGGTGAAGCACATGAGTCTCGATGATATCATGGAAGATGTGAGGTCCGATG
AATCCGAACTTTCTATCGATAGTAGCAGCAGCACCCTTAGCGAAAGTCCATTCCTCAGCGTTGTAATGAGGCATAGTAGG
ATCAGTGTGCTGAAGGAATGTGATGAAAACGAGCCAGTGGTTAACCCAGATGTAAGGAACGAACCAGTTGATGAAAAGGG
ACCATCCTCCGAATTTCTTGTACCAAAGAGTAAGAACGATTCCCTGGGTGAGGATTCCAAGATCAGAAAGGAAGATGTAG
AGAGCATCTCTTTGCTCGAAAAGTGGGAGAGGTAAGCCAGAAGTGGTTCCATTTCCAAGAAGGAACATCAGGGTAAGGTTG
TCCTGTAACGTTAACGAAGAGGTAAGCGATCCATCCTCCAAGTTGTTGAACAAGAAGCTCGTAAAGGGTTCTAAGTGGAG
AATCCTCAGAGTACTCAGCGAGGTTACCGAAGAAGTTCCTAGACTTCTTGAATTCCTCTTTGGTGGCAGGAACGAAAACC
ATATCTCTGGTCATGTGTCCAGTAGCCTTATGGTGCTTTCATGAGAGTACTTCCAGCTGAAGTAAGGAACCATAAGGTA
AGAGTGAAGGGTCCATCCAACGAAATCGTTCACGATTCCGTAATCAGAGAAAGCTTGATGTCCACACTCATGAGCGAGAA
CCCAGATTCCGGTTCCGAAAAGTCCTTGAACGTAAGTGTAAAGGGCCCAGAAAGTGAACTTGATGATGCTGTTAGAGGTG
TAAGAGATGAGGAGAGGGTAAAGGATCTTATGGGTAAGGTATCCGGTGGTAAGCATGCAGAAGATATCTCTGAACACGTA
GTAGAGAGAGGTAGCCAATCTTCTCTCGTAACACTCATGAGGGATAGCTCCAAGGATGTCCTTGATGGTGAAATCAGGAA
CAGAGAACACGTTTCCGTTGGTATCGATAGCAACTTTTGGAACCTCTTGCTCGGTGTTGCTAGAAGATCCTCTGTTCTTA
```

FIG. 6 (con't)

```
GGATCAGATCCAGTAACGGTAACAGCGCTCATGGTATGGTAATTGTAAATGTAATTGTAATGTTGTTTGTTGTTTGTTGT
TGTTGGTAATTGTTGTAAAATTTTTGGTGGTGATTGGTTCTTTAAGGTGTGAGAGTGAGTTGTGAGTTGTGTGGTGGGTT
TGGTGAGATTGGGGATGGTGGGTTTATATAGTGGAGACTGAGGAATGGGGTCGTGAGTGTTAACTTTGCATGGGCTACAC
GTGGGTTCTTTTGGGCTTACACGTAGTATTATTCATGCAAATGCAGCCAATACATATACGGTATTTTAATAATGTGTGGG
AATACAATATGCCGAGTATTTTACTAATTTTGGCAATGACAAGTGTACATTTGGATTATCTTACTTGGCCTCTCTTGCTT
TAATTTGGATTATTTTTATTCTCTTACCTTGGCCGTTCATATTCACATCCCTAAAGGCAAGACAGAATTGAATGGTGGCC
AAAAATTAAAACGATGGATATGACCTACATAGTGTAGGATCAATTAACGTCGAAGGAAAATACTGATTCTGCCCGTTCGA
CTCAGATCTTCCAAGGCCTCGTCTCCGAGTCCGCTGCTTCTCGCCGCGCCGATCACTTCTCCGCCGCCAACAAGGCTTGT
AGTTAATAGGAATCATTCAGGGATTGTGATTCCGGGCAGTAGTAATTAATAATATAGTATTAGTATAGATAATATGTTTC
GTTTGGGATCTTTGGAACGTTGCTCTGTTCCTTGTTGTTCATTTTAAAGCTTTTGAGGGATAGTTGCAGAACTGTTCGGT
GATGCTTCATCCTCTCAAGAACTAGATTTGGGTAAAGAAACATCCATGCATGGATATGGAATGTTGTTCTTCCGATTGGA
GATTATTTTATAAAATTTAAAATTCATGATTTAAAAAAACACATAAAAACCACAAAATTCATGATTTATTGACAATACGA
TACAAAATTAGCACCACCGGCTACTGGCTCATTACACATTTCCCCTTCCCCTCATTCTCACTTTGTGGCTTTATTATTAT
TATTATTACATATATTTTACCGTTATTATTTCACGTCACATAAGCTTGTCATTACTCAGCCTTAGATCTAGGCCTTCTTC
CAAGAGCGTACATATGTCTGAGGGTAGAAGCAAGGTTAGACCAGATAGTAGGGTAGTGCTTGTACTCGATTCCTCTAGCC
TCAAGCTCAGCCTTAACAAGAGGAGCAAGTCTAGGGTAGAATCCATGGTGAACTCTAGGGAACAAGTGATGCTCAATTTG
GTAGTTGAGTCCACCGTTAAGAGTAGCAAGAAGAGGTCCTCCAACGTTAGAAGAAGTCTCAGCTTGTCTCTTAAGGAAGC
TAGCACCTCTAGTCATAGAAGTGATAGATCCATCAGGTCCAACAGAAGCAACACCCTCGAAGTTGTGGGAGATGAAGAAG
AAGAAAGCGAGGTAGAAAGATCCAGTCATAACAGTAGCAGCGATACACACAGCAGTATGAACAGAAGGAGCAAGGTAAAG
AGGCAAAGCAACGAATCTAGCCCAGAAGGTAAGCTTGAGAAGCAAAGAAGGCATAAAGAGGTATCCAGCAAGCTTAGAGA
TAGGCTCACCCTCCCAACGCCACATAACAAGCTCAGAGATGTCGAGGAACAAAAGCTTGAAAGCGTACATAGTCTCACCA
GGCAAAAGGTAAAGATGCTGAAGCCAATGCATAGGTGACCAAGCATCAGTAGGCTTGAGTCTAAGAGCACCGTGAGCCTT
TTGATCAGGATCCTTATCAACATCGTTAGTGTGGAGGTGGTGCATAACAACATGCTCTTGAAGCCAAAGGATCATAGATC
CTCCGATCCAATCCTGACAAAGTCCAAGAGCAAGGTTAACAGAAGCAGACTTAGACAAAGCACCATGGTTAGCATCATGC
TGGATGTTAAGACCGATAAGAGCGAAAAGCCATCCAAGAACGATAGAAGGGAGAAGTCTCTTTCCAGCGTAAAGCATGTA
AGCCTCAAGAGCGATAGCAGATCCAAGGATAAGTCCAGCCTTAACCCAGTAAGAAGCAGGAGCGAATCCAGAAGAAACAG
AAGGCACCATCTTAGCGATCCTAGCACAAAGTTGAAGGTATCCCTCATCAGCAGCAACAGGTTCCTCAGTAGAAGCAAGA
GATCCAACGTGGAATCTAGACATTCTAGACTTAGGCCAAGCCCTTCTATGGTATTCCATGAAAGCCTCAGTAGCATCTCT
TCCTCCGAACAAAGAAACGAAATGAGCACCACCAGGATGCTCGATCTGAAAGCCTTAGCATCGTAAACAGAATCTCCAA
CGATGGTGAGATCAGGTCTATCAGCAACATCCTTTCTGGTGAAAGCAGAAGAGTCAGTAACACCAGCATGAACACCAGTA
GAAGCTCCCATTTGCTTAGCAGCGCTAGGTGGCATGGTATGGTAATTGTAAATGTAATTGTAATGTTGTTTGTTGTTTGT
TGTTGTTGGTAATTGTTGTAAAAGTGGGTATCTTTTGGATGGATAAGCAAGTAGTGATGATGTTCTAGGTGAAGTGATGG
GGGTGTTTTATAGCGGGAGATGGTGAAATGGATGGTCGCCACATAAGAAATGGAGGGGAAGGGTTCTTGCGCCATTCTTC
AGTTTGCATGGATGCATGGGTTTCATTTTGTAACACGTAATAAGGACAATGAAGTGCAGGTGTCTCTCAAGTTTCAGAGG
GGATATGTGGACAGAAGAAGAACGGCGATGATATTGATGGAAATGGCCATCTAGTGTGAATCTATTCGGTTGATAATACT
AGTGCATTTTGGCCGTTAATCCCTTCAATTAACTGCACAAACTTCAGTTGAGTATTGATTATTTGATTATAGGTTCTGTA
AACACAATACCAAGTTTATTTAGAGGGGAGACATACAAATAGTTTCGATATAAATAATAGAGTGGTTAAACTTAGTTATT
AAAACTATATATAAAGTCTAAAAGTTAAATTATTTTTTTAATTGCAAATATATAAAGTCTAAAGGGGTTACATTATTTCT
TAAGAGATGTAACTCTGTTGGAATCTGACTTAATCCGTCTCATCACTCTGGTTTCCAGTTCTAATCTAATGAATTGTTTT
CTGCCAAAGAATTTGAAGCAAGAAGTAAATTGATCAATGCCGTCAACCCACACCAAACCGTCAACCCACTACCATCGCCG
CGGAGACCCCCAAACTCAACCTCCACCCATCGGTAAGAAGCACAGGGCAGCCCGCACCACCACCAATTTGGCGTGCATGA
CACCTAGGGACTTGGCACGGGAGGCGGCGCACGTGGATGCAAATGACGGGATATCAGATGACAGGAAACGACGTTGAGAG
ACCATACGATGTAGAATATGAGCTCACCATCAACGAGAAACTAGGAAAATCACAAAAAAAACAACTCTCGTAATTGTACG
AGTGGCACAGATGGGTCTGCCTCAACATATCTCTAATACGGCGAAGCCTGCCCAACACGTAGTTGCCGGAATCCGGTGTG
GAGCTCACGACTCTGAAAGATAGGCGCTTCCTGTTTCGTTTCGCTCACCCACTGGACGTCCGTCATGTGATGGATTTCGG
TCATTGGTTTGCTGACAACCACATTCTGAAGCTCCATGAGATGAGTCTTCACAATAGGTCCTGCTCAATACCGTGGAGTT
ATGGTTGCAAGTCCATAACTTGCCGTTCGAATATTTTGCGGAGCCAGTCGGACGGGAATTGGCGAGCTCGGCTGACACCT
ATAAAGGCCATGACAAGAAGAACCAAAAGTTCTTCCCTAATGCTTTCATGAGGCTTCGGGTCGTTATGGATGTCGGAAAA
CCCCTCTTGAAGGAACGAGACGTTATTATGCATGACGGTAAGACTATTACTTGTCAGTATAAGTATGAAAGATTACCTGT
CTTCTGCTTTGTTTGTGGATTGATTGGACACGTTGAAAAAAAATGTGCACTTCGATTTCAATACTCAGAGATCGACTTCC
CTTTTCTCTAGGAGTATTCGATCAAGGCATTAACATGGAAGGAAGCTCAAGCTCTAAAGGCTTCACAATGGAACCTGAAA
AATTTCAACAAGCCTAAACTGAAATCGAAGTCAAATCACCCAACCGGGAGCTCTAAATCAGCAAACACTCCTCCTCCACA
GTATCCAATCATCGTGCACGATGCTCCAGGTATTGCAAGCCAGGTATTGCAAGCTAGGAGTAGGATAGAGACCTTAAACG
TCGTTGGTGTGAAGAGTCATCTTCAGACCTAATGGAGATAGATGTAGACGGCGGCACGAAGACTCTGAAACACCAGAAAG
GCTAGTCCAGGATAAGGATCTGCTATCCCAACTGACCTCTCGTTAGTCCCAAGGCCTCTCAACTAGAGCAGGAGGAAGGA
TGGTCACAAGACTAGGATAATGATGTTTCCAATATGAACCTGAATGTCCATAGCTAATTTTTTAGTCTTGCTTCTGCAC
```

FIG. 6 (con't)

```
TTTTTGTTTATTATGTTCTGGTGACTATGTTATTTACCCTTGTCCGTATGCTTGAGAGAATCAGTATTTTCCTTCGACGT
TAATTGATCCTACACTATGTAGGTCATATCCATCGTTTTAATTTTTGGCCACCATTCAATTCTGTCTTGCCTTTAGGGAT
GTGAATATGAACGGCCAAGGTAAGAGAATAAAAATAATCCAAATTAAAGCAAGAGAGGCCAAGTAAGATAATCCAAATGT
ACACTTGTCATTGCCAAAATTAGTAAAATACTCGGCATATTGTATTCCCACACATTATTAAAATACCGTATATGTATTGG
CTGCATTTGCATGAATAATACTACGTGTAAGCCCAAAAGAACCCACGTGTAGCCCATGCAAAGTTAACACTCACGACCCC
ATTCCTCAGTCTCCACTATATAAACCCACCATCCCCAATCTCACCAAACCCACCACACAACTCACAACTCACTCTCACAC
CTTAAAGAACCAATCACCACCAAAAATTTTACAACAATTACCAACAACAACAAACAACAAACAACATTACAATTACATTT
ACAATTACCATACCATGTCTAAGGTTACCGTGTCTGGATCTGAGATCCTTGAGGGATCTACTAAGACCGTTAGGCGTTCT
GGAAACGTTGCATCTTTCAAGCAGCAAAAGACCGCTATCGATACCTTCGGAAACGTTTTCAAGGTGCCAGATTACACCAT
CAAGGATATCCTTGACGCTATCCCTAAGCACTGTTACGAGAGATCTCTCGTGAAGTCTATGTCTTACGTGGTGAGAGATA
TCGTGGCTATCTCTGCTATCGCTTACGTTGGACTTACCTACATCCCTCTTCTCCCTAACGAATTCCTTAGATTCGCTGCT
TGGTCTGCTTACGTGTTCTCTATCTCTTGTTTCGGATTCGGAATCTGGATCCTTGGACATGAGTGTGGACATTCTGCTTT
CTCTAACTACGGATGGGTTAACGATACCGTTGGATGGGTTCTCCACTCTCTTGTTATGGTTCCTTACTTCAGCTGGAAGT
TCTCTCATGCTAAGCACCATAAGGCTACTGGACACATGACCAGAGATATGGTTTTCGTTCCTTACACCGCCGAGGAATTC
AAAGAGAAGCACCAAGTTACCAGCCTTCACGATATCGCTGAGGAAACTCCTATCTACTCTGTTTTCGCTCTCTTGTTCCA
ACAGCTTGGAGGACTTTCTCTTTACCTTGCTACTAACGCTACTGGACAACCTTACCCTGGTGTTTCTAAGTTCTTCAAGT
CTCACTACTGGCCTTCTAGCCCTGTTTTCGATAAGAAGGACTACTGGTACATCGTTCTTTCTGATCTTGGAATCCTTGCT
ACCCTCACTTCTGTTTACACCGCTTACAAGGTTTTCGGATTCTGGCCTACTTTCATCACATGGTTCTGTCCTTGGATCCT
TGTTAACCACTGGCTTGTTTTCGTTACCTTCCTTCAGCACACCGATTCTTCTATGCCTCATTACGATGCTCAAGAGTGGA
CTTTCGCTAAGGGTGCTGCTGCTACTATCGATAGAGAGTTCGGAATCCTCGGAATCATCTTCCATGACATCATCGAGACT
CATGTGCTCCATCACTACGTTTCAAGGATCCCATTCTACCATGCTAGAGAAGCTACCGAGTGCATCAAGAAAGTTATGGG
AGAGCACTACAGACACACCGATGAGAACATGTGGGTTAGCCTTTGGAAAACTTGGAGATCTTGCCAGTTCGTTGAGAACC
ATGATGGTGTGTACATGTTCCGTAACTGCAACAACGTTGGAGTGAAGCCTAAGGATACCTGATGAAGGGGTGATCGATTA
TGAGATCGTACAAAGACACTGCTAGGTGTTAAGGATGGATAATAATAATAATAATGAGATGAATGTGTTTTAAGTTAGTG
TAACAGCTGTAATAAAGAGAGAGAGAGAGAGAGAGAGAGAGAGAGAGAGAGAGAGAGAGAGGCTGATGAAATGT
TATGTATGTTTCTTGGTTTTTAAAATAAATGAAAGCACATGCTCGTGTGGTTCTATCGAATTATTCGGCGGTTCCTGTGG
GAAAAAGTCCAGAAGGGCGGCGGCAGCTACTACTACAACCAAGGCCGTGGAGGAGGGCAACAGAGCCAGCACTTCGATAG
CTGCTGCGATGATCTTAAGCAATTGAGGAGCGAGTGCACATGCAGGGGACTGGAGCGTGCAATCGGCCAGATGAGGCAGG
ACATCCAGCAGCAGGGACAGCAGCAGGAAGTTGAGAGGTGGTCCCATCAATCTAAACAAGTCGCTAGGGACCTTCCGGGA
CAGTCGGCACCCAGCCTAGCCGATGCCAGCTCCAGGGGCAGCAGCAGTCTGCATGGTTTTGAAGTGGTGATCGATGAGA
TCGTATAAAGACACTGCTAGGTGTTAAGGATGGGATAATAAGATGTGTTTTAAGTCATTAACCGTAATAAAAAGAGAGAG
AGGCTGATGGAATGTTATGTATGTATGTTTCTTGGTTTTTAAAATTAAATGGAAAGCACATGCTCGTGTGGGTTCTATCA
CTATTTTCAGAAGAAGTTCCCAATAGTAGTCCAAAATTTTTGTAACGAAGGGAGCATAATAGTTACATGCAAAGGAAAAC
TGCCATTCTTTAGAGGGGATGCTTGTTTAAGAACAAAAAATATATCACTTTCTTTTGTTCCAAGTCATTGCGTATTTTTT
TAAAAATATTTGTTCCTTCGTATATTTCGAGCTTCAATCACTTTATGGTTCTTTGTATTCTGGCTTTGCTGTAAATCGTA
GCTAACCTTCTTCCTAGCAGAAATTATTAATACTTGGGATATTTTTTAGAATCAAGTAAATTACATATTACCACCACAT
CGAGCTGCTTTTAAATTCATATTACAGCCATATAGGCTTGATTCATTTTGCAAAATTTCCAGGATATTGACAACGTTAAC
TTAATAATATCTTGAAATATTAAAGCTATTATGATTAGGGGTGCAAATGGACCGAGTTGGTTCGGTTTATATCAAAATCA
AACCAAACCAACTATATCGGTTTGGATTGGTTCGGTTTTGCCGGGTTTTCAGCATTTTCTGGTTTTTTTTTGTTAGATG
AATATTATTTTAATCTTACTTTGTCAAATTTTTGATAAGTAAATATATGTGTTAGTAAAAATTAATTTTTTTTACAAACA
TATGATCTATTAAAATATTCTTATAGGAGAATTTTCTTAATAACACATGATATTTATTTATTTTAGTCGTTTGACTAATT
TTTCGTTGATGTACACTTTCAAAGTTAACCAAATTTAGTAATTAAGTATAAAAATCAATATGATACCTAAATAATGATAT
GTTCTATTTAATTTTAAATTATCGAAATTTCACTTCAAATTCGAAAAGATATATAAGAATTTTGATAGATTTTGACATA
TGAATATGGAAGAACAAAGAGATTGACGCATTTTAGTAACACTTGATAAGAAAGTGATCGTACAACCAATTATTTAAAGT
TAATAAAAATGGAGCACTTCATATTTAACGAAATATTACATGCCAGAAGAGTCGCAAATATTTCTAGATATTTTTTAAAG
AAAATTCTATAAAAAGTCTTAAAGGCATATATATAAAAACTATATATTTATATTTTGGTTTGGTTCGAATTTGTTTTACT
CAATACCAAACTAAATTAGACCAAATATAATTGGGATTTTTAATCGACCGATCTAGTAACATAGATGACACCGCGCGCGA
TAATTTATCCTAGTTTGCGCGCTATATTTTGTTTTCTATCGCGTATTAAATGTATAATTGCGGGACTCTAATCATAAAAA
CCCATCTCATAAATAACGTCATGCATTACATGTTAATTATTACGTGCTTAACGTAATTCAACAGAAATTATATGATAATC
ATCGCAAGACCGGCAACAGGATTCAATCTTAAGAAACTTTATTGCCAAATGTTTGAACGATCTCATTACTGCATTTTCTT
CTCAGGAGCATGGGCAACGTTATCAAGGTTAGCGAAAGTATCAGCCATAGCCTCGAAGTATCCTCTAACATCGTAGTGAA
GTCCGTGCTTCTCGAAAAGCTGCTTAACTCTAGGAGCGATCTTAGGGTGTCTGAATTGAGGCATAGAAGGGTAAAGGTGG
TGCTCGATCTGGTAGTTAAGGTAAGACATCCACCAATCACACCACCAAGATGGAGAACAGTTAGTAGTGTGGTTAGCAGC
GTACTCAACCCAAGTAGCATGCTCGTTAGGCTCAACAACAGGGAGGTGAGTATGAGAAACAGCGAAGTTGCAGAAGATGT
ACATAGCTCCAAGCTGAACGTAAAGAAGGTAACAAGCGAGAACGTATCCAGCACCGTAGTTAGCAGCAAGGTATCCAACA
AGTCCGTATCTGATTCCGAGCATAGCAAGCTCATCGTAGTGCTTAGTCCTGAGCATGTGTCTAGGATGAAGGTAAAGCTG
CCATCCAAGAGCAACAAGAAGAGTGGTAACAGGAGCGAAAAGCTTAGCTTGCATAGAAAGCCAAGCCTTCATAGCAGGAG
ACTTAACCTTAGCAGCGATTCTCTCATGGAAAGCAACGAGAGGAAGGGTATCAAGATCAACATCGTGCTGAAGCTTTTGA
```

FIG. 6 (con't)

```
GGAGTAGCATGGTGCTTGTTATGCTGGTTACGCCACCAAGCACCAGACATTCCACATCCAAGTCCGTAACAAGCAACTTG
GATAGCTCTGTCGAAAGCAATGTTTCCAGTGAGAGAGTAATGTCCACCCTCATGCATAAGCCATCCACATCTTCCCTGAA
CAACTCCAAGCATAGCGATTCCAGCGAAAGTGTATCCATGCCAGATAAGAGCAGCACCAGCAACATGCATAGCGATAACC
TCAGCAAGTCTGTAAGCAACATGAGGAAGAGAAGGCTCGAACATTCCCTCAGCCTCAAGTTGCTTGGTGAACTCTTGGAA
ATCAGCGATAAGATCAGCCCTTCTTGGAGAGTATCCCTTGTGAACAGGACGAGAAGGAAGAGACTTAAGCATCTTGTCAG
CCTTAGCAGATCTAACATGGAACTGCTTGTAAGCATCGGTAGCATCAGTTCCAACTTGGTAAGCAATGATCTTTCCACCA
GGGTGTCTCTTAACGAAGTTGGTAACATCGTAAGCCCTATCTCCGATAACAAGCTCTTTCTTGTCGTGCTCTTGAGGAGT
ATCAACTTCGTGAAGTTGAGCAGAAGGAGGAGCAGCATAAGAGTAAGAGTCCCTTGGAGGCATGGTATGGTAATTGTAAA
TGTAATTGTAATGTTGTTTGTTGTTTGTTGTTGGTAATTGTTGTAAAAGATCCTCGTGTATGTTTTAATCTTGTTT
GTATCGATGAGTTTTGGTTTGAGTAAAGAGTGAAGCGGATGAGTTAATTTATAGGCTATAAAGGAGATTTGCATGGCGAT
CACGTGTAATAATGCATGCACGCATGTGATTGTATGTGTGTGCTGTGAGAGAGAAGCTCTTAGGTGTTTGAAGGGAGTGA
CAAGTGGCGAAGAAAACAATTCTCCGCGGCTGCATGCTATGTGTAACGTGTAGCTAATGTTCTGGCATGGCATCTTATG
AACGATTCTTTTAAAAACAAGGTAAAAACTTAACTTCATAAAATTAAAAAAAAAAACGTTTACTAAGTTGGTTTAAAAG
GGGATGAGACTAGAATCTAATTATTCTATTCAGACTAAATTAGTATAAGTATTTTTTAATCAATAAATAATAATTAATA
ATTTATTAGTAGGAGTGATTGAATTTATAATATATTTTTTTAATCATTTAAAGAATCTTATATCTTTAAATTGACAAGA
GTTTTAAATGGGGAGAGTGTTATCATATGACAAGTAGGATTAATGTGTTATAGTTTCACATGCATTACGATAAGTTGTGA
AAGATAACATTATTATATATAACAATGACAATCACTAGCGATCGAGTAGTGAGAGTCGTCTTATTACACTTCTTCCTTC
GATCTGTCACATGGCGGCGGCCCGGCGCGCCGCGCGCCTTATCACTGCTTCTTAGCACCCTTAGACTTGTACCTCTTACG
GTAGAAGTTGGCGAAGAGAACGAACATGTTCACCATAACCCAGAGTTGAAGGTAAGGAAGCCAGAAAGCGGTATTCTGAA
CGTAAGCGGTGTAGATAGAGTGAGAAGCACAGATACAGAACTGAAGCATCTGGATCTGGGTGATGTACTTCTTCCAGAAA
CAGTTAACTCCAAGAGCAGCAAGTCCGTAGTAAGAGTACATGATCACGTGCACGAAGGTGTTAACAGAAGATCCGAAGTA
GCAATCTCCAACAGGCTCAAGCTTCATAACAACGAACCATGACCAGATGAGAAGAGTGTGGTGGTAGATGTGAAGGAAAG
AAAGCTGGTCGAACTTCTTCCTCATCACCATGAAGAAGGTGTCGAGAAGCTCAACGTACTTGTTGTTGTAGTGAAGCCAG
ATAACCTGAGAGATTCCCCAAGAGTTAGCAGTCATATCAGGGATGTTTCCCCAAACCTTAAGTCCCTGAGCCCTATGAGA
AGTAACGAAAAGGTAGATGCAGTAGCTGTTGAAGAAGGTCTGGTAGAAGTTGTAAACGAGCATAGCGTTCTTGAGTCCGA
AAGGTTGAGATCTGTTCTGCATGATACGCTTTCCGAAGTAGATGAAGAGGAGGTATCCAATAGTTCCGATAGTAGGTCCC
CAGTACTCAACCTGCATGAAGTAAGCAGGAACTTTCTCAGAAGCTGGGATATCAGGGTTAGCCACATTGTAGGTAACGTA
TCCAAGAGTTCCAGCAAGAGCAGCAGGGATAGCGATAGAGGCCATGGTATGGTAATTGTAAATGTAATTGTAATGTTGTT
TGTTGTTTGTTGTTGGTAATTGTTGTAAAATGCTCTGTTTGTGTCGGAAAATAATGGAGGAAGCTATGAGATGTATT
TGTATGGATCCTCTTTTGTGGTCCGTTACGTTTTACAAAGCATGCATTTAGACATGTGTATACTCAAACTCATGCATCCA
TACACATTGTAATAAAGTAGTAGTCCACTGAAAGTTGCCAAAATAGCAAAATAGTACATTGCAGAAATATATATACTAAA
TTCATATATTTCGATGGAAAATTTCGGTTTTCCACTTAAAATAAAATGTACGTATAAACTTAGTCTTCTTTTAACGCCAA
AAAAAAGTCTACAAATTTCTGTCTTTAATACTACATTATTTTTGAATTGTGCTAAACTATGATTACATGTGCATTAAAAT
TTGAGGGAATGTGTGTTCTTAGATCTGATTGGCATACCCTCTGACTAATTATGGGATCATGAGTATTTCTCGGGAATGTG
TTTATTCGCAAGTCTATTCTCTAACCTCAGTAAATAATGAGTGGAAGTTTAGTTAAGGCCAAATAGTCTAAAATATATTA
TTTGTAGTTTTGTACACAGCCAGGATTGAATCTTAAGAGACTCTTTAAGTCTAAAATTACAATCAGATCCTAGACCACTT
TCTATTTGCATGAACGTAACCGGATACTGATTTTTTAAATGTTTTCTTTGGTTCAAAATCGCCACTATCTTTGACAAAAA
CATTCTCGAATAGGATTCAAACCTAAGAGCCTTTCAAATTCGTTCTTAATTATGTCATCATCTTTAGTTCTGCTCCCATC
TCTCATCGGTCTCAAGAACCACTCCAGTCATTTAAGTACTACGTTTTATACACATTACATATACATACATTTACACAAC
TAGGAATTGAGTAGGGAACAAAGTTTCAACTTTCAACTAATAGGGTAAGCCTTCTGGTACATGGAAACCAACCAACCAAT
CTACTAGGGTACCCTCAAGCATACGGACAAGGGTAAATAACATAGTCACCAGAACATAATAAACAAAAAGTGCAGAAGCA
AGACTAAAAAATTAGCTATGGACATTCAGGTTCATATTGGAAACATCATTATCCTAGTCTTGTGACCATCCTTCCTCCT
GCTCTAGTTGAGAGGCCTTGGGACTAACGAGAGGTCAGTTGGGATAGCAGATCCTTATCCTGGACTAGCCTTTCTGGTGT
TTCAGAGTCTTCGTGCCGCCGTCTACATCTATCTCCATTAGGTCTGAAGATGACTCTTCACACCAACGACGTTTAAGGTC
TCTATCCTACTCCAGCTTGCAATACCTGGCTTGCAATACCTGGAGCATCGTGCACGATGATTGGATACTGTGGAGGAGG
AGTGTTTGCTGATTTAGAGCTCCCGGTTGGGTGATTTGACTTCGATTTCAGTTTAGGCTTGTTGAAATTTTTCAGGTTCC
ATTGTGAAGCCTTTAGAGCTTGAGCTTCCTTCCATGTTAATGCCTTGATCGAATACTCCTAGAGAAAAGGGAAGTCGATC
TCTGAGTATTGAAATCGAAGTGCACATTTTTTTCAACGTGTCCAATCAATCCACAAACAAAGCAGAAGACAGGTAATCT
TTCATACTTATACTGACAAGTAATAGTCTTACCGTCATGCATAATAACGTCTCGTTCCTTCAAGAGGGGTTTTCCGACAT
CCATAACGACCCGAAGCCTCATGAAAGCATTAGGGAAGAACTTTTGGTTCTTCTTGTCATGGCCTTTATAGGTGTCAGCC
GAGCTCGCCAATTCCCGTCCGACTGGCTCCGCAAAATATTCGAACGGCAAGTTATGGACTTGCAACCATAACTCCACGGT
ATTGAGCAGGACCTATTGTGAAGACTCATCTCATGGAGCTTCAGAATGTGGTTGTCAGCAAACCAATGACCGAAATCCAT
CACATGACGGACGTCCAGTGGGTGAGCGAAACGAAACAGGAAGCGCCTATCTTTCAGAGTCGTGAGCTCCACACCGGATT
CCGGCAACTACGTGTTGGGCAGGCTTCGCCGTATTAGAGATATGTTGAGGCAGACCCATCTGTGCCACTCGTACAATTAC
GAGAGTTGTTTTTTTGTGATTTTCCTAGTTTCTCGTTGATGGTGAGCTCATATTCTACATCGTATGGTCTCTCAACGTC
GTTTCCTGTCATCTGATATCCCGTCATTTGCATCCACGTGCGCCGCCTCCCGTGCCAAGTCCCTAGGTGTCATGCACGCC
AAATTGGTGGTGGTGCGGGCTGCCCTGTGCTTCTTACCGATGGGTGGAGGTTGAGTTTGGGGGTCTCCGCGGCGATGGTA
GTGGGTTGACGGTTTGGTGTGGGTTGACGGCATTGATCAATTTACTTCTTGCTTCAAATTCTTTGGCAGAAAACAATTCA
```

FIG. 6 (con't)

```
TTAGATTAGAACTGGAAACCAGAGTGATGAGACGGATTAAGTCAGATTCCAACAGAGTTACATCTCTTAAGAAATAATGT
AACCCCTTTAGACTTTATATATTTGCAATTAAAAAAATAATTTAACTTTTAGACTTTATATATAGTTTTAATAACTAAGT
TTAACCACTCTATTATTTATATCGAAACTATTTGTATGTCTCCCCTCTAAATAAACTTGGTATTGTGTTTACAGAACCTA
TAATCAAATAATCAATACTCAACTGAAGTTTGTGCAGTTAATTGAAGGGATTAACGGCCAAAATGCACTAGTATTATCAA
CCGAATAGATTCACACTAGATGGCCATTTCCATCAATATCATCGCCGTTCTTCTTCTGTCCACATATCCCCTCTGAAACT
TGAGAGACACCTGCACTTCATTGTCCTTATTACGTGTTACAAAATGAAACCCATGCATCCATGCAAACTGAAGAATGGCG
CAAGAACCCTTCCCCTCCATTTCTTATGTGGCGACCATCCATTTCACCATCTCCCGCTATAAAACACCCCCATCACTTCA
CCTAGAACATCATCACTACTTGCTTATCCATCCAAAAGATACCCACTTAATTAATTTTACAACAATTACCAACAACAACA
AACAACAAACAACATTACAATTACATTTACAATTACCATACCATGTGCCCTCCTAAGACTGATGGAAGATCTTCTCCTAG
ATCTCCACTTACCAGGTCTAAATCTTCTGCTGAGGCTCTTGATGCTAAGGATGCTTCTACTGCTCCTGTTGATCTTAAGA
CTCTTGAGCCTCATGAGCTTGCTGCTACTTTCGAGACTAGATGGGTTAGAGTTGAGGACGTTGAGTACGATGTGACTAAC
TTCAAGCACCCTGGTGGATCTGTGATCTTCTACATGCTTGCTAACACTGGTGCTGATGCTACTGAGGCTTTCAAAGAATT
CCACATGCGTTCTCTCAAGGCTTGGAAGATGCTTAGAGCTTTGCCTTCTAGACCTGCTGAGATCAAGAGATCTGAGTCTG
AGGATGCTCCTATGCTTGAGGATTTCGCTAGATGGCGTGCTGAGCTTGAGAGAGATGGATTCTTCAAGCCTTCTATCACC
CATGTGGCTTACAGACTTCTCGAGCTTCTTGCTACATTCGCTCTTGGAACTGCTCTTATGTACGCTGGATACCCTATCAT
TGCTTCTGTTGTTTACGGTGCTTTCTTCGGAGCTAGATGTGGATGGGTTCAACATGAGGGTGGACATAACTCTCTTACCG
GATCTGTTTACGTGGACAAGAGACTTCAGGCTATGACTTGTGGATTCGGACTTTCTACTTCTGGTGAGATGTGGAACCAG
ATGCATAACAAGCACCATGCTACCCCTCAAAAGGTTAGACACGATATGGATCTTGATACCACTCCTGCTGTGGCTTTCTT
CAACACTGCTGTTGAGGATAACAGACCTAGAGGATTCTCTAGAGCTTGGGCTAGACTTCAAGCTTGGACTTTCGTTCCTG
TTACCTCTGGACTTCTTGTTCAAGCTTTCTGGATCTACGTTCTCCACCCTAGACAAGTTCTCCGTAAGAAGAACTACGAA
GAGGCTTCTTGGATGCTCGTTTCTCATGTTGTTAGAACCGCTGTTATCAAGCTTGCTACTGGATACTCTTGGCCTGTTGC
TTACTGGTGGTTCACTTTCGGAAACTGGATCGCTTACATGTACCTTTTCGCTCACTTCTCTACTTCTCATACTCACCTCC
CTGTTGTTCCATCTGATAAGCACCTTTCTTGGGTTAACTACGCTGTTGATCACACCGTTGATATCGATCCTTCTAGAGGA
TACGTGAACTGGCTTATGGGATACCTTAACTGTCAGGTTATCCACCACCTCTTCCCTGATATGCCTCAATTCAGACAGCC
TGAGGTTAGCAGAAGATTCGTTCCTTTCGCTAAGAAGTGGGGACTCAACTACAAGGTGCTCTCTTACTACGGTGCTTGGA
AGGCTACTTTCTCTAACCTTGATAAGGTGGGACAGCACTACTACGTTAACGGAAAGGCTGAGAAGGCTCACTAATGATTA
ATTAACAAGCTTATGTGACGTGAAATAATAACGGTAAAATATATGTAATAATAATAATAATAAAGCCACAAAGTGAGAAT
GAGGGGAAGGGGAAATGTGTAATGAGCCAGTAGCCGGTGGTGCTAATTTTGTATCGTATTGTCAATAAATCATGAATTTT
GTGGTTTTTATGTGTTTTTTTAAATCATGAATTTTAAATTTTATAAAATAATCTCCAATCGGAAGAACAACATTCCATAT
CCATGCATGGATGTTTCTTTACCCAAATCTAGTTCTTGAGAGGATGAAGCATCACCGAACAGTTCTGCAACTATCCCTCA
AAAGCTTTAAAATGAACAACAAGGAACAGAGCAACGTTCCAAAGATCCCAAACGAAACATATTATCTATACTAATACTAT
ATTATTAATTACTACTGCCCGGAATCACAATCCCTGAATGATTCCTATTAACTACAAGCCTTGTTGGCGGCGGAGAAGTG
ATCGGCGCGGCGAGAAGCAGCGGACTCGGAGACGAGGCCTTGGAAGATCTGAGTCGAACGGGCGGTACCGCGGCCGCAAG
CTTTCCGCGGGGCGCCCGTTTTACAACGTCGTGACTGGGAGATCCACTAGCAGATTGTCGTTTCCGCCTTCAGTTTAAA
CTATCAGTGTTTAAGGACAGACCCACCCAAGAACACACCAGTCATTCAGATGCAGCCTATCTCCGTGCCGGCTATTCCA
GCTGATGAGTTGAAGGATATAACTGATAACTATGGTTCCAAGTCCTTGATTGGTGAGGGCTCTTATGGAAGAGTGTTTTA
CGGTGTTCTTAGAAGCGGCAAGGCAGCTGCCATTAAGAAGCTGGATTCTAGTAAGCAGCCTGATCAAGAGTTTCTCGCAC
AGGTACAAATGCTACTTAAGTAAATCAAACCGTTAAAGTTGAGTTGCTGCTTAGTTACTGATGTAAATAATGTTAATTAG
GTATCAATGGTTTCGAGATTGAGACAAGACAATGTTGTTGCACTTCTGGGATATTGCGTTGATGGCCCACTCCGTGTTCT
TGCTTATGAGTTTGCTCCTAATGGATCTCTTCATGATATTCTTCATGGTAAGTTATTAAGTCTAAAACATTGATTCGGTA
CGACTTGTAGATGTGAAGCTATTAACTAATGAAATGTGGTGAGTTTGTTGGGTGTAGGTAGGAAAGGAGTGAAAGGAGCA
CAGCCAGGACCTGTTCTGTCGTGGAACCAGAGAGTTAAAATTGCTGTTGGTGCGGCTAGGGGACTCGAGTACTTGCATGA
GAAGGCGAACCCTCATGTTGTCCACCGAGACATCAAATCCAGCAATGTGCTTTTGTTTGACGATGATGTTGCCAAGATTG
CTGACTTCGATCTGTCTAACCAAGCCCCTGACATGGCTGCTCGCCTTCACTCAACTCGTGTGCTGGGAACCTTTGGTTAT
CACGCTCCAGAGTAAGCCCTTTACTTGTTTATTTGAATTGTTTTGTTCAGACTAATCAATGTGGTTACATTCAACTTGT
GCTCAAAGACTTTTGGTTATTATTATCTTATGTTTTGAGGCACTAAGTCCTTCCTTGGAATAATCTTTGACATTATTTTG
GATTGCATCTCTTCTAATTGACCATACTAGAGTCTTAAACACAAACATTTTTGTTTTGGTTCTGCATTTTCAGGTATGCA
ATGACAGGGACATTGAGCACAAAGAGTGATGTCTATAGTTTTGGAGTTGTTCTGCTAGAGCTCCTCACAGGTCGTAAGCC
AGTTGATCATACCTTACCACGAGGACAGCAGAGTCTCGTTACATGGGTAATGCTTAGTGCAGCTCTGCTTCTTTTTCTG
GTTTACTCATATTGAGAAGAAAGGGAATGTGTCTGCACAATCATGTTGATTTGTGAGAGATTAGATAAACTCATTATT
AAATGAAAACGCGTTTGTGTGTGTATCAGGCAACTCCTAAACTGAGTGAAGACAAGGTGAAGCAATGCGTTGATGCAA
GACTAAACGGAGAATATCCTCCCAAAGCTGTTGCCAAGGTAACCTTTTGTCATAGTGTCGTTGTGTCAGTAGAGAAGGTT
TACCTTAGGACACGACTTAGAAACTGCTTCTCCATCACTTCCATCGTTTTCGGTTCCTTCTTAATGTATCCCTGTTGTAG
GCCTAGATTGAAATACAAGTCTCTTCTAAGGACAATAGAACCTAAGCATTGATGTATGATTTTTTGGGAGTCTGATTTT
GGTTTTTTCTCTCTTATATGACTCCGGTAATGATCAGCTGGCTGCTGTAGCTGCGCTATGTGTGCAATACGAAGCAGACT
TCAGGCCAAACATGAGCATAGTGGTGAAGGCTCTTCAGCCTCTCCTCAATCCTCCTCGCTCTGCTCCTCAAACTCCTCAC
AGGAACAATCCTTATTGATGTCCTCCAATCTGATGCCACGCTTCTTCATCATATCACTTATTTCATTTGTTTTTGTTTGA
```

FIG. 6 (con't)

ATCCAATTTGTGTAAATTCGTGAAAATAGGCTTTTTATTTCTCACAATAGACATGAAAGTCTCACTTCCAAACCTGAATG
GTGTTGCTCTATTTGTTTATGTTATTTCATGCCTGCGATTGTAAGTTTCTACTAATTATACAATATGCGAGGAATGGATT
ATTCATAATATACTCATTGTGTTTGTGCC
(SEQ ID NO:41)

SEQUENCE LISTING

<160> NUMBER OF SEQ ID NOS: 66

<210> SEQ ID NO 1
<211> LENGTH: 44
<212> TYPE: DNA
<213> ORGANISM: Artificial Sequence
<220> FEATURE:
<223> OTHER INFORMATION: KASP primer

<400> SEQUENCE: 1
gaaggtgacc aagttcatgc tccaagcacc gtagtaagag agca                44

```
<210> SEQ ID NO 2
<211> LENGTH: 26
<212> TYPE: DNA
<213> ORGANISM: Artificial Sequence
<220> FEATURE:
<223> OTHER INFORMATION: KASP primer

<400> SEQUENCE: 2
gctaagaagt ggggactcaa ctacaa                                          26

<210> SEQ ID NO 3
<211> LENGTH: 41
<212> TYPE: DNA
<213> ORGANISM: Artificial Sequence
<220> FEATURE:
<223> OTHER INFORMATION: KASP primer

<400> SEQUENCE: 3
gaaggtgacc aagttcatgc tgctcttgct ggaactcttg g                         41

<210> SEQ ID NO 4
<211> LENGTH: 26
<212> TYPE: DNA
<213> ORGANISM: Artificial Sequence
<220> FEATURE:
<223> OTHER INFORMATION: KASP primer

<400> SEQUENCE: 4
gggttagcca cattgtaggt aacgta                                          26

<210> SEQ ID NO 5
<211> LENGTH: 44
<212> TYPE: DNA
<213> ORGANISM: Artificial Sequence
<220> FEATURE:
<223> OTHER INFORMATION: KASP primer

<400> SEQUENCE: 5
gaaggtgacc aagttcatgc ttaagagaca ccctggtgga aaga                      44

<210> SEQ ID NO 6
<211> LENGTH: 28
<212> TYPE: DNA
<213> ORGANISM: Artificial Sequence
<220> FEATURE:
<223> OTHER INFORMATION: KASP primer

<400> SEQUENCE: 6
tagcatcagt tccaacttgg taagcaat                                        28

<210> SEQ ID NO 7
<211> LENGTH: 44
<212> TYPE: DNA
<213> ORGANISM: Artificial Sequence
<220> FEATURE:
<223> OTHER INFORMATION: KASP primer

<400> SEQUENCE: 7
gaaggtgacc aagttcatgc tgaacacgta agcagaccaa gcag                      44

<210> SEQ ID NO 8
<211> LENGTH: 25
<212> TYPE: DNA
<213> ORGANISM: Artificial Sequence
<220> FEATURE:
<223> OTHER INFORMATION: KASP primer
```

```
<400> SEQUENCE: 8
ccctcttctc cctaacgaat tcctt                                           25

<210> SEQ ID NO 9
<211> LENGTH: 44
<212> TYPE: DNA
<213> ORGANISM: Artificial Sequence
<220> FEATURE:
<223> OTHER INFORMATION: KASP primer

<400> SEQUENCE: 9
gaaggtgacc aagttcatgc tgaggaacct gttgctgctg atga                      44

<210> SEQ ID NO 10
<211> LENGTH: 26
<212> TYPE: DNA
<213> ORGANISM: Artificial Sequence
<220> FEATURE:
<223> OTHER INFORMATION: KASP primer

<400> SEQUENCE: 10
gcgatcctag cacaaagttg aaggta                                          26

<210> SEQ ID NO 11
<211> LENGTH: 44
<212> TYPE: DNA
<213> ORGANISM: Artificial Sequence
<220> FEATURE:
<223> OTHER INFORMATION: KASP primer

<400> SEQUENCE: 11
gaaggtgacc aagttcatgc tggatggatc gcttacctct tcgt                      44

<210> SEQ ID NO 12
<211> LENGTH: 25
<212> TYPE: DNA
<213> ORGANISM: Artificial Sequence
<220> FEATURE:
<223> OTHER INFORMATION: KASP primer

<400> SEQUENCE: 12
cagggtaagg ttgtcctgta acgtt                                           25

<210> SEQ ID NO 13
<211> LENGTH: 42
<212> TYPE: DNA
<213> ORGANISM: Artificial Sequence
<220> FEATURE:
<223> OTHER INFORMATION: KASP primer

<400> SEQUENCE: 13
gaaggtgacc aagttcatgc tctattggat ggggactcaa gc                        42

<210> SEQ ID NO 14
<211> LENGTH: 26
<212> TYPE: DNA
<213> ORGANISM: Artificial Sequence
<220> FEATURE:
<223> OTHER INFORMATION: KASP primer

<400> SEQUENCE: 14
gggagatcct tagtagcaga agagat                                          26

<210> SEQ ID NO 15
<211> LENGTH: 44
```

<212> TYPE: DNA
<213> ORGANISM: Artificial Sequence
<220> FEATURE:
<223> OTHER INFORMATION: KASP primer

<400> SEQUENCE: 15
gaaggtgacc aagttcatgc tcctgagagg cgtcctgttg aaat       44

<210> SEQ ID NO 16
<211> LENGTH: 25
<212> TYPE: DNA
<213> ORGANISM: Artificial Sequence
<220> FEATURE:
<223> OTHER INFORMATION: KASP primer

<400> SEQUENCE: 16
aacagcagcc atatcagcag cagta                           25

<210> SEQ ID NO 17
<211> LENGTH: 45
<212> TYPE: DNA
<213> ORGANISM: Artificial Sequence
<220> FEATURE:
<223> OTHER INFORMATION: KASP primer

<400> SEQUENCE: 17
gaaggtgacc aagttcatgc ttgttcttgg gtgggtctgt ccttc     45

<210> SEQ ID NO 18
<211> LENGTH: 46
<212> TYPE: DNA
<213> ORGANISM: Artificial Sequence
<220> FEATURE:
<223> OTHER INFORMATION: KASP primer

<400> SEQUENCE: 18
gaaggtcgga gtcaacggat tgtgttcttg ggtgggtctg tcctta    46

<210> SEQ ID NO 19
<211> LENGTH: 25
<212> TYPE: DNA
<213> ORGANISM: Artificial Sequence
<220> FEATURE:
<223> OTHER INFORMATION: KASP primer

<400> SEQUENCE: 19
atccactagc agattgtcgt ttccc                           25

<210> SEQ ID NO 20
<211> LENGTH: 22
<212> TYPE: DNA
<213> ORGANISM: Artificial Sequence
<220> FEATURE:
<223> OTHER INFORMATION: KASP primer

<400> SEQUENCE: 20
gttggctaag gtcacggtgg ag                              22

<210> SEQ ID NO 21
<211> LENGTH: 48
<212> TYPE: DNA
<213> ORGANISM: Artificial Sequence
<220> FEATURE:
<223> OTHER INFORMATION: KASP primer

<400> SEQUENCE: 21

```
gaaggtgacc aagttcatgc tccgccttca gtttaaacta tcagtgtt          48

<210> SEQ ID NO 22
<211> LENGTH: 41
<212> TYPE: DNA
<213> ORGANISM: Artificial Sequence
<220> FEATURE:
<223> OTHER INFORMATION: KASP primer

<400> SEQUENCE: 22
gaaggtcgga gtcaacggat tggtcacggt ggaggtcacc a                 41

<210> SEQ ID NO 23
<211> LENGTH: 22
<212> TYPE: DNA
<213> ORGANISM: Artificial Sequence
<220> FEATURE:
<223> OTHER INFORMATION: KASP primer

<400> SEQUENCE: 23
ggtgtgttct tgggtgggtc tg                                      22

<210> SEQ ID NO 24
<211> LENGTH: 49
<212> TYPE: DNA
<213> ORGANISM: Artificial Sequence
<220> FEATURE:
<223> OTHER INFORMATION: KASP primer

<400> SEQUENCE: 24
gaaggtgacc aagttcatgc tactttttttt tcaactgttg gctaaggta        49

<210> SEQ ID NO 25
<211> LENGTH: 49
<212> TYPE: DNA
<213> ORGANISM: Artificial Sequence
<220> FEATURE:
<223> OTHER INFORMATION: KASP primer

<400> SEQUENCE: 25
gaaggtcgga gtcaacggat tactttttttt tcaactgttg gctaaggtc        49

<210> SEQ ID NO 26
<211> LENGTH: 21
<212> TYPE: DNA
<213> ORGANISM: Artificial Sequence
<220> FEATURE:
<223> OTHER INFORMATION: KASP primer

<400> SEQUENCE: 26
gtgtgttctt gggtgggtct g                                       21

<210> SEQ ID NO 27
<211> LENGTH: 21
<212> TYPE: DNA
<213> ORGANISM: Artificial Sequence
<220> FEATURE:
<223> OTHER INFORMATION: KASP primer

<400> SEQUENCE: 27
gtcgtttccc gccttcagtt t                                       21

<210> SEQ ID NO 28
<211> LENGTH: 46
<212> TYPE: DNA
<213> ORGANISM: Artificial Sequence
```

-continued

```
<220> FEATURE:
<223> OTHER INFORMATION: KASP primer

<400> SEQUENCE: 28
gaaggtgacc aagttcatgc taaactatca gtgtttgaac acctcc        46

<210> SEQ ID NO 29
<211> LENGTH: 44
<212> TYPE: DNA
<213> ORGANISM: Artificial Sequence
<220> FEATURE:
<223> OTHER INFORMATION: KASP primer

<400> SEQUENCE: 29
gaaggtcgga gtcaacggat tacaacttgt cgtgctacac acct         44

<210> SEQ ID NO 30
<211> LENGTH: 22
<212> TYPE: DNA
<213> ORGANISM: Artificial Sequence
<220> FEATURE:
<223> OTHER INFORMATION: KASP primer

<400> SEQUENCE: 30
ggttgtgtga aaacgtgtga gc                                22

<210> SEQ ID NO 31
<211> LENGTH: 51
<212> TYPE: DNA
<213> ORGANISM: Artificial Sequence
<220> FEATURE:
<223> OTHER INFORMATION: KASP primer

<400> SEQUENCE: 31
gaaggtgacc aagttcatgc tcttttagct aaataagagg ttctgtatac t    51

<210> SEQ ID NO 32
<211> LENGTH: 51
<212> TYPE: DNA
<213> ORGANISM: Artificial Sequence
<220> FEATURE:
<223> OTHER INFORMATION: KASP primer

<400> SEQUENCE: 32
gaaggtcgga gtcaacggat tcttttagct aaataagagg ttctgtatac a    51

<210> SEQ ID NO 33
<211> LENGTH: 19
<212> TYPE: DNA
<213> ORGANISM: Artificial Sequence
<220> FEATURE:
<223> OTHER INFORMATION: KASP primer

<400> SEQUENCE: 33
gattgtgatt ccgggcagt                                    19

<210> SEQ ID NO 34
<211> LENGTH: 21
<212> TYPE: DNA
<213> ORGANISM: Artificial Sequence
<220> FEATURE:
<223> OTHER INFORMATION: KASP primer

<400> SEQUENCE: 34
gtgtgaaaac gtgtgagcaa t                                 21
```

<210> SEQ ID NO 35
<211> LENGTH: 40
<212> TYPE: DNA
<213> ORGANISM: Artificial Sequence
<220> FEATURE:
<223> OTHER INFORMATION: KASP primer

<400> SEQUENCE: 35
gaaggtgacc aagttcatgc tttgtgattc cgggcagtag        40

<210> SEQ ID NO 36
<211> LENGTH: 41
<212> TYPE: DNA
<213> ORGANISM: Artificial Sequence
<220> FEATURE:
<223> OTHER INFORMATION: KASP primer

<400> SEQUENCE: 36
gaaggtcgga gtcaacggat tgtgagcaa ttgttggagg t        41

<210> SEQ ID NO 37
<211> LENGTH: 31
<212> TYPE: DNA
<213> ORGANISM: Artificial Sequence
<220> FEATURE:
<223> OTHER INFORMATION: KASP primer

<400> SEQUENCE: 37
tcttatcaac attaagaaca taatcttta g        31

<210> SEQ ID NO 38
<211> LENGTH: 15
<212> TYPE: DNA
<213> ORGANISM: Artificial Sequence
<220> FEATURE:
<223> OTHER INFORMATION: Insertion deletion on Brassica chromosome A02

<400> SEQUENCE: 38
gtagcacgac aagtt        15

<210> SEQ ID NO 39
<211> LENGTH: 20
<212> TYPE: DNA
<213> ORGANISM: Artificial Sequence
<220> FEATURE:
<223> OTHER INFORMATION: Insertion deletion Brassica chromosome A05

<400> SEQUENCE: 39
cacggtggag gtcaccatgt        20

<210> SEQ ID NO 40
<211> LENGTH: 15004
<212> TYPE: DNA
<213> ORGANISM: Artificial Sequence
<220> FEATURE:
<223> OTHER INFORMATION: Transgene insert and Brassica flanking regions

<400> SEQUENCE: 40
gagccttgag tgctactttg ggaacaaaaa cttggtttga tgctatccta gtcttttct        60 cttttataaa ctattattag ataaaaacta aaaatagta tttatgagat ttgtcttttt        120
ttcacaatat aaattatttt aggtataaaa ataaataata gaattagtat tattagatat        180
ataaaataca tttaatttaa ttaataatat aactgtaaag tataattaag ttatacaata        240
tctaataaat ataaaaattg tattaaaata tgggaaaaca atattatatt ttaaagcgat        300

```
cttactcgat ctctctttga tcccaaagtt ttcattcctt ttaattatat ttgttgcaga    360
atattaaaac cagtgatttc tggggtttga taggattaag acacgatcgc agagaaagta    420
gaatcaatcg tggaagggaa gggatattcg aaaccctaat ttcgatcgta tccccatctt    480
ctacgaaagc atcgatcgac ttttttctga ttcagtgaga gtttgaaatc aaagtttgat    540
tttttcgacc tgatgggttt cttaaagaag ttaacgggga ttttcgggtt cgggcacaac    600
gatggtgggc acgagctgc tgcgagagac gaagatggtg aagggataa cactggatca    660 gtctctgagg acggagataa acgccgggag ggtaatcagg caaggttccg tgaaaccgga    720
cttccaagga ggggttttgg agttccggtt caagtagccg tcgaacggtc tagtcctggt    780
cctattcttc agccttgtgc tgcttctgac ggtggagttc aggtttgtct ttctttcatg    840
gttgtgattt taactgtgta gaagtctagg gactgaagaa attaatgaga atttgagggt    900
tgctagtttt gattctgatc ttgtaatgtg gctacagtgt tgtacttgtc ttgttgcagg    960
atcgttaaat ccatttgttt ggttccgatc atcctatgtt agttggtaaa attggtcttg   1020
tgagtttgtt taagttgttt ttgtgtcttc attcattttc taagcttagc attgatgaac   1080
agttgaattt agaatctttg ttctaagctt aacattaatg aatatcgaat ctttgttcta   1140
ctcagtcctt tctttgtttt tggttgtgat atgttctcgt ttcaacgtag tttatgttct   1200
tcttgtgatt ggctttacat tctgcacggt ttccgcttta gttaggtgtc tgcattatag   1260
ttagttcatt gctatcttaa attctctgtt cattcatctc tatatatcaa attaaagagt   1320
ggcagtgaag tttatgacag gacacgatat atgttttagc ttgattagtt gcggttaaag   1380
caaaaagttt ttgtttcact ctgtctgcta cagaacctgt aatttagaaa tgatgatgga   1440
tctcatgtct taacggtttc gtattcatca tgagtcacga ggctgctata gagtttgaat   1500
cttaattggt tctgttgttg gggaaagaca ataatccagt ctttaagaag ctagtggggt   1560
tgattcatcc ccaagactat tcgattgtcc aaacgcattg atatgttttt tttaatcaag   1620
tttttgttga tggcaataaa ctaacatccc agcatagtta ttgactcgac ttagttttac   1680
cattagggac tacgatggta ctcaatgcgg ctaaggattg atgaagatgg agatgttgca   1740
gatgagttct tggaagatga taactgtaag actttgccca gaaaatgcaa aacaaaagct   1800
gcaaaagtga gaggtttagt gatatcttct gatgggaaac ttcagccatt aatgcattga   1860
gcagtgaaca ccaaggataa atatttactg attagtgtgt gattgaatca agaaaaggtt   1920
agaatctggt tttcatttag ccattcaatc tcgatgtaaa atcggttaga ttctggttgt   1980
tgatacttga gaacttgaaa tgttttgtaa ctgtgaattt tgttttgaaa atagacaagt   2040
gaatctgttt ggggttgtgt gaaaacgtgt gagcaattgt tggaggtgtt caaacactga   2100
tagtttaaac tgaaggcggg aaacgacaat ctgctagtgg atctcccagt cacgacgttg   2160
taaaacgggc gccccgcgga aagcttgcgg ccgcggtacc gcccgttcga ctcagatctt   2220
ccaaggcctc gtctccgagt ccgctgcttc tcgccgcgcc gatcacttct ccgccgccaa   2280
caaggcttgt agttaatagg aatcattcag ggattgtgat tccgggcagt agtaattaat   2340
aatatagtat tagtatagat aatatgtttc gtttgggatc tttggaacgt tgctctgttc   2400
cttgttgttc attttaaagc ttttgaggga tagttgcaga actgttcggt gatgcttcat   2460
cctctcaaga actagatttg ggtaaagaaa catccatgca tggatatgga atgttgttct   2520
tccgattgga gattatttta taaaatttaa aattcatgat ttaaaaaaac acataaaaac   2580
cacaaaattc atgatttatt gacaatacga tacaaaatta gcaccaccgg ctactggctc   2640
```

```
attacacatt tcccttccc ctcattctca ctttgtggct ttattattat tattattaca    2700
tatattttac cgttattatt tcacgtcaca taagcttgtt aattaatcat tagtgagcct    2760
tctcagcctt tccgttaacg tagtagtgct gtcccacctt atcaaggtta gagaaagtag    2820
ccttccaagc accgtagtaa gagagcacct tgtagttgag tccccacttc ttagcgaaag    2880
gaacgaatct tctgctaacc tcaggctgtc tgaattgagg catatcaggg aagaggtggt    2940
ggataacctg acagttaagg tatcccataa gccagttcac gtatcctcta gaaggatcga    3000
tatcaacggt gtgatcaaca gcgtagttaa cccaagaaag gtgcttatca gatggaacaa    3060
cagggaggtg agtatgagaa gtagagaagt gagcgaaaag gtacatgtaa gcgatccagt    3120
ttccgaaagt gaaccaccag taagcaacag gccaagagta tccagtagca agcttgataa    3180
cagcggttct aacaacatga gaaacgagca tccaagaagc ctcttcgtag ttcttcttac    3240
ggagaacttg tctagggtgg agaacgtaga tccagaaagc ttgaacaaga agtccagagg    3300
taacaggaac gaaagtccaa gcttgaagtc tagcccaagc tctagagaat cctctaggtc    3360
tgttatcctc aacagcagtg ttgaagaaag ccacagcagg agtggtatca agatccatat    3420
cgtgtctaac cttttgaggg gtagcatggt gcttgttatg catctggttc cacatctcac    3480
cagaagtaga aagtccgaat ccacaagtca tagcctgaag tctcttgtcc acgtaaacag    3540
atccggtaag agagttatgt ccaccctcat gttgaaccca tccacatcta gctccgaaga    3600
aagcaccgta acaacagaa gcaatgatag ggtatccagc gtacataaga gcagttccaa    3660
gagcgaatgt agcaagaagc tcgagaagtc tgtaagccac atgggtgata aaggcttga    3720 agaatccatc tctctcaagc tcagcacgcc atctagcgaa atcctcaagc ataggagcat    3780
cctcagactc agatctcttg atctcagcag gtctagaagg caaagctcta agcatcttcc    3840
aagccttgag agaacgcatg tggaattctt tgaaagcctc agtagcatca gcaccagtgt    3900
tagcaagcat gtagaagatc acagatccac cagggtgctt gaagttagtc acatcgtact    3960
caacgtcctc aactctaacc catctagtct cgaaagtagc agcaagctca tgaggctcaa    4020
gagtcttaag atcaacagga gcagtagaag catccttagc atcaagagcc tcagcagaag    4080
atttagacct ggtaagtgga gatctaggag aagatcttcc atcagtctta ggagggcaca    4140
tggtatggta attgtaaatg taattgtaat gttgtttgtt gtttgttgtt gttggtaatt    4200
gttgtaaaat taattaagtg ggtatctttt ggatggataa gcaagtagtg atgatgttct    4260
aggtgaagtg atgggggtgt tttatagcgg gagatggtga aatggatggt cgccacataa    4320
gaaatggagg ggaagggttc ttgcgccatt cttcagtttg catggatgca tgggtttcat    4380
tttgtaacac gtaataagga caatgaagtg caggtgtctc tcaagtttca gagggatat    4440 gtggacagaa gaagaacggc gatgatattg atggaaatgg ccatctagtg tgaatctatt    4500
cggttgataa tactagtgca ttttggccgt taatcccttc aattaactgc acaaacttca    4560
gttgagtatt gattatttga ttataggttc tgtaaacaca ataccaagtt tatttagagg    4620
ggagacatac aaatagtttc gatataaata atagagtggt taaacttagt tattaaaact    4680
atatataaag tctaaaagtt aaattatttt tttaattgca aatatataaa gtctaaaggg    4740
gttacattat ttcttaagag atgtaactct gttggaatct gacttaatcc gtctcatcac    4800
tctggtttcc agttctaatc taatgaattg ttttctgcca aagaatttga agcaagaagt    4860
aaattgatca atgccgtcaa cccacaccaa accgtcaacc cactaccatc gccgcggaga    4920
cccccaaact caacctccac ccatcggtaa gaagcacagg gcagcccgca ccaccaccaa    4980
tttggcgtgc atgacaccta gggacttggc acgggaggcg gcgcacgtgg atgcaaatga    5040
```

```
cgggatatca gatgacagga aacgacgttg agagaccata cgatgtagaa tatgagctca   5100
ccatcaacga gaaactagga aaatcacaaa aaaaacaact ctcgtaattg tacgagtggc   5160
acagatgggt ctgcctcaac atatctctaa tacggcgaag cctgcccaac acgtagttgc   5220
cggaatccgg tgtggagctc acgactctga agataggcg cttcctgttt cgtttcgctc   5280
acccactgga cgtccgtcat gtgatggatt tcggtcattg gtttgctgac aaccacattc   5340
tgaagctcca tgagatgagt cttcacaata ggtcctgctc aataccgtgg agttatggtt   5400
gcaagtccat aacttgccgt tcgaatattt tgcggagcca gtcggacggg aattggcgag   5460
ctcggctgac acctataaag gccatgacaa gaagaaccaa aagttcttcc ctaatgcttt   5520
catgaggctt cgggtcgtta tggatgtcgg aaaacccctc ttgaaggaac gagacgttat   5580
tatgcatgac ggtaagacta ttacttgtca gtataagtat gaaagattac ctgtcttctg   5640
cttgtttgt ggattgattg gacacgttga aaaaaaatgt gcacttcgat ttcaatactc   5700
agagatcgac ttcccttttc tctaggagta ttcgatcaag gcattaacat ggaaggaagc   5760
tcaagctcta aaggcttcac aatggaacct gaaaaatttc aacaagccta aactgaaatc   5820
gaagtcaaat cacccaaccg ggagctctaa atcagcaaac actcctcctc cacagtatcc   5880
aatcatcgtg cacgatgctc caggtattgc aagccaggta ttgcaagcta ggagtaggat   5940
agagacctta aacgtcgttg gtgtgaagag tcatcttcag acctaatgga gatagatgta   6000
gacggcggca cgaagactct gaaacaccag aaaggctagt ccaggataag gatctgctat   6060
cccaactgac ctctcgttag tcccaaggcc tctcaactag agcaggagga aggatggtca   6120
caagactagg ataatgatgt ttccaatatg aacctgaatg tccatagcta atttttttag   6180
tcttgcttct gcacttttg tttattatgt tctggtgact atgttattta cccttgtccg   6240
tatgcttgag ggtaccctag tagattggtt ggttggtttc catgtaccag aaggcttacc   6300
ctattagttg aaagttgaaa ctttgttccc tactcaattc ctagtgtgt aaatgtatgt   6360
atatgtaatg tgtataaaac gtagtactta aatgactagg agtggttctt gagaccgatg   6420
agagatggga gcagaactaa agatgatgac ataattaaga acgaatttga aaggctctta   6480
ggtttgaatc ctattcgaga atgttttgt caaagatagt ggcgattttg aaccaaagaa   6540
aacatttaaa aaatcagtat ccggttacgt tcatgcaaat agaaagtggt ctaggatctg   6600
attgtaattt tagacttaaa gagtctctta agattcaatc ctggctgtgt acaaaactac   6660
aaataatata tttagacta tttggcctta actaaacttc cactcattat ttactgaggt   6720
tagagaatag acttgcgaat aaacacattc ccgagaaata ctcatgatcc cataattagt   6780
cagagggtat gccaatcaga tctaagaaca cacattccct caaattttaa tgcacatgta   6840
atcatagttt agcacaattc aaaaataatg tagtattaaa gacagaaatt tgtagacttt   6900
tttttggcgt taaaagaaga ctaagtttat acgtacattt tattttaagt ggaaaaccga   6960
aattttccat cgaaatatat gaattagta tatatatttc tgcaatgtac tattttgcta   7020
ttttggcaac tttcagtgga ctactacttt attacaatgt gtatggatgc atgagtttga   7080
gtatacacat gtctaaatgc atgctttgta aaacgtaacg gaccacaaaa gaggatccat   7140
acaaatacat ctcatagctt cctccattat tttccgacac aaacagagca ttttacaaca   7200
attaccaaca acaacaaaca acaaacaaca ttacaattac atttacaatt accataccat   7260
ggcctctatc gctatccctg ctgctcttgc tggaactctt ggatacgtta cctacaatgt   7320
ggctaaccct gatatcccag cttctgagaa agttcctgct tacttcatgc aggttgagta   7380
```

```
ctggggacct actatcggaa ctattggata cctcctcttc atctacttcg gaaagcgtat    7440
catgcagaac agatctcaac ctttcggact caagaacgct atgctcgttt acaacttcta    7500
ccagaccttc ttcaacagct actgcatcta ccttttcgtt acttctcata gggctcaggg    7560
acttaaggtt tggggaaaca tccctgatat gactgctaac tcttgggaa  tctctcaggt    7620
tatctggctt cactacaaca acaagtacgt tgagcttctc gacaccttct tcatggtgat    7680
gaggaagaag ttcgaccagc tttctttcct tcacatctac caccacactc ttctcatctg    7740
gtcatggttc gttgttatga agcttgagcc tgttggagat tgctacttcg gatcttctgt    7800
taacaccttc gtgcacgtga tcatgtactc ttactacgga cttgctgctc ttggagttaa    7860
ctgtttctgg aagaagtaca tcacccagat ccagatgctt cagttctgta tctgtgcttc    7920
tcactctatc tacaccgctt acgttcagaa taccgctttc tggcttcctt accttcaact    7980
ctgggttatg gtgaacatgt tcgttctctt cgccaacttc taccgtaaga ggtacaagtc    8040
taagggtgct aagaagcagt gataaggcgc gcggcgcgcc gggccgccgc catgtgacag    8100
atcgaaggaa gaaagtgtaa taagacgact ctcactactc gatcgctagt gattgtcatt    8160
gttatatata ataatgttat cttttcacaac ttatcgtaat gcatgtgaaa ctataacaca    8220
ttaatcctac ttgtcatatg ataacactct ccccatttaa aactcttgtc aatttaaaga    8280
tataagattc tttaaatgat taaaaaaaat atattataaa ttcaatcact cctactaata    8340
aattattaat tattatttat tgattaaaaa aatacttata ctaatttagt ctgaatagaa    8400
taattagatt ctagtctcat ccccttttaa accaacttag taaacgtttt ttttttttaat    8460
tttatgaagt taagttttta ccttgttttt aaaaagaatc gttcataaga tgccatgcca    8520
gaacattagc tacacgttac acatagcatg cagccgcgga gaattgtttt tcttcgccac    8580
ttgtcactcc cttcaaacac ctaagagctt ctctctcaca gcacacacat acaatcacat    8640
gcgtgcatgc attattacac gtgatcgcca tgcaaatctc ctttatagcc tataaattaa    8700
ctcatccgct tcactcttta ctcaaaccaa aactcatcga tacaaacaag attaaaaaca    8760
tacacgagga tcttttacaa caattaccaa caacaacaaa caacaaacaa cattacaatt    8820
acatttacaa ttaccatacc atgcctccaa gggactctta ctcttatgct gctcctcctt    8880
ctgctcaact tcacgaagtt gatactcctc aagagcacga caagaaagag cttgttatcg    8940
gagatagggc ttcgatgtt  accaacttcg ttaagagaca ccctggtgga aagatcattg    9000
cttaccaagt tggaactgat gctaccgatg cttacaagca gttccatgtt agatctgcta    9060
aggctgacaa gatgcttaag tctcttcctt ctcgtcctgt tcacaaggga tactctccaa    9120
gaagggctga tcttatcgct gatttccaag agttcaccaa gcaacttgag gctgagggaa    9180
tgttcgagcc ttctcttcct catgttgctt acagacttgc tgaggttatc gctatgcatg    9240
ttgctggtgc tgctcttatc tggcatggat acactttcgc tggaatcgct atgcttggag    9300
ttgttcaggg aagatgtgga tggccttatgc atgagggtgg acattactct ctcactggaa    9360
acattgcttt cgacagagct atccaagttg cttgttacgg acttggatgt ggaatgtctg    9420
gtgcttggtg gcgtaaccag cataacaagc accatgctac tcctcaaaag cttcagcacg    9480
atgttgatct tgataccctt cctctccgttg ctttccatga gagaatcgct gctaaggtta    9540
agtctcctgc tatgaaggct tggctttcta tgcaagctaa gcttttcgct cctgttacca    9600
ctcttctttgt tgctcttgga tggcagcttt accttcatcc tagacacatg ctcaggacta    9660
agcactacga tgagcttgct atgctcggaa tcagatacgg acttgttgga taccttgctg    9720
ctaactacgg tgctggatac gttctcgctt gttaccttct ttacgttcag cttggagcta    9780
```

-continued

```
tgtacatctt ctgcaacttc gctgtttctc atactcacct ccctgttgtt gagcctaacg   9840
agcatgctac ttgggttgag tacgctgcta accacactac taactgttct ccatcttggt   9900
ggtgtgattg gtggatgtct taccttaact accagatcga gcaccacctt tacccttcta   9960
tgcctcaatt cagacaccct aagatcgctc ctagagttaa gcagcttttc gagaagcacg  10020
gacttcacta cgatgttaga ggatacttcg aggctatggc tgatactttc gctaaccttg  10080
ataacgttgc ccatgctcct gagaagaaaa tgcagtaatg agatcgttca aactttggc   10140 aataaagttt cttaagattg aatcctgttg ccggtcttgc gatgattatc ataatttc    10200 tgttgaatta cgttaagcac gtaataatta acatgtaatg catgacgtta tttatgagat  10260 gggttttat gattagagtc ccgcaattat acatttaata cgcgatagaa acaaaatat    10320 agcgcgcaaa ctaggataaa ttatcgcgcg cggtgtcatc tatgttacta gatcggtcga  10380
ttaaaaatcc caattatatt tggtctaatt tagtttggta ttgagtaaaa caaattcgaa  10440
ccaaaccaaa atataaatat atagtttta tatatatgcc tttaagactt tttatagaat   10500 tttcttaaa aaatatctag aaatatttgc gactcttctg gcatgtaata tttcgttaaa   10560
tatgaagtgc tccattttta ttaactttaa ataattggtt gtacgatcac tttcttatca  10620
agtgttacta aaatgcgtca atctctttgt tcttccatat tcatatgtca aaatctatca  10680
aaattcttat atatcttttt cgaatttgaa gtgaaatttc gataatttaa aattaaatag  10740
aacatatcat tatttaggta tcatattgat ttttatactt aattactaaa tttggttaac  10800
tttgaaagtg tacatcaacg aaaaattagt caaacgacta aaataaataa atatcatgtg  10860
ttattaagaa aattctccta taagaatatt ttaatagatc atatgtttgt aaaaaaaatt  10920
aatttttact aacacatata tttacttatc aaaaatttga caaagtaaga ttaaaataat  10980
attcatctaa caaaaaaaaa accagaaaat gctgaaaacc cggcaaaacc gaaccaatcc  11040
aaaccgatat agttggtttg gtttgatttt gatataaacc gaaccaactc ggtccatttg  11100 caccctaat cataatagct ttaatatttc aagatattat taagttaacg ttgtcaatat   11160
cctggaaatt ttgcaaaatg aatcaagcct atatggctgt aatatgaatt taaaagcagc  11220
tcgatgtggt ggtaatatgt aatttacttg attctaaaaa aatatcccaa gtattaataa  11280
tttctgctag gaagaaggtt agctacgatt tacagcaaag ccagaataca aagaaccata  11340
aagtgattga agctcgaaat atacgaagga acaaatattt ttaaaaaaat acgcaatgac  11400
ttggaacaaa agaaagtgat atattttttg ttcttaaaca agcatcccct ctaaagaatg  11460
gcagttttcc tttgcatgta actattatgc tcccttcgtt acaaaaattt tggactacta  11520
ttgggaactt cttctgaaaa tagtgataga acccacacga gcatgtgctt tccatttaat  11580
tttaaaaacc aagaaacata catacataac attccatcag cctctctctc tttttattac  11640
ggttaatgac ttaaaacaca tcttattatc ccatccttaa cacctagcag tgtctttata  11700
cgatctcatc gatcaccact tcaaaaccat gcagactgct gctgcccctg gagctggcat  11760
cggctaggct gggtgccgca ctgtcccgga aggtccctag cgacttgttt agattgatgg  11820
gaccacctct caacttcctg ctgctgtccc tgctgctgga tgtcctgcct catctggccg  11880
attgcacgct ccagtcccct gcatgtgcac tcgctcctca attgcttaag atcatcgcag  11940
cagctatcga agtgctggct ctgttgccct cctccacggc cttggttgta gtagtagctg  12000
ccgccgccct tctggacttt ttcccacagg aaccgccgaa taattcgata gaaccacacg  12060
agcatgtgct ttcattatt ttaaaaacca agaaacatac ataacatttc atcagcctct   12120
```

```
ctctctctct ctctctctct ctctctctct ctctctctct ctctctcttt attacagctg    12180
ttacactaac ttaaaacaca ttcatctcat tattattatt attatccatc cttaacacct    12240
agcagtgtct ttgtacgatc tcataatcga tcaccccttc atcaggtatc cttaggcttc    12300
actccaacgt tgttgcagtt acggaacatg tacacaccat catggttctc aacgaactgg    12360
caagatctcc aagttttcca aaggctaacc cacatgttct catcggtgtg tctgtagtgc    12420
tctcccataa ctttcttgat gcactcggta gcttctctag catggtagaa tgggatcctt    12480
gaaacgtagt gatggagcac atgagtctcg atgatgtcat ggaagatgat tccgaggatt    12540
ccgaactctc tatcgatagt agcagcagca cccttagcga aagtccactc ttgagcatcg    12600
taatgaggca tagaagaatc ggtgtgctga aggaaggtaa cgaaaacaag ccagtggtta    12660
acaaggatcc aaggacagaa ccatgtgatg aaagtaggcc agaatccgaa aaccttgtaa    12720
gcggtgtaaa cagaagtgag ggtagcaagg attccaagat cagaaagaac gatgtaccag    12780
tagtccttct tatcgaaaac agggctagaa ggccagtagt gagacttgaa gaacttagaa    12840
acaccagggt aaggttgtcc agtagcgtta gtagcaaggt aaagagaaag tcctccaagc    12900
tgttggaaca agagagcgaa aacagagtag ataggagttt cctcagcgat atcgtgaagg    12960
ctggtaactt ggtgcttctc tttgaattcc tcggcggtgt aaggaacgaa aaccatatct    13020
ctggtcatgt gtccagtagc cttatggtgc ttagcatgag agaacttcca gctgaagtaa    13080
ggaaccataa caagagagtg gagaacccat ccaacgtat cgttaaccca tccgtagtta    13140
gagaaagcag aatgtccaca ctcatgtcca aggatccaga ttccgaatcc gaaacaagag    13200
atagagaaca cgtaagcaga ccaagcagcg aatctaagga attcgttagg gagaagaggg    13260
atgtaggtaa gtccaacgta agcgatagca gagatagcca cgatatctct caccacgtaa    13320
gacatagact tcacgagaga tctctcgtaa cagtgcttag ggatagcgtc aaggatatcc    13380
ttgatggtgt aatctggcac cttgaaaacg tttccgaagg tatcgatagc ggtcttttgc    13440
tgcttgaaag atgcaacgtt tccagaacgc ctaacggtct tagtagatcc ctcaaggatc    13500
tcagatccag acacggtaac cttagacatg gtatggtaat tgtaaatgta attgtaatgt    13560
tgtttgttgt ttgttgttgt tggtaattgt tgtaaaattt tggtggtga ttggttcttt    13620 aaggtgtgag agtgagttgt gagttgtgtg gtgggtttgg tgagattggg gatggtgggt    13680
ttatatagtg gagactgagg aatggggtcg tgagtgttaa cttgtcatgg gctacacgtg    13740 ggttctttg ggcttacacg tagtattatt catgcaaatg cagccaatac atatacggta    13800
ttttaataat gtgtgggaat acaatatgcc gagtatttta ctaatttgg caatgacaag    13860 tgtacatttg gattatctta cttggcctct cttgctttaa tttggattat ttttattctc    13920
ttaccttggc cgttcatatt cacatcccta aaggcaagac agaattgaat ggtggccaaa    13980
aattaaaacg atggatatga cctacatagt gtaggatcaa ttaacgtcga aggaaaatac    14040
tgattctgcc cgttcgactc agatcttcca aggcctcgtc tccgagtccg ctgcttctcg    14100
ccgcgccgat cacttctccg ccgccaacaa ggcttgtagt aataggaat cattcaggga    14160 ttgtgattcc gggcagtagt aattaataat atagtattag tatacagaac ctcttattta    14220
gctaaaagat tatgttctta atgttgataa gaagtttgag aaacaaatat aattgagctt    14280
ctgattagtt gatcgtaatt ggtcattaat aattgtatct aaccagtgca gtataagagc    14340
gtataagagc atcttcaaaa agactttatt ttagagttaa tcagtgcagt ataagagcat    14400
ctctaaaaaa actctaatta tagagttttg caaactctat atttgaagtt ttaaggtgtt    14460 ttttttttcaa aagcaaaact tcaaatttaa cttcaaaatt atttgtaatt tacactatgc    14520
```

```
tctttatatt tatcataatt aatataaggg ggtgttagtg ggacttagat ttctatagag    14580
tttgttgatt ttaaaagttg agagatttgt taaatttaga aagagatgta gagaattttg    14640
tctattgtga aaatctatga aaatagagta atgtaatgat tctaagaatt caaagtaaac    14700
atgtagtatt ctcaaaatct aaatttgtga aacagtggtc ccagatttc aagactcaga    14760 ctaaaggcta tggaggaagc tagggttttg gcgattggcg acactagggt ttcgagtacg    14820
gcagatttgg atgaaactat gatggatgtg ggggagagag ggagaccgcc aggagatccg    14880
ccagataagt taacctcatg ggtagcgaag gtggtggaga cggctgaggg agggatgcca    14940
gtaccggagg ttttgattgc agattctttt gtgtcggaga gggtacgggt agaatttccg    15000
aatg                                                                15004

<210> SEQ ID NO 41
<211> LENGTH: 49789
<212> TYPE: DNA
<213> ORGANISM: Artificial Sequence
<220> FEATURE:
<223> OTHER INFORMATION: Chimeric 16 transgene inserted into Brassica

<400> SEQUENCE: 41
aaaaaataca accaaagaaa aatataccag aaggttgtga tttggtccat tatataaaaa      60
ttacgaaatg aatttcttta tcctttttatc tcaaatttta ttgaagactt ttgtaggatt    120
atagttgact ttatgctcac atatatatac actgatcaaa acttttttaaa aacataaaga    180 aattgtgaaa caataaaaat aaaatgaaat gagtaattaa tgagtagatt aagacattgg    240
accctccaca ggcgataaag taaaataatc agaagttgca ggaggcaaag gaggactact    300
actaatactt ggaacttgga agtagctatc gtgcgcatct gcctccaagt ccaacaccct    360
ataacaaatt tccgccggga agaagaaaaa gtctctctgc cctctcttct ttagcctcca    420
gcttctgcaa accatacgta caaacaagat agacacaatc ctccctacct ccttcttcta    480
tcttcatcga aagattcaac caccactcaa gtcttctctc tcttttttgg aaagaaaaaa    540
ggtaaaagct ttcttcttc tgagcaaact cccatgaatt tccctttgg gggtttaggg     600 tctttccttt tatgttccta cttcggtata attcgatttc atgcgaactt agattataaa    660
aatttgatct tttttttgtg gggtttgaaa ttgaaatcca ttttaggggt taccatcgtt    720
gaccaaatgt ctcgactttg ttcgaatcat gatgttactt aatcatggag gagaagaagg    780
atttttataa ccatgtctct gttgcttgct gcttaaaccc tatataattg gaaactttt    840 gttttagtct gtgtctgaaa gtttctatat tcgtattgtc tattttgtaa agactaaaac    900
aaaaatgcct attttagtt tgttcttgtt ccgcaacacc gttactgaac tcttcgttca    960
cttaaacagt ttgtgtgtgt gagaaacagc gtaatgagct gctttggttg ttgtggtggt   1020
gacgattttc gtcgagttgc tgaaactgga cccaagccag tgtacggcgc aggaggtact   1080
ttaagcttat aacccttgt ctatccttg gctagcggct aatgttgatg aactttttta    1140
ttcaaccgtt ggctaaggta acactgatag tttaaactga aggcgggaaa cgacaatctg   1200
ctagtggatc tcccagtcac gacgttgtaa aacgggcgcc ccgcggaaag cttgcggccg   1260
cggtaccgcc cgttcgactc agatcttcca aggcctcgtc tccgagtccg ctgcttctcg   1320
ccgcgccgat cacttctccg ccgccaacaa ggcttgtagt taataggaat cattcaggga   1380
ttgtgattcc gggcagtagt aattaataat atagtattag tatagataat atgtttcgtt   1440
tgggatcttt ggaacgttgc tctgttcctt gttgttcatt ttaaagcttt tgagggatag   1500
```

```
ttgcagaact gttcggtgat gcttcatcct ctcaagaact agatttgggt aaagaaacat    1560
ccatgcatgg atatggaatg ttgttcttcc gattggagat tattttataa aatttaaaat    1620
tcatgattta aaaaacaca taaaaaccac aaaattcatg atttattgac aatacgatac     1680
aaaattagca ccaccggcta ctggctcatt acacatttcc ccttcccctc attctcactt    1740
tgtggcttta ttattattat tattacatat attttaccgt tattatttca cgtcacataa    1800
gcttgttaat taatcattag tgagccttct cagccttttcc gttaacgtag tagtgctgtc   1860
ccaccttatc aaggttagag aaagtagcct tccaagcacc gtagtaagag agcaccttgt    1920
agttgagtcc ccacttctta gcgaaaggaa cgaatcttct gctaacctca ggctgtctga    1980
attgaggcat atcagggaag aggtggtgga taacctgaca gttaaggtat cccataagcc    2040
agttcacgta tcctctagaa ggatcgatat caacggtgtg atcaacagcg tagttaaccc    2100
aagaaaggtg cttatcagat ggaacaacag ggaggtgagt atgagaagta gagaagtgag    2160
cgaaaaggta catgtaagcg atccagtttc cgaaagtgaa ccaccagtaa gcaacaggcc    2220
aagagtatcc agtagcaagc ttgataacag cggttctaac aacatgagaa cgagcatcc    2280 aagaagcctc ttcgtagttc ttcttacgga gaacttgtct agggtggaga acgtagatcc    2340
agaaagcttg aacaagaagt ccagaggtaa caggaacgaa agtccaagct tgaagtctag    2400
cccaagctct agagaatcct ctaggtctgt tatcctcaac agcagtgttg aagaaagcca    2460
cagcaggagt ggtatcaaga tccatatcgt gtctaacctt ttgagggggta gcatggtgct    2520 tgttatgcat ctggttccac atctcaccag aagtagaaag tccgaatcca caagtcatag    2580
cctgaagtct cttgtccacg taaacagatc cggtaagaga gttatgtcca ccctcatgtt    2640
gaacccatcc acatctagct ccgaagaaag caccgtaaac aacagaagca atgatagggt    2700
atccagcgta cataagagca gttccaagag cgaatgtagc aagaagctcg agaagtctgt    2760
aagccacatg ggtgatagaa ggcttgaaga atccatctct ctcaagctca gcacgccatc    2820
tagcgaaatc ctcaagcata ggagcatcct cagactcaga tctcttgatc tcagcaggtc    2880
tagaaggcaa agctctaagc atcttccaag ccttgagaga acgcatgtgg aattctttga    2940
aagcctcagt agcatcagca ccagtgttag caagcatgta gaagatcaca gatccaccag    3000
ggtgcttgaa gttagtcaca tcgtactcaa cgtcctcaac tctaacccat ctagtctcga    3060
aagtagcagc aagctcatga ggctcaagag tcttaagatc aacaggagca gtagaagcat    3120
ccttagcatc aagagcctca gcagaagatt tagacctggt aagtggagat ctaggagaag    3180
atcttccatc agtcttagga gggcacatgg tatggtaatt gtaaatgtaa ttgtaatgtt    3240
gtttgttgtt tgttgttgtt ggtaattgtt gtaaaattaa ttaagtgggt atcttttgga    3300
tggataagca agtagtgatg atgttctagg tgaagtgatg ggggtgtttt atagcgggag    3360
atggtgaaat ggatggtcgc cacataagaa atggagggga agggttcttg cgccattctt    3420
cagtttgcat ggatgcatgg gtttcatttt gtaacacgta ataaggacaa tgaagtgcag    3480
gtgtctctca gtttcagag gggatatgtg gacagaagaa gaacggcgat gatattgatg     3540
gaaatggcca tctagtgtga atctattcgg ttgataatac tagtgcattt tggccgttaa    3600
tcccttcaat taactgcaca aacttcagtt gagtattgat tatttgatta taggttctgt    3660
aaacacaata ccaagtttat ttagagggga gacatacaaa tagtttcgat ataaataata    3720
gagtggttaa acttagttat taaaactata tataaagtct aaaagttaaa ttatttttt    3780 aattgcaaat atataaagtc taaggggtt acattatttc ttaagagatg taactctgtt    3840
ggaatctgac ttaatccgtc tcatcactct ggtttccagt tctaatctaa tgaattgttt    3900
```

```
tctgccaaag aatttgaagc aagaagtaaa ttgatcaatg ccgtcaaccc acaccaaacc    3960
gtcaacccac taccatcgcc gcggagaccc ccaaactcaa cctccaccca tcggtaagaa    4020
gcacagggca gcccgcacca ccaccaattt ggcgtgcatg acacctaggg acttggcacg    4080
ggaggcggcg cacgtggatg caaatgacgg gatatcagat gacaggaaac gacgttgaga    4140
gaccatacga tgtagaatat gagctcacca tcaacgagaa actaggaaaa tcacaaaaaa    4200
aacaactctc gtaattgtac gagtggcaca gatgggtctg cctcaacata tctctaatac    4260
ggcgaagcct gcccaacacg tagttgccgg aatccggtgt ggagctcacg actctgaaag    4320
ataggcgctt cctgtttcgt ttcgctcacc cactggacgt ccgtcatgtg atggatttcg    4380
gtcattggtt tgctgacaac cacattctga agctccatga atgagtctt cacaataggt    4440 cctgctcaat accgtggagt tatggttgca agtccataac ttgccgttcg aatattttgc    4500
ggagccagtc ggacgggaat tggcgagctc ggctgacacc tataaaggcc atgacaagaa    4560
gaaccaaaag ttcttcccta atgctttcat gaggcttcgg gtcgttatgg atgtcggaaa    4620 accctcttg aaggaacgag acgttattat gcatgacggt aagactatta cttgtcagta    4680
taagtatgaa agattacctg tcttctgctt tgtttgtgga ttgattggac acgttgaaaa    4740
aaaatgtgca cttcgatttc aatactcaga gatcgacttc ccttttctct aggagtattc    4800
gatcaaggca ttaacatgga aggaagctca agctctaaag gcttacaat ggaacctgaa    4860 aaatttcaac aagcctaaac tgaaatcgaa gtcaaatcac ccaaccggga gctctaaatc    4920
agcaaacact cctcctccac agtatccaat catcgtgcac gatgctccag gtattgcaag    4980
ccaggtattg caagctagga gtaggataga gaccttaaac gtcgttggtg tgaagagtca    5040
tcttcagacc taatggagat agatgtagac ggcggcacga agactctgaa acaccagaaa    5100
ggctagtcca ggataaggat ctgctatccc aactgacctc tcgttagtcc caaggcctct    5160
caactagagc aggaggaagg atggtcacaa gactaggata atgatgtttc caatatgaac    5220
ctgaatgtcc atagctaatt tttttagtct tgcttctgca cttttttgttt attatgttct    5280 ggtgactatg ttatttaccc ttgtccgtat gcttgagggt accctagtag attggttggt    5340
tggtttccat gtaccagaag gcttacccta ttagttgaaa gttgaaactt tgttccctac    5400
tcaattccta gttgtgtaaa tgtatgtata tgtaatgtgt ataaaacgta gtacttaaat    5460
gactaggagt ggttcttgag accgatgaga gatgggagca gaactaaaga tgatgacata    5520
attaagaacg aatttgaaag gctcttaggt ttgaatccta ttcgagaatg tttttgtcaa    5580
agatagtggc gattttgaac caaagaaaac atttaaaaaa tcagtatccg gttacgttca    5640
tgcaaataga aagtggtcta ggatctgatt gtaattttag acttaaagag tctcttaaga    5700
ttcaatcctg gctgtgtaca aaactacaaa taatatattt tagactattt ggccttaact    5760
aaacttccac tcattattta ctgaggttag agaatagact tgcgaataaa cacattcccg    5820
agaaatactc atgatcccat aattagtcag agggtatgcc aatcagatct aagaacacac    5880
attccctcaa attttaatgc acatgtaatc atagtttagc acaattcaaa ataatgtag    5940 tattaaagac agaaatttgt agactttttt ttggcgttaa aagaagacta agtttatacg    6000
tacattttat tttaagtgga aaaccgaaat tttccatcga aatatatgaa tttagtatat    6060
atatttctgc aatgtactat tttgctattt tggcaacttt cagtggacta ctactttatt    6120
acaatgtgta tggatgcatg agtttgagta tacacatgtc taaatgcatg ctttgtaaaa    6180
cgtaacggac cacaaaagag gatccataca aatacatctc atagcttcct ccattatttt    6240
```

```
ccgacacaaa cagagcattt tacaacaatt accaacaaca acaaacaaca aacaacatta   6300
caattacatt tacaattacc ataccatggc ctctatcgct atccctgctg ctcttgctgg   6360
aactcttgga tacgttacct acaatgtggc taaccctgat atcccagctt ctgagaaagt   6420
tcctgcttac ttcatgcagg ttgagtactg gggacctact atcggaacta ttggatacct   6480
cctcttcatc tacttcggaa agcgtatcat gcagaacaga tctcaacctt tcggactcaa   6540
gaacgctatg ctcgtttaca acttctacca gaccttcttc aacagctact gcatctacct   6600
tttcgttact tctcataggg ctcagggact taaggtttgg ggaaacatcc ctgatatgac   6660
tgctaactct tggggaatct ctcaggttat ctggcttcac tacaacaaca agtacgttga   6720
gcttctcgac accttcttca tggtgatgag gaagaagttc gaccagcttt ctttccttca   6780
catctaccac cacactcttc tcatctggtc atggttcgtt gttatgaagc ttgagcctgt   6840
tggagattgc tacttcggat cttctgttaa caccttcgtg cacgtgatca tgtactctta   6900
ctacggactt gctgctcttg gagttaactg tttctggaag aagtacatca cccagatcca   6960
gatgcttcag ttctgtatct gtgcttctca ctctatctac accgcttacg ttcagaatac   7020
cgctttctgg cttccttacc ttcaactctg ggttatggtg aacatgttcg ttctcttcgc   7080
caacttctac cgtaagaggt acaagtctaa gggtgctaag aagcagtgat aaggcgcgcg   7140
gcgcgccggg ccgccgccat gtgacagatc gaaggaagaa agtgtaataa gacgactctc   7200
actactcgat cgctagtgat tgtcattgtt atatataata atgttatctt tcacaactta   7260
tcgtaatgca tgtgaaacta taacacatta atcctacttg tcatatgata acactctccc   7320
catttaaaac tcttgtcaat ttaaagatat aagattcttt aaatgattaa aaaaaatata   7380
ttataaattc aatcactcct actaataaat tattaattat tatttattga ttaaaaaaat   7440
acttatacta atttagtctg aatagaataa ttagattcta gtctcatccc cttttaaacc   7500
aacttagtaa acgttttttt ttttaatttt atgaagttaa gttttttacct tgttttttaaa   7560
aagaatcgtt cataagatgc catgccagaa cattagctac acgttacaca tagcatgcag   7620
ccgcggagaa ttgttttttct tcgccacttg tcactcccctt caaacaccta agagcttctc   7680
tctcacagca cacacataca atcacatgcg tgcatgcatt attacacgtg atcgccatgc   7740
aaatctcctt tatagcctat aaattaactc atccgcttca ctctttactc aaaccaaaac   7800
tcatcgatac aaaacaagatt aaaaacatac acgaggatct tttacaacaa ttaccaacaa   7860
caacaaacaa caaacaacat tacaattaca tttacaatta ccataccatg cctccaaggg   7920
actcttactc ttatgctgct cctccttctg ctcaacttca cgaagttgat actcctcaag   7980
agcacgacaa gaaagagctt gttatcggag atagggctta cgatgttacc aacttcgtta   8040
agagacaccc tggtggaaag atcattgctt accaagttgg aactgatgct accgatgctt   8100
acaagcagtt ccatgttaga tctgctaagg ctgacaagat gcttaagtct cttccttctc   8160
gtcctgttca aagggatac tctccaagaa gggctgatct tatcgctgat ttccaagagt   8220
tcaccaagca acttgaggct gagggaatgt tcgagccttc tcttcctcat gttgcttaca   8280
gacttgctga ggttatcgct atgcatgttg ctggtgctgc tcttatctgg catggataca   8340
ctttcgctgg aatcgctatg cttggagttg ttcagggaag atgtggatgg cttatgcatg   8400
agggtggaca ttactctctc actggaaaca ttgctttcga cagagctatc caagttgctt   8460
gttacggact tggatgtgga atgtctggtg cttggtggcg taaccagcat aacaagcacc   8520
atgctactcc tcaaaagctt cagcacgatg ttgatcttga tacccttcct ctcgttgctt   8580
tccatgagag aatcgctgct aaggttaagt ctcctgctat gaaggcttgg ctttctatgc   8640
```

```
aagctaagct tttcgctcct gttaccactc ttcttgttgc tcttggatgg cagctttacc    8700
ttcatcctag acacatgctc aggactaagc actacgatga gcttgctatg ctcggaatca    8760
gatacggact tgttggatac cttgctgcta actacggtgc tggatacgtt ctcgcttgtt    8820
accttcttta cgttcagctt ggagctatgt acatcttctg caacttcgct gtttctcata    8880
ctcacctccc tgttgttgag cctaacgagc atgctacttg ggttgagtac gctgctaacc    8940
acactactaa ctgttctcca tcttggtggt gtgattggtg gatgtcttac cttaactacc    9000
agatcgagca ccacctttac ccttctatgc ctcaattcag acaccctaag atcgctccta    9060
gagttaagca gcttttcgag aagcacggac ttcactacga tgttagagga tacttcgagg    9120
ctatggctga tactttcgct aaccttgata cgttgccca tgctcctgag aagaaaatgc    9180
agtaatgaga tcgttcaaac atttggcaat aaagtttctt aagattgaat cctgttgccg    9240
gtcttgcgat gattatcata taatttctgt tgaattacgt taagcacgta ataattaaca    9300
tgtaatgcat gacgttattt atgagatggg ttttatgat tagagtcccg caattataca     9360
tttaatacgc gatagaaaac aaaatatagc gcgcaaacta ggataaatta tcgcgcgcgg    9420
tgtcatctat gttactagat cggtcgatta aaaatcccaa ttatatttgg tctaatttag    9480
tttggtattg agtaaaacaa attcgaacca aaccaaaata taaatatata gttttatat     9540 atatgccttt aagactttt atagaattt ctttaaaaaa tatctagaaa tatttgcgac     9600
tcttctggca tgtaatattt cgttaaatat gaagtgctcc atttttatta actttaaata    9660
attggttgta cgatcacttt cttatcaagt gttactaaaa tgcgtcaatc tctttgttct    9720
tccatattca tatgtcaaaa tctatcaaaa ttcttatata tcttttcga atttgaagtg     9780 aaatttcgat aatttaaaat taaatagaac atatcattat ttaggtatca tattgatttt    9840
tatacttaat tactaaattt ggttaacttt gaaagtgtac atcaacgaaa aattagtcaa    9900
acgactaaaa taaataaata tcatgtgtta ttaagaaaat tctcctataa gaatatttta    9960
atagatcata tgtttgtaaa aaaaattaat ttttactaac acatatattt acttatcaaa   10020
aatttgacaa agtaagatta aaataatatt catctaacaa aaaaaaaacc agaaaatgct   10080
gaaaacccgg caaaaccgaa ccaatccaaa ccgatatagt tggtttggtt tgattttgat   10140
ataaaccgaa ccaactcggt ccatttgcac ccctaatcat aatagcttta atatttcaag   10200
atattattaa gttaacgttg tcaatatcct ggaaattttg caaatgaat caagcctata    10260 tggctgtaat atgaatttaa aagcagctcg atgtggtggt aatatgtaat ttacttgatt   10320
ctaaaaaaat atcccaagta ttaataattt ctgctaggaa gaaggttagc tacgatttac   10380
agcaaagcca gaatacaaag aaccataaag tgattgaagc tcgaaatata cgaaggaaca   10440
aatattttta aaaaaatacg caatgacttg gaacaaaaga aagtgatata ttttttgttc   10500
ttaaacaagc atcccctcta agaatggca gttttccttt gcatgtaact attatgctcc    10560
cttcgttaca aaaattttgg actactattg ggaacttctt ctgaaaatag tgatagaacc   10620
cacacgagca tgtgctttcc atttaatttt aaaaaccaag aaacatacat acataacatt   10680
ccatcagcct ctctctcttt ttattacggt taatgactta aaacacatct tattatccca   10740
tccttaacac ctagcagtgt ctttatacga tctcatcgat caccacttca aaaccatgca   10800
gactgctgct gcccctggag ctggcatcgg ctaggctggg tgccgcactg tcccggaagg   10860
tccctagcga cttgtttaga ttgatgggac cacctctcaa cttcctgctg ctgtccctgc   10920
tgctggatgt cctgcctcat ctggccgatt gcacgctcca gtcccctgca tgtgcactcg   10980
```

```
ctcctcaatt gcttaagatc atcgcagcag ctatcgaagt gctggctctg ttgccctcct    11040
ccacggcctt ggttgtagta gtagctgccg ccgcccttct ggactttttc ccacaggaac    11100
cgccgaataa ttcgatagaa ccacacgagc atgtgctttc atttatttta aaaaccaaga    11160
aacatacata acatttcatc agcctctctc tctctctctc tctctctctc tctctctctc    11220
tctctctctc tctctttatt acagctgtta cactaactta aaacacattc atctcattat    11280
tattattatt atccatcctt aacacctagc agtgtctttg tacgatctca taatcgatca    11340
cccctttcatc aggtatcctt aggcttcact ccaacgttgt tgcagttacg aacatgtac    11400
```
(partial — see below)

```
ctcctcaatt gcttaagatc atcgcagcag ctatcgaagt gctggctctg ttgccctcct    11040
ccacggcctt ggttgtagta gtagctgccg ccgcccttct ggactttttc ccacaggaac    11100
cgccgaataa ttcgatagaa ccacacgagc atgtgctttc atttatttta aaaaccaaga    11160
aacatacata acatttcatc agcctctctc tctctctctc tctctctctc tctctctctc    11220
tctctctctc tctctttatt acagctgtta cactaactta aaacacattc atctcattat    11280
tattattatt atccatcctt aacacctagc agtgtctttg tacgatctca taatcgatca    11340
cccttcatc aggtatcctt aggcttcact ccaacgttgt tgcagttacg aacatgtac     11400
acaccatcat ggttctcaac gaactggcaa gatctccaag ttttccaaag gctaacccac   11460
atgttctcat cggtgtgtct gtagtgctct cccataactt tcttgatgca ctcggtagct   11520
tctctagcat ggtagaatgg gatccttgaa acgtagtgat ggagcacatg agtctcgatg   11580
atgtcatgga agatgattcc gaggattccg aactctctat cgatagtagc agcagcaccc   11640
ttagcgaaag tccactcttg agcatcgtaa tgaggcatag aagaatcggt gtgctgaagg   11700
aaggtaacga aaacaagcca gtggttaaca aggatccaag gacagaacca tgtgatgaaa   11760
gtaggccaga atccgaaaac cttgtaagcg gtgtaaacag aagtgagggt agcaaggatt   11820
ccaagatcag aaagaacgat gtaccagtag tccttcttat cgaaacagg gctagaaggc   11880
cagtagtgag acttgaagaa cttagaaaca ccagggtaag gttgtccagt agcgttagta   11940
gcaaggtaaa gagaaagtcc tccaagctgt tggaacaaga gagcgaaaac agagtagata   12000
ggagtttcct cagcgatatc gtgaaggctg gtaacttggt gcttctcttt gaattcctcg   12060
gcggtgtaag gaacgaaaac catatctctg gtcatgtgtc cagtagcctt atggtgctta   12120
gcatgagaga acttccagct gaagtaagga accataacaa gagagtggag aacccatcca   12180
acggtatcgt taacccatcc gtagttagag aaagcagaat gtccacactc atgtccaagg   12240
atccagattc cgaatccgaa acaagagata gagaacacgt aagcagacca agcagcgaat   12300
ctaaggaatt cgttagggag aagagggatg taggtaagtc caacgtaagc gatagcagag   12360
atagccacga tatctctcac cacgtaagac atagacttca cgagagatct ctcgtaacag   12420
tgcttaggga tagcgtcaag gatatccttg atggtgtaat ctggcacctt gaaaacgttt   12480
ccgaaggtat cgatagcggt cttttgctgc ttgaaagatg caacgtttcc agaacgccta   12540
acggtcttag tagatccctc aaggatctca gatccagaca cggtaacctt agacatggta   12600
tggtaattgt aaatgtaatt gtaatgttgt ttgttgtttg ttgttgtttg taattgttgt   12660
aaaattttttg gtggtgattg gttctttaag gtgtgagagt gagttgtgag ttgtgtggtg   12720
ggtttggtga gattggggat ggtgggttta tatagtggag actgaggaat ggggtcgtga   12780
gtgttaactt tgcatgggct acacgtgggt tcttttgggc ttacacgtag tattattcat   12840
gcaaatgcag ccaatacata tacggtattt taataatgtg tgggaataca atatgccgag   12900
tattttacta attttggcaa tgacaagtgt acatttggat tatcttactt ggcctctctt   12960
gctttaattt ggattatttt tattctctta ccttggccgt tcatattcac atccctaaag   13020
gcaagacaga attgaatggt ggccaaaaat taaaacgatg gatatgacct acatagtgta   13080
ggatcaatta acgtcgaagg aaaatactga ttctctcaag catacggaca agggtaaata   13140
acatagtcac cagaacataa taaacaaaaa gtgcagaagc aagactaaaa aaattagcta   13200
tggacattca ggttcatatt ggaaacatca ttatcctagt cttgtgacca tccttcctcc   13260
tgctctagtt gagaggcctt gggactaacg agaggtcagt tgggatagca gatccttatc   13320
ctggactagc ctttctggtg tttcagagtc ttcgtgccgc cgtctacatc tatctccatt   13380
```

```
aggtctgaag atgactcttc acaccaacga cgtttaaggt ctctatccta ctcctagctt    13440
gcaatacctg gcttgcaata cctggagcat cgtgcacgat gattggatac tgtggaggag    13500
gagtgtttgc tgatttagag ctcccggttg ggtgatttga cttcgatttc agtttaggct    13560
tgttgaaatt tttcaggttc cattgtgaag cctttagagc ttgagcttcc ttccatgtta    13620
atgccttgat cgaatactcc tagagaaaag ggaagtcgat ctctgagtat tgaaatcgaa    13680
gtgcacattt tttttcaacg tgtccaatca atccacaaac aaagcagaag acaggtaatc    13740
tttcatactt atactgacaa gtaatagtct taccgtcatg cataataacg tctcgttcct    13800
tcaagagggg ttttccgaca tccataacga cccgaagcct catgaaagca ttagggaaga    13860
acttttggtt cttcttgtca tggcctttat aggtgtcagc cgagctcgcc aattcccgtc    13920
cgactggctc cgcaaaatat tcgaacggca agttatggac ttgcaaccat aactccacgg    13980
tattgagcag gacctattgt gaagactcat ctcatggagc ttcagaatgt ggttgtcagc    14040
aaaccaatga ccgaaatcca tcacatgacg gacgtccagt gggtgagcga aacgaaacag    14100
gaagcgccta tctttcagag tcgtgagctc cacaccggat tccggcaact acgtgttggg    14160
caggcttcgc cgtattagag atatgttgag gcagacccat ctgtgccact cgtacaatta    14220
cgagagttgt ttttttttgtg attttcctag tttctcgttg atggtgagct catattctac    14280
atcgtatggt ctctcaacgt cgtttcctgt catctgatat cccgtcattt gcatccacgt    14340
gcgccgcctc ccgtgccaag tccctaggtg tcatgcacgc caaattggtg gtggtgcggg    14400
ctgccctgtg cttcttaccg atgggtggag gttgagtttg ggggtctccg cggcgatggt    14460
agtgggttga cggtttggtg tgggttgacg gcattgatca atttacttct tgcttcaaat    14520
tctttggcag aaaacaattc attagattag aactggaaac cagagtgatg agacggatta    14580
agtcagattc caacagagtt acatctctta agaaataatg taacccctttt agactttata    14640 tatttgcaat taaaaaaata atttaacttt tagactttat atatagtttt aataactaag    14700
tttaaccact ctattattta tatcgaaact atttgtatgt ctcccctcta aataaacttg    14760
gtattgtgtt tacagaacct ataatcaaat aatcaatact caactgaagt ttgtgcagtt    14820
aattgaaggg attaacggcc aaaatgcact agtattatca accgaataga ttcacactag    14880
atggccattt ccatcaatat catcgccgtt cttcttctgt ccacatatcc cctctgaaac    14940
ttgagagaca cctgcacttc attgtcctta ttacgtgtta caaaatgaaa cccatgcatc    15000
catgcaaact gaagaatggc gcaagaaccc ttcccctcca tttcttatgt ggcgaccatc    15060
catttcacca tctcccgcta taaaacaccc ccatcacttc acctagaaca tcatcactac    15120
ttgcttatcc atccaaaaga tacccacttt tacaacaatt accaacaaca acaaacaaca    15180
aacaacatta caattacatt tacaattacc ataccatgcc acctagcgct gctaagcaaa    15240
tgggagcttc tactggtgtt catgctggtg ttactgactc ttctgctttc accagaaagg    15300
atgttgctga tagacctgat ctcaccatcg ttggagattc tgtttacgat gctaaggctt    15360
tcagatctga gcatcctggt ggtgctcatt tcgtttcttt gttcggagga agagatgcta    15420
ctgaggcttt catggaatac catagaaggg cttggcctaa gtctagaatg tctagattcc    15480
acgttggatc tcttgcttct actgaggaac ctgttgctgc tgatgaggga taccttcaac    15540
tttgtgctag gatcgctaag atggtgcctt ctgtttcttc tggattcgct cctgcttctt    15600
actgggttaa ggctggactt atccttggat ctgctatcgc tcttgaggct tacatgcttt    15660
acgctggaaa gagacttctc ccttctatcg ttcttggatg gcttttcgct cttatcggtc    15720
```

```
ttaacatcca gcatgatgct aaccatggtg ctttgtctaa gtctgcttct gttaaccttg   15780
ctcttggact ttgtcaggat tggatcggag gatctatgat cctttggctt caagagcatg   15840
ttgttatgca ccacctccac actaacgatg ttgataagga tcctgatcaa aaggctcacg   15900
gtgctcttag actcaagcct actgatgctt ggtcacctat gcattggctt cagcatcttt   15960 acctttgcc tggtgagact atgtacgctt tcaagctttt gttcctcgac atctctgagc    16020
ttgttatgtg gcgttgggag ggtgagccta tctctaagct tgctggatac ctctttatgc   16080
cttctttgct tctcaagctt accttctggg ctagattcgt tgctttgcct cttaccttg    16140 ctccttctgt tcatactgct gtgtgtatcg ctgctactgt tatgactgga tctttctacc   16200
tcgctttctt cttcttcatc tcccacaact tcgagggtgt tgcttctgtt ggacctgatg   16260
gatctatcac ttctatgact agaggtgcta gcttccttaa gagacaagct gagcttctt    16320 ctaacgttgg aggacctctt cttgctactc ttaacggtgg actcaactac caaattgagc   16380
atcacttgtt ccctagagtt caccatggat tctaccctag acttgctcct cttgttaagg   16440
ctgagcttga ggctagagga atcgagtaca agcactaccc tactatctgg tctaaccttg   16500
cttctaccct cagacatatg tacgctcttg gaagaaggcc tagatctaag gctgagtaat   16560
gacaagctta tgtgacgtga ataataacg gtaaaatata tgtaataata ataataataa    16620
agccacaaag tgagaatgag gggaagggga aatgtgtaat gagccagtag ccggtggtgc   16680
taattttgta tcgtattgtc aataaatcat gaattttgtg gtttttatgt gtttttttaa   16740
atcatgaatt ttaaatttta taaaataatc tccaatcgga agaacaacat tccatatcca   16800
tgcatggatg tttctttacc caaatctagt tcttgagagg atgaagcatc accgaacagt   16860
tctgcaacta tccctcaaaa gctttaaaat gaacaacaag gaacagagca acgttccaaa   16920
gatcccaaac gaaacatatt atctatacta atactatatt attaattact actgcccgga   16980
atcacaatcc ctgaatgatt cctattaact acaagccttg ttggcggcgg agaagtgatc   17040
ggcgcggcga gaagcagcgg actcggagac gaggccttgg aagatctgag tcgaacgggc   17100
agaatcagta ttttccttcg acgttaattg atcctacact atgtaggtca tatccatcgt   17160
tttaattttt ggccaccatt caattctgtc ttgcctttag ggatgtgaat atgaacggcc   17220
aaggtaagag aataaaaata atccaaatta aagcaagaga ggccaagtaa gataatccaa   17280
atgtacactt gtcattgcca aaattagtaa aatactcggc atattgtatt cccacacatt   17340
attaaaatac cgtatatgta ttggctgcat ttgcatgaat aatactacgt gtaagcccaa   17400
aagaacccac gtgtagccca tgcaaagtta acactcacga ccccattcct cagtctccac   17460
tatataaacc caccatcccc aatctcacca aacccaccac acaactcaca actcactctc   17520 acacettaaa gaaccaatca ccaccaaaaa ttttacaaca attaccaaca acaacaaaca   17580
acaaacaaca ttacaattac atttacaatt accataccat gagcgctgtt accgttactg   17640
gatctgatcc taagaacaga ggatcttcta gcaacaccga gcaagaggtt ccaaaagttg   17700
ctatcgatac caacggaaac gtgttctctg ttcctgattt caccatcaag gacatccttg   17760
gagctatccc tcatgagtgt tacgagagaa gattggctac ctctctctac tacgtgttca   17820
gagatatctt ctgcatgctt accaccggat accttaccca taagatcctt taccctctcc   17880
tcatctctta cacctctaac agcatcatca agttcacttt ctgggcccctt tacacttacg   17940 ttcaaggact tttcggaacc ggaatctggg ttctcgctca tgagtgtgga catcaagctt   18000
tctctgatta cggaatcgtg aacgatttcg ttggatggac ccttcactct taccttatgg   18060
ttccttactt cagctggaag tactctcatg gaaagcacca taaggctact ggacacatga   18120
```

```
ccagagatat ggttttcgtt cctgccacca agaggaatt  caagaagtct aggaacttct  18180
tcggtaacct cgctgagtac tctgaggatt ctccacttag aacccttac  gagcttcttg  18240
ttcaacaact tggaggatgg atcgcttacc tcttcgttaa cgttacagga caaccttacc  18300
ctgatgttcc ttcttggaaa tggaaccact tctggcttac ctctccactt ttcgagcaaa  18360
gagatgctct ctacatcttc ctttctgatc ttggaatcct cacccaggga atcgttctta  18420
ctctttggta caagaaattc ggaggatggt ccctttcat  caactggttc gttccttaca  18480
tctgggttaa ccactggctc gttttcatca cattccttca gcacactgat cctactatgc  18540
ctcattacaa cgctgaggaa tggactttcg ctaagggtgc tgctgctact atcgatagaa  18600
agttcggatt catcggacct cacatcttcc atgatatcat cgagactcat gtgcttcacc  18660
actactgttc taggatccca ttctacaacg ctagacctgc ttctgaggct atcaagaaag  18720
ttatgggaaa gcactacagg tctagcgacg agaacatgtg gaagtcactt tggaagtctt  18780
tcaggtcttg ccaatacgtt gacggtgata acggtgttct catgttccgt aacatcaaca  18840
actgcggagt tggagctgct gagaagtaat gaaggggtga tcgattatga gatcgtacaa  18900
agacactgct aggtgttaag gatggataat aataataata atgagatgaa tgtgttttaa  18960
gttagtgtaa cagctgtaat aaagagagag agagagagag agagagagag agagagagag  19020
agagagagag agaggctgat gaaatgttat gtatgtttct tggttttaa  aataaatgaa  19080
agcacatgct cgtgtggttc tatcgaatta ttcggcggtt cctgtgggaa aaagtccaga  19140
agggccgccg cagctactac tacaaccaag gccgtggagg agggcaacag agccagcact  19200
tcgatagctg ctgcgatgat cttaagcaat tgaggagcga gtgcacatgc aggggactgg  19260
agcgtgcaat cggccagatg aggcaggaca tccagcagca gggacagcag caggaagttg  19320
agaggtggtc ccatcaatct aaacaagtcg ctagggacct tccgggacag tgcggcaccc  19380
agcctagccg atgccagctc caggggcagc agcagtctgc atggttttga agtggtgatc  19440
gatgagatcg tataaagaca ctgctaggtg ttaaggatgg gataataaga tgtgttttaa  19500
gtcattaacc gtaataaaaa gagagagagg ctgatggaat gttatgtatg tatgtttctt  19560
ggtttttaaa attaaatgga aagcacatgc tcgtgtgggt tctatctcga ttaaaaatcc  19620
caattatatt tggtctaatt tagtttggta ttgagtaaaa caaattcgaa ccaaaccaaa  19680
atataaatat atagttttta tatatatgcc tttaagactt tttatagaat tttctttaaa  19740
aaatatctag aaatatttgc gactcttctg gcatgtaata tttcgttaaa tatgaagtgc  19800
tccatttta  ttaactttaa ataattggtt gtacgatcac tttcttatca agtgttacta  19860
aaatgcgtca atctctttgt tcttccatat tcatatgtca aaatctatca aaattcttat  19920
atatcttttt cgaatttgaa gtgaaatttc gataatttaa aattaaatag aacatatcat  19980
tatttaggta tcatattgat ttttatactt aattactaaa tttggttaac tttgaaagtg  20040
tacatcaacg aaaaattagt caaacgacta aaataaataa atatcatgtg ttattaagaa  20100
aattctccta taagaatatt ttaatagatc atatgtttgt aaaaaaaatt aattttact   20160
aacacatata tttacttatc aaaaatttga caaagtaaga ttaaataat  attcatctaa  20220
caaaaaaaaa accagaaaat gctgaaaacc cggcaaaacc gaaccaatcc aaaccgatat  20280
agttggtttg gtttgatttt gatataaacc gaaccaactc ggtccatttg caccccctaat 20340
cataatagct ttaatatttc aagatattat taagttaacg ttgtcaatat cctggaaatt  20400
ttgcaaaatg aatcaagcct atatggctgt aaatatgaatt taaaagcagc tcgatgtggt  20460
```

```
ggtaatatgt aatttacttg attctaaaaa aatatcccaa gtattaataa tttctgctag   20520
gaagaaggtt agctacgatt tacagcaaag ccagaataca aagaaccata aagtgattga   20580
agctcgaaat atacgaagga acaaatattt ttaaaaaaat acgcaatgac ttggaacaaa   20640
agaaagtgat atattttttg ttcttaaaca agcatcccct ctaaagaatg gcagttttcc   20700
tttgcatgta actattatgc tcccttcgtt acaaaaattt tggactacta ttgggaactt   20760
cttctgaaaa tagtcctgca ggctagtaga ttggttggtt ggtttccatg taccagaagg   20820
cttaccctat tagttgaaag ttgaaacttt gttccctact caattcctag ttgtgtaaat   20880
gtatgtatat gtaatgtgta taaaacgtag tacttaaatg actaggagtg gttcttgaga   20940
ccgatgagag atgggagcag aactaaagat gatgacataa ttaagaacga atttgaaagg   21000
ctcttaggtt tgaatcctat tcgagaatgt ttttgtcaaa gatagtggcg attttgaacc   21060
aaagaaaaca tttaaaaaat cagtatccgg ttacgttcat gcaaatagaa agtggtctag   21120
gatctgattg taattttaga cttaaagagt ctcttaagat tcaatcctgg ctgtgtacaa   21180
aactacaaat aatatatttt agactatttg gccttaacta aacttccact cattatttac   21240
tgaggttaga gaatagactt gcgaataaac acattcccga gaaatactca tgatcccata   21300
attagtcaga gggtatgcca atcagatcta agaacacaca ttccctcaaa ttttaatgca   21360
catgtaatca tagtttagca caattcaaaa ataatgtagt attaaagaca gaaatttgta   21420
gacttttttt tggcgttaaa agaagactaa gtttatacgt acatttttatt ttaagtggaa   21480 aaccgaaatt ttccatcgaa atatatgaat ttagtatata tatttctgca atgtactatt   21540
ttgctatttt ggcaactttc agtggactac tactttatta caatgtgtat ggatgcatga   21600
gtttgagtat acacatgtct aaatgcatgc tttgtaaaac gtaacggacc acaaaagagg   21660
atccatacaa atacatctca tagcttcctc cattattttc cgacacaaac agagcatttt   21720
acaacaatta ccaacaacaa caaacaacaa acaacattac aattacattt acaattacca   21780
taccatggaa tttgctcaac ctctcgttgc tatggctcaa gagcagtacg ctgctatcga   21840
tgctgttgtt gctcctgcta tcttctctgc taccgactct attggatggg gactcaagcc   21900
tatctcttct gctactaagg atctccctct cgttgaatct cctacccctc ttatcctttc   21960
tctcctcgct tacttcgcta tcgttggttc tggactcgtt taccgtaaag tgttccctag   22020
aaccgttaag ggacaggatc cttttccttct caaggctctt atgctcgctc acaacgtttt   22080
ccttatcgga ctcagccttt acatgtgcct caagctcgtt tacgaggctt acgtgaacaa   22140
gtactccttc tggggaaacg cttacaaccc tgctcaaacc gagatggcta aggtgatctg   22200
gatcttctac gtgtccaaga tctacgagtt catggacacc ttcatcatgc ttctcaaggg   22260
aaacgttaac caggtttcct tcctccatgt ttaccaccac ggatctatct ctggaatctg   22320
gtggatgatc acttatgctg ctccaggtgg agatgcttac ttctctgctg ctctcaactc   22380
ttgggttcat gtgtgcatgt acacctacta cttcatggct gctgttcttc ctaaggacga   22440
aaagaccaag agaaagtacc tttggtgggg aagataccct tacccagatgc aaatgttcca   22500 gttcttcatg aaccttctcc aggctgttta cctcctctac tcttcttctc cttacccctaa   22560 gttcattgct caactcctcg ttgtttacat ggttacccctc ctcatgcttt tcggaaactt   22620
ctactacatg aagcaccacg cttctaagtg ataagggccg ccgccatgtg acagatcgaa   22680
ggaagaaagt gtaataagac gactctcact actcgatcgc tagtgattgt cattgttata   22740
tataataatg ttatctttca caacttatcg taatgcatgt gaaactataa cacattaatc   22800
ctacttgtca tatgataaca ctctcccccat ttaaaactct tgtcaattta aagatataag   22860
```

-continued

```
attctttaaa tgattaaaaa aaatatatta taaattcaat cactcctact aataaattat   22920
taattattat ttattgatta aaaaaatact tatactaatt tagtctgaat agaataatta   22980
gattctagcc tgcagggcgg ccgcggatcc catggagtca agattcaaa tagaggacct   23040 aacagaactc gccgtaaaga ctggcgaaca gttcatacag agtctcttac gactcaatga   23100
caagaagaaa atcttcgtca acatggtgga gcacgacaca cttgtctact ccaaaaatat   23160
caaagataca gtctcagaag accaaagggc aattgagact tttcaacaaa gggtaatatc   23220
cggaaacctc ctcggattcc attgcccagc tatctgtcac tttattgtga agatagtgga   23280
aaaggaaggt ggctcctaca aatgccatca ttgcgataaa ggaaaggcca tcgttgaaga   23340
tgcctctgcc gacagtggtc ccaaagatgg accccaccc acgaggagca tcgtggaaaa   23400
agaagacgtt ccaaccacgt cttcaaagca agtggattga tgtgatatct ccactgacgt   23460
aagggatgac gcacaatccc actatccttc gcaagaccct tcctctatat aaggaagttc   23520
atttcatttg gagagaacac gggggactga attaaatatg agccctgaga ggcgtcctgt   23580
tgaaatcaga cctgctactg ctgctgatat ggctgctgtt tgtgatatcg tgaaccacta   23640
catcgagact tctaccgtta acttcagaac tgagcctcaa actcctcaag agtggatcga   23700
tgatcttgag agactccaag atagataccc ttggcttgtt gctgaggttg agggtgttgt   23760
tgctggaatc gcttacgctg gaccttggaa ggctagaaac gcttacgatt ggactgttga   23820
gtctaccgtt tacgtttcac acagacatca gagacttgga cttggatcta ccctttacac   23880
tcaccttctc aagtctatgg aagctcaggg attcaagtct gttgttgctg ttatcggact   23940
ccctaacgat ccttctgtta gacttcatga ggctcttgga tacactgcta gaggaactct   24000
tagagctgct ggatacaagc acggtggatg gcatgatgtt ggattctggc aaagagattt   24060
cgagcttcct gctcctccta gacctgttag accagttact cagatctgaa tttgcgtgat   24120
cgttcaaaca tttggcaata aagtttctta agattgaatc ctgttgccgg tcttgcgatg   24180
attatcatat aatttctgtt gaattacgtt aagcatgtaa taattaacat gtaatgcatg   24240
acgttattta tgagatgggt ttttatgatt agagtcccgc aattatacat ttaatacgcg   24300
atagaaaaca aaatatagcg cgcaaactag gataaaattat cgcgcgcggt gtcatctatg   24360
ttactagatc actagtgatg tacggttaaa accaccccag tacattaaaa acgtccgcaa   24420
tgtgttatta agttgtctaa gcgtcaattt gtttacacca caatatattg tggtgtaaac   24480
aaattgacgc ttagacaact taataacaca ttgcggacgt ttttaatgta ctggggtggt   24540
tttaaccgta catcactagt gatctagtaa catagatgac accgcgcgcg ataatttatc   24600
ctagtttgcg cgctatattt tgttttctat cgcgtattaa atgtataatt gcgggactct   24660
aatcataaaa acccatctca taaataacgt catgcattac atgttaatta ttacatgctt   24720
aacgtaattc aacagaaatt atatgataat catcgcaaga ccggcaacag gattcaatct   24780
taagaaactt tattgccaaa tgtttgaacg atcacgcaaa ttcagatctg agtaactggt   24840
ctaacaggtc taggaggagc aggaagctcg aaatctcttt gccagaatcc aacatcatgc   24900
catccaccgt gcttgtatcc agcagctcta agagttcctc tagcagtgta tccaagagcc   24960
tcatgaagtc taacagaagg atcgttaggg agtccgataa cagcaacaac agacttgaat   25020
ccctgagctt ccatagactt gagaaggtga gtgtaaaggg tagatccaag tccaagtctc   25080
tgatgtctgt gtgaaacgta aacggtagac tcaacagtcc aatcgtaagc gtttctagcc   25140
ttccaaggtc cagcgtaagc gattccagca acaacaccct caacctcagc aacaagccaa   25200
```

```
gggtatctat cttggagtct ctcaagatca tcgatccact cttgaggagt ttgaggctca   25260
gttctgaagt taacggtaga agtctcgatg tagtggttca cgatatcaca aacagcagcc   25320
atatcagcag cagtagcagg tctgatttca acaggacgcc tctcagggct catatttaat   25380
tcagtccccc gtgttctctc caaatgaaat gaacttcctt atatagagga agggtcttgc   25440
gaaggatagt gggattgtgc gtcatccctt acgtcagtgg agatatcaca tcaatccact   25500
tgctttgaag acgtggttgg aacgtcttct ttttccacga tgctcctcgt gggtgggggt   25560
ccatctttgg gaccactgtc ggcagaggca tcttcaacga tggcctttcc tttatcgcaa   25620
tgatggcatt tgtaggagcc accttccttt tccactatct tcacaataaa gtgacagata   25680
gctgggcaat ggaatccgag gaggtttccg gatattaccc tttgttgaaa agtctcaatt   25740
gcccttggt cttctgagac tgtatctttg atattttgg agtagacaag tgtgtcgtgc   25800
tccaccatgt tgacgaagat tttcttcttg tcattgagtc gtaagagact ctgtatgaac   25860
tgttcgccag tctttacggc gagttctgtt aggtcctcta tttgaatctt tgactccatg   25920
ggatccgcgg ccgccctgca ggctagaatc taattattct attcagacta aattagtata   25980
agtatttttt taatcaataa ataataatta ataatttatt agtaggagtg attgaattta   26040
taatatattt tttttaatca tttaaagaat cttatatctt taaattgaca agagtttttaa   26100
atggggagag tgttatcata tgacaagtag gattaatgtg ttatagttc acatgcatta   26160
cgataagttg tgaaagataa cattattata tataacaatg acaatcacta gcgatcgagt   26220
agtgagagtc gtcttattac actttcttcc ttcgatctgt cacatggcgg cggcccttat   26280
cacttagaag cgtggtgctt catgtagtag aagtttccga aaagcatgag gagggtaacc   26340
atgtaaacaa cgaggagttg agcaatgaac ttagggtaag gagaagaaga gtagaggagg   26400
taaacagcct ggagaaggtt catgaagaac tggaacattt gcatctgggt aaggtatctt   26460
ccccaccaaa ggtactttct cttggtcttt tcgtccttag gaagaacagc agccatgaag   26520
tagtaggtgt acatgcacac atgaacccaa gagttgagag cagcagagaa gtaagcatct   26580
ccacctggag cagcataagt gatcatccac cagattccag agatagatcc gtggtggtaa   26640
acatggagga aggaaacctg gttaacgttt cccttgagaa gcatgatgaa ggtgtccatg   26700
aactcgtaga tcttggacac gtagaagatc cagatcacct tagccatctc ggtttgagca   26760
gggttgtaag cgtttccca gaaggagtac ttgttcacgt aagcctcgta acgagcttg   26820
aggcacatgt aaaggctgag tccgataagg aaaacgttgt gagcgagcat aagagccttg   26880
agaaggaaag gatcctgtcc cttaacggtt ctagggaaca ctttacggta aacgagtcca   26940
gaaccaacga tagcgaagta agcgaggaga gaaaggataa gagggtagg agattcaacg   27000
agagggagat ccttagtagc agaagagata ggcttgagtc cccatccaat agagtcggta   27060
gcagagaaga tagcaggagc aacaacagca tcgatagcag cgtactgctc ttgagccata   27120
gcaacgagag gttgagcaaa ttccatggta tggtaattgt aaatgtaatt gtaatgttgt   27180
ttgttgtttg ttgttgttgg taattgttgt aaaatgctct gtttgtgtcg gaaaataatg   27240
gaggaagcta tgagatgtat ttgtatggat cctcttttgt ggtccgttac gttttacaaa   27300
gcatgcattt agacatgtgt atactcaaac tcatgcatcc atacacattg taataaagta   27360
gtagtccact gaaagttgcc aaaatagcaa aatagtacat tgcagaaata tatatactaa   27420
attcatatat ttcgatggaa aatttcggtt ttccacttaa aataaaatgt acgtataaac   27480
ttagtcttct tttaacgcca aaaaaaagtc tacaaatttc tgtctttaat actacattat   27540
ttttgaattg tgctaaacta tgattacatg tgcattaaaa tttgagggaa tgtgtgttct   27600
```

```
tagatctgat tggcataccc tctgactaat tatgggatca tgagtatttc tcgggaatgt   27660
gtttattcgc aagtctattc tctaacctca gtaaataatg agtggaagtt tagttaaggc   27720
caaatagtct aaaatatatt atttgtagtt ttgtacacag ccaggattga atcttaagag   27780
actctttaag tctaaaatta caatcagatc ctagaccact ttctatttgc atgaacgtaa   27840
ccggatactg atttttaaa tgttttcttt ggttcaaaat cgccactatc tttgacaaaa     27900
acattctcga ataggattca aacctaagag cctttcaaat tcgttcttaa ttatgtcatc   27960
atctttagtt ctgctcccat ctctcatcgg tctcaagaac cactcctagt catttaagta   28020
ctacgtttta tacacattac atatacatac atttacacaa ctaggaattg agtagggaac   28080
aaagtttcaa ctttcaacta atagggtaag ccttctggta catggaaacc aaccaaccaa   28140
tctactagcc tgcaggacta ttttcagaag aagttcccaa tagtagtcca aaattttgt    28200 aacgaaggga gcataatagt tacatgcaaa ggaaaactgc cattctttag aggggatgct   28260
tgtttaagaa caaaaaatat atcactttct tttgttccaa gtcattgcgt attttttaa    28320 aaatatttgt tccttcgtat atttcgagct tcaatcactt tatggttctt tgtattctgg   28380
ctttgctgta aatcgtagct aaccttcttc ctagcagaaa ttattaatac ttgggatatt   28440 ttttagaat caagtaaatt acatattacc accacatcga gctgctttta aattcatatt    28500
acagccatat aggcttgatt cattttgcaa aatttccagg atattgacaa cgttaactta   28560
ataatatctt gaaatattaa agctattatg attaggggtg caaatggacc gagttggttc   28620
ggtttatatc aaaatcaaac caaaccaact atatcggttt ggattggttc ggttttgccg   28680
ggttttcagc attttctggt ttttttttg ttagatgaat attattttaa tcttactttg     28740 tcaaatttt gataagtaaa tatatgtgtt agtaaaaatt aatttttttt acaaacatat     28800
gatctattaa aatattctta taggagaatt ttcttaataa cacatgatat ttatttattt   28860
tagtcgtttg actaatttt cgttgatgta cactttcaaa gttaaccaaa tttagtaatt    28920
aagtataaaa atcaatatga tacctaaata atgatatgtt ctatttaatt ttaaattatc   28980
gaaatttcac ttcaaattcg aaaaagatat ataagaattt tgatagattt tgacatatga   29040
atatggaaga acaaagagat tgacgcattt tagtaacact tgataagaaa gtgatcgtac   29100
aaccaattat ttaaagttaa taaaaatgga gcacttcata tttaacgaaa tattacatgc   29160
cagaagagtc gcaaatattt ctagatattt tttaaagaaa attctataaa aagtcttaaa   29220
ggcatatata taaaaactat atatttatat tttggtttgg ttcgaatttg ttttactcaa   29280
taccaaacta aattagacca aatataattg ggatttttaa tcgagataga acccacacga   29340
gcatgtgctt tccatttaat tttaaaaacc aagaaacata catacataac attccatcag   29400
cctctctctc tttttattac ggttaatgac ttaaaacaca tcttattatc ccatccttaa   29460
cacctagcag tgtctttata cgatctcatc gatcaccact tcaaaaccat gcagactgct   29520
gctgcccctg gagctggcat cggctaggct gggtgccgca ctgtcccgga aggtccctag   29580
cgacttgttt agattgatgg gaccacctct caacttcctg ctgctgtccc tgctgctgga   29640
tgtcctgcct catctggccg attgcacgct ccagtcccct gcatgtgcac tcgctcctca   29700
attgcttaag atcatcgcag cagctatcga agtgctggct ctgttgccct cctccacggc   29760
cttggttgta gtagtagctg cggcggccct tctggacttt tcccacagg aaccgccgaa     29820 taattcgata gaaccacacg agcatgtgct ttcattatt ttaaaaacca agaaacatac     29880
ataacatttc atcagcctct ctctctctct ctctctctct ctctctctct ctctctctct   29940
```

```
ctctctcttt attacagctg ttacactaac ttaaaacaca ttcatctcat tattattatt    30000
attatccatc cttaacacct agcagtgtct ttgtacgatc tcataatcga tcaccccttc    30060
attacttctc agcagctcca actccgcagt tgttgatgtt acggaacatg agaacaccgt    30120
tatcaccgtc aacgtattgg caagacctga aagacttcca aagtgacttc cacatgttct    30180
cgtcgctaga cctgtagtgc tttcccataa ctttcttgat agcctcagaa gcaggtctag    30240
cgttgtagaa tgggatccta gaacagtagt ggtgaagcac atgagtctcg atgatatcat    30300
ggaagatgtg aggtccgatg aatccgaact ttctatcgat agtagcagca gcacccttag    30360
cgaaagtcca ttcctcagcg ttgtaatgag gcatagtagg atcagtgtgc tgaaggaatg    30420
tgatgaaaac gagccagtgg ttaacccaga tgtaaggaac gaaccagttg atgaaaaggg    30480
accatcctcc gaatttcttg taccaaagag taagaacgat tccctgggtg aggattccaa    30540
gatcagaaag gaagatgtag agagcatctc tttgctcgaa aagtggagag gtaagccaga    30600
agtggttcca tttccaagaa ggaacatcag ggtaaggttg tcctgtaacg ttaacgaaga    30660
ggtaagcgat ccatcctcca agttgttgaa caagaagctc gtaaagggtt ctaagtggag    30720
aatcctcaga gtactcagcg aggttaccga agaagttcct agacttcttg aattcctctt    30780
tggtggcagg aacgaaaacc atatctctgg tcatgtgtcc agtagcctta tggtgctttc    30840
catgagagta cttccagctg aagtaaggaa ccataaggta agagtgaagg gtccatccaa    30900
cgaaatcgtt cacgattccg taatcagaga aagcttgatg tccacactca tgagcgaaa     30960 cccagattcc ggttccgaaa agtccttgaa cgtaagtgta aagggcccag aaagtgaact    31020
tgatgatgct gttagaggtg taagagatga ggagagggta aaggatctta tgggtaaggt    31080
atccggtggt aagcatgcag aagatatctc tgaacacgta gtagagagag gtagccaatc    31140
ttctctcgta acactcatga gggatagctc caaggatgtc cttgatggtg aaatcaggaa    31200
cagagaacac gtttccgttg gtatcgatag caacttttgg aacctcttgc tcggtgttgc    31260
tagaagatcc tctgttctta ggatcagatc cagtaacggt aacagcgctc atggtatggt    31320
aattgtaaat gtaattgtaa tgttgtttgt tgtttgttgt tgttggtaat tgttgtaaaa    31380
tttttggtgg tgattggttc tttaaggtgt gagagtgagt tgtgagttgt gtggtgggtt    31440
tggtgagatt ggggatggtg ggtttatata gtggagactg aggaatgggg tcgtgagtgt    31500
taactttgca tgggctacac gtgggttctt ttgggcttac acgtagtatt attcatgcaa    31560
atgcagccaa tacatatacg gtattttaat aatgtgtggg aatacaatat gccgagtatt    31620
ttactaattt tggcaatgac aagtgtacat ttggattatc ttacttggcc tctcttgctt    31680
taatttggat tattttttatt ctcttacctt ggccgttcat attcacatcc ctaaaggcaa    31740
gacagaattg aatggtggcc aaaaattaaa acgatggata tgacctacat agtgtaggat    31800
caattaacgt cgaaggaaaa tactgattct gcccgttcga ctcagatctt ccaaggcctc    31860
gtctccgagt ccgctgcttc tcgccgcgcc gatcacttct ccgccgccaa caaggcttgt    31920
agttaatagg aatcattcag ggattgtgat tccgggcagt agtaattaat aatatagtat    31980
tagtatagat aatatgtttc gtttgggatc tttggaacgt tgctctgttc cttgttgttc    32040
attttaaagc ttttgaggga tagttgcaga actgttcggt gatgcttcat cctctcaaga    32100
actagatttg ggtaaagaaa catccatgca tggatatgga atgttgttct tccgattgga    32160
gattatttta taaatttaa aattcatgat ttaaaaaaac acataaaaac cacaaaattc    32220
atgatttatt gacaatacga tacaaaatta gcaccaccgg ctactggctc attacacatt    32280
tccccttccc ctcattctca ctttgtggct ttattattat tattattaca tatattttac    32340
```

```
cgttattatt tcacgtcaca taagcttgtc attactcagc cttagatcta ggccttcttc   32400
caagagcgta catatgtctg agggtagaag caaggttaga ccagatagta gggtagtgct   32460
tgtactcgat tcctctagcc tcaagctcag ccttaacaag aggagcaagt ctagggtaga   32520
atccatggtg aactctaggg aacaagtgat gctcaatttg gtagttgagt ccaccgttaa   32580
gagtagcaag aagaggtcct ccaacgttag aagaagtctc agcttgtctc ttaaggaagc   32640
tagcacctct agtcatagaa gtgatagatc catcaggtcc aacagaagca acaccctcga   32700
agttgtggga gatgaagaag aagaaagcga ggtagaaaga tccagtcata acagtagcag   32760
cgatacacac agcagtatga acagaaggag caaggtaaag aggcaaagca acgaatctag   32820
cccagaaggt aagcttgaga agcaaagaag gcataaagag gtatccagca agcttagaga   32880
taggctcacc ctcccaacgc cacataacaa gctcagagat gtcgaggaac aaaagcttga   32940
aagcgtacat agtctcacca ggcaaaaggt aaagatgctg aagccaatgc ataggtgacc   33000
aagcatcagt aggcttgagt ctaagagcac cgtgagcctt ttgatcagga tccttatcaa   33060
catcgttagt gtggaggtgg tgcataacaa catgctcttg aagccaaagg atcatagatc   33120
ctccgatcca atcctgacaa agtccaagag caaggttaac agaagcagac ttagacaaag   33180
caccatggtt agcatcatgc tggatgttaa gaccgataag agcgaaaagc catccaagaa   33240
cgatagaagg gagaagtctc tttccagcgt aaagcatgta agcctcaaga gcgatagcag   33300
atccaaggat aagtccagcc ttaacccagt aagaagcagg agcgaatcca gaagaaacag   33360
aaggcaccat cttagcgatc ctagcacaaa gttgaaggta tccctcatca gcagcaacag   33420
gttcctcagt agaagcaaga gatccaacgt ggaatctaga cattctagac ttaggccaag   33480
cccttctatg gtattccatg aaagcctcag tagcatctct tcctccgaac aaagaaacga   33540
aatgagcacc accaggatgc tcagatctga aagccttagc atcgtaaaca gaatctccaa   33600
cgatggtgag atcaggtcta tcagcaacat cctttctggt gaaagcagaa gagtcagtaa   33660
caccagcatg aacaccagta gaagctccca tttgcttagc agcgctaggt ggcatggtat   33720
ggtaattgta aatgtaattg taatgttgtt tgttgtttgt tgttgttggt aattgttgta   33780
aaagtgggta tcttttggat ggataagcaa gtagtgatga tgttctaggt gaagtgatgg   33840
gggtgtttta tagcgggaga tggtgaaatg gatggtcgcc acataagaaa tggaggggaa   33900
gggttcttgc gccattcttc agtttgcatg gatgcatggg tttcattttg taacacgtaa   33960
taaggacaat gaagtgcagg tgtctctcaa gtttcagagg ggatatgtgg acagaagaag   34020
aacggcgatg atattgatgg aaatggccat ctagtgtgaa tctattcggt tgataatact   34080
agtgcatttt ggccgttaat cccttcaatt aactgcacaa acttcagttg agtattgatt   34140
atttgattat aggttctgta aacacaatac caagtttatt tagaggggag acatacaaat   34200
agtttcgata taaataatag agtggttaaa cttagttatt aaaactatat ataaagtcta   34260
aaagttaaat tatttttta attgcaaata tataaagtct aaaggggtta cattatttct   34320
taagagatgt aactctgttg gaatctgact taatccgtct catcactctg gtttccagtt   34380
ctaatctaat gaattgtttt ctgccaaaga atttgaagca agaagtaaat tgatcaatgc   34440
cgtcaaccca caccaaaccg tcaacccact accatcgccg cggagacccc caaactcaac   34500
ctccacccat cggtaagaag cacagggcag cccgcaccac caccaatttg cgtgcatga   34560 cacctaggga cttggcacgg gaggcggcgc acgtggatgc aaatgacggg atatcagatg   34620
acaggaaacg acgttgagag accatacgat gtagaatatg agctcaccat caacgagaaa   34680
```

```
ctaggaaaat cacaaaaaaa acaactctcg taattgtacg agtggcacag atgggtctgc   34740
ctcaacatat ctctaatacg gcgaagcctg cccaacacgt agttgccgga atccggtgtg   34800
gagctcacga ctctgaaaga taggcgcttc ctgtttcgtt tcgctcaccc actggacgtc   34860
cgtcatgtga tggatttcgg tcattggttt gctgacaacc acattctgaa gctccatgag   34920
atgagtcttc acaataggtc ctgctcaata ccgtggagtt atggttgcaa gtccataact   34980
tgccgttcga atattttgcg gagccagtcg gacgggaatt ggcgagctcg gctgacacct   35040
ataaaggcca tgacaagaag aaccaaaagt tcttccctaa tgctttcatg aggcttcggg   35100
tcgttatgga tgtcggaaaa cccctcttga aggaacgaga cgttattatg catgacggta   35160
agactattac ttgtcagtat aagtatgaaa gattacctgt cttctgcttt gtttgtggat   35220
tgattggaca cgttgaaaaa aaatgtgcac ttcgatttca atactcagag atcgacttcc   35280
cttttctcta ggagtattcg atcaaggcat taacatggaa ggaagctcaa gctctaaagg   35340
cttcacaatg gaacctgaaa aatttcaaca agcctaaact gaaatcgaag tcaaatcacc   35400
caaccgggag ctctaaatca gcaaacactc ctcctccaca gtatccaatc atcgtgcacg   35460
atgctccagg tattgcaagc caggtattgc aagctaggag taggatagag accttaaacg   35520
tcgttggtgt gaagagtcat cttcagacct aatggagata gatgtagacg gcggcacgaa   35580
gactctgaaa caccagaaag gctagtccag gataaggatc tgctatccca actgacctct   35640
cgttagtccc aaggcctctc aactagagca ggaggaagga tggtcacaag actaggataa   35700
tgatgtttcc aatatgaacc tgaatgtcca tagctaattt ttttagtctt gcttctgcac   35760
tttttgttta ttatgttctg gtgactatgt tatttacccct tgtccgtatg cttgagagaa   35820
tcagtatttt ccttcgacgt taattgatcc tacactatgt aggtcatatc catcgtttta   35880
attttttggcc accattcaat tctgtcttgc ctttagggat gtgaatatga acggccaagg   35940
taagagaata aaaataatcc aaattaaagc aagagaggcc aagtaagata atccaaatgt   36000
acacttgtca ttgccaaaat tagtaaaata ctcggcatat tgtattccca cacattatta   36060
aaataccgta tatgtattgg ctgcatttgc atgaataata ctacgtgtaa gcccaaaaga   36120
acccacgtgt agcccatgca aagttaacac tcacgacccc attcctcagt ctccactata   36180
taaacccacc atccccaatc tcaccaaacc caccacacaa ctcacaactc actctcacac   36240
cttaaagaac caatcaccac caaaaatttt acaacaatta ccaacaacaa caaacaacaa   36300
acaacattac aattacattt acaattacca taccatgtct aaggttaccg tgtctggatc   36360
tgagatcctt gagggatcta ctaagaccgt taggcgttct ggaaacgttg catctttcaa   36420
gcagcaaaag accgctatcg ataccttcgg aaacgttttc aaggtgccag attacaccat   36480
caaggatatc cttgacgcta tccctaagca ctgttacgag agatctctcg tgaagtctat   36540
gtcttacgtg gtgagagata tcgtggctat ctctgctatc gcttacgttg gacttaccta   36600
catccctctt ctccctaacg aattccttag attcgctgct tggtctgctt acgtgttctc   36660
tatctcttgt ttcggattcg gaatctggat ccttggacat gagtgtggac attctgcttt   36720
ctctaactac ggatgggtta acgataccgt tggatgggtt ctccactctc ttgttatggt   36780
tccttacttc agctggaagt tctctcatgc taagcaccat aaggctactg acacacatgac   36840
cagagatatg gttttcgttc cttacaccgc cgaggaattc aaagagaagc accaagttac   36900
cagccttcac gatatcgctg aggaaactcc tatctactct gttttcgctc tcttgttcca   36960
acagcttgga ggactttctc tttaccttgc tactaacgct actggacaac cttaccctgg   37020
tgtttctaag ttcttcaagt ctcactactg gccttctagc cctgttttcg ataagaagga   37080
```

```
ctactggtac atcgttcttt ctgatcttgg aatccttgct accctcactt ctgtttacac    37140
cgcttacaag gttttcggat tctggcctac tttcatcaca tggttctgtc cttggatcct    37200
tgttaaccac tggcttgttt tcgttacctt ccttcagcac accgattctt ctatgcctca    37260
ttacgatgct caagagtgga ctttcgctaa gggtgctgct gctactatcg atagagagtt    37320
cggaatcctc ggaatcatct tccatgacat catcgagact catgtgctcc atcactacgt    37380
ttcaaggatc ccattctacc atgctagaga agctaccgag tgcatcaaga aagttatggg    37440
agagcactac agacacaccg atgagaacat gtgggttagc ctttggaaaa cttggagatc    37500
ttgccagttc gttgagaacc atgatggtgt gtacatgttc cgtaactgca acaacgttgg    37560
agtgaagcct aaggatacct gatgaagggg tgatcgatta tgagatcgta caaagacact    37620
gctaggtgtt aaggatggat aataataata ataatgagat gaatgtgttt taagttagtg    37680
taacagctgt aataaagaga gagagagaga gagagagaga gagagagaga gagagagaga    37740
gagagaggct gatgaaatgt tatgtatgtt tcttggtttt taaaataaat gaaagcacat    37800
gctcgtgtgg ttctatcgaa ttattcggcg gttcctgtgg gaaaaagtcc agaagggcgg    37860
cggcagctac tactacaacc aaggccgtgg aggagggcaa cagagccagc acttcgatag    37920
ctgctgcgat gatcttaagc aattgaggag cgagtgcaca tgcagggac tggagcgtgc    37980 aatcggccag atgaggcagg acatccagca gcagggacag cagcaggaag ttgagaggtg    38040
gtcccatcaa tctaaacaag tcgctaggga ccttccggga cagtgcggca cccagcctag    38100
ccgatgccag ctccagggggc agcagcagtc tgcatggttt tgaagtggtg atcgatgaga    38160
tcgtataaag acactgctag gtgttaagga tgggataata agatgtgttt taagtcatta    38220
accgtaataa aaagagagag aggctgatgg aatgttatgt atgtatgttt cttggttttt    38280
aaaattaaat ggaaagcaca tgctcgtgtg ggttctatca ctattttcag aagaagttcc    38340
caatagtagt ccaaaatttt tgtaacgaag ggagcataat agttacatgc aaaggaaaac    38400
tgccattctt tagaggggat gcttgtttaa gaacaaaaaa tatatcactt tcttttgttc    38460
caagtcattg cgtatttttt taaaaatatt tgttccttcg tatatttcga gcttcaatca    38520
ctttatggtt ctttgtattc tggctttgct gtaaatcgta gctaaccttc ttcctagcag    38580
aaattattaa tacttgggat attttttttag aatcaagtaa attacatatt accaccacat    38640
cgagctgctt ttaaattcat attacagcca tataggcttg attcattttg caaaatttcc    38700
aggatattga caacgttaac ttaataatat cttgaaatat taaagctatt atgattaggg    38760
gtgcaaatgg accgagttgg ttcggtttat atcaaaatca aaccaaacca actatatcgg    38820
tttggattgg ttcggtttttg ccgggtttttc agcatttttct ggtttttttt tgttagatg    38880 aatattattt taatcttact ttgtcaaatt tttgataagt aaatatatgt gttagtaaaa    38940
attaattttt tttacaaaca tatgatctat taaaatattc ttataggaga atttttcttaa    39000 taacacatga tatttattta tttttagtcgt ttgactaatt tttcgttgat gtacactttc    39060
aaagttaacc aaatttagta attaagtata aaaatcaata tgatacctaa ataatgatat    39120 gttctatttta atttttaaatt atcgaaattt cacttcaaat tcgaaaaaga tatataagaa    39180
ttttgataga ttttgacata tgaatatgga agaacaaaga gattgacgca ttttagtaac    39240
acttgataag aaagtgatcg tacaaccaat tatttaaagt taataaaaat ggagcacttc    39300
atatttaacg aaatattaca tgccagaaga gtcgcaaata tttctagata ttttttaaag    39360
aaaattctat aaaaagtctt aaaggcatat atataaaaac tatatattta tattttggtt    39420
```

| | |
|---|---|
| tggttcgaat ttgttttact caataccaaa ctaaattaga ccaaatataa ttgggatttt | 39480 |
| taatcgaccg atctagtaac atagatgaca ccgcgcgcga taatttatcc tagtttgcgc | 39540 |
| gctatatttt gttttctatc gcgtattaaa tgtataattg cgggactcta atcataaaaa | 39600 |
| cccatctcat aaataacgtc atgcattaca tgttaattat tacgtgctta acgtaattca | 39660 |
| acagaaatta tatgataatc atcgcaagac cggcaacagg attcaatctt aagaaacttt | 39720 |
| attgccaaat gtttgaacga tctcattact gcattttctt ctcaggagca tgggcaacgt | 39780 |
| tatcaaggtt agcgaaagta tcagccatag cctcgaagta tcctctaaca tcgtagtgaa | 39840 |
| gtccgtgctt ctcgaaaagc tgcttaactc taggagcgat cttagggtgt ctgaattgag | 39900 |
| gcatagaagg gtaaaggtgg tgctcgatct ggtagttaag gtaagacatc caccaatcac | 39960 |
| accaccaaga tggagaacag ttagtagtgt ggttagcagc gtactcaacc caagtagcat | 40020 |
| gctcgttagg ctcaacaaca gggaggtgag tatgagaaac agcgaagttg cagaagatgt | 40080 |
| acatagctcc aagctgaacg taaagaaggt aacaagcgag aacgtatcca gcaccgtagt | 40140 |
| tagcagcaag gtatccaaca agtccgtatc tgattccgag catagcaagc tcatcgtagt | 40200 |
| gcttagtcct gagcatgtgt ctaggatgaa ggtaaagctg ccatccaaga gcaacaagaa | 40260 |
| gagtggtaac aggagcgaaa agcttagctt gcatagaaag ccaagccttc atagcaggag | 40320 |
| acttaacctt agcagcgatt ctctcatgga aagcaacgag aggaagggta tcaagatcaa | 40380 |
| catcgtgctg aagcttttga ggagtagcat ggtgcttgtt atgctggtta cgccaccaag | 40440 |
| caccagacat tccacatcca agtccgtaac aagcaacttg gatagctctg tcgaaagcaa | 40500 |
| tgtttccagt gagagagtaa tgtccaccct catgcataag ccatccacat cttccctgaa | 40560 |
| caactccaag catagcgatt ccagcgaaag tgtatccatg ccagataaga gcagcaccag | 40620 |
| caacatgcat agcgataacc tcagcaagtc tgtaagcaac atgaggaaga gaaggctcga | 40680 |
| acattccctc agcctcaagt tgcttggtga actcttggaa atcagcgata agatcagccc | 40740 |
| ttcttggaga gtatcccttg tgaacaggac gagaaggaag agacttaagc atcttgtcag | 40800 |
| ccttagcaga tctaacatgg aactgcttgt aagcatcggt agcatcagtt ccaacttggt | 40860 |
| aagcaatgat ctttccacca gggtgtctct taacgaagtt ggtaacatcg taagccctat | 40920 |
| ctccgataac aagctctttc ttgtcgtgct cttgaggagt atcaacttcg tgaagttgag | 40980 |
| cagaaggagg agcagcataa gagtaagagt cccttggagg catggtatgg taattgtaaa | 41040 |
| tgtaattgta atgttgtttg ttgtttgttg ttgttggtaa ttgttgtaaa agatcctcgt | 41100 |
| gtatgttttt aatcttgttt gtatcgatga gttttggttt gagtaaagag tgaagcggat | 41160 |
| gagttaatttt ataggctata aaggagatttt gcatggcgat cacgtgtaat aatgcatgca | 41220 |
| cgcatgtgat tgtatgtgtg tgctgtgaga gagaagctct taggtgtttg aagggagtga | 41280 |
| caagtggcga agaaaaacaa ttctccgcgg ctgcatgcta tgtgtaacgt gtagctaatg | 41340 |
| ttctggcatg gcatcttatg aacgattctt tttaaaaaca aggtaaaaac ttaacttcat | 41400 |
| aaaattaaaa aaaaaaacgt ttactaagtt ggtttaaaag gggatgagac tagaatctaa | 41460 |
| ttattctatt cagactaaat tagtataagt atttttttaa tcaataaata ataattaata | 41520 |
| atttattagt aggagtgatt gaatttataa tatatttttt ttaatcattt aaagaatctt | 41580 |
| atatctttaa attgacaaga gttttaaatg gggagagtgt tatcatatga caagtaggat | 41640 |
| taatgtgtta tagtttcaca tgcattacga taagttgtga aagataacat tattatatat | 41700 |
| aacaatgaca atcactagcg atcgagtagt gagagtcgtc ttattacact ttcttccttc | 41760 |
| gatctgtcac atggcggcgg cccggcgcgc cgcgcgcctt atcactgctt cttagcaccc | 41820 |

```
ttagacttgt acctcttacg gtagaagttg gcgaagagaa cgaacatgtt caccataacc  41880
cagagttgaa ggtaaggaag ccagaaagcg gtattctgaa cgtaagcggt gtagatagag  41940
tgagaagcac agatacagaa ctgaagcatc tggatctggg tgatgtactt cttccagaaa  42000
cagttaactc caagagcagc aagtccgtag taagagtaca tgatcacgtg cacgaaggtg  42060
ttaacagaag atccgaagta gcaatctcca acaggctcaa gcttcataac aacgaaccat  42120
gaccagatga gaagagtgtg gtggtagatg tgaaggaaag aaagctggtc gaacttcttc  42180
ctcatcacca tgaagaaggt gtcgagaagc tcaacgtact tgttgttgta gtgaagccag  42240
ataacctgag agattcccca agagttagca gtcatatcag ggatgtttcc ccaaacctta  42300
agtccctgag ccctatgaga agtaacgaaa aggtagatgc agtagctgtt gaagaaggtc  42360
tggtagaagt tgtaaacgag catagcgttc ttgagtccga aaggttgaga tctgttctgc  42420
atgatacgct ttccgaagta gatgaagagg aggtatccaa tagttccgat agtaggtccc  42480
cagtactcaa cctgcatgaa gtaagcagga actttctcag aagctgggat atcagggtta  42540
gccacattgt aggtaacgta tccaagagtt ccagcaagag cagcagggat agcgatagag  42600
gccatggtat ggtaattgta aatgtaattg taatgttgtt tgttgtttgt tgttgttggt  42660
aattgttgta aaatgctctg tttgtgtcgg aaaataatgg aggaagctat gagatgtatt  42720
tgtatggatc ctcttttgtg gtccgttacg ttttacaaag catgcattta gacatgtgta  42780
tactcaaact catgcatcca tacacattgt aataaagtag tagtccactg aaagttgcca  42840
aaatagcaaa atagtacatt gcagaaatat atatactaaa ttcatatatt tcgatggaaa  42900
atttcggttt tccacttaaa ataaaatgta cgtataaact tagtcttctt ttaacgccaa  42960
aaaaaagtct acaaatttct gtctttaata ctacattatt tttgaattgt gctaaactat  43020
gattacatgt gcattaaaat ttgagggaat gtgtgttctt agatctgatt ggcataccct  43080
ctgactaatt atgggatcat gagtatttct cgggaatgtg tttattcgca agtctattct  43140
ctaacctcag taaataatga gtggaagttt agttaaggcc aaatagtcta aaatatatta  43200
tttgtagttt tgtacacagc caggattgaa tcttaagaga ctctttaagt ctaaaattac  43260
aatcagatcc tagaccactt tctatttgca tgaacgtaac cggatactga ttttttaaat  43320
gttttctttg gttcaaaatc gccactatct ttgacaaaaa cattctcgaa taggattcaa  43380
acctaagagc ctttcaaatt cgttcttaat tatgtcatca tctttagttc tgctcccatc  43440
tctcatcggt ctcaagaacc actcctagtc atttaagtac tacgttttat acacattaca  43500
tatacataca tttacacaac taggaattga gtagggaaca aagtttcaac tttcaactaa  43560
tagggtaagc cttctggtac atggaaacca accaaccaat ctactagggt accctcaagc  43620
atacggacaa gggtaaataa catagtcacc agaacataat aaacaaaaag tgcagaagca  43680
agactaaaaa aattagctat ggacattcag gttcatattg gaaacatcat tatcctagtc  43740
ttgtgaccat ccttcctcct gctctagttg agaggcttg ggactaacga gaggtcagtt  43800
gggatagcag atccttatcc tggactagcc tttctggtgt tcagagtct tcgtgccgcc  43860
gtctacatct atctccatta ggtctgaaga tgactcttca caccaacgac gtttaaggtc  43920
tctatcctac tcctagcttg caatacctgg cttgcaatac ctggagcatc gtgcacgatg  43980
attggatact gtggaggagg agtgtttgct gatttagagc tcccggttgg gtgatttgac  44040
ttcgatttca gttaggctt gttgaaattt tcaggttcc attgtgaagc ctttagagct  44100
tgagcttcct tccatgttaa tgccttgatc gaatactcct agagaaaagg gaagtcgatc  44160
```

| | |
|---|---|
| tctgagtatt gaaatcgaag tgcacatttt ttttcaacgt gtccaatcaa tccacaaaca | 44220 |
| aagcagaaga caggtaatct ttcatactta tactgacaag taatagtctt accgtcatgc | 44280 |
| ataataacgt ctcgttcctt caagaggggt tttccgacat ccataacgac ccgaagcctc | 44340 |
| atgaaagcat tagggaagaa cttttggttc ttcttgtcat ggcctttata ggtgtcagcc | 44400 |
| gagctcgcca attcccgtcc gactggctcc gcaaaatatt cgaacggcaa gttatggact | 44460 |
| tgcaaccata actccacggt attgagcagg acctattgtg aagactcatc tcatggagct | 44520 |
| tcagaatgtg gttgtcagca aaccaatgac cgaaatccat cacatgacgg acgtccagtg | 44580 |
| ggtgagcgaa acgaaacagg aagcgcctat ctttcagagt cgtgagctcc acaccggatt | 44640 |
| ccggcaacta cgtgttgggc aggcttcgcc gtattagaga tatgttgagg cagacccatc | 44700 |
| tgtgccactc gtacaattac gagagttgtt ttttttgtga ttttcctagt ttctcgttga | 44760 |
| tggtgagctc atattctaca tcgtatggtc tctcaacgtc gtttcctgtc atctgatatc | 44820 |
| ccgtcatttg catccacgtg cgccgcctcc cgtgccaagt ccctaggtgt catgcacgcc | 44880 |
| aaattggtgg tggtgcgggc tgccctgtgc ttcttaccga tgggtggagg ttgagtttgg | 44940 |
| gggtctccgc ggcgatggta gtgggttgac ggtttggtgt gggttgacgg cattgatcaa | 45000 |
| tttacttctt gcttcaaatt ctttggcaga aaacaattca ttagattaga actggaaacc | 45060 |
| agagtgatga gacggattaa gtcagattcc aacagagtta catctcttaa gaaataatgt | 45120 |
| aaccccttta gactttatat atttgcaatt aaaaaaataa tttaacttttt agactttata | 45180 |
| tatagtttta ataactaagt ttaaccactc tattatttat atcgaaacta tttgtatgtc | 45240 |
| tccctctaa ataaacttgg tattgtgttt acagaaccta taatcaaata atcaatactc | 45300 |
| aactgaagtt tgtgcagtta attgaaggga ttaacggcca aaatgcacta gtattatcaa | 45360 |
| ccgaatagat tcacactaga tggccatttc catcaatatc atcgccgttc ttcttctgtc | 45420 |
| cacatatccc ctctgaaact tgagagacac ctgcacttca ttgtccttat tacgtgttac | 45480 |
| aaaatgaaac ccatgcatcc atgcaaactg aagaatggcg caagaaccct tcccctccat | 45540 |
| ttcttatgtg gcgaccatcc atttcaccat ctcccgctat aaaacacccc catcacttca | 45600 |
| cctagaacat catcacactact tgcttatcca tccaaaagat acccacttaa ttaattttac | 45660 |
| aacaattacc aacaacaaca aacaacaaac aacattacaa ttacatttac aattaccata | 45720 |
| ccatgtgccc tcctaagact gatggaagat cttctcctag atctccactt accaggtcta | 45780 |
| aatcttctgc tgaggctctt gatgctaagg atgcttctac tgctcctgtt gatcttaaga | 45840 |
| ctcttgagcc tcatgagctt gctgctactt tcgagactag atgggttaga gttgaggacg | 45900 |
| ttgagtacga tgtgactaac ttcaagcacc ctggtggatc tgtgatcttc tacatgcttg | 45960 |
| ctaacactgg tgctgatgct actgaggctt tcaaagaatt ccacatgcgt tctctcaagg | 46020 |
| cttggaagat gcttagagct ttgccttcta gacctgctga gatcaagaga tctgagtctg | 46080 |
| aggatgctcc tatgcttgag gatttcgcta gatggcgtgc tgagcttgag agagatggat | 46140 |
| tcttcaagcc ttctatcacc catgtggctt acagacttct cgagcttctt gctacattcg | 46200 |
| ctcttggaac tgctcttatg tacgctggat accctatcat tgcttctgtt gtttacggtg | 46260 |
| cttttcttcgg agctagatgt ggatgggttc aacatgaggg tggacataac tctcttaccg | 46320 |
| gatctgttta cgtggacaag agacttcagg ctatgacttg tggattcgga cttttctactt | 46380 |
| ctggtgagat gtggaaccag atgcataaca agcaccatgc taccccctcaa aaggttagac | 46440 |
| acgatatgga tcttgatacc actcctgctg tggcttcttt caacactgct gttgaggata | 46500 |
| acagacctag aggattctct agagcttggg ctagacttca agcttggact ttcgttcctg | 46560 |

```
ttacctctgg acttcttgtt caagctttct ggatctacgt tctccaccct agacaagttc    46620
tccgtaagaa gaactacgaa gaggcttctt ggatgctcgt ttctcatgtt gttagaaccg    46680
ctgttatcaa gcttgctact ggatactctt ggcctgttgc ttactggtgg ttcactttcg    46740
gaaactggat cgcttacatg taccttttcg ctcacttctc tacttctcat actcacctcc    46800
ctgttgttcc atctgataag cacctttctt gggttaacta cgctgttgat cacaccgttg    46860
atatcgatcc ttctagagga tacgtgaact ggcttatggg ataccttaac tgtcaggtta    46920
tccaccacct cttccctgat atgcctcaat tcagacagcc tgaggttagc agaagattcg    46980
ttcctttcgc taagaagtgg ggactcaact acaaggtgct ctcttactac ggtgcttgga    47040
aggctacttt ctctaacctt gataaggtgg gacagcacta ctacgttaac ggaaaggctg    47100
agaaggctca ctaatgatta attaacaagc ttatgtgacg tgaaataata acggtaaaat    47160
atatgtaata ataataataa taaagccaca aagtgagaat gaggggaagg ggaaatgtgt    47220
aatgagccag tagccggtgg tgctaatttt gtatcgtatt gtcaataaat catgaatttt    47280
gtggttttta tgtgtttttt taaatcatga attttaaatt ttataaaata atctccaatc    47340
ggaagaacaa cattccatat ccatgcatgg atgtttcttt acccaaatct agttcttgag    47400
aggatgaagc atcaccgaac agttctgcaa ctatccctca aaagctttaa aatgaacaac    47460
aaggaacaga gcaacgttcc aaagatccca aacgaaacat attatctata ctaatactat    47520
attattaatt actactgccc ggaatcacaa tccctgaatg attcctatta actacaagcc    47580
ttgttggcgg cggagaagtg atcggcgcgg cgagaagcag cggactcgga gacgaggcct    47640
tggaagatct gagtcgaacg ggcggtaccg cggccgcaag ctttccgcgg ggcgcccgtt    47700
ttacaacgtc gtgactggga gatccactag cagattgtcg tttcccgcct tcagtttaaa    47760
ctatcagtgt ttgaaggaca gacccaccca agaacacacc agtcattcag atgcagccta    47820
tctccgtgcc ggctattcca gctgatgagt tgaaggatat aactgataac tatggttcca    47880
agtccttgat tggtgagggc tcttatggaa gagtgtttta cggtgttctt agaagcggca    47940
aggcagctgc cattaagaag ctggattcta gtaagcagcc tgatcaagag tttctcgcac    48000
aggtacaaat gctacttaag taaatcaaac cgttaaagtt gagttgctgc ttagttactg    48060
atgtaaataa tgttaattag gtatcaatgg tttcgagatt gagacaagac aatgttgttg    48120
cacttctggg atattgcgtt gatggcccac tccgtgttct tgcttatgag tttgctccta    48180
atggatctct tcatgatatt cttcatggta agttattaag tctaaaacat tgattcggta    48240
cgacttgtag atgtgaagct attaactaat gaaatgtggt gagtttgttg ggtgtaggta    48300
ggaaaggagt gaaaggagca cagccaggac ctgttctgtc gtggaaccag agagttaaaa    48360
ttgctgttgg tgcggctagg ggactcgagt acttgcatga gaaggcgaac cctcatgttg    48420
tccaccgaga catcaaatcc agcaatgtgc ttttgtttga cgatgatgtt gccaagattg    48480
ctgacttcga tctgtctaac caagcccctg acatggctgc tcgccttcac tcaactcgtg    48540
tgctgggaac ctttggttat cacgctccag agtaagccct ttacttgttt atttgaattg    48600
tttttgttca gactaatcaa tgtggttaca ttcaacttgt gctcaaagac ttttggttat    48660
tattatctta tgttttgagg cactaagtcc ttccttggaa taatctttga cattattttg    48720
gattgcatct cttctaattg accatactag agtcttaaac acaaacattt ttgttttggt    48780
tctgcatttt caggtatgca atgacaggga cattgagcac aaagagtgat gtctatagtt    48840
ttggagttgt tctgctagag ctcctcacag gtcgtaagcc agttgatcat accttaccac    48900
```

```
gaggacagca gagtctcgtt acatgggtaa tgcttagtgc agctctgctt cttttttctg    48960
gtttactcat attgagaaga aaagggaatg tgtctgcaca atcatgttga ttttgtgaga    49020
gattagataa actcattatt aaatgaaaac gcgtttgtgt gtgtgtatca ggcaactcct    49080
aaactgagtg aagacaaggt gaagcaatgc gttgatgcaa gactaaacgg agaatatcct    49140
cccaaagctg ttgccaaggt aacctttgt catagtgtcg ttgtgtcagt agagaaggtt     49200
taccttagga cacgacttag aaactgcttc tccatcactt ccatcgtttt cggttccttc    49260
ttaatgtatc cctgttgtag gcctagattg aaatacaagt ctcttctaag gacaatagaa    49320
cctaagcatt gatgtatgat ttttttggga gtctgatttt ggtttttct ctcttatatg     49380 actccggtaa tgatcagctg gctgctgtag ctgcgctatg tgtgcaatac gaagcagact    49440
tcaggccaaa catgagcata gtggtgaagg ctcttcagcc tctcctcaat cctcctcgct    49500
ctgctcctca aactcctcac aggaacaatc cttattgatg tcctccaatc tgatgccacg    49560
cttcttcatc atatcactta tttcatttgt ttttgtttga atccaatttg tgtaaattcg    49620
tgaaaatagg cttttattt ctcacaatag acatgaaagt ctcacttcca aacctgaatg     49680
gtgttgctct atttgtttat gttatttcat gcctgcgatt gtaagtttct actaattata    49740
caatatgcga ggaatggatt attcataata tactcattgt gtttgtgcc               49789

<210> SEQ ID NO 42
<211> LENGTH: 18
<212> TYPE: DNA
<213> ORGANISM: Artificial Sequence
<220> FEATURE:
<223> OTHER INFORMATION: Junction at 5' end of transgene

<400> SEQUENCE: 42
tggaggtgtt caaacact                                                  18

<210> SEQ ID NO 43
<211> LENGTH: 18
<212> TYPE: DNA
<213> ORGANISM: Artificial Sequence
<220> FEATURE:
<223> OTHER INFORMATION: Junction of 5' end of 4-transgene-insert on
      chr. A02.

<400> SEQUENCE: 43
tggaggtgtt caaacact                                                  18

<210> SEQ ID NO 44
<211> LENGTH: 18
<212> TYPE: DNA
<213> ORGANISM: Artificial Sequence
<220> FEATURE:
<223> OTHER INFORMATION: Junction of 3' end of 4-trangene-insert and
      chr. A02

<400> SEQUENCE: 44
atagtattag tatacaga                                                  18

<210> SEQ ID NO 45
<211> LENGTH: 18
<212> TYPE: DNA
<213> ORGANISM: Artificial Sequence
<220> FEATURE:
<223> OTHER INFORMATION: Junction of  5' end of 16-transgene insert in
      chr. A05

<400> SEQUENCE: 45
```

```
ggctaaggta acactgat                                                     18
```

<210> SEQ ID NO 46
<211> LENGTH: 18
<212> TYPE: DNA
<213> ORGANISM: Artificial Sequence
<220> FEATURE:
<223> OTHER INFORMATION: Junction of 3' end of 16-transgene insert and
      chr. A05

<400> SEQUENCE: 46

```
cagtgtttga aggacaga                                                     18
```

<210> SEQ ID NO 47
<211> LENGTH: 470
<212> TYPE: DNA
<213> ORGANISM: Artificial Sequence
<220> FEATURE:
<223> OTHER INFORMATION: 470 bp chimeric 5' junction of transgenic
      insert and Brassica chr. A02

<400> SEQUENCE: 47

```
cattgagcag tgaacaccaa ggataaatat ttactgatta gtgtgtgatt gaatcaaaga       60
aaggttagaa tctggttttc atttagccat tcaatctcga tgtaaaatcg gttagattct     120
ggttgttgat acttgagaac ttgaaatgtt ttgtaactgt gaattttgtt ttgaaaatag     180
acaagtgaat ctgtttgggg ttgtgtgaaa acgtgtgagc aattgttgga ggtgttcaaa     240
cactgatagt ttaaactgaa ggcgggaaac gacaatctgc tagtggatct cccagtcacg     300
acgttgtaaa acgggcgccc cgcggaaagc ttgcggccgc ggtaccgccc gttcgactca     360
gatcttccaa ggcctcgtct ccgagtccgc tgcttctcgc cgcgccgatc acttctccgc     420
cgccaacaag gcttgtagtt aataggaatc attcagggat tgtgattccg                470
```

<210> SEQ ID NO 48
<211> LENGTH: 470
<212> TYPE: DNA
<213> ORGANISM: Artificial Sequence
<220> FEATURE:
<223> OTHER INFORMATION: 470 bp chimeric 3' junction of transgenic
      insert and Brassica chr. A02

<400> SEQUENCE: 48

```
ttgaatggtg gccaaaaatt aaaacgatgg atatgaccta catagtgtag gatcaattaa       60
cgtcgaagga aaatactgat tctgcccgtt cgactcagat cttccaaggc ctcgtctccg     120
agtccgctgc ttctcgccgc gccgatcact tctccgccgc caacaaggct tgtagttaat     180
aggaatcatt cagggattgt gattccgggc agtagtaatt aataatatag tattagtata     240
cagaacctct tatttagcta aaagattatg ttcttaatgt tgataagaag tttgagaaac     300
aaatataatt gagcttctga ttagttgatc gtaattggtc attaataatt gtatctaacc     360
agtgcagtat aagagcgtat aagagcatct tcaaaaagac tttatttag agttaatcag     420
tgcagtataa gagcatctct aaaaaaactc taattataga gttttgcaaa                470
```

<210> SEQ ID NO 49
<211> LENGTH: 470
<212> TYPE: DNA
<213> ORGANISM: Artificial Sequence
<220> FEATURE:
<223> OTHER INFORMATION: 470 bp chimeric 5' junction of transgene insert
      and chr. A05

<400> SEQUENCE: 49

```
cttgttccgc aacaccgtta ctgaactctt cgttcactta aacagtttgt gtgtgtgaga      60
aacagcgtaa tgagctgctt tggttgttgt ggtggtgacg attttcgtcg agttgctgaa     120
actggaccca agccagtgta cggcgcagga ggtactttaa gcttataacc ctttgtctat     180
cctttggcta gcggctaatg ttgatgaact tttttattca accgttggct aaggtaacac     240
tgatagttta aactgaaggc gggaaacgac aatctgctag tggatctccc agtcacgacg     300
ttgtaaaacg gccgcccgc ggaaagcttg cggccgcggt accgcccgtt cgactcagat      360
cttccaaggc ctcgtctccg agtccgctgc ttctcgccgc gccgatcact tctccgccgc     420
caacaaggct tgtagttaat aggaatcatt cagggattgt gattccgggc               470
```

<210> SEQ ID NO 50
<211> LENGTH: 470
<212> TYPE: DNA
<213> ORGANISM: Artificial Sequence
<220> FEATURE:
<223> OTHER INFORMATION: 470 bp chimeric 3' junction of transgene insert
      and chr. A05

<400> SEQUENCE: 50

```
ttattaatta ctactgcccg gaatcacaat ccctgaatga ttcctattaa ctacaagcct      60
tgttggcggc ggagaagtga tcggcgcggc gagaagcagc ggactcggag acgaggcctt     120
ggaagatctg agtcgaacgg gcggtaccgc ggccgcaagc tttccgcggg cgcccgtttt     180
tacaacgtcg tgactgggag atccactagc agattgtcgt ttcccgcctt cagttaagga     240
cagacccacc caagaacaca ccagtcattc agatgcagcc tatctccgtg ccggctattc     300
cagctgatga gttgaaggat ataactgata actatggttc caagtccttg attggtgagg     360
gctcttatgg aagagtgttt tacggtgttc ttagaagcgg caaggcagct gccattaaga     420
agctggattc tagtaagcag cctgatcaag agtttctcgc acaggtacaa               470
```

<210> SEQ ID NO 51
<211> LENGTH: 24
<212> TYPE: DNA
<213> ORGANISM: Artificial Sequence
<220> FEATURE:
<223> OTHER INFORMATION: Forward primer for amplicon diagnostic for
      NS-B50027-4

<400> SEQUENCE: 51

```
aattgttgga ggtgttcaaa cact                                             24
```

<210> SEQ ID NO 52
<211> LENGTH: 24
<212> TYPE: DNA
<213> ORGANISM: Artificial Sequence
<220> FEATURE:
<223> OTHER INFORMATION: Reverse primer for amplicon diagnostic for
      NS-B50027-4

<400> SEQUENCE: 52

```
cggaatcaca atccctgaat gatt                                             24
```

<210> SEQ ID NO 53
<211> LENGTH: 20
<212> TYPE: DNA
<213> ORGANISM: Artificial Sequence
<220> FEATURE:
<223> OTHER INFORMATION: Sense primer for detection of codon-optimized
      delta12-desaturase

<400> SEQUENCE: 53
tggagctatc cctcatgagt                                                    20

<210> SEQ ID NO 54
<211> LENGTH: 21
<212> TYPE: DNA
<213> ORGANISM: Artificial Sequence
<220> FEATURE:
<223> OTHER INFORMATION: Antisense primer for detection of
      codon-optimized delta12-desaturase

<400> SEQUENCE: 54
gatcctagaa cagtagtggt g                                                  21

<210> SEQ ID NO 55
<211> LENGTH: 21
<212> TYPE: DNA
<213> ORGANISM: Artificial Sequence
<220> FEATURE:
<223> OTHER INFORMATION: Sense primer for detecting codon-optimized
      delta15/omega3-desaturase

<400> SEQUENCE: 55
gacgctatcc ctaagcactg t                                                  21

<210> SEQ ID NO 56
<211> LENGTH: 20
<212> TYPE: DNA
<213> ORGANISM: Artificial Sequence
<220> FEATURE:
<223> OTHER INFORMATION: Antisense primer for detecting codon-optimized
      delta15/omega3-desaturase

<400> SEQUENCE: 56
gtccactctt gagcatcgta                                                    20

<210> SEQ ID NO 57
<211> LENGTH: 21
<212> TYPE: DNA
<213> ORGANISM: Artificial Sequence
<220> FEATURE:
<223> OTHER INFORMATION: Sense primer for detecting codon-optimized
      delta6-desaturase

<400> SEQUENCE: 57
gagcaccttg tagttgagtc c                                                  21

<210> SEQ ID NO 58
<211> LENGTH: 21
<212> TYPE: DNA
<213> ORGANISM: Artificial Sequence
<220> FEATURE:
<223> OTHER INFORMATION: Antisense primer for detecting codon-optimized
      delta6-desaturase

<400> SEQUENCE: 58
agtctgagga tgctcctatg c                                                  21

<210> SEQ ID NO 59
<211> LENGTH: 20
<212> TYPE: DNA
<213> ORGANISM: Artificial Sequence
<220> FEATURE:
<223> OTHER INFORMATION: Sense primer for detecting codon-optimized
      delta6-elongase

<400> SEQUENCE: 59
tgttgctatg gctcaagagc                                           20

<210> SEQ ID NO 60
<211> LENGTH: 20
<212> TYPE: DNA
<213> ORGANISM: Artificial Sequence
<220> FEATURE:
<223> OTHER INFORMATION: Antisense prmer for detecting codon-optimized
      delta6-elongase

<400> SEQUENCE: 60
ctagcgtggt gcttcatgta                                           20

<210> SEQ ID NO 61
<211> LENGTH: 20
<212> TYPE: DNA
<213> ORGANISM: Artificial Sequence
<220> FEATURE:
<223> OTHER INFORMATION: Sense primer for detection codon-optimized
      delta5-desaturase

<400> SEQUENCE: 61
gctaccgatg cttacaagca                                           20

<210> SEQ ID NO 62
<211> LENGTH: 20
<212> TYPE: DNA
<213> ORGANISM: Artificial Sequence
<220> FEATURE:
<223> OTHER INFORMATION: Antisense primer for detecting codon-optimized
      delta5-desaturase

<400> SEQUENCE: 62
tagtgaagtc cgtgcttctc                                           20

<210> SEQ ID NO 63
<211> LENGTH: 20
<212> TYPE: DNA
<213> ORGANISM: Artificial Sequence
<220> FEATURE:
<223> OTHER INFORMATION: Sense primer for detection of delta5-elongase

<400> SEQUENCE: 63
tgctggaact cttggatacg                                           20

<210> SEQ ID NO 64
<211> LENGTH: 20
<212> TYPE: DNA
<213> ORGANISM: Artificial Sequence
<220> FEATURE:
<223> OTHER INFORMATION: Antisense primer for detection of
      codon-optimized delta5-elongase

<400> SEQUENCE: 64
ctgggtgatg tacttcttcc                                           20

<210> SEQ ID NO 65
<211> LENGTH: 20
<212> TYPE: DNA
<213> ORGANISM: Artificial Sequence
<220> FEATURE:
<223> OTHER INFORMATION: Sense primer for detecting codon-optimized
      delta4-desaturase

<400> SEQUENCE: 65
ggctttcaga tctgagcatc                                           20

```
<210> SEQ ID NO 66
<211> LENGTH: 20
<212> TYPE: DNA
<213> ORGANISM: Artificial Sequence
<220> FEATURE:
<223> OTHER INFORMATION: Antisense primer for detecting codon-optimized
      delta4-desaturase

<400> SEQUENCE: 66
ctcagcctta acaagaggag                                                    20
```

ELITE EVENT CANOLA NS-B50027-4

RELATED APPLICATION

This Application claims priority benefit of U.S. Provisional Application No. 62/351,246, filed Jun. 16, 2016, which is incorporated fully herein for all purposes.

SEQUENCE LISTING

The instant application contains a Sequence Listing which has been submitted in ASCII format via EFS-Web and is hereby incorporated by reference in its entirety.

FIELD

The present embodiments relate to the field of canola breeding and agricultural products, specifically to elite event NS-B50027-4.

BACKGROUND

Canola is an important oil crop in many areas of the world. The fatty acid composition of canola oil is rich in both mono-unsaturated and polyunsaturated fatty acids including short chain omega-3, but lacks in long-chain omega-3 fatty acids. Long chain omega-3 (LC-ω3) fatty acids have established health benefits, but currently LC-ω3 fatty acids are obtained primarily from algae directly or from algae-eating ocean fish. Recognition of dietary LC-ω3 fatty acids, especially docosahexaenoic acid (22:6 n-3; DHA) and eicosapentaenoic acid (20:5 n-3; EPA), has contributed to a dramatic increase in the demand for consumable fish oil. Thus, there is a need for alternative, direct sources of LC-ω3 fatty acids for human consumption. Additionally, because farmed fish, such as Atlantic salmon, accumulate fatty acids in proportion to dietary fatty acids, there is a need to sustain the amount of LC polyunsaturated fatty acids (LC-PUFAs) in fish feed, and in turn ensure the presence of these fatty acids in farmed fish. Accordingly, there is a need for LC-PUFA-rich sources that can be used in aquaculture. For example, there is a need for canola that can produce LC-PUFA, particularly LC-ω3 fatty acid such as DHA, for use in aquaculture as well as for direct human consumption. Despite achievements in plant breeding and manipulation by molecular genetics, however, there are no commercial sources of canola oil that have the content of LC-PUFA approaching those produced in wild fishes. Further, a canola cultivar (not F1 hybrid) should be homogenous, homozygous, and reproducible to be useful for the production of a commercial crop on a reliable basis. Therefore, there remains a need for a canola line that can be grown as a sustainable crop, the seeds of which provide commercially viable amounts of LC-ω3 fatty acids such as DHA.

SUMMARY

The embodiments described herein provide an inbred recombinant canola line, designated NS-B50027-4, the seeds of which comprise advantageous levels of ω3 and LC-ω3 fatty acid, thus providing a renewable, land-based system to produce these valuable oils. A representative sample of seeds of inbred canola line NS-B50027-4 was deposited according to the Budapest Treaty at the American Type Culture Collection (ATCC®) (Manassas, Va.) on Jun. 9, 2016, and assigned Accession Number PTA-123186 (see Appendix A). Also described herein are cells, tissues, seeds, and oil of inbred canola line NS-B50027-4. The combination of selection and breeding with transgenic manipulation enables variation in a species where that variation does not exist. For example, the fatty acid profile of canola line NS-B50027-4 described herein does not exist in native *B. napus*; and the traits described herein, particularly the advantageous trait of producing DHA, were developed with significant technical intervention by man.

An aspect of the present embodiments provides seed of canola (*Brassica napus* L.) line NS-B50027-4, a genetically modified canola of cultivar AV Jade that was selected and bred to a stable, uniform breeding line that accumulates in its seeds a high proportion (percent) of ω3 and LC-ω3 fatty acids relative to the total fatty acid content. Inbred line NS-B50027-4 was developed to provide canola plants that produce seeds comprising LC-ω3 fatty acids, particularly DHA, at levels approaching those found in some wild fish oil. Edible oil derived from NS-B50027-4 has significantly higher DHA content than other *B. napus* plants. The novel, uniform breeding line NS-B50027-4 was developed by genetic transformation, followed by rigorous selection and breeding for the high DHA trait in a stable, high-yielding, morphologically fit canola line.

Accordingly, at least one embodiment described herein relates to the seeds of inbred canola line NS-B50027-4; to the plants cultivated from the seeds of inbred canola line NS-B50027-4, and parts thereof, such as pollen, ovule, or seed; and to methods for producing seed from a canola plant by cultivating inbred canola line NS-B50027-4, or by crossing inbred canola line NS-B50027-4 with itself or with another canola or *Brassica* line and obtaining seed from the cultivated progeny.

At least one embodiment provides seed from a population of canola plants produced by the method described herein, said population deriving, on average, 10% to 100% of its alleles from canola line NS-B50027-4. Similarly, the present embodiments provide use of canola line NS-B50027-4, a sub-line of NS-B50027-4, progeny of NS-B50027-4 or the sub-line, or a plant produced by crossing NS-B50027-4 with a second canola or *Brassica* plant, for breeding, or for cultivating a plant for seed, oil, meal, or protein production.

At least one embodiment provides a seed of an oilseed rape plant, such as a *Brassica napus* plant, comprising in its genome at least a portion of the genome of inbred line NS-B50027-4. At least one embodiment provides a plant, such as a *B. napus* plant, comprising in its genome at least a portion of the genome of inbred line NS-B50027-4. At least one embodiment provides a cell of an oilseed rape plant, such as a *B. napus* plant, comprising in its genome at least a portion of the genome of inbred line NS-B50027-4. Another embodiment provides a genomic DNA of an oilseed rape plant, such as a *B. napus* plant, comprising the at least a portion of the genome of line NS-B50027-4. At least one embodiment further relates to seeds, cells, tissues, tissue cultures, progeny, and descendants from a plant comprising at least a portion of the genome of NS-B50027-4 grown from seed deposited at the ATCC® having Accession No. PTA-123186. Another embodiment further provides plants obtainable from (such as by propagation of or breeding with) a canola plant comprising at least a portion of the genome of NS-B50027-4 (such as a plant grown from the seed deposited at the ATCC® having Accession No. PTA-123186).

At least one embodiment provides a seed of an oilseed rape plant, such as a *B. napus* plant, comprising in its genome the elite event of line NS-B50027-4. At least one embodiment provides a plant, such as a *B. napus* plant, comprising in its genome the elite event of inbred line NS-B50027-4. Another embodiment provides a genomic DNA of an oilseed rape plant, such as a *B. napus* plant, comprising the elite event of line NS-B50027-4. At least one embodiment further relates to seeds, cells, tissues, progeny, and descendants from a plant comprising the elite event of NS-B50027-4 grown from seed deposited at the ATCC® having Accession No. PTA-123186. Another embodiment further provides plants obtainable from (such as by propagation of or breeding with) a canola plant comprising the elite event (such as a plant grown from the seed deposited at the ATCC® having Accession No. PTA-123186. The embodiments also relate to canola plants comprising elite event NS-B50027-4.

Reference seed of inbred line NS-B50027-4 of the present embodiments has been deposited with ATCC® under Accession No. PTA-123186. At least one embodiment provides the seed of NS-B50027-4 deposited as Accession No. PTA-123186, which grows into a canola plant the seed of which, at conventional harvest, comprises at least 5% DHA, about 6% DHA, about 7% DHA, about 8% DHA, about 9% DHA, about 10% DHA, about 11% DHA, about 12% DHA, about 13% DHA, about 14% DHA, about 15% DHA, about 16% DHA, about 17% DHA, inclusive, or more DHA, as wt. % of the total fatty acids of the seed.

In at least one embodiment, the seed of ATCC® Accession No. PTA-123186 is a seed lot consisting of at least about 95% inbred transgenic seeds having the transgenes of elite event of NS-B50027-4, that grow into a canola plant the seed of that comprises at least 5% DHA, about 6% DHA, about 7% DHA, about 8% DHA, about 9% DHA, about 10% DHA, about 11% DHA, about 12% DHA, about 13% DHA, about 14% DHA, about 15% DHA, about 16% DHA, about 17% DHA, inclusive, or more DHA, as wt. % of the total fatty acids of the seed. The seed of ATCC® deposit Accession No. PTA-123186 is a seed lot consisting of at least about 95% transgenic seeds homozygous for the transgene DNA, comprising the elite event of NS-B50027-4, that grow into a canola plant the seed of which comprises at least 5% LC-PUFA, about 6% LC-PUFA, about 7% LC-PUFA, about 8% LC-PUFA, about 9% LC-PUFA, about 10% LC-PUFA, about 11% LC-PUFA, about 12% LC-PUFA, about 13% LC-PUFA, about 14% LC-PUFA, about 15% LC-UFA, about 16% LC-PUFA, about 17% LC-PUFA, about 18% LC-PUFA, about 19% LC-PUFA, about 20% LC-PUFA, about 21% LC-PUFA, inclusive, or more LC-PUFA, as the sum of EPA, DPA, and DHA as wt. % of the total fatty acids of the seed.

In another embodiment, the seed or progeny seed obtainable or obtained from the deposited seed (e.g., following crossing with a canola or *Brassica* plant with the same or a different genetic background) can be sown, and the growing plants may have substantially the same phenotype as that of NS-B50027-4. In at least one embodiment, at conventional harvest the fatty acid content of NS-B50027-4-progeny seed comprises at least 5% DHA, about 6%, about 7% DHA, about 8% DHA, about 9% DHA, about 10% DHA, about 11% DHA, about 12% DHA, about 13% DHA, about 14% DHA, about 15% DHA, about 17% DHA, about 18% DHA, about 19% DHA, about 20% DHA, about 21% DHA, about 22% DHA, about 23% DHA, about 24% DHA, inclusive, or more DHA, as wt. % of the total fatty acids of the seed. In at least one embodiment, at conventional harvest the fatty acid content of NS-B50027-4 progeny seed comprises at least 5% LC-PUFA, about 6% LC-PUFA, about 7% LC-PUFA, about 8% LC-PUFA, about 9% LC-PUFA, about 10% LC-PUFA, about 11% LC-PUFA, about 12% LC-PUFA, about 13% LC-PUFA, about 14% LC-PUFA, about 15% LC-UFA, about 16% LC-PUFA, about 17% LC-PUFA, about 18% LC-PUFA, about 19% LC-PUFA, about 20% LC-PUFA, about 21% LC-PUFA, about 22% LC-PUFA, about 23% LC-PUFA, about 24% LC-PUFA, about 25% LC-PUFA, inclusive, or more LC-PUFA, as the sum of EPA, DPA, and DHA as wt. % of the total fatty acids of the seed.

The seed of NS-B50027-4 also contains substantially more ω3 ALA than conventional canola varieties. In at least one embodiment, at conventional harvest the fatty acid content of NS-B50027-4 progeny seed comprises at least 15% ALA, about 16% ALA, about 17% ALA, about 18% ALA, about 19% ALA, about 20% ALA, about 21% ALA, about 22% ALA, about 23% ALA, about 24% ALA, inclusive, or more ALA as wt. % of the total fatty acids of the seed.

Another aspect of the present embodiments provides oil with advantageous ω3 fatty acid and LC-ω3 fatty acid levels, in which the fatty acid content contains a higher ratio of ω3:ω6 fatty acid than that of regular canola oil. For example, AV Jade has no EPA/DPA/DHA(ω3) to compare with LA(ω6), in one embodiment seed oil from NS-B50027-4 has an EPA/DPA/DHA(ω3):LA(ω6) ratio of about 1 to about 7, such as about 1.25. The ratio of ω3:ω6 fatty acid from NS-B50027-4 is particularly advantageous regarding palmitic acid. Oil from the parent line AV Jade has no DHA, and thus no DHA:palmitate ratio; oil from NS-B50027-4 has a DHA:palmitate ratio of, for example, about 2.12; oil from farm-raised salmon, in comparison, has a reported DHA:palmitate ratio of 0.59; and oil from wild salmon has a reported DHA:palmitate ratio of 1.02. In at least one embodiment, the ratio of ω3:ω6 fatty acid in seed oil of NS-B50027-4 is about 3 to about:7, such as a ratio of about 6.

In another aspect of the present embodiments, oil, lipid, ω3-FA, LC-PUFA, or DHA from inbred line NS-B50027-4 seed is used as or in a foodstuff (food or edible material including beverages) or as nutritional supplements (food additives) for humans or animals. In at least one embodiment, oil, lipid, ω3-FA, LC-PUFA, or DHA from event NS-B50027-4 seed is used to supplement feed or as a feed additive for use in aquaculture. In at least one embodiment, oil, lipid, ω3-FA, LC-PUFA, or DHA from event NS-B50027-4 seed is used as or in a pharmaceutical composition. In at least one other embodiment, the seed meal or protein obtained of concentrated from the seed of NS-B50027-4 or its progeny is as or in a foodstuff (food or edible material) or as nutritional supplements (food additives) for humans or animals. In particular embodiments, oil, lipids, meal, or proteins from seed of NS-B50027-4 or its progeny is used as feed for aquaculture.

An aspect of the present embodiments provides a method of increasing the LC-PUFA in a plant by providing (e.g., by genetic transformation or breeding) the plant with multiple copies of genetic constructs expressing some enzymes of the "front end" of the LC-PUFA biosynthetic pathway. For example, although not all of the enzymes Δ6-desaturases, Δ5-desaturases, Δ5-elongases, and ω3/Δ15-desaturases may be considered exclusively as the front end enzymes, in particular embodiments these genes are assembled into an artificial locus that enhances the production of LC-PUFA, such as DHA, in a plant that produces LC-PUFA. In particular embodiments, the artificial locus comprising some front end genes includes *Micromonas pusilla*-derived Δ6-desaturase, *Pyramimonas cordata*-derived Δ5-elongase, *Pavlova salina*-derived Δ5-desaturase, and *Pichia pastoris*-derived Δ15/ω3-desaturase.

An aspect of the described embodiments provides a new canola breeding line, designated NS-B50027-4, and an oilseed rape plant, such as *Brassica napus* L., comprising in its nuclear genome the elite event of NS-B50027-4. *Brassica* plants comprising the genetic event of line NS-B50027-4 are capable of seed-specific production of fatty acids that comprise more unsaturated, longer chains than the fatty acids produced in conventional canola plants. Inbred canola line NS-B50027-4 plants exhibit other agronomic performance traits that are substantially equivalent to non-transgenic isogenic canola plant lines; but such traits are distinct from other lines as to provide an independent line or cultivar. A representative sample of inbred canola line NS-B50027-4 seeds has been deposited at the ATCC®, Accession No. PTA-123186.

At least one embodiment relates to a transgenic canola seeds, plants or plant parts, tissues or cells thereof, having stably integrated into the genome at least one transgenic insert comprising an expression cassette comprising sixteen heterologous genes, the transgenes being codon-optimized for plant expression and encoding *Pavlova salina*-derived Δ4-desaturase, *Pavlova salina*-derived Δ5-desaturase, *Pyramimonas cordata*-derived Δ5-elongase, *Micromonas pusilla*-derived Δ6-desaturase, *Pyramimonas cordata*-derived Δ6-elongase, *Lachancea kluyveri*-derived Δ12-desaturase, *Pichia pastoris*-derived Δ15/ω3-desaturase, and at least one *Nicotiana tabacum*-derived matrix attachment region (MAR), and a selectable marker gene; and at least one transgenic insert comprising an expression cassette four heterologous genes, the transgenes being codon-optimized for plant expression and encoding *Micromonas pusilla*-derived Δ6-desaturase, *Pyramimonas cordata*-derived Δ5-elongase, *Pavlova salina*-derived Δ5-desaturase, *Pichia pastoris*-derived Δ15/ω3-desaturase transgenes, and a least one *Nicotiana tabacum*-derived MAR. Inbred transgenic line NS-B50027-4 exemplifies this embodiment, and a representative sample of seeds with these heterologous genes has been deposited at the ATCC®, Accession No. PTA-123186.

Another aspect of the present embodiments provides isolated or purified genomic DNA obtained from inbred canola line NS-B50027-4 or canola plants comprising the elite event of line NS-B50027-4, seed of which having been deposited as ATCC Accession No. PTA-123186. Such genomic DNA may be used, for example, as reference control material in identification assays herein described. At least one embodiment provides for genome of *Brassica napus* L., having a deletion in the 3' UTR of a HPP gene located on chrUn_random of *B. napus* reference genome (2n=AACC; var. Darmor) at position 118589903-118591677, and at chromosome A02 of *B. rapa* reference genome (2n=AA, var. Chiifu) at position 18569298-18571066, wherein the deletion is GTAGCACGACAAGTT (SEQ ID NO:38). A 15-bp deletion was located on chrUn_random of *B. napus* reference genome at position 118589927-118589941 and on chromosome A02 of *B. rapa* reference genome at position 18569316-18569330. At least one embodiment provides for a *Brassica napus* L. plant having a deletion in the second exon of the gene encoding the Pto-interacting protein (PTI), located on chromosome A05 of *B. napus* reference (var. Darmor) genome at position 17267746-17270700, which deletion disrupts the expression of PTI, wherein the deletion is CACGGTGGAGGTCACCATGT (SEQ ID NO:39). These deletions are a characteristic of the genome of inbred canola line NS-B50027-4, and can be used to identify line NS-B50027-4 and progeny derived from line NS-B50027-4.

Accordingly, the present embodiments further provides methods for identifying a transgenic plant, or cells or tissues thereof, comprising the transgenic aspect (elite event) of inbred canola line NS-B50027-4, which method is based on identifying the presence of characterizing DNA molecules as having particular nucleotide sequences or encoding particular amino acids. For example, such characterizing DNA molecules comprise sequences of 15 base pairs (bp), at least 15 bp, 20 bp, at least 20 bp, at least 24 bp, at least 30 bp, or more than 30 bp that comprise the insertion junction site of the event, i.e., both a part of the inserted foreign DNA comprising LC-ω3 fatty acid synthesis genes or ("genes" including regulatory sequences for expression, etc.) and a part of the canola or *Brassica* genome (either the 5' or 3' flanking regions for each insertion) contiguous therewith, allowing specific identification of the elite event. For example, junction sequences of the 5' end of the four-gene insert in chromosome A02 of NS-B50027-4 comprise SEQ ID NO:43; junction sequences of the 3' end of the four-gene insert in chromosome A02 comprise SEQ ID NO:44; junction sequences of the 5' end of the sixteen-gene insert in chromosome A05 of NS-B50027-4 comprise SEQ ID NO:45; and the junction sequences of the 3' end of the sixteen-gene insert in chromosome A05 comprise SEQ ID NO:46. The embodiments also relate to plants comprising the elite event of inbred canola line NS-B50027-4 identified by such methods.

Another aspect of the present embodiments provides nucleic acid molecules (e.g., polynucleotides or DNA) comprising the insertion site of the NS-B50027-4 elite event and sufficient length of polynucleotides of both the canola genomic DNA and the transgenic DNA so as to be useful for the detection of the elite event of inbred line NS-B50027-4, and to characterize plants comprising the NS-B50027-4 elite event or are related to inbred line NS-B50027-4. Such molecules may comprise, for example, at least nine nucleotides of the canola genomic DNA and a similar number of nucleotides of the transgene DNA at each side of the junction site respectively. For example, such DNA molecules comprise at least nine nucleotides of the canola genomic DNA and a similar number of nucleotides of the transgene (foreign) DNA comprising genetic regions contiguous with the insertion site in SEQ ID NO:40 (e.g., nucleotides 2081 to 2098 and nucleotides 14193 to 14210), SEQ ID NO:41 (e.g., nucleotides 1151 to 1168 and nucleotides 47765 to 47782). In one aspect of the invention, canola plants are provided comprising such specific nucleic acid molecules.

At least one embodiment relates to transgenic *Brassica* or canola seed, or plant cells, plants, plant parts, or tissues thereof, having stably integrated into the genome at least one transgenic insert comprising an expression cassette(s) comprising sixteen heterologous genes, the transgenes being plant codon-optimized *Micromonas pusilla*-derived Δ6-desaturase, Δ6-elongase, *Pyramimonas cordata*-derived Δ5-elongase, *Pavlova salina*-derived Δ5-desaturase, *Pichia pastoris*-derived Δ15/ω3-desaturase, *Pavlova salina*-derived Δ4-desaturase, and *Lachancea kluyveri*-derived Δ12-desaturase, at least one *Nicotiana tabacum*-derived matrix attachment region (MAR), and a selectable marker gene; the sixteen-transgene insert characterized by nucleotides 1268 to 47773 of SEQ ID NO:41; and at least one transgenic insert comprising an expression cassette (s) of four heterologous genes, the genes being codon-optimized for plant expression and encoding *Micromonas pusilla*-derived Δ6-desaturase, *Pyramimonas cordata*-derived Δ5-elongase, *Pavlova salina*-derived Δ5-desaturase, *Pichia pastoris*-derived Δ15/ω3-desaturase transgenes, and a least one *Nicotiana tabacum*-derived MAR; the four-gene insert characterized by nucleotides 2090 to 14201 of SEQ ID NO:40. In at least one embodiment, the two expression cassettes are located in two different chromosomes in the plant genome.

Another embodiment provides a recombinant nucleic acid molecule having the nucleic acid sequence of SEQ ID NO:40, SEQ ID NO:41, or complements thereof. Another embodiment provides a recombinant nucleic acid molecule having the nucleic acid sequence of positions 2090 to 14201 of SEQ ID NO:40, or a complement thereof. Another embodiment provides a recombinant nucleic acid molecule having the nucleic acid sequence of positions 1160 to 47773 of SEQ ID NO:41, or a complement thereof. The present embodiments also provide transgenic *Brassica* or canola seeds comprising a nucleic acid molecule having the nucleic acid sequence of nucleotides 2090 to 14201 of SEQ ID NO:40, or a complement thereof; and *Brassica* or canola seeds comprising a nucleic acid molecule having the nucleic acid sequence of nucleotides 1160 to 47773 of SEQ ID NO:41, or complements thereof. Another embodiment provides seeds or cells comprising such nucleic acid molecules.

Another embodiment provides a DNA molecule comprising an artificial genetic locus comprising, in order, the following nucleotide sequences: (a) the nucleotide sequence of SEQ ID NO:40 from nucleotide 2747 to nucleotide 6250; (b) the nucleotide sequence of SEQ ID NO:40 from nucleotide 6257 to nucleotide 8414; (c) the nucleotide sequence of SEQ ID NO:40 from nucleotide 8415 to nucleotide 10374; (d) the nucleotide sequence of SEQ ID NO:40 from nucleotide 10375 to nucleotide 11544; and (e) the nucleotide sequence of SEQ ID NO:40 from nucleotide 11545 to nucleotide 14049; (f) a molecule with at least 80%, 95%, 97%, 98%, 99%, or 99.5%, sequence identity to the nucleotide sequences (a) through (e); or (g) complements thereof. A related embodiment provides plant cells, plant materials, or plant seeds comprising this artificial genetic locus.

Another embodiment provides a DNA molecule comprising an artificial genetic locus comprising, in order, the following nucleotide sequences: (a) the nucleotide sequence of SEQ ID NO:41 from nucleotide 1268 to nucleotide 5317; (b) the nucleotide sequence of SEQ ID NO:41 from nucleotide 5324 to nucleotide 7481; (c) the nucleotide sequence of SEQ ID NO:41 from nucleotide 7482 to nucleotide 9443; (d) the nucleotide sequence of SEQ ID NO:41 from nucleotide 9444 to nucleotide 10611; (e) the nucleotide sequence of SEQ ID NO:41 from nucleotide 10612 to nucleotide 13116); (f) the nucleotide sequence of SEQ ID NO:41 from nucleotide 13117 to nucleotide 17000); (g) the nucleotide sequence of SEQ ID NO:41 from nucleotide 17001 to nucleotide 19606); (h) the nucleotide sequence of SEQ ID NO:41 from nucleotide 19607 to nucleotide 29773; (i) the nucleotide sequence of SEQ ID NO:41 from nucleotide 20783 to nucleotide 22987; (j) the nucleotide sequence of SEQ ID NO:41 from nucleotide 23011 to 24370; (k) the nucleotide sequence of SEQ ID NO:41 from nucleotide 42561 to nucleotide 25920; (l) the nucleotide sequence of SEQ ID NO:41 from nucleotide 25943 to nucleotide 29324; (m) the nucleotide sequence of SEQ ID NO:41 from nucleotide 28157 to nucleotide 29324; (n) the nucleotide sequence of SEQ ID NO:41 from nucleotide 29324 to nucleotide 31830; (p) the nucleotide sequence of SEQ ID NO:41 from nucleotide 31831 to nucleotide 35816; (q) the nucleotide sequence of SEQ ID NO:41 from nucleotide 35817 to nucleotide 38319; (r) the nucleotide sequence of SEQ ID NO:41 from nucleotide 38320 to nucleotide 39488; (s) the nucleotide sequence of SEQ ID NO:41 from nucleotide 39489 to nucleotide 41449; (t) the nucleotide sequence of SEQ ID NO:41 from nucleotide 41450 to nucleotide 43607; (u) the nucleotide sequence of SEQ ID NO:41 from nucleotide 43614 to nucleotide 47662; (v) a molecule with at least 80%, 95%, 97%, 98%, 99%, or 99.5%, sequence identity to the nucleotide sequences (a) through (u), (a) through (j), (k) through (u); or (w) complements thereof. A related embodiment provides plant cells, materials, or seed comprising this artificial genetic locus.

Another embodiment provides a DNA molecule comprising an artificial genetic locus comprising, in order, the following nucleotide sequences: (a) the nucleotide sequence of SEQ ID NO:40 from nucleotide 2747 to nucleotide 4141; (b) the nucleotide sequence of the complement of the nucleotide sequence of SEQ ID NO:40 from nucleotide 7259 to nucleotide 8065; (c) the nucleotide sequence of SEQ ID NO:40 from nucleotide 8841 to nucleotide 10121; (d) the nucleotide sequence of SEQ ID NO:40 from nucleotide 12281 to nucleotide 13531; (e) a molecule with at least 80%, 95%, 97%, 98%, 99%, or 99.5%, sequence identity to the nucleotide sequences (a) through (d); or (f) complements thereof; wherein the artificial locus includes regulatory regions (e.g., promoters, leader sequences, terminators) to provide expression of (a) through (d) or (e) or (f). A related embodiment provides plant cells, plant materials, or plant seeds comprising this artificial genetic locus.

Another embodiment provides a DNA molecule comprising an artificial genetic locus comprising, in order, the following nucleotide sequences: (a) the nucleotide sequence of SEQ ID NO:41 from nucleotide 1820 to nucleotide 3208; (b) the nucleotide sequence of SEQ ID NO:41 from nucleotide 6326 to nucleotide 7126; (c) the nucleotide sequence of SEQ ID NO:41 from nucleotide 7908 to nucleotide 9192; (d) the nucleotide sequence of SEQ ID NO:41 from nucleotide 11352 to nucleotide 12596; (e) the nucleotide sequence of SEQ ID NO:41 from nucleotide 15216 to nucleotide 16556; (f) the nucleotide sequence of SEQ ID NO:41 from nucleotide 17619 to nucleotide 18866; (g) the nucleotide sequence of SEQ ID NO:41 from nucleotide 21895 to nucleotide 22647; (h) the nucleotide sequence of SEQ ID NO:41 from nucleotide 25943 to nucleotide 26283; (i) the nucleotide sequence of SEQ ID NO:41 from nucleotide 30066 to nucleotide 31313; (j) the nucleotide sequence of SEQ ID NO:41 from nucleotide 31831 to nucleotide 35816; (k) the nucleotide sequence of SEQ ID NO:41 from nucleotide 36335 to nucleotide 38319; (l) the nucleotide sequence of SEQ ID NO:41 from nucleotide 39749 to nucleotide 41023; (m) the nucleotide sequence of SEQ ID NO:41 from nucleotide 41805 to nucleotide 42605; (n) the nucleotide sequence of SEQ ID NO:41 from nucleotide 45724 to nucleotide 47111; (o) a molecule with at least 80%, 95%, 97%, 98%, 99%, or 99.5%, sequence identity to the nucleotide sequences (a) through (u), (a) through (j), (k) through (u); or (p) complements thereof; wherein the artificial locus includes regulatory regions (e.g., promoters, leader sequences, terminators) to provide expression of (a) through (n) or (o) or (p). A related embodiment provides plant cells, plant materials, or plant seeds comprising this artificial genetic locus.

In one embodiment, the transgenes of inbred line NS-B50027-4 as described herein have the nucleotide sequence of SEQ ID NO:40 from nucleotide positions 2090 to 14201, or its complement, or comprises a molecule with at least 80%, 95%, 97%, 98%, 99%, or 99.5%, sequence identity to the nucleotide sequence of SEQ ID NO:40 from nucleotide position 2090 to nucleotide position 14201, or its complement. In one embodiment, the transgenes of inbred line NS-B50027-4 as described herein have the nucleotide sequence of SEQ ID NO:41 from nucleotide positions 1268 to 47662, or its complement, or comprises a molecule with at least 80%, 95%, 97%, 98%, 99%, or 99.5%, sequence identity to the nucleotide sequence of SEQ ID NO:41 from nucleotide position 1268 to nucleotide position 47662, or its complement.

Also provided herein is a *Brassica* or canola plant, plant cell, tissue, or seed, comprising in its genome a nucleic acid molecule comprising the nucleotide sequence of SEQ ID NO:40 from nucleotide positions 2090 to 14201, or its complement, or comprises a molecule with at least 95%, 97%, 98%, 99%, or 99.5% sequence identity to the nucleotide sequence of SEQ ID NO:40 from nucleotide position 2090 to nucleotide position 14201, or its complement. Another embodiment provides a *Brassica* or canola plant, plant cell, tissue, or seed, comprising in its genome a nucleic acid molecule comprising the nucleotide sequence of SEQ ID NO:41 from nucleotide positions 1268 to 47662, or its complement, or comprises a molecule with at least 80%, 95%, 97%, 98%, 99%, or 99.5%, sequence identity to the nucleotide sequence of SEQ ID NO:41 from nucleotide position 1268 to nucleotide position 47662, or its complement.

Another aspect of the present embodiments provides kits and methods for determining whether a canola plant is or is related to inbred line NS-B50027-4, or a canola plant that comprises at least part of genetic elite event of line NS-B50027-4. Compositions and method for simple and unequivocal techniques for identification of elite event NS-B50027-4 in biological samples are described herein. For example, a kit includes at least one set of sense (forward) and antisense (backward) primers specific for the junction of *Brassica* chromosomal DNA and the inserted transgene. For example, the DNA junctions comprising sequences SEQ ID NO:43 (TGGAGGTGTTCAAACACT), NO:44 (ATAGT-ATTAGTATACAGA), NO:45 (GGCTAAGGTAACACT-GAT), and NO:46 (CAGTGTTTGAAGGACAGA) are novel DNA sequences of elite event NS-B50027-4, and are diagnostic for canola plant NS-B50027-4 and progeny thereof. More specifically, the junction sequences in SEQ ID NO:43 and SEQ ID NO:44 represent nine polynucleotides on each side of an insertion site of the transgene sequence fragment and canola genomic chromosome A02 DNA; and the junction sequences in SEQ ID NO:45 and SEQ ID NO:46 represent nine polynucleotides on each side of an insertion site of the transgene sequence fragment and canola genomic chromosome A05 DNA. Longer or shorter polynucleotides can be selected from the flanking regions described herein.

The present embodiments further provide methods for identifying the elite event of inbred canola line NS-B50027-4 in a biological sample, based on primers or probes that specifically recognize the 5' or 3' flanking regions the foreign DNA inserts comprising the genetic event of elite event NS-B50027-4. More specifically, an example method comprises amplifying a nucleic acid present in a biological sample by a polymerase chain reaction with at least two primers, one of which recognizes the 5' or 3' *Brassica* flanking regions of the inserted foreign DNAs (heterologous or transgenic DNAs) of elite event NS-B50027-4, the other of which recognizes a sequence within the foreign DNA comprising, for example, foreign desaturase or elongase genes, to obtain a DNA fragment of between 100 bp and 800 bp. Primers or probes may identify NS-B50027-4 via a recognition of a sequence within the 5' region of chromosome A02 flanking the insert: SEQ ID NO:40 from positions 1 to 2089 (or complements thereof), or within the 3' region of chromosome A02 flanking the insert: SEQ ID NO:40 from positions 14202 to 15006 (or complements thereof); a sequence within the 5' region of chromosome A05 flanking the insert: SEQ ID NO:41 from positions 1 to 1159 (or complements thereof), or within the 3' region of chromosome A05 flanking the insert: SEQ ID NO:41 from positions 47774 to 49789 (or complements thereof); and at least one sequence within the foreign DNA comprising, for example, SEQ ID NO:40 from position 2090 to 14201 (or a complement thereof) or SEQ ID NO:41 from position 1160 to 47773 (or a complement thereof).

At least one embodiment further provides compositions useful in kompetitive allele specific PCR (KASP) assays (two allele-specific forward primers recognize SNP), droplet digital PCR (ddPCR) assays, quantitative PCR (qPCR) assays, paralog-specific assays, or assays for adventitious presence (AP) testing. Specific embodiments of primers useful for conducting KASP assays to detect NS-B50027-4 genetic traits, particularly useful in introgression studies and hybrid development, include at least ten contiguous nucleotides of the primers of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, or complements thereof. The preceding primers or their complements may be included in a kit for the identification of NS-B50027-4, progeny of NS-B50027-4, or other plants or plant materials comprising at least a partial genome of NS-B50027-4. A related embodiment provides for plant material identified by such primers.

For example, at least one embodiment provides an isolated primer pair of DNA molecules, wherein a first primer comprises at least eleven contiguous nucleotides from nucleotide 1 to 235 of a 5' canola flanking genomic region of SEQ ID NO:47 or full complements thereof, and a second primer comprises at least eleven contiguous nucleotides of a transgene region from nucleotide 236 to 470 of SEQ ID NO:47 or full complements thereof, wherein the primer pair of DNA molecules when used together in a DNA amplification reaction produces a diagnostic amplicon comprising SEQ ID NO:43 for canola event NS-B50027-4 or progeny thereof.

At least one embodiment provides a composition comprising an isolated primer pair of DNA molecules, wherein a first primer comprises at least eleven contiguous nucleotides from nucleotide 1 to 235 of a transgene region of SEQ ID NO:48 or full complements thereof, and a second primer comprises at least eleven contiguous nucleotides of a 3' canola flanking genomic DNA region from nucleotide 236 to 470 of SEQ ID NO:48 or full complements thereof, wherein the primer pair of DNA molecules when used together in a DNA amplification reaction produces a diagnostic amplicon comprising SEQ ID NO:44 for canola event NS-B50027-4 or progeny thereof.

At least one embodiment provides an isolated primer pair of DNA molecules, wherein a first primer comprises at least eleven contiguous nucleotides from nucleotide 1 to 235 of a 5' canola flanking genomic region of SEQ ID NO:49 or full complements thereof, and a second primer comprises at least eleven contiguous nucleotides of a transgene region from nucleotide 236 to 470 of SEQ ID NO:49 or full complements thereof, wherein the primer pair of DNA molecules when used together in a DNA amplification reaction produces a diagnostic amplicon comprising SEQ ID NO:45 for canola event NS-B50027-4 or progeny thereof.

At least one embodiment provides an isolated primer pair of DNA molecules, wherein a first primer comprises at least eleven contiguous nucleotides from nucleotide 1 to 235 of a transgene region of SEQ ID NO:50 or full complements thereof, and a second primer comprises at least eleven contiguous nucleotides of a 3' canola flanking genomic DNA region from nucleotide 236 to 470 of SEQ ID NO:50 or full complements thereof, wherein the primer pair of DNA molecules when used together in a DNA amplification reaction produces a diagnostic amplicon comprising SEQ ID NO:46 for canola event NS-B50027-4 or progeny thereof.

Additionally, DNA event primer pairs can also be used to produce an amplicon diagnostic for NS-B50027-4 event. These event primer pairs include, for example, AATTGT-TGGAGGTGTTCAAACACT (SEQ ID NO:51) and CGGAATCACAATCCCTGAATGATT (SEQ ID NO:52) or the complements thereof. The amplicon produced by SEQ ID NO:51 and SEQ ID NO:52 is about 250 polynucleotides. In addition to these primer pairs, any primer pair derived from SEQ ID NO:47, NO:48, NO:49, or NO:50, or the complements thereof, that when used in a DNA amplification reaction produces an amplicon diagnostic for NS-B50027-4 event is an aspect of the present embodiments.

Another embodiment provides at least one set of primers for one of a *Pavlova salina*-derived Δ4-desaturase, *Pavlova salina*-derived Δ5-desaturase, *Pyramimonas cordata*-derived Δ5-elongase, *Micromonas pusilla*-derived Δ6-desaturase, *Pyramimonas cordata*-derived Δ6-elongase, *Lachancea kluyveri*-derived Δ12-desaturase, *Pichia pastoris*-derived Δ15/ω3-desaturase; and at least one set of primers specific for the 5' junction between the insert and the native *Brassica* chromosome A02 DNA, such as a junction from nucleotides 2033 to 2132 of SEQ ID NO:40, a 100 bp region comprising 43 bp of the insert and 57 bp of *Brassica* chromosome A02 DNA, or at least one set of primers specific for the 3' junction between the insert and the native *Brassica* chromosome A02 DNA, such as a junction from nucleotides 14156 to 14255 of SEQ ID NO:40, a 100 bp region comprising 46 bp of the insert and 54 bp of *Brassica* chromosome A02 DNA; at least one set of primers specific for the 5' junction between the insert and the native *Brassica* chromosome A05 DNA, such as a junction from nucleotides 47724 to 47823 of SEQ ID NO:41, a 100 bp region comprising 50 bp of the insert and 50 bp of *Brassica* chromosome A05 DNA, or at least one set of primers specific for the 3' junction between the insert and the native *Brassica* chromosome A05 DNA, such as a junction from nucleotides 47724 to 47823 of SEQ ID NO:41, a 100 bp region comprising 50 bp of the insert and 50 bp of *Brassica* chromosome A05 DNA.

Another embodiment provides primers that recognizes a sequence within the foreign DNA of NS-B50027-4, comprising, for example, at least one primer of *Micromonas pusilla* derived Δ6-desaturase DNA having the sequence of SEQ ID NO:57, SEQ ID NO:58, or complements thereof; *Pyramimonas cordata* derived Δ5-elongase having the sequence of SEQ ID NO:63, SEQ ID NO:64, or complements thereof; *Pavlova salina* derived Δ5-desaturase having the sequence of SEQ ID NO:61, SEQ ID NO:62, or complements thereof; *Pichia pastoris* derived Δ15/ω3-desaturase having the sequence of SEQ ID NO:55, SEQ ID NO:56, or complements thereof; *Pavlova salina* derived Δ4-desaturase having the sequence of SEQ ID NO:65, SEQ ID NO:66, or complements thereof; *Lachancea kluyveri* derived Δ12-desaturase having the nucleotide sequence of SEQ ID NO:53, SEQ ID NO:54, or complements thereof; or *Pyramimonas cordata*-derived Δ6-elongase having the sequence of SEQ ID NO:59, SEQ ID NO:60, or complements thereof. Accordingly, the present embodiments provide specific primers and the specific DNA amplified using such primers, and to primers that can be derived from the sequence information provided herein.

In accord with methods for identifying NS-B50027-4 and progeny thereof, kits may comprise, in addition to a primer that specifically recognizes the 5' or 3' flanking region of elite event NS-B50027-4, a second primer that specifically recognizes a sequence within the foreign DNA comprising at least one of *Micromonas pusilla* derived Δ6-desaturase, *Pyramimonas cordata* derived Δ5-elongase, *Pavlova salina* derived Δ5-desaturase, *Pichia pastoris* derived Δ15/ω3-desaturase, *Pavlova salina* derived Δ4-desaturase, *Pyramimonas cordata*-derived Δ6-elongase, or *Lachancea kluyveri* derived Δ12-desaturase, for use in a PCR identification protocol. The kits of the may comprise at least two specific primers, one of which recognizes a sequence within the 5' flanking region of elite event NS-B50027-4, and the other that recognizes a sequence within the foreign DNA comprising at least one of *Micromonas pusilla* derived Δ6-desaturase, *Pyramimonas cordata* derived Δ5-elongase, *Pavlova salina* derived Δ5-desaturase, *Pichia pastoris* derived Δ15/ω3-desaturase, *Pavlova salina* derived Δ4-desaturase, or *Lachancea kluyveri* derived Δ12-desaturase.

The invention further relates to a kit for identifying elite event NS-B50027-4 in biological samples, said kit comprising the PCR primers comprising or consisting (essentially) of the nucleotide sequences of SEQ ID NO:1 to NO:37, or complements thereof, for use in the elite event NS-B50027-4 identification protocol described herein.

At least one embodiment relates to a transgenic canola seeds, plants or plant parts, tissues or cells thereof, having stably integrated into the genome at least one transgenic insert comprising an expression cassette comprising sixteen heterologous genes, the transgenes being plant codon-optimized *Micromonas pusilla*-derived Δ6-desaturase, *Pyramimonas cordata*-derived Δ5-elongase, *Pavlova salina*-derived Δ5-desaturase, *Pichia pastoris*-derived Δ15/ω3-desaturase, *Pavlova salina*-derived Δ4-desaturase, *Pyramimonas cordata*-derived Δ6-elongase, and *Lachancea kluyveri*-derived Δ12-desaturase, at least one *Nicotiana tabacum*-derived matrix attachment region (MAR), and a selectable marker gene; and at least one transgenic insert comprising an expression cassette the four heterologous genes, the genes being codon-optimized for plant expression and encoding *Micromonas pusilla*-derived Δ6-desaturase, *Pyramimonas cordata*-derived Δ5-elongase, *Pavlova salina*-derived Δ5-desaturase, *Pichia pastoris*-derived Δ15/ω3-desaturase transgenes, and a least one *Nicotiana tabacum*-derived MAR, the four-gene expression cassette characterized as nucleotides 2090 to 14201 of SEQ ID NO:40. In at least one embodiment, the two expression cassettes are located in two different chromosomes in the plant genome.

Another embodiment provides a recombinant nucleic acid molecule having the nucleic acid sequence of FIG. 5 (SEQ ID NO:40), or a complement thereof. Another embodiment provides a recombinant nucleic acid molecule having the nucleic acid sequence of FIG. 6 (SEQ ID NO:41), or a complement thereof. In one embodiment, the transgenes of inbred line NS-B50027-4 as described herein has the nucleotide sequence of SEQ ID NO:40 from nucleotide positions 2090 to 14201, or its complement, or comprises a molecule with at least 95%, 97%, 98%, 99%, or 99.5% sequence identity to the nucleotide sequence of SEQ ID NO:40 from nucleotide position 2090 to nucleotide position 14201, or its complement. Also provided herein is a canola plant, plant cell, tissue, or seed, comprising in its genome a nucleic acid molecule comprising the nucleotide sequence of SEQ ID NO:40 from nucleotide positions 2090 to 14201, or its complement, or comprises a molecule with at least 95%, 97%, 98%, 99%, or 99.5% sequence identity to the nucleotide sequence of SEQ ID NO:40 from nucleotide position 2090 to nucleotide position 14201, or its complement. In another embodiment, the transgenes of inbred line NS-B50027-4 as described herein has the nucleotide sequence of SEQ ID NO:41 from nucleotide positions 1268 to 47662, or its complement, or comprises a molecule with at least 95%, 97%, 98%, 99%, or 99.5% sequence identity to the nucleotide sequence of SEQ ID NO:41 from nucleotide position 1268 to nucleotide position 47662, or its complement. Also provided herein is a canola plant, plant cell, tissue, or seed, comprising in its genome a nucleic acid molecule comprising the nucleotide sequence of SEQ ID NO:41 from nucleotide positions 1268 to 47662, or its complement, or comprises a molecule with at least 95%, 97%, 98%, 99%, or 99.5% sequence identity to the nucleotide sequence of SEQ ID NO:41 from nucleotide position 1268 to nucleotide position 47662, or its complement.

Another aspect of the present embodiments provides kits and methods for determining whether a canola plant is or is related to inbred line NS-B50027-4, or a canola plant that comprises at least part of genetic elite event of line NS-B50027-4. Compositions and method for simple and unequivocal techniques for identification of elite event NS-B50027-4 in biological samples are described herein. For example, a kit includes at least one set of sense (forward) and antisense (backward) primers specific for the junction of *Brassica* chromosomal DNA and the inserted transgene. The junction sequences, SEQ ID NO:43 (TGGAGGTGT-TCAAACACT), NO:44 (ATAGTATTAGTATACAGA), NO:45 (GGCTAAGGTAACACTGAT), and NO:46 (CA-GTGTTTGAAGGACAGA) are novel DNA sequences in NS-B50027-4 event, and are diagnostic for canola plant NS-B50027-4 and progeny thereof. The junction sequences in SEQ ID NO:43 and SEQ ID NO:44 represent nine polynucleotides on each side of an insertion site of the transgene sequence fragment and canola genomic chromosome A02 DNA; and the junction sequences in SEQ ID NO:45 and SEQ ID NO:46 represent nine polynucleotides on each side of an insertion site of the transgene sequence fragment and canola genomic chromosome A05 DNA. Longer or shorter polynucleotides can be selected from the flanking regions described herein.

Additionally, DNA event primer pairs can also be used to produce an amplicon diagnostic for NS-B50027-4 event. These event primer pairs include, for example, AATTGT-TGGAGGTGTTCAAACACT (SEQ ID NO:51) and CGGAATCACAATCCCTGAATGATT (SEQ ID NO:52) or the complements thereof. The amplicon produced by SEQ ID NO:51 and SEQ ID NO:52 is about 250 polynucleotides. In addition to these primer pairs, any primer pair derived from SEQ IDs NO:43, NO:44, NO:45, or NO:46, or the complements thereof, that when used in a DNA amplification reaction produces an amplicon diagnostic for NS-B50027-4 event is an aspect of the present invention.

Another embodiment provides at least one set of primers for one of a Δ6-desaturase derived from the micro alga *Micromonas pusilla*, a Δ5-elongase derived from the micro alga *Pyramimonas cordata*, a Δ6-elongase derived from *Pyramimonas cordata*, a Δ5-desaturase derived from the marine microalga *Pavlova salina*, a Δ15/ω3-desaturase derived from the yeast *Pichia pastoris*, a Δ4-desaturase derived from *Pavlova salina*, or a Δ12-desaturase derived from the yeast *Lachancea kluyveri*; and at least one set of primers specific for the 5' junction between the insert and the native *Brassica* chromosome A02 DNA, such as a junction from nucleotides 2033 to 2132 of SEQ ID NO:40, a 100 bp region comprising 43 bp of the insert and 57 bp of *Brassica* chromosome A02 DNA, or at least one set of primers specific for the 3' junction between the insert and the native *Brassica* chromosome A02 DNA, such as a junction from nucleotides 14156 to 14255 of SEQ ID NO:40, a 100 bp region comprising 46 bp of the insert and 54 bp of *Brassica* chromosome A02 DNA; at least one set of primers specific for the 5' junction between the insert and the native *Brassica* chromosome A05 DNA, such as a junction from nucleotides 11109 to 11209 of SEQ ID NO:41, a 100 bp region comprising 50 bp of the insert and 50 bp of *Brassica* chromosome A05 DNA, or at least one set of primers specific for the 3' junction between the insert and the native *Brassica* chromosome A05 DNA, such as a junction from nucleotides 47724 to 47823 of SEQ ID NO:41, a 100 bp region comprising 50 bp of the insert and 50 bp of *Brassica* chromosome A05 DNA.

A further aspect of the embodiments described herein provide kits for identifying elite event NS-B50027-4 in biological samples, said kits comprising at least one primer or probe that specifically recognizes the 5' or 3' *Brassica* regions that flank the foreign DNA, and at least one primer or probe that specifically recognizes least one insert DNA of *Micromonas pusilla*-derived Δ6 desaturase, which may comprise the nucleotide sequence of GAGCACCTTG-TAGTTGAGTCC (SEQ ID NO:57), AGTCTGAGGAT-GCTCCTATGC (SEQ ID NO:58), or complements thereof; *Pyramimonas cordata* derived Δ5-elongase, which may comprise the nucleotide sequence TGCTGGAACTCTTG-GATACG (SEQ ID NO:63), CTGGGTGATGTACTTCT-TCC (SEQ ID NO:64), or complements thereof; *Pavlova salina* derived Δ5-desaturase, which may comprise the nucleotide sequence GCTACCGATGCTTACAAGCA (SEQ ID NO:61), TAGTGAAGTCCGTGCTTCTC (SEQ ID NO:62), or complements thereof; *Pichia pastoris* derived Δ15/ω3-desaturase, which may comprise the nucleotide sequence GACGCTATCCCTAAGCACTGT (SEQ ID NO:55), GTCCACTCTTGAGCATCGTA (SEQ ID NO:56), or complements thereof; *Pavlova salina* derived Δ4-desaturase, which may comprise the nucleotide sequence GGCTTTCAGATCTGAGCATC (SEQ ID NO:65), CTCA-GCCTTAACAAGAGGAG (SEQ ID NO:66), or complements thereof; *Lachancea kluyveri* derived Δ12-desaturase, which may comprise the nucleotide sequence TGGAGC-TATCCCTCATGAGT (SEQ ID NO:53), GATCCTA-GAACAGTAGTGGTG (SEQ ID NO:54), or complements thereof; *Pyramimonas* CS0140 derived Δ6 elongase, which may comprise the nucleotide sequence TGTTGCTATG-GCTCAAGAGC (SEQ ID NO:59), CTAGCGTGGTGCT-TCATGTA (SEQ ID NO:60), or complements thereof.

The kit of this embodiment may comprise, in addition to a primer that specifically recognizes at least one of the 5' or 3' flanking regions of elite event NS-B50027-4; and at a primer that specifically recognizes a sequence within the foreign DNA comprising at least one of *Micromonas pusilla* derived Δ6-desaturase, *Pyramimonas cordata* derived Δ5-elongase, *Pavlova salina* derived Δ5-desaturase, *Pichia pastoris* derived Δ15/ω3-desaturase, *Pavlova salina* derived Δ4-desaturase, *Pyramimonas cordata*-derived Δ6-elongase, or *Lachancea kluyveri* derived Δ12-desaturase, for use in a PCR identification protocol. The kit may comprise at least two specific primers, one of which recognizes a sequence within the 5' flanking region of elite event NS-B50027-4, and the other that recognizes a sequence within the foreign DNA comprising at least one of *Micromonas pusilla* derived Δ6-desaturase, *Pyramimonas cordata* derived Δ5-elongase, *Pavlova salina* derived Δ5-desaturase, *Pichia pastoris* derived Δ15/ω3-desaturase, *Pavlova salina* derived Δ4-desaturase, *Pyramimonas cordata*-derived Δ6-elongase, or *Lachancea kluyveri*-derived Δ12-desaturase.

A related aspect provides genomic DNA obtained or derived from plants, comprising at least part of the elite event of line NS-B50027-4. Such genomic DNA may be used as reference control material in the identification assays herein described.

BRIEF DESCRIPTION OF THE DRAWINGS

FIG. 5 shows the DNA sequence of the four-gene transgenic insert and its flanking *B. napus* sequences (bold) (SEQ ID NO:40).

FIG. 6 shows the DNA sequence of the sixteen-gene insert and its flanking *B. napus* sequences (bold) (SEQ ID NO:41).

DETAILED DESCRIPTION

Figure 1:
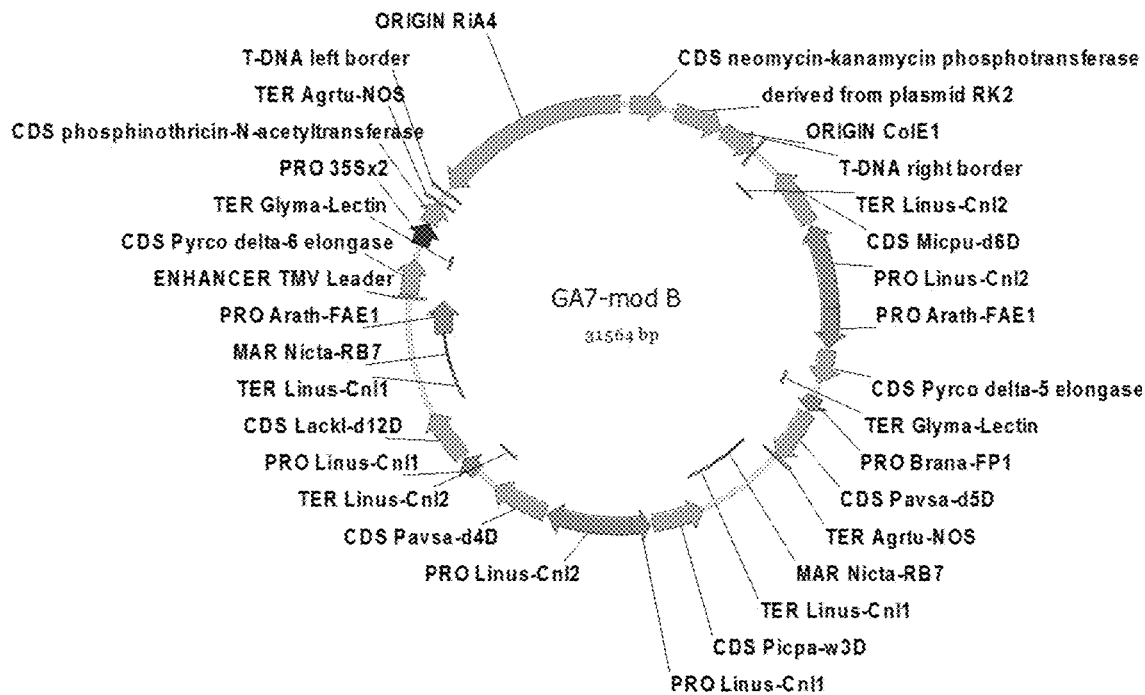
FIG. 1 provides a scheme (map) of the GA7-modB transformation cassette.
Figure 2:
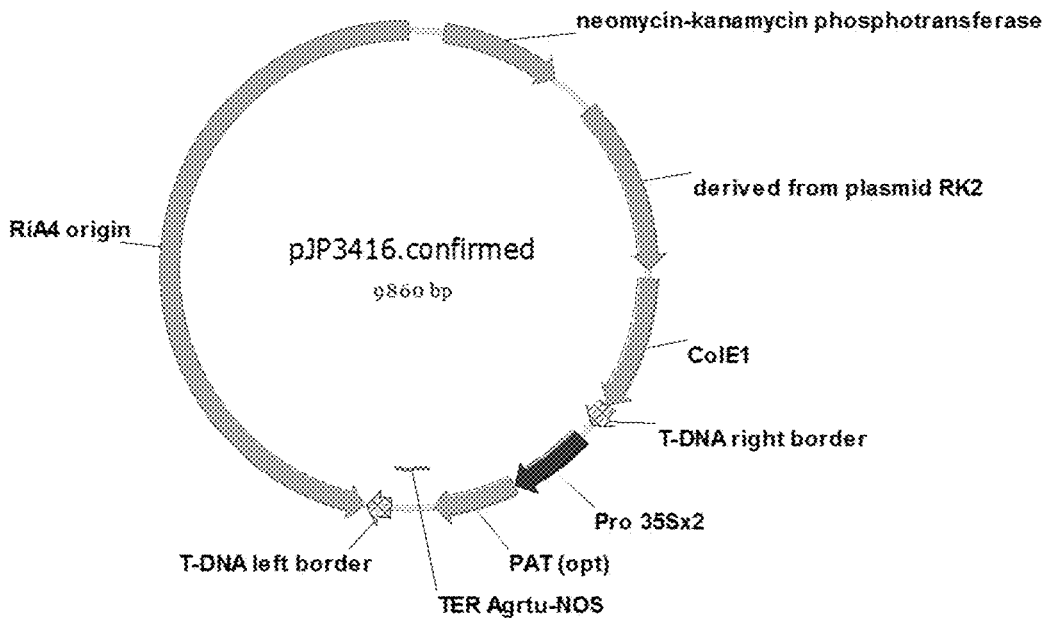
FIG. 2 is a plasmid map of the binary vector, pJP3416.
Figure 3:
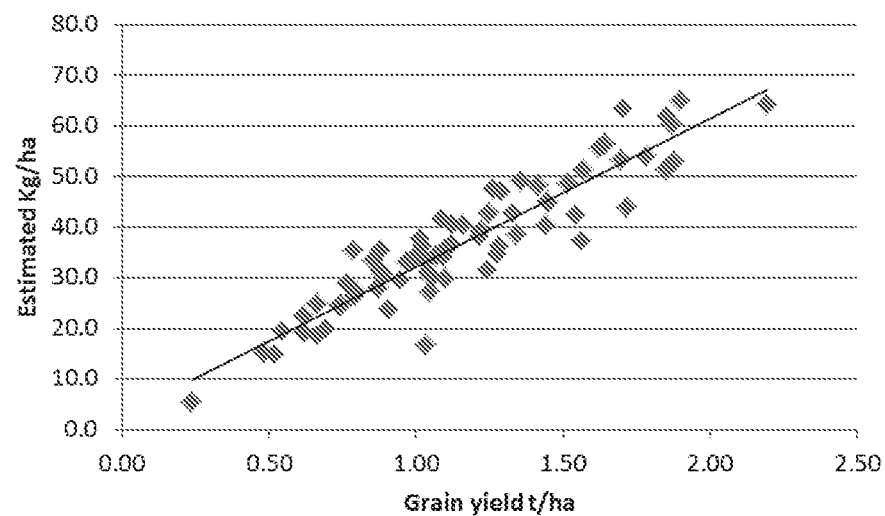
FIG. 3 depicts grain yield plotted against predicted DHA, in kg/ha, across eight cultivation sites. ♦ is DHA Kg/ha; -- is linear DHA Kg/ha; y=29.296x+2.8315; $R^2$=0.8567.
Figure 4:
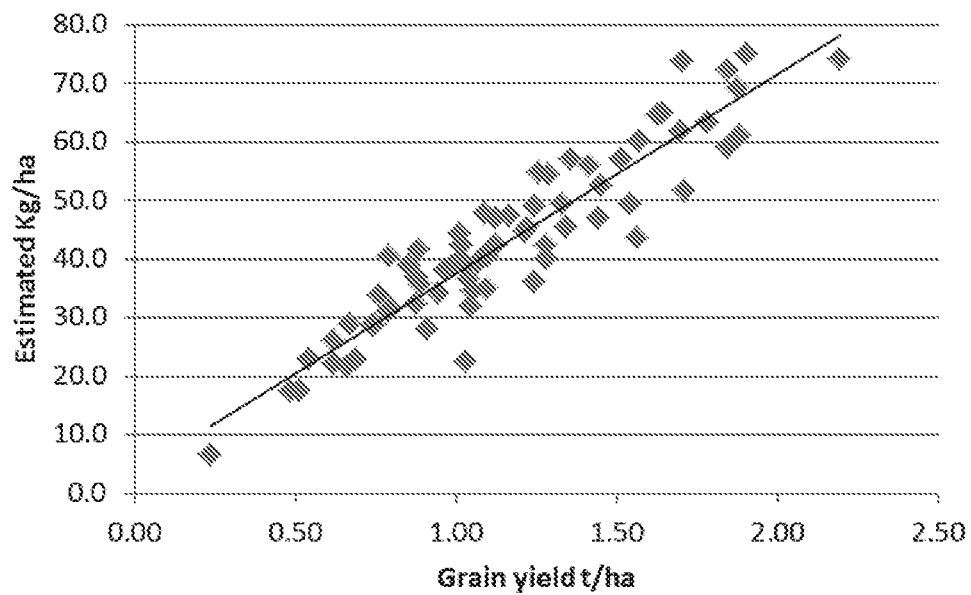
FIG. 4 depicts grain yield graphed against predicted LC-PUFA (EPA, DPA, and DHA), in kg/ha, across eight sites. ♦ is LC-PFU Kg/ha; -- is linear LC-PUF Kg/ha; y=34.043x+3.4049; $R^2$=0.8636.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

As used herein and in the claims, the singular forms "a," "an," and "the" include the plural reference unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Thus, unless context indicates otherwise, the word "or" means any one member of a particular list and also includes any combination of members of that list.

All values are approximate as there is some fluctuation in fatty acid composition due to environmental conditions. Values are typically expressed as percent by weight of total fatty acid, or percent weight of the total seed. Accordingly, other than in the operating examples, or where otherwise indicated, all numbers expressing quantities or reaction conditions used herein should be understood as modified in all instances by the term "about."

Recombinant DNA techniques can be carried out according to standard protocols as known in the art. See Sambrook et al., MOLECULAR CLONING: LAB. MANUAL (2nd Ed., Cold Spring Harbor Lab. Press, NY (1989); Ausubel et al., CURRENT PROTOCOLS MOLEC. BIOL. (1994 and updates); DNA CLONING: PRACTICAL APPROACH, Vols. 1-4 (Glover & Hames, Eds., IRL Press 1995, 1996), Croy, PLANT MOLEC. BIOL. LABFAX (BIOS Sci. Pub. Ltd. & Blackwell Sci. Pub., UK, 1993); WO 2015089587.

Headings are provided for convenience only and are not to be construed to limit the invention in any way. Unless defined otherwise, all technical and scientific terms used herein have the same meaning as those commonly understood to one of ordinary skill in the art. The terminology used herein is for the purpose of describing particular embodiments only, and is not intended to limit the scope of the present invention, which is defined solely by the claims. In order that the present disclosure can be more readily understood, certain terms are first defined. Additional definitions are set forth throughout the detailed description.

A "line" is a group of plants that displays very little overall variation among individuals sharing that designation. "Line" also refers to a homogeneous assemblage of plants carrying substantially the same genetic material that display little or no genetic variation between individuals for at least one trait. "Variety" or "cultivar" may be used interchangeably with "line," but in general the former two terms refer to a line that is suitable for commercial production. "Genetically derived" as used for example in the phrase "genetically derived from the parent lines" means that the characteristic in question is dictated wholly or in part by an aspect of the genetic makeup of the plant in question.

"*Brassica*" plant as used herein refers to plants of the family of the Brassicaceae. The *Brassica* plant may belong to one of the species *Brassica napus, B. rapa* (or *campestris*), or *B. juncea*. Alternatively, the plant can belong to a species originating from intercrossing of these *Brassica* species, such as *B. napocampestris*, or of an artificial crossing of one of these *Brassica* species with another species of the Cruciferacea. Ploidy refers to whether the number of chromosomes exhibited by a cultivar is diploid or tetraploid. Because *Brassica napus* is an allotetraploid (amphidiploid) arising from the cross and retention of both genomes of *Brassica rapa* (previously *B. campestris*) and *B. oleracea*, a *B. napus* plant comprising transgenic event NS-B50027-4 may be used with breeding methods to introduce the NS-B50027-4 event, and thus the "trait" of producing LC-ω3 fatty acids as described herein, into other members of the *Brassica* genus. Accordingly, examples of members of the *Brassica* genus useful in practicing the present embodiments include but are not limited to *B. juncea, B. napobrassica, B. oleracea, B. carinata, B. napus, B. rapa,* and *B.* campestris, as well as any other plants belonging to the genus Brassica that permit breeding between Brassica species. Generally, "oilseed plant" refers to any one of the species B. napus, B. rapa (or campestris), or B. juncea.

Brassica napus is commonly known as rapeseed or oilseed rape and specific cultivars may be referred to as canola. As used herein, the term "canola" or "canola plant" refers to a Brassica plant capable of being used to produce canola oil (i.e., an oil meeting a specific quality designation of containing less than 2% erucic acid) and includes varieties of Brassica napus, B. napobrassica, B. rapa, B. juncea, and B. campestris. Canola is an amphidiploid (also called an allotetraploid), an interspecific hybrid having a complete diploid chromosome set from each parent form, with genome AACC.

"Canola" and "canola plant" typically refers to Brassica napus, but includes all plant varieties that can be bred with canola. "Canola" and "canola plant" also includes plant parts. "Canola oil" must contain less than 2% erucic acid; and one gram of air-dry, oil-free solid canola seed must contain less than 30 μmoles of 3-butenyl glucosinolate, 4-pentenyl glucosinolate, 2-hydroxy-3 butenyl glucosinolate, 2-hydroxy-4-pentenyl glucosinolate, or a mixture thereof. See, e.g., CODEX ALIMENTARIUS: FATS, OILS & RELATED PRODUCTS, VOL. 8 (2nd ed., Food & Agriculture Org. United Nations, Rome, Italy, 2001).

"Plant part" includes plant cells, plant organs, plant protoplasts, plant cell tissue cultures from which plants can be regenerated, plant calli, plant clumps, and plant cells that are intact in plants or parts of plants such as embryos, pollen, ovules, seeds, pods, leaves, flowers, branches, fruit, stalks, roots, root tips, anthers, cotyledons, hypocotyls, radicles, single cells, gametes, cell cultures, tissue cultures, and the like. A cotyledon is a type of seed leaf; a small leaf contained on a plant embryo. A cotyledon contains the food storage tissues of the seed. The embryo is a small plant contained within a mature seed. "Plant cells" also encompasses non-regenerable plant cells. Progeny, derivatives, variants, and mutants of regenerated plants are also included within the scope of the present embodiments, provided that these parts comprise event NS-B50027-4 nucleic acid molecules. The present embodiments are also directed to the use of elite event NS-B50027-4 transgenes in plant cell culture and tissue culture. The embodiments include plants and plant parts from the elite event NS-B50027-4 line, as well as other plants produced by the described methods.

"Allele" is any of one or more alternative forms of a gene which relate to one trait or characteristic. In a diploid cell or organism, the two alleles of a given gene occupy corresponding loci on a pair of homologous chromosomes.

A "locus" confers one or more traits such as, for example, modified fatty acid metabolism, modified phytic acid metabolism, modified carbohydrate metabolism, male sterility, herbicide tolerance, insect resistance, disease resistance, or modified protein metabolism. The trait may be, for example, conferred by a naturally occurring gene introduced into the genome of the line by backcrossing, a natural or induced mutation, or a transgene introduced through genetic transformation techniques. A locus may comprise one or more alleles integrated at a single chromosomal location. Quantitative trait loci (QTL) refer to genetic loci that control, to at least some degree, numerically representable traits that are usually continuously distributed.

An "event" is an artificial genetic locus that, as a result of genetic manipulation, carries a foreign DNA comprising at least one copy of the genes of interest. The typical allelic states of an event are the presence or absence of the foreign DNA. An event may be characterized phenotypically by the expression of one or more transgenes. At the genetic level, an event is part of the genetic makeup of a plant. At the molecular level, an event is characterized by the restriction map (e.g., as determined by Southern blotting) or by the upstream or downstream flanking sequences of the transgene, or the molecular configuration of the transgene. Usually transformation of plant cells or plant parts with a transforming DNA leads to a multitude of events, each of which is unique.

The term "gene" refers to a DNA molecule typically comprising several operably linked DNA regions, such as a promoter and a 5' untranslated region (5'UTR or 5' noncoding sequences) which together form the promoter region; a coding region (which may or may not code for a protein); and an untranslated 3' region (3'UTR or 3' noncoding sequences) comprising a polyadenylation site. Typically in plant cells, the 5'UTR, coding, and 3'UTR regions are transcribed into an RNA molecule which, in the case of a protein-encoding gene, is translated into protein. "Coding sequence" thus refers to the sequence of nucleotides in a DNA molecule providing codons that translate a specific sequence of amino acids. A gene may include additional DNA regions such as, for example, introns. "Genotype" refers to the genetic constitution of a cell or organism. A "genetic locus" is generally the position of a given gene in the genome of a plant.

The term "transgene" refers to a gene of interest as incorporated in the genome of a plant. Accordingly, a "transgenic plant" comprises at least one transgene in the genome of all of its cells. The transgenes of the present embodiments comprise at least one copy of a gene of interest, more specifically at least one copy of: Δ4-desaturase derived from Pavlova salina, Δ5-desaturase derived from the marine microalga Pavlova salina, Δ5-elongase derived from the micro alga Pyramimonas cordata, Δ6-desaturase derived from the micro alga Micromonas pusilla, Δ6-elongase derived from Pyramimonas cordata, Δ12-desaturase from the yeast Lachancea kluyveri, and Δ15/ω3-desaturase derived from the yeast Pichia pastoris; and at least one additional copy of Δ6-desaturase derived from the micro alga Micromonas pusilla, Δ5-elongase derived from Pyramimonas cordata, Δ5-desaturase derived from the marine microalga Pavlova salina, and Δ15/ω3-desaturase derived from the yeast Pichia pastoris. The transgenes are arranged in a binary fashion in expression cassettes that include the appropriate regulatory regions. The transgenes described above are artificial in that they have been designed using codon optimization strategy, and thus the transgenes do not otherwise exist in nature. The transgenic expression cassette may include at least one matrix attachment region (MAR) from Nicotiana tabacum. The transgene cassette may also include a selectable marker gene. See U.S. Pat. No. 8,816,111.

"Foreign" or "heterologous" when referring to a gene or a DNA molecule with respect to a plant species, indicates that the gene or DNA molecule, or a portion thereof (e.g., a particular region), is not naturally found in that plant species, or is not naturally found in that genetic locus in that plant species. The term "foreign DNA" also refers to a DNA molecule that will or has been incorporated into the genome of a plant as a result of transformation. In the context of this disclosure, a transgene, transgenic cassette, or transgenic expression cassette comprises at least one foreign or heterologous DNA.

The term "chimeric" when referring to a gene or DNA molecule is used to indicate that the gene or DNA molecule comprises at least two functionally relevant DNA regions (such as promoter, 5'UTR, coding region, 3'UTR, intron) that are not naturally associated with each other, and originate from different sources such that at least one DNA region is foreign to another DNA region in the chimeric molecule.

The terms "plasmid", "vector" and refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. In relation to transgenic plants, such plasmids or vectors may contain regions of T-DNA to facilitate insertion to transgene(s) into the plant genome.

"Expression cassette" refers to a genetic construct containing a transgene and having elements in addition to the foreign gene that allow for expression of that gene in a foreign host; and may refer to the cassette before and after insertion into the genome of the plant. In other words, a transgenic insert comprises an expression cassette.

The "transforming DNA" refers to a recombinant DNA molecule used for transformation, e.g., an expression vector. The transforming DNA usually comprises at least one "gene of interest" (e.g., a chimeric gene) that is capable of conferring one or more specific characteristics to the transformed plant.

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" organisms.

The term "recombinant DNA molecule" is used to exemplify and thus can include an isolated nucleic acid molecule that can be DNA and that can be obtained through recombinant or other procedures such as synthetic DNA synthesis or PCR. PCR (polymerase chain reaction) is a reaction in which replicate copies of a target polynucleotide are made using primers consisting of "upstream" and a "downstream" primer, and a catalyst of polymerization, such as a DNA polymerase, and typically a thermally-stable polymerase enzyme. Methods for PCR are known in the art. See, e.g., PCR (McPherson & Moller, eds., BIOS Sci. Publ. Ltd., Oxford, 2000). PCR can be performed on genomic DNA or cDNA.

"Insert DNA" refers to the heterologous DNA introduced to plant material via the transformation process and includes DNA which differs from the original DNA used for such transformation as explained herein. Insert DNA is typically a transgenic expression cassette. "Elite event NS-B50027-4 insert nucleic acid" and "event "NS-B50027-4 insert DNA" refer to a nucleic acid molecule characterized as consisting of the sequence of nucleotides 2090 to 14201 of SEQ ID NO:1, or a complement thereof; and a nucleic acid molecule characterized as comprising the sequence of nucleotides positions 987 to 1894 of SEQ ID NO:2, or 1 to 910 of SEQ ID NO:3, or complements thereof.

"Suitable regulatory sequences" refer to nucleotide sequences located upstream (e.g., 5'UTR), within, or downstream (3'UTR) of a coding sequence; which influence the transcription, RNA processing or stability, or translation of the associated coding sequence. Regulatory sequences may include promoters, enhancer elements, translation leader sequences, introns, polyadenylation recognition sequences, RNA processing sites, effector binding sites, and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequences" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) derived from the nucleic acids of the invention. Expression may also refer to translation of mRNA into a polypeptide.

Reference to a cell includes a plant cell, whether isolated, in tissue culture, or incorporated in a plant or plant part, unless otherwise stated or clear from context.

"Progeny" means all descendants including offspring and derivatives of a plant or plants and includes the first, second, third, and subsequent generations; and may be produced by self-pollination or crossing with plants with the same or different genotypes, and may be modified by a range of suitable genetic engineering techniques. Cultigen generally relates to plants that have been deliberately altered and selected by human. "T0" refers to the first generation of transformed plant material, "T1" refers to the seed produced on T0 plants, T1 seed gives rise to plants that produce T2 seed, etc., to subsequent Tx progeny.

"Breeding" includes all methods of developing or propagating plants and includes both intra- and inter-species and intra- and inter-line crosses as well as all suitable conventional breeding and artificial breeding techniques. Desired traits (e.g., NS-B50027-4 DHA trait) may be transferred to other canola or *B. napus* lines, cultivars, or cultigens; or through conventional breeding methods and can also be transferred to other *Brassica* species, such as *B. juncea* and *B. rapa* through inter-specific crossing. Conventional breeding methods and inter-specific crossing methods, as well as other methods of transferring genetic material between plants, are well-known in the art.

"Backcrossing" is a process in which a breeder repeatedly crosses hybrid progeny back to a parental line, for example, a first generation hybrid F1 with one of the parental genotypes of the F1 hybrid.

"Fatty acid composition" or "fatty acid content" generally refer to percentages by weight of various fatty acids present in the endogenously formed oil of the mature, whole, partially dried seeds. The common industry practice is to report fatty acid composition as area percentage (area normalized), rather than absolute quantities. Area percentage is easy to calculate and readily compared with the results of the many others in the industry who report the same way. Area percentage is not the same as absolute weight percentage, but approximates it. Absolute results can be calculated using individual reference standards of known concentration and an internal standard to calculate results on a mg/kg basis. It is also possible to use correction factors to calculate masses of fatty acids without the use of individual fatty acid standards, although an internal standard may still be needed. Commonly, fatty acid content is determined by crushing seed and extracting fatty acids as fatty acid methyl esters (FAME) which can be analyzed for fatty acid content by a variety of techniques that generate data as area percent or from which area percent can be derived. Example analytical approaches include gas chromatography (GC), GC-mass spectrometry (GC-MS), liquid chromatography-mass spectrometry (LC-MS), nuclear magnetic resonance (NMR), or near infrared reflectance spectroscopy. Total lipid may be separated by techniques known in the art to purify fractions, for example, such as the TAG fraction. Other methods of characterizing fatty acid compositions are known to those skilled in the art. See, e.g., Tinoco et al., 3 Anal. Biochem. 514 (1962); CANOLA: CHEMISTRY, PRODUCTION, PROCESSING & UTILIZATION (Daun et al., eds., AOCS Press, Urbana, Ill., 2011) (Daun et al., 2011); US 2015/0166928; US 20160002566.

Similarly, "oil content" is the typical percentage by weight oil present in the mature, whole, partially dried seeds (typically containing about 6% or 7% moisture). Percent oil is calculated as the weight of the oil divided by the weight of the seed at 0% moisture. Oil content can be characteristic of different varieties. It can be determined using various analytical techniques such as NMR (MQC, Oxford Instruments), NIR, and Soxhlet extraction. For example, canola oil content can be measured by nuclear magnetic resonance techniques (Rossell & Pritchar, ANALYSIS OF OILSEEDS, FATS & FATTY FOODS 48-53 (Elsevier Sci. Pub. Ltd, London, 1991), by a pulsed wave NMS 100 Minispec (Balker Pty Ltd Scientific Instruments, Germany), which simultaneously measures moisture content. Seed oil content can also be measured by near infrared reflectance (NIR) spectroscopy. Li et al. 67 Phytochem. 904 (2006).

The phrases "extracted plant lipid," "isolated plant lipid," "extracted lipid," and the like, refer to compositions comprising lipids that have been extracted from, for example, crushed plant or plant parts, such as seed. The extracted lipid can be a relatively crude composition obtained by, for example, crushing a plant material, such as seed; or a more purified composition in which most, if not all, of the water, nucleic acids, proteins, or carbohydrates derived from the plant material have been removed from the oil. Examples of purification methods are known in the art. In some embodiments, the extracted or isolated plant lipid comprises at least about 60%, at least about 70%, at least about 80%, at least about 90%, or at least about 95% (w/w) lipid by weight of the composition. The extracted lipid may be solid or liquid at room temperature, the latter being considered "oil." In some embodiments, extracted lipid has not been blended with another lipid, such as DHA, produced by another source (e.g., DHA from fish oil). In some embodiments, following extraction the ratio of oleic acid to DHA, palmitic acid to DHA, linoleic acid to DHA, or total $\omega 6$ fatty acids to total $\omega 3$ fatty acids has not been altered significantly (for example, no greater than a 10% or 5% alteration) compared with the ratio in the intact seed or cell. In other words, the extracted lipid has not been enriched for a particular fatty acid, e.g., DHA. In other embodiments, the extracted plant lipid has not been exposed to a procedure, such as hydrogenation or fractionation, which alters the ratio of oleic acid to DHA, palmitic acid to DHA, linoleic acid to DHA, or total $\omega 6$ fatty acids to total $\omega 3$ fatty acids, when compared with the ratio in the intact seed or cell. In other words, the extracted lipid has not been enriched for a particular fatty acid, e.g., DHA. When the extracted plant lipid of the present embodiments is oil, the oil may further comprise non-fatty acid molecules such as sterols.

As noted above, the phrases "extracted plant oil" and "isolated plant oil" refer to compositions comprising extracted plant lipid or isolated plant lipid that is a liquid at room temperature. The oil is obtained from a plant or part thereof, such as seed. The extracted or isolated oil can be a relatively crude composition obtained by, for example, crushing a plant seed; or a more purified composition where most, if not all, of the water, nucleic acids, proteins, or carbohydrates derived from the plant material has been removed from the oil. The composition may comprise other components which may be lipid or non-lipid, e.g., non-fatty acid molecules such as sterols. In an embodiment, the oil composition comprises at least about 60%, at least about 70%, at least about 80%, at least about 90%, or at least about 95% (w/w) extracted plant lipid. In an embodiment, extracted oil of the invention has not been blended with another oil or fatty acid, such as DHA produced by another source (e.g., DHA from fish oil). In one embodiment, following extraction, the ratios of fatty acids have not been altered significantly (for example, no greater than a 10% or 5% alteration) compared with the ratio in the intact seed or cell; nor has the extracted plant oil been exposed to a procedure, such as hydrogenation or fractionation, that significantly alters the ratio of fatty acids in the extract compared with the ratios in the intact seed or cell. In other words, the extracted oil has not been enriched for a particular fatty acid, e.g., DHA.

As used herein, "oil" is a composition comprising predominantly lipid and which is a liquid at room temperature. For instance, oil of the invention preferably comprises at least 75%, at least 80%, at least 85% or at least 90% lipid by weight. Typically, purified plant oil comprises at least 90% triacylglycerols (TAG) by weight of the lipid in the oil. Minor components of oil, such as diacylglycerols (DAG), free fatty acids (FFA), phospholipid, or sterols, may be present in oil.

As used herein, the term "fatty acid" refers to a carboxylic acid often with a long aliphatic tail, either saturated or unsaturated. Typically, fatty acids have a carbon-carbon bonded chain of at least eight carbon atoms in length, for example at least 12 carbons, 16 carbons, 18 carbons, 20 carbons, or 22 carbons in length. Most naturally occurring fatty acids have an even number of carbon atoms because their biosynthesis involves acetate which has two carbon atoms. The fatty acids may be in a free state (non-esterified); in an esterified form such as part of a triglyceride (TAG), diacylglyceride (DAG), monoacylglyceride; or be acyl-CoA (thio-ester)-bound or in another bound form. The fatty acid may be esterified as a phospholipid, such as a phosphatidylcholine, phosphatidylethanolamine, phosphatidylserine, phosphatidylglycerol, phosphatidylinositol, or diphosphatidylglycerol.

"Saturated fatty acids" do not contain carbon-carbon double bonds (alkenes) or other functional groups along the chain. "Saturated" refers to the presence of hydrogen at all possible carbons (apart from the carboxylic acid [—COOH] group). In other words, in a saturated fatty acid the omega (w) end (also called the n-end) of the fatty acid contains three hydrogens (—$CH_3$), and each carbon within the chain contains two hydrogens (—$CH_2$—).

"Unsaturated fatty acids" share a similar backbone with saturated fatty acids, except they include at least one alkene group (—CH=CH—) in the carbon chain. The two flanking carbon atoms (bound to either side of the alkene group) can occur in a cis or trans configuration. "Monounsaturated fatty acids" refers to fatty acids that have at least twelve carbon atoms but only one alkene group in the carbon chain. "Polyunsaturated fatty acids" or "PUFAs" refer to fatty acids that have at least twelve carbon atoms and at least two alkene groups in the carbon chain. "Long-chain polyunsaturated fatty acids" and "LC-PUFAs" refer to fatty acids that have at least twenty carbon atoms in the carbon chain and have at least two alkene groups. "Very long-chain polyunsaturated fatty acids" and "VLC-PUFAs" refer to fatty acids that have at least twenty-two carbon atoms and at least three alkene groups in the carbon chain. A reference to LC-PUFA includes VLC-PUFA. Ordinarily, the number of carbon atoms in the carbon chain of fatty acids refers to an unbranched carbon chain. If the carbon chain is branched, the number of carbon atoms excludes those in side-groups.

In one embodiment, the LC-PUFA is an ω3 fatty acid: it has a desaturation (alkene group) at the third carbon-carbon bond from the methyl end of the fatty acid. In another embodiment, the LC-PUFA is an ω6 fatty acid: it has a desaturation (alkene group) in the sixth carbon-carbon bond from the methyl end of the fatty acid. The position of the alkene (double bond) in the fatty acid chain is also annotated using A (or delta), in which the position of the alkene is numbered with reference to the carboxylic end of the fatty acid. For example, linoleic acid can also be designated "cis-Δ9, cis-Δ12 octadecadienoic acid" or $\Delta^{9,12}$ octadecadienoic acid." Fatty acids can also be identified with reference to a "C:D" lipid number, in which C is the number of carbons and D is the number of double bonds in the carbon backbone. For example, arachidonic acid can be annotated 20:4$\Delta^{5,8,11,14}$ meaning a twenty-carbon chain with four alkene groups, located at carbons 5, 8, 11 and 14 from the carboxylic end of the fatty acid. This name also indicates that arachidonic acid is an ω6 fatty acid, because if there are twenty carbons and an alkene at C14 from the carboxylic end, the first alkene from the methyl end must be at C6.

In a further embodiment, the LC-PUFA is selected from the group consisting of; arachidonic acid (ARA, 20:4$\Delta^{5,8,11,14}$; ω6), eicosatetraenoic acid (ETA, 20:4$4^{8,11,14,17}$; ω0), eicosapentaenoic acid (EPA, 20:5$\Delta^{5,8,11,14,17}$; ω3), docosapentaenoic acid (DPA, 22:5$\Delta^{7,10,13,16,19}$; ω3), or docosahexaenoic acid (DHA, 22:6$\Delta^{4,7,10,13,16,19}$; ω3). The LC-PUFA may also be dihomo-γ-linoleic acid (DGLA) or eicosatrienoic acid (ETrA, 20:3$\Delta^{11,14,17}$; ω3). The LC-PUFA produced according to the present embodiments may be a mixture of any or all of the above, and may include other LC-PUFAs or derivatives of any of these LC-PUFAs. The LC-PUFAs produced in the elite event canola, however, is generally purer than that derived from fish oil. In at least one embodiment, the ω3 fatty acids are at least one of DHA; DPA and DHA; or EPA, DPA, and DHA.

Furthermore, as noted above a LC-PUFA and VLC-PUFA can be a free fatty acid (non-esterified), esterified, or in another bound form. Thus, the LC-PUFA of the present embodiments may be present as a mixture of forms in the lipid of a cell, extracted lipid, or purified oil. In at least one embodiment, the oil comprising at least 75% or at least 85% triacylglycerols, with the remainder present as other forms of lipid such as those mentioned, with the triacylglycerols comprising at least one LC-PUFA. The oil may subsequently be further purified or treated, for example by hydrolysis with a strong base to release the free fatty acids, or by distillation or the like.

Accordingly, "total ω3 fatty acids," "total ω3 fatty acid content," and the like, refers to the sum of all ω3 fatty acids, esterified and non-esterified, in extracted lipid, oil, recombinant cell, plant part or seed, as the context determines, typically expressed as a percentage of the total fatty acid content. These ω3 fatty acids include ALA, SDA, ETrA, ETA, EPA, DPA, or DHA, and exclude any ω6 fatty acids or monounsaturated fatty acids. "New ω3 fatty acids," "new ω3 fatty acid content," and the like, refers to the sum of all ω3 fatty acids excluding ALA, esterified and non-esterified, in the extracted lipid, oil, recombinant cell, plant part or seed, as the context determines, expressed as a percentage of the total fatty acid content. These new ω3 fatty acids are the fatty acids that are produced in the cells, plants, plant parts and seeds of the present embodiments by the expression of elite event transgenic constructs, and if present include SDA, ETrA, ETA, EPA, DPA, or DHA, but exclude ALA, any ω6 fatty acids, or monounsaturated fatty acids. Exemplary total ω3 fatty acid contents and new ω3 fatty acid contents can be determined by conversion of fatty acids in a sample to FAME and analysis by GC using methods known in the art. See, e.g., American Oilseed Chemists' Society (AOCS) method Celd-91.

Similarly, "total ω6 fatty acids," "total ω6 fatty acid content," and the like, refer to the sum of all the ω6 fatty acids, esterified and non-esterified, in the extracted lipid, oil, recombinant cell, plant part or seed, as the context determines, expressed as a percentage of the total fatty acid content. "Total ω6 fatty acids," if present, may include LA, GLA, DGLA, ARA, EDA, or ω6-DPA, and excludes any ω3 fatty acids or monounsaturated fatty acids. "New ω6 fatty acids," "new ω6 fatty acid content," and the like, refers to the sum of all ω6 fatty acids excluding LA, esterified and non-esterified, in the extracted lipid, oil, recombinant cell, plant part or seed, as the context determines, expressed as a percentage of the total fatty acid content. These new ω6 fatty acids are the fatty acids that are produced in the cells, plants, plant parts, or seeds as described herein, through expression of the elite event transgenes, and may include GLA, DGLA, ARA, EDA, or ω6-DPA, but exclude LA, any ω3 fatty acids, or monounsaturated fatty acids.

"Half-seed analysis" is a procedure whereby fatty acid analysis is carried out on one of the two cotyledons (half-seed) and the remaining seedling carrying the second cotyledon forms a plant.

"Protein content" is the typical percentage by weight of protein in the oil free meal of the mature whole dried seeds is determined by methods known in the art. See, e.g., Daun et al., 2011; AOCS Official Meth. Ba 4e-93 Combustion Meth. Determination Crude Protein.

Mature seed produced by commercial growers for purposes other than growing or reproducing the species is sometimes referred to as "grain."

Genetic Events

The phenotypic expression of transgenes in canola is determined both by the structure of the transgene cassette itself and by its insert location in the plant genome: the presence of transgenes at particular locations in the plant genome may influence the expression of the transgene and the overall phenotype of the plant. The agronomically or industrially successful introduction of a commercially interesting trait in a plant by genetic manipulation can be a lengthy procedure dependent on different factors. The actual transformation and regeneration of genetically transformed plants are only the first in a series of selection steps, which include extensive genetic characterization, breeding, and evaluation in field trials, eventually leading to the selection of an elite event.

An aspect of the present embodiments involves the surprising number of copies of expressible transgenes in a plant genome. "Expressible" means that the primary structure of the DNA molecule, i.e., the coding sequence of the transgene, indicates that the gene encodes an active protein. Expressible coding sequences may not be expressed, however, because 'gene silencing' occurs via various mechanisms of homologous transgene inactivation in vivo. Homologous transgene inactivation has been described in plants in which a transgene has been inserted in the sense orientation, with the unexpected result that both the gene and the transgene were down-regulated. Napoli et al., 2 Plant Cell 279 (1990). Possible mechanisms for inactivation of homologous genetic sequences include transcriptional inactivation via methylation, in which duplicated DNA regions signal endogenous mechanisms for gene silencing, and post-transcriptional silencing, in which the combined levels of mRNA from both the endogenous gene and transgene trigger threshold-induced degradation of both messages. van Bokland et al., 6 Plant J. 861 (1994). Surprisingly, however, although there are at least three copies of several transgenes in NS-B50027-4, some of which are disposed in the same orientation, NS-B50027-4 exhibits synergistic DHA expression.

An elite genetic event can be characterized by the location(s) and the configuration at the site(s) of incorporation of the recombinant DNA molecule(s) in the plant genome. The site in the plant genome where a recombinant DNA cassette has been inserted is also referred to as the "insertion site" or "target site." A "flanking region" or "flanking sequence" is a region of DNA, for example, at least 20 base pairs, at least 50 base pairs, or up to 5,000 base pairs of the plant genome located either immediately upstream of and contiguous with, or immediately downstream of and contiguous with, the transgenic cassette. Transformation that leads to random integration of the foreign DNA results in transformants with different flanking regions, which are characteristic and unique for each transformant (elite event).

Generally, when the transgene is introduced into a plant through traditional crossing, its insertion site in the plant genome and its flanking regions are not changed. An "insertion region" refers to the region corresponding to a region of at least 40 base pairs, such as at least 100 base pairs, or up to more than 10,000 base pairs, encompassed by the upstream and the downstream flanking regions of a transgene in the (untransformed) plant genome and including the insertion site (and possible target site deletion). Taking into consideration minor differences due to mutations within a species, an insertion region may retain at least 85%, such as 90%, 95%, or 100% sequence identity with the upstream and downstream flanking regions of the foreign DNA in a given plant of that species. Insertion of the transgenic cassette into the plant genome can sometimes be associated, however, with deletion of plant DNA, referred to as "target site deletion."

Expression of genes of interest refers to the fact that the transgenes confer on the plant one or more phenotypic traits (e.g., production of LC-ω3 fatty acids) that were intended to be conferred by the introduction of the transforming DNA (on the basis of the structure and function of some or all of the genes of interest). In the present embodiments, several transgenes provide the biosynthetic pathway for the production of LC-ω3 fatty acids in the transformed plant.

An "elite event," as used herein, is an event selected from a group of events, obtained by transformation with the same transforming DNA or by back-crossing with plants obtained by such transformation, based on the expression and stability of the transgene construct(s), its compatibility with optimal agronomic characteristics of the plant comprising it, and realization of the desired phenotypic trait. Thus, the criteria for elite event selection are at least one, and advantageously all, of the following:

(a) the presence of the transgene does not unduly compromise other desired characteristics of the plant, such as those relating to agronomic performance or commercial value;

(b) the event is characterized by a well-defined molecular configuration that is stably inherited and for which appropriate diagnostic tools for identity control can be developed;

(c) the genes of interest in the transgene cassette show a correct, appropriate and stable spatial and temporal phenotypic expression, both in heterozygous (or hemizygous) and homozygous condition of the event, at a commercially acceptable level in a range of environmental conditions in which the plants carrying the event are likely to be exposed in normal agronomic use. The foreign DNA may also be associated with a position in the plant genome that allows introgression into further desired commercial genetic backgrounds.

The status of an event as an elite event may be confirmed by introgression of the elite event in different relevant genetic backgrounds and observing compliance with at least one of the criteria, e.g., (a), (b) and (c) above. Additionally, selection of the elite events may also be determined on the compatibility, more specifically that the progeny resulting from a cross between a plant carrying elite event NS-B50027-4 and a plant carrying at least one other event, such that progeny carry both events. Accordingly, an "elite event" refers to a genetic locus comprising a transgenic cassette that answers to the above-described criteria. A plant, seeds, plant material or progeny can comprise one or more elite events in its genome.

Elite event NS-B50027-4 was selected as an elite event in the development of canola that produces LC-PUFA, particularly LC-ω3 fatty acids, and more particularly DHA. The incorporation of a recombinant DNA molecule in the plant genome typically results from transformation of a cell or tissue (or from another genetic manipulation). The particular site(s) of incorporation may be a matter of chance or predetermined (if a process of targeted integration is used). Canola line NS-B50027-4 is a stable and uniform breeding line, as described herein. It has been bred with careful attention to uniformity of plant type. The line has been increased with continued observation for uniformity. Canola line NS-B50027-4 is not a parent of any other canola cultivar commercialized at the time of the patent filing for line NS-B50027-4.

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner Any DNA molecules, whether from a different species or from the same species, that are inserted into the genome of the species using transformation are referred to herein collectively as "transgenes". The process of "transforming" is the insertion of DNA into the genome. Several methods for producing transgenic plants have been developed, and the present invention, in particular embodiments, also relates to transformed versions of the claimed canola line NS-B50027-4.

Numerous methods for plant transformation have been developed, including biological and physical, plant transformation protocols. In addition, expression vectors and in vitro culture methods for plant cell or tissue transformation and regeneration of plants are available. See, e.g., Miki et al., *Procedures for introducing foreign DNA into plants*, in METH. PLANT MOLEC. BIOL. & BIOTECHNOL. at 63 (Glick & Thompson, eds., CRC Press, Boca Raton, 1993); Gruber et al., *Vectors for plant transformation, id.* at R 89; *Genetic transformation for the improvement of Canola*, PROC. WORLD CONF. BIOTECHNOL. FATS & OILS INDUS. at 43-46 (Am. Oil. Chem. Soc., Champaign, Ill., 1988).

The most prevalent types of plant transformation involve the construction of an expression vector. Such a vector comprises a DNA molecule that contains a coding region under the control of or operatively linked to a regulatory region, for example a promoter. The vector may contain one or more genes and one or more regulatory elements. At least one of the coding regions and their respective regulatory elements can be arranged in opposite orientation within the vector, providing a binary vector. In theory, arrangement of genes susceptible to gene silencing in binary fashion may minimize gene silencing.

For example, an initial transformation cassette, pJP3416_GA7-modB, included seven genes capable of promoting the accumulation of omega-3 fatty acids in canola seed, and one selectable marker gene to facilitate the selection of putative transgenic plants in vitro. See WO 2013/185184; U.S. Patent Publ'n No. 2015/0374654; U.S. Pat. Nos. 8,816,111 and 8,946,460; Petrie et al., 6 Plant Meth. 8 (2010).

The expressed genes were all synthetic—codon optimized and synthesized—hence the transgenic DNA molecules are not found in any natural organisms. The original sequences that were used as a template for codon optimization have been described. See Petrie et al., 12 Metab. Eng'g 233 (2010a); Petrie et al., 11 Plant Methods 6 (2010b); Petrie et al., 21 Transgenic Res. 139 (2012).

As is well-known in the art, functional gene promoters are regions of DNA that are important for gene transcription, but do not encode functional products such as peptides. For example, a common promoter for constitutive expression is derived from Cauliflower Mosaic Virus. Kay et al., 236 Science 1299 (1987); Coutu et al., 16 Transgenic Res. 771 (2007). Terminator regions, which include polyadenylation signals, are required for the production of complete and stable mRNA molecules. For example, the *A. tumefaciens* nopaline synthase (NOS) terminator provides a useful terminator. Bevan, 12 Nucl. Acid Res. 8711 (1984); Rogers et al., in BIOTECHNOL. PLANT SCI. at 219 (Acad. Press, Inc., New York, N.Y., 1985); Sanders et al., 15 Nucl. Acids Res. 1543 (1987). A range of regulatory sequences were used in combination to drive and terminate transcription the various expression cassettes. The seed-specific promoters used in GA7-modB have been described previously: *A. thaliana* FAE1 (Rossack et al., 46 Plant Molec. Biol. 717 (2001)); *L. usitatissimum* Cn11 and Cn12 (Chaudhary et al., WO 2001/016340); and truncated *B. napus* napin promoter (Stalberg et al., 23 Plant Molec. Biol. 671 (1993)). See also U.S. Pat. No. 8,816,111.

A more detailed description of transgenes comprising open reading frames 5' and 3' regulatory regions and other non-coding regions of the transgenic expression cassettes used to introduce LC-PUFA pathways into canola are shown in Table 1.

TABLE 1

Genetic elements in Elite Event NS-B50027-4

| Promoter (PRO) | | Coding sequence (CDS) | | Termination (TER) | | MAR |
|---|---|---|---|---|---|---|
| Name | Source | Name | Source | Name | Source | |
| PRO Linus-Cnl2 | *Linum usitatissimum* conlinin2 promoter w/ tobacco mosaic virus (TMV) 5' UTR enhancer leader | CDS Micpu-d6D | Δ6-desaturase *Micromonas pusilla* | TER Linus-Clnl2 | *Linum usitatissimum* conlinin2 terminator | — |
| PRO Arath-FAE1 | *Arabidopsis thaliana* fatty acid elongase promoter TMV leader | CDS Pyrco delta-5 elongase | Δ5-elongase *Pyramimonas cordata* | TER Glyma-Lectin | Glycine max lectin terminator | — |
| PRO Brana-FP1 | *Brassica napus* napin promoter TMV leader | CDS Pavsa-d5D | Δ5-desaturase *Pavlova salina* | TER Agrtu-NOS | *Agrobacterium tumerfaciens* nopaline synthase terminator | MAR Nicta-RB7 |

TABLE 1-continued

Genetic elements in Elite Event NS-B50027-4

| Promoter (PRO) | | Coding sequence (CDS) | | Termination (TER) | | MAR |
|---|---|---|---|---|---|---|
| Name | Source | Name | Source | Name | Source | |
| PRO Linus-Cnl1 | *L. usitatissimum* conlinin1 promoter TMV leader | CDS Picpa-w3D | Δ15/ω3-desaturase *Pichia pastoris* | TER Linus-Cnl1 | *L. usitatissimum* conlinin1 terminator | — |
| PRO Linus-Cnl2 | *L. usitatissimum* conlinin2 promoter | CDS Pavsa-d4D | Δ4-desaturase *Pavlova salina* | TER Linus-Cnl2 | *L. usitatissimum* conlinin2 terminator | — |
| PRO Linus-Cnl2 | *L. usitatissimum* conlinin1 promoter | CDS Lack1-d12D | Δ12-desaturase *Lachancea kluyveri* | TER Linus-Cnl1 | *L. usitatissimum* conlinin1 terminator | MAR Nicta-RB7 |
| PRO Arath-FAE1::ENHANCER TMV Leader | *A. thaliana* fatty acid elongase promoter TMV leader | CDS Pyrco delta-6 elongase | Δ6-elongase *Pyramimonas cordata* | TER Glyma-Lectin | *G. max* lectin terminator | — |
| PRO 35S x2 | Cauliflower Mosaic Virus | CDS phosphinothricin N-acetyl transferase | *Streptomyces viridochromogenes* | TER Agrtu-NOS | *A. tumefaciens* nopaline synthase terminator | — |

Accordingly, to determine whether a biological sample comprises at least part of the LC-PUFA pathway as present in NS-B50027-4 primers and probes can be used to detect transgenes. Particular primers useful for detecting transgenes are shown in Table 2, in which each primer has an annealing temperature of 62, and the size (bp) refers to the number of base pairs in the PCR product.

TABLE 2

Example PCR primer sets for the detection of expression cassette genes

| Target gene | sense primer | antisense primer |
|---|---|---|
| Δ12 desaturase | TGGAGCTATCCCTCATGAGT (SEQ ID NO: 53) | GATCCTAGAACAGTAGTGGTG (SEQ ID NO: 54) |
| Δ15/ω3 desaturase | GACGCTATCCCTAAGCACTGT (SEQ ID NO: 55) | GTCCACTCTTGAGCATCGTA (SEQ ID NO: 56) |
| Δ6 desaturase | GAGCACCTTGTAGTTGAGTCC (SEQ ID NO: 57) | AGTCTGAGGATGCTCCTATGC (SEQ ID NO: 58) |
| Δ6 Elongase | TGTTGCTATGGCTCAAGAGC (SEQ ID NO: 59) | CTAGCGTGGTGCTTCATGTA (SEQ ID NO: 60) |
| Δ5 desaturase | GCTACCGATGCTTACAAGCA (SEQ ID NO: 61) | TAGTGAAGTCCGTGCTTCTC (SEQ ID NO: 62) |
| Δ5 elongase | TGCTGGAACTCTTGGATACG (SEQ ID NO: 63) | CTGGGTGATGTACTTCTTCC (SEQ ID NO: 64) |
| Δ4 desaturase | GGCTTTCAGATCTGAGCATC (SEQ ID NO: 65) | CTCAGCCTTAACAAGAGGAG (SEQ ID NO: 66) |

Initial transformants cultivated from *Brassica napus* L. (var. AV Jade) germline exhibited a wide variation in levels of fatty acid production, particularly in EPA and DHA levels. For the second and third generations, selection was based primarily on DHA and EPA content of transgenic seeds. In some cases, particularly T2 or T3 generations, segregation patterns (determined by growing twenty to forty individual seeds from one plant to twenty to forty offspring, and then measuring the DHA and EPA content of the individual seeds of those offspring) also exhibited scattered results, indicating complex or multi-copy insertions had occurred. Many of the initial T2 or T3 generations of plants were thus discarded. Initially, it was concluded that multiple copies of the transgenic insert would yield unstable transformants, and also exhibit classic gene silencing seen in homozygous genotypes. Therefore, if PCR analysis of transformed plants indicated copy number>1, those transformants were often discarded.

Surprisingly, elite event NS-B50027-4 was found to contain a multi-copy event: a sixteen-gene insertion including two eight-gene-T-DNA-bordered cassettes arranged in binary (inverted) left-border-to-left-border fashion (analogous to a massive palindrome); and a separate, smaller four-gene cassette; and this combination of transgene inserts act synergistically in the production of DHA in inbred line NS-B50027-4. More specifically, a combination of crossing, backcrossing, and self-crossing segregated the sixteen-gene insert to chromosome A05 (also called N05), and the four-gene insert to chromosome A02 (also called N02). The contribution of each transgenic chromosome was determined by breeding each segregant to obtain pure homozygous lines of each event. For example, in one experiment the segregant comprising the sixteen-gene insert produced about 4% DHA; and segregant comprising the four-gene insert produced no DHA; but when the segregants were bred to combine the transgenic chromosome A02 locus and transgenic chromosome A05 locus, the combination of the two transgenic inserts provided a plant that produced at least about 7% DHA to at least about 14% DHA, inclusive, in its seed. This result was unexpected. As noted, despite the unusual genetic makeup of elite event NS-B50027-4, the line has proved stable and consistent in fatty acid production.

Regarding the smaller, four-gene insert located on A02, this insert replaced about 15 bp of the 3' UTR region of a gene of unknown function (HPP gene). The partial insert and its flanking *B. napus* sequences are well-characterized herein. The four-gene insert includes the Δ6-desaturase, Δ5-elongase, Δ5-desaturase, and Δ15/ω3-desaturase transgenes; but does not include the Δ4-desaturase, Δ12-desaturase, Δ6-elongase genes, nor the genetic selection marker PAT. Because Δ4-desaturase is required for DHA production in the plant seed cell, it was unexpected and surprising that the four-gene insert contributed synergistically to the production of DHA in transgenic line NS-B50027-4. The four-gene insert and its flanking *B. napus* regions on A02 are shown in FIG. 5 (SEQ ID NO:40). In particular, nucleotides 1 to 2089 of SEQ ID NO:40 are a 5' (upstream) flanking region of the insertion site of the small insert; nucleotides 2090 to 14201 of SEQ ID NO:40 provides the heterologous nucleic acid from the transgenic cassette; and nucleotides 14202 to 15006 of SEQ ID NO:40 are a 808 bp 3' (downstream) region of the insertion site. Nucleotides 1 to 2089 and 14202 to 15006 of SEQ ID NO:40 are native to the *B. napus* chromosome A02. Genetic analysis comparing the native *B. napus* sequence and the insertion site revealed an insertion deletion: the transgene insert replaced a 15-bp-fragment (GTAGCACGACAAGTT; SEQ ID NO:38) that would otherwise be located on chrUn_random of *B. napus* cultivar Darmor reference (2n=AACC) at position 118589927-118589941, and on chromosome A02 of a reference genome from *B. rapa* cultivar Chiifu (2n=AA) at position 18569316-18569330. See Chalhoub et al., 345 Sci. 950 (2014); NCBI Ref. Seq. NC_024796.1; Wang et al., 43 Nat. Genet. 1035 (2011); NCBI Ref. Seq. XM_009130638.

The sixteen-gene insert was confirmed to be located in a *Brassica* gene encoding the Pto-interacting protein (PTI), a serine-threonine kinase that would otherwise be involved in hypersensitive response-mediated signaling. The PTI gene is located on chromosome A05 of reference genome *B. napus* (cultivar Darmor), at position 17267746-17270700. This larger insert is also associated with an insertion deletion, having replaced a 20-bp stretch of DNA (CACGGTGGAGGTCACCATGT; SEQ ID NO:39) in the second exon of the PTI protein; and thereby disrupted expression of PTI. This 20-bp deletion was located on chromosome A05 of the reference genome at position 17269790-17269809. The DNA sequence of the sixteen-gene insert and its flanking *B. napus* regions on A05 is shown in FIG. 6 (SEQ ID NO:41). In particular, nucleotides 1 to 1159 of SEQ ID NO:41 are a 5' (upstream) flanking region of the insertion site of the large insert; nucleotides 47774 to 49789 of SEQ ID NO:41 are a 3' (downstream) flanking region of the insertion site. Nucleotides 1 to 1159 of SEQ ID NO:41 and 47774 to 49789 of SEQ ID NO:41 of are native to the *Brassica napus* chromosome A05.

Accordingly, another embodiment provides a DNA molecule comprising an artificial, binary genetic locus comprising, in order, the following nucleotide sequences (arrows indicate direction of transcription in relation to referenced 5' to 3' DNA sequence):
 (a) the nucleotide sequence of SEQ ID NO:40 from nucleotide 2747 to nucleotide 6250 (Micpu-d6D←including PRO, leader, TER);
 (b) the nucleotide sequence of SEQ ID NO:40 from nucleotide 6257 to nucleotide 8414 (→Pyrco-d5E including PRO, leader, TER);
 (c) the nucleotide sequence of SEQ ID NO:40 from nucleotide 8415 to nucleotide 10374 (→Paysa-d5D including PRO, leader, TER);
 (d) the nucleotide sequence of SEQ ID NO:40 from nucleotide 10375 to nucleotide 11544 (→MAR); and
 (e) the nucleotide sequence of SEQ ID NO:40 from nucleotide 11545 to nucleotide 14049 (Picpa-w3/d15D←including PRO, leader, TER);
 (f) a molecule with at least 80%, 95%, 97%, 98%, 99%, or 99.5%, sequence identity to the nucleotide sequences
  (a) through (e); or
 (g) complements thereof.
A related embodiment provides plant cells, plant materials, or plant seeds comprising this artificial binary genetic locus.

Another embodiment provides a DNA molecule comprising an artificial binary genetic locus comprising, in order, the following nucleotide sequences:
 (a) the nucleotide sequence of SEQ ID NO:41 from nucleotide 1268 to nucleotide 5317 (Cn12 PRO thru leader thru coding region for Micpu-d6D←thru TER);
 (b) the nucleotide sequence of SEQ ID NO:41 from nucleotide 5324 to nucleotide 7481 (PRO thru→Pyrco-d5E thru TER);
 (c) the nucleotide sequence of SEQ ID NO:41 from nucleotide 7482 to nucleotide 9443 (PRO thru leader and→Paysa-d5D thru TER);
 (d) the nucleotide sequence of SEQ ID NO:41 from nucleotide 9444 to nucleotide 10611 (→MAR);
 (e) the nucleotide sequence of SEQ ID NO:41 from nucleotide 10612 to nucleotide 13116 (PRO thru leader and Picpa-w3/d15D←thru TER);
 (f) the nucleotide sequence of SEQ ID NO:41 from nucleotide 13117 to nucleotide 17000 (PRO thru→Paysa d4D thru TER);
 (g) the nucleotide sequence of SEQ ID NO:41 from nucleotide 17001 to nucleotide 19606 (PRO thru→Lack-d12D thru TER);
 (h) the nucleotide sequence of SEQ ID NO:41 from nucleotide 19607 to nucleotide 29773 (→MAR);
 (i) the nucleotide sequence of SEQ ID NO:41 from nucleotide 20783 to nucleotide 22987 (PRO thru→Pyrco-d6E thru TER);
 (j) the nucleotide sequence of SEQ ID NO:41 from nucleotide 23011 to 24370 (PRO thru→PAT thru TER);
 (k) the nucleotide sequence of SEQ ID NO:41 from nucleotide 42561 to nucleotide 25920 (PRO thru PAT←thru TER);
 (l) the nucleotide sequence of SEQ ID NO:41 from nucleotide 25943 to nucleotide 29324 (PRO thru Pyrco-d6E←thru TER);
 (m) the nucleotide sequence of SEQ ID NO:41 from nucleotide 28157 to nucleotide 29324 (MAR←);

(n) the nucleotide sequence of SEQ ID NO:41 from nucleotide 29324 to nucleotide 31830 (PRO thru Lack-d12D←thru TER);
(p) the nucleotide sequence of SEQ ID NO:41 from nucleotide 31831 to nucleotide 35816 (PRO thru Paysa d4D←thru TER);
(q) the nucleotide sequence of SEQ ID NO:41 from nucleotide 35817 to nucleotide 38319 (PRO thru leader and→Picpa-w3/d15D thru TER);
(r) the nucleotide sequence of SEQ ID NO:41 from nucleotide 38320 to nucleotide 39488 (MAR←);
(s) the nucleotide sequence of SEQ ID NO:41 from nucleotide 39489 to nucleotide 41449 (PRO thru Paysa-d5D←thru TER);
(t) the nucleotide sequence of SEQ ID NO:41 from nucleotide 41450 to nucleotide 43607 (PRO thru Pyrco-d5E←thru TER);
(u) the nucleotide sequence of SEQ ID NO:41 from nucleotide 43614 to nucleotide 47662 (PRO→Micpu-d6D thru TER);
(v) a molecule with at least 80%, 95%, 97%, 98%, 99%, or 99.5%, sequence identity to the nucleotide sequences (a) through (u), (a) through (j), (k) through (u); or
(w) complements thereof.

A related embodiment provides plant cells, materials, or seed comprising this artificial binary genetic locus.

Another embodiment provides a DNA molecule comprising an artificial binary genetic locus comprising, in order, the following nucleotide sequences:
(a) the nucleotide sequence of SEQ ID NO:40 from nucleotide 2747 to nucleotide 4141 (Micpu-d6D←);
(b) the nucleotide sequence of the complement of the nucleotide sequence of SEQ ID NO:40 from nucleotide 7259 to nucleotide 8065 (→Pyrco-d5E);
(c) the nucleotide sequence of SEQ ID NO:40 from nucleotide 8841 to nucleotide 10121 (→Paysa-d5D);
(d) the nucleotide sequence of SEQ ID NO:40 from nucleotide 12281 to nucleotide 13531 (Picpa-w3/d15D←);
(e) a molecule with at least 80%, 95%, 97%, 98%, 99%, or 99.5%, sequence identity to the nucleotide sequences (a) through (d); or
(f) complements thereof;
wherein the artificial locus includes regulatory regions (e.g., promoters, leader sequences, terminators) to provide expression of (a) through (d) or (e) or (f). A related embodiment provides plant cells, plant materials, or plant seeds comprising this artificial binary genetic locus.

Another embodiment provides a DNA molecule comprising an artificial binary genetic locus comprising, in order, the following nucleotide sequences:
(a) the nucleotide sequence of SEQ ID NO:41 from nucleotide 1820 to nucleotide 3208 (Micpu-d6D4←);
(b) the nucleotide sequence of SEQ ID NO:41 from nucleotide 6326 to nucleotide 7126 (→Pyrco-d5E);
(c) the nucleotide sequence of SEQ ID NO:41 from nucleotide 7908 to nucleotide 9192 (→Paysa-d5D);
(d) the nucleotide sequence of SEQ ID NO:41 from nucleotide 11352 to nucleotide 12596 (Picpa-w3/d15D4←);
(e) the nucleotide sequence of SEQ ID NO:41 from nucleotide 15216 to nucleotide 16556 (→Paysa d4D);
(f) the nucleotide sequence of SEQ ID NO:41 from nucleotide 17619 to nucleotide 18866 (→Lack-d12D);
(g) the nucleotide sequence of SEQ ID NO:41 from nucleotide 21895 to nucleotide 22647 (→Pyrco-d6E);
(h) the nucleotide sequence of SEQ ID NO:41 from nucleotide 25943 to nucleotide 26283 (Pyrco-d6E4←);
(i) the nucleotide sequence of SEQ ID NO:41 from nucleotide 30066 to nucleotide 31313 (Lack-d12D4←);
(j) the nucleotide sequence of SEQ ID NO:41 from nucleotide 31831 to nucleotide 35816 (Paysa-d4D4←);
(k) the nucleotide sequence of SEQ ID NO:41 from nucleotide 36335 to nucleotide 38319 (→Picpa-w3/d15D);
(l) the nucleotide sequence of SEQ ID NO:41 from nucleotide 39749 to nucleotide 41023 (Paysa-d5D4←);
(m) the nucleotide sequence of SEQ ID NO:41 from nucleotide 41805 to nucleotide 42605 (Pyrco-d5E4←);
(n) the nucleotide sequence of SEQ ID NO:41 from nucleotide 45724 to nucleotide 47111 (→Micpu-d6D);
(o) a molecule with at least 80%, 95%, 97%, 98%, 99%, or 99.5%, sequence identity to the nucleotide sequences (a) through (u), (a) through (j), (k) through (u); or
(p) complements thereof;
wherein the artificial locus includes regulatory regions (e.g., promoters, leader sequences, terminators) to provide expression of (a) through (n) or (o) or (p). A related embodiment provides plant cells, plant materials, or plant seeds comprising this artificial binary genetic locus.

A genetic trait such that has been engineered into a particular canola plant using transformation techniques, such as described herein, can be moved into another canola or *Brassica* line using traditional breeding techniques that are well known in the plant breeding arts. For example, plants harboring elite event NS-B50027-4 can, for example, be obtained from the seeds deposited at the ATCC. Such plants can be further propagated and/or used in a conventional breeding scheme to introduce elite event NS-B50027-4 into other cultivars of the same plant species. The deposited seeds belong to the species *Brassica napus*. Nevertheless, methods to introduce alleles or transgenes located on the A-genome or C-genome from *B. napus* to *B. juncea* are well known in the art and include repeated back-crossing. A backcrossing approach can be used to move a transgene from a transformed canola plant to an elite inbred line and the resulting progeny comprise the transgene. Also, if an inbred line is used for the transformation, then the transgenic plants can be crossed to a different line in order to produce a transgenic hybrid canola plant. As used herein, "crossing" can refer to a simple X by Y cross, or the process of backcrossing, depending on the context. Various genetic elements can further be introduced into the plant genome using transformation. These elements include but are not limited to genes; coding sequences; inducible, constitutive, and tissue specific promoters; enhancing sequences; and signal and targeting sequences.

Inbred Canola Line NS-B50027-4

Canola line NS-B50027-4 is a stable and uniform breeding line, as described herein. It has been bred with careful attention to uniformity of plant type, and the line has been increased with continued observation for uniformity. NS-B50027-4 is distinguished particularly for the production in its seeds of LC-PUFA, particularly LC-ω3 fatty acids, and more particularly DHA. Canola line NS-B50027-4 is not a parent of any other canola cultivar commercialized at the time of the patent filing for line NS-B50027-4.

Inbred transgenic canola line NS-B50027-4 has the following morphology and physiological characteristics (based primarily on data collected and averaged from eight different locations in Australia during 2015):

TABLE 3

Description Information: NS-B50027-4 and AV Jade

| | NS-B50027-4 | Comparator: AV Jade |
|---|---|---|
| Species | Brassica napus | Brassica napus |
| Leaf: Green color | medium | medium |
| Leaf: Lobes | present | present |
| Leaf: Number of lobes | medium | medium |
| Leaf: Dentation of margin | medium | medium |
| Leaf: Length | medium | medium |
| Time of Flowering | medium to late | medium |
| Flower: Color of petals | yellow | yellow |
| Flower: Width of petals | medium | medium |
| Flower: Production of pollen | present | present |
| Plant: Seedling vigor | medium to high | medium |
| Plant: Height at full flowering | medium | medium |
| Plant: Lodging at maturity | low | low |
| Blackleg Disease Resistance | present | present |
| Silique: Length | medium to long | medium to long |
| Silique: Length of beak | medium | medium |
| Silique: Length of peduncle | medium to long | medium to long |
| Seed Shattering | low | low |
| Seed: Yield | high | high |
| Seed % Oil | moderate | moderate |
| Seed: % Erucic Acid | nil | nil |
| Seed: % EPA C20:5n3 | present | absent |
| Seed: % DPA C22:5n3 | present | absent |
| Seed: % DHA C22:6n3 | present | absent |

Another aspect provides a method for producing a NS-B50027-4-derived *Brassica napus* plant, or parts thereof such as seed, comprising crossing the *B. napus* plant, or parts thereof, described above comprising obtaining the *Brassica* plant described above and growing the plant under *Brassica* plant growing conditions. Another aspect provides a method of growing *B. napus* line NS-B50027-4, representative seed of said line having been deposited under ATCC Accession No. PTA-123186, a sub-line of NS-B50027-4, progeny of NS-B50027-4 or the sub-line, or a plant produced by crossing NS-B50027-4 with a second canola or *Brassica* plant comprising: obtaining the *Brassica* seed described above and growing the plant under *Brassica* plant growing conditions. Another aspect provides a method for producing a NS-B50027-4-derived *Brassica napus* plant, or parts thereof such as seed, comprising crossing the *Brassica napus* plant, or parts thereof.

LC-ω3 Fatty Acids

With canola line NS-B50027-4 plants, according to the present embodiments, LC-ω3 fatty acids can be produced in commercial quantities from NS-B50027-4 canola seed. Thus, techniques for the selection and propagation of transformed plants yield a plurality of plants with advantageous traits of NS-B50027-4, that are harvested in a conventional manner and the fatty acids extracted from a tissue of interest, e.g., seeds.

As noted above, "fatty acid content" or "fatty acid composition" generally refers to percentages by weight of various fatty acids present in the endogenously formed oil of the mature, whole, partially dried seeds (typically containing about 6% or 7% moisture), calculated as percent particular fatty acid as area normalized; or against a known standard; or as a weight ratio of fatty acid per gram of seeds (e.g., mg DHA/g seeds).

A common industry practice reports fatty acid composition as area percentage (area normalized), rather than as absolute quantities. For example, chromatography often generates data as peaks, and the area under each peak is integrated and presented as a percentage of the total area under all the peaks for fatty acids in the chromatogram. Area percentage is easy to calculate and compare with results reported by others in the industry who also report area percentage. Area percentage is not absolute, but provides a acceptable approximation. Absolute mg/kg results can be calculated, for example, by including reference standards of known concentration and an internal standard. Correction factors can also be used to calculate mass amounts of fatty acids.

For example, in determining the fatty acid content the seeds may be crushed, the oil triacylglycerides (TAG) extracted, followed by saponification and methylation with methanol and sodium methoxide, or by reaction with 1.25% 3-(trifluoromethyl)phenyl-trimethylammonium hydroxide in methanol (Meth Prep II™, Fischer Scientific Cat #AT18007), to form fatty acid methyl esters. The resulting fatty acid methyl esters (FAME) can be analyzed by gas-liquid chromatography (GLC), using a capillary column that separates the FAME based on the degree of unsaturation and fatty acid chain length. FAME can also be analyzed by, for example, GC, LC-MS, GC-MS, NMR or near infrared reflectance spectroscopy. Fatty acid composition may also be determined from whole seeds, e.g., by breaking the seed coats and subjecting the broken seeds to direct methylation. Total lipid may be separated by techniques known in the art to purify fractions such as the TAG fraction. For example, thin-layer chromatography (TLC) may be performed at an analytical scale to separate TAG from other lipid fractions such as DAG, acyl-CoAs or phospholipid in order to determine the fatty acid composition specifically of TAG. A number of other analytical techniques may be used as known to those skilled in the art. See, e.g., Tinoco et al., 3 Anal. Biochem. 514 (1962); CANOLA: CHEMISTRY, PRODUCTION, PROCESSING & UTILIZATION (Daun et al., eds., AOCS Press, Urbana, Ill., 2011) (Daun et al., 2011); US 2015/0166928; US 20160002566.

In a further embodiment, extracted plant lipid can be treated to increase the level of DHA as a percentage of the total fatty acid content. For example, the treatment comprises hydrolysis of the esterified fatty acids to produce free fatty acids, or transesterification. For example, canola oil may be treated to convert the fatty acids in the oil to alkyl esters such as methyl or ethyl esters, which may then be purified or fractionated to enrich the lipid or oil for DHA. In embodiments, the fatty acid composition of the lipid after such treatment comprises at least 40%, at least 50%, at least 60%, at least 70%, at least 80%, or at least 90% DHA.

The present embodiments also include progeny and descendants of these new *B. napus* lines from line NS-B50027-4. The progeny or descendants can be developed by methods of breeding or tissue culture as are known to those skilled in the art. For example, the progeny or descendants can contain the canola fatty acid profile developed in these lines. Accordingly, the descendants or progeny can have any number of genes from the developed lines. The descendants or progeny can include only those genes that provide the canola fatty acid phenotype provided herein, or additional genes. This can be determined by molecular analysis as is known to those skilled in the art.

An aspect provides a method for developing a *Brassica napus* seed having the same phenotype as that of NS-B50027-4. For example, the DHA fatty acid content of NS-B50027-4 seeds comprise at least about 7%, at least about 8%, at least about 9%, at least about 10% DHA, at least about 11% DHA, at least about 12%, at least about 13%, at least about 14%, at least about 15% or more DHA (% fatty acids). For example, the LC-PUFA fatty acid content of NS-B50027-4 seeds comprise at least about 10% LC-PUFA, at least about 11%, at least about 12%, at least about 13%, at least about 14%, at least about 15%, at least about 16%, at least about 17%, at least about 18%, or more LC-PUFA (sum of EPA, DPA, DHA as % fatty acids).

Another aspect provides a homogeneous assemblage of crushed *Brassica napus* seed produced from the plants of described herein, wherein the crushed *B. napus* seed have at least about 30%, at least about 35%, such as about 36% to about 40%, inclusive, by weight, of total fatty acids (% wt. seed). In particular embodiments, for example, the fatty acid content of a homogeneous assemblage of crushed *B. napus* seed comprises at least about 7% DHA, at least about 8% DHA, at least about 9% DHA, at least about 10% DHA, at least about 11% DHA, at least about 12% DHA, at least about 13% DHA, at least about 14% DHA, at least about 15% DHA, or more DHA (% fatty acids). In particular embodiments, for example, the fatty acid content of a homogeneous assemblage of crushed *B. napus* seed comprises at least about 8% LC-PUFA, at least about 9% LC-PUFA, at least about 10% LC-PUFA, at least about 11% LC-PUFA, at least about 12% LC-PUFA, at least about 13%, at least about 14% LC-PUFA, at least about 15% LC-PUFA, at least about 16%, at least about 17%, at least about 18% or more LC-PUFA (sum of EPA, DPA, DHA as % fatty acids). Also provided is the oil and meal from such crushed seed.

Also provided is a homogeneous assemblage of crushed line NS-B50027-4 seed, or a homogeneous assemblage of crushed *B. napus* seed from a progeny or descendent of NS-B50027-4, wherein the crushed seeds have a DHA content of at least about 7% DHA, at least about 8% DHA, at least about 9% DHA, at least about 10% DHA, at least about 11% DHA, at least about 12% DHA, at least about 13% DHA, at least about 14% DHA, at least about 15% DHA, or more DHA (% fatty acids). For example, a homogeneous assemblage of crushed *Brassica napus* NS-B50027-4 seed, or a homogeneous assemblage of crushed *B. napus* seed from a progeny or descendent of NS-B50027-4, wherein the homogeneous assemblage of crushed seed comprises at least about 8% LC-PUFA, at least about 9% LC-PUFA, at least about 10% LC-PUFA, at least about 11% LC-PUFA, at least about 12% LC-PUFA, at least about 13%, at least about 14% LC-PUFA, at least about 15% LC-PUFA, at least about 16%, at least about 17%, at least about 18% or more LC-PUFA (sum of EPA, DPA, DHA as % fatty acids). Also provided is the oil and meal from such crushed seed.

Another aspect described herein provides a method of producing oil or meal from *Brassica napus* line NS-B50027-4, representative seed of said line having been deposited under ATCC Accession No. PTA-123186, a sub-line of NS-B50027-4, progeny of NS-B50027-4 or the sub-line, or a plant produced by crossing NS-B50027-4 with a second canola or *Brassica* plant comprising: growing the plant described above under *Brassica* plant growing conditions; harvesting the seed; and extracting oil or meal.

Another aspect described herein provides a method of producing oil from *Brassica napus* line NS-B50027-4, representative seed of said line having been deposited under ATCC Accession No. PTA-123186, a sub-line of NS-B50027-4, progeny of NS-B50027-4 or the sub-line, or a plant produced by crossing NS-B50027-4 with a second *Brassica* plant, comprising: crushing seeds of line NS-B50027-4, representative seed of said line having been deposited under ATCC Accession No. PTA-123186, a sub-line of NS-B50027-4, progeny of NS-B50027-4 or the sub-line, or a plant produced by crossing NS-B50027-4 with a second canola or *Brassica* plant; and extracting oil from said seeds.

Another aspect provides meal and protein, as well as oil, from NS-B50027-4 seed or NS-B50027-4-derived progeny seed. Protein extraction from plant biomass can be accomplished by known methods. See, e.g., Heney & Orr, 114 Anal. Biochem. 92 (1981). Meal from NS-B50027-4 may prove particularly advantageous because it contains at least some DHA and other ω3 fatty acids. Similarly, the protein fraction from NS-B50027-4 comprises at least some beneficial DHA and other ω3 fatty acids.

Despite having lower oleic acid content than oils alleged to lend stability to DHA and other LC-PUFAs via high oleic acid content, LC-PUFA ω3 fatty acid oil from the seed of NS-B50027-4 exhibit surprising stability. More specifically, LC-PUFA ω3 fatty acids are notoriously unstable and particularly susceptible to oxidation. It is understood in the art that encapsulation, blending with other oils, particularly high oleic acid oils, or adding antioxidants are required to extend the shelf life of LC-PUFAs and foods containing LC-PUFAs. Despite a lack of such treatments, however, some evidence suggests that crude oil extracted from crushed NS-B50027-4 seed retains freshness for months at room temperature.

Another aspect of the present embodiments provides a source of DHA and LC-PUFA for use in nutritional supplements and food for humans and non-human animals. In particular, oil from NS-B50027-4 seed provides a sustainable source of DHA and LC-PUFA for use in aquaculture. Due to the high global demands for fish and the resulting overfishing of the seas, marine and freshwater aquaculture has taken on increasing importance. Betancor et al., 4 Sci. Rep. 8104 (2014). For example, farming and consumption of salmonids has dramatically increased during the past 20 years. The diet of wild fish is very different from that of their fellow species in aquaculture, however. In fact, aquaculture is still highly dependent upon marine-capture fisheries to provide key dietary nutrients, such as fish meal and fish oil. Indeed, fish meal and fish oil are the primary sources of ω3-LC PUFA in aquaculture. Because marine fish oils comprise a limiting factor for the strongly growing fish farming industry (5% to 10% per annum), aquaculture diets contain a wide variety of alternative plant-based ingredients such as legume seeds, oilseed cakes, leaf meals, and an increasing portion of vegetable oil. Replacing fish oils with vegetable oils that are traditionally low in LC-PUFA means that less LC-PUFA are available in the fish diet, even though some oils such as flaxseed oil contain a quantity of ALA that can be converted, albeit only to a limited extent, into LC metabolites in fish. In general, current vegetable oils in fish feed can have a detrimental effect on the FA distribution in fish, and they can alter the ω3/ω6 ratio.

For example, typical vegetable oils contain high amounts of ω6 PUFA, mainly as linoleic acid (C18:2 ω6; LA). Oil from the parent line AV Jade has no DHA, therefore no DHA:LA ratio; oil from NS-B50027-4 has a DHA:LA ratio of 1.048; compared with oil from farm-raised salmon having a DHA:LA ratio of 0.908. Strobel et al., 11 Lipids Health Dis. 144 (2012). Interestingly, the ratios of ω3 FAs from NS-B50027-4 are particularly advantageous regarding palmitic acid, a saturated fatty acid associated with cardiovascular disease and dyslipidemia. *Diet, Nutrition & Prevention of Chronic Dis.*, WHO Tech. Rep. Series 916, Report of a Joint WHO/FAO Expert Consultation, 88 (World Health Organization, Geneva, 2003). Oil from the parent line AV Jade has no DHA, and thus no DHA:palmitate ratio; oil from NS-B50027-4 has a DHA:palmitate ratio of 2.122; oil from farm-raised salmon, in comparison, has a DHA:palmitate ratio of 0.591; and oil from wild salmon has a DHA:

palmitate ratio of 1.018. Strobel et al., 2012. The preparation of aquaculture feeds including LC-PUFAs is otherwise known in the art. See Betancor et al., 2014; Petrie et al., 9 PLOS ONE 1, 2014; Tocher, Aquaculture (2015). Therefore the scope of the present embodiments encompasses the use of oil from NS-B50027-4 as a source of ω3 fatty acids for aquaculture feed and aquaculture feed comprising oil obtained from NS-B50027 and its progeny.

Identification of NS-B50027-4 and Progeny Thereof

An elite genetic event can be characterized by the location(s) and the configuration at the site(s) of incorporation of the recombinant DNA molecule(s) in the plant genome. The site in the plant genome where a recombinant DNA cassette has been inserted is also referred to as the "insertion site" or "target site." A "flanking region" or "flanking sequence" is a region of DNA, for example, at least 20 base pairs, at least 50 base pairs, or up to 5,000 base pairs of the plant genome located either immediately upstream of and contiguous with, or immediately downstream of and contiguous with, the transgenic cassette. Transformation that leads to random integration of the foreign DNA results in transformants with different flanking regions, which are characteristic and unique for each transformant (elite event).

Another aspect provides a method for producing a NS-B50027-4-derived *Brassica napus* plant, or parts thereof comprising crossing the *Brassica napus* plant, or parts thereof, described above, with a second plant to produce a first generation progeny seed; growing said first generation progeny seed to produce an F1 generation plant; optionally, repeating the steps of crossing and growing to obtain successive filial generations of said seed to obtain a breeding line NS-B50027-4-derived *Brassica napus* seed, plant, or parts thereof. The plant or plant parts (including any hybrid) produced by this method are also provided. In an embodiment, a genetic trait that has been engineered into the genome of a particular canola plant may be moved into the genome of another cultivar using traditional breeding techniques that are well known in the plant breeding arts. For example, a backcrossing approach may be used to move a transgene from a transformed canola cultivar into an already developed canola cultivar, and the resulting backcross conversion plant would then comprise the transgene(s).

Accordingly, another aspect of the present embodiments provides compositions, methods, and kits for detection of NS-B50027-4. It would be advantageous to be able to detect the presence of a particular event in order to determine whether progeny of a sexual cross contain a transgene of interest. In addition, a method for detecting a particular event would be helpful for complying with regulations requiring the premarket approval and labeling of foods derived from recombinant crop plants, for example. It is possible to detect the presence of a transgene by any well-known nucleic acid detection method such as the polymerase chain reaction (PCR) or DNA hybridization using nucleic acid probes. These detection methods generally focus on frequently used genetic elements, such as promoters, terminators, marker genes, etc. As a result, such methods may not be useful for discriminating between different events, particularly those produced using the same DNA construct unless the sequence of chromosomal DNA adjacent to the inserted DNA ("flanking DNA") is known. Event-specific PCR assays have been described. See, e.g., Windels et al., (Med. Fac. Landbouww, Univ. Gent 64/5b: 459-462, 1999) (identifying glyphosate tolerant soybean event by PCR using a primer set spanning the junction between the insert and flanking DNA, specifically one primer that included sequence from the insert and a second primer that included sequence from flanking DNA). Additionally, the sixteen-gene insert of NS-B50027-4 disrupted the expression of the *Brassica* gene encoding the Pto-interacting protein (PTI), a serine-threonine kinase involved in the hypersensitive response-mediated signaling located on chromosome A05. Although no phenotypic change was observed, this provides another marker for identification of NS-B50027-4 or NS-B50027-4-derived progeny Methods and kits herein are useful for identifying in biological samples the presence of plant material comprising specifically the transgenes in NS-B50027-4, as well as transgenic canola plants, plant materials, and seeds containing such event. The elite event NS-B50027-4 described herein can be identified by genotype, which can be characterized through a genetic marker profile that can identify plants of the same cultivar or a related cultivar or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs).

For example, the elite event NS-B50027-4 described herein can be identified by generation of a genetic map from a sample of plant material. A genetic map can be generated by conventional RFLP, Polymerase Chain Reaction (PCR) analysis, or SSR which identifies the approximate chromosomal location of the integrated DNA molecule coding for the foreign protein. See Glick & Thompson, METHODS IN PLANT MOLEC. BIOL. & BIOTECHNOL. 269 (CRC Press, Boca Raton, Fla., 1993). Map information concerning chromosomal location is useful for proprietary protection of a subject transgenic plant. For example, the map of the integration region can be compared to similar maps for suspect plants to determine if the latter have a common parentage with the subject plant. Map comparisons can involve hybridizations, RFLP, PCR, SSR and sequencing, all of which are conventional techniques.

Another aspect of the present embodiments provides kits and methods for determining whether a canola plant is or is related to inbred line NS-B50027-4, or a canola plant that comprises at least part of genetic elite event of line NS-B50027-4. Compositions and method for simple and unequivocal techniques for identification of elite event NS-B50027-4 in biological samples are described herein.

For example, a kit can include at least one set of primers for identification of one or more genetic markers of NS-B50027-4, such as a set of sense (forward) and antisense (backward) primers. See Table 2. Specific embodiments of primers include the following primers useful in kits for conducting KASP assays to detect NS-B50027-4 genetic traits, particularly useful in introgression studies and hybrid development. See Example 2. These primers may consist of a nucleic acid molecule comprising at least ten consecutive nucleic acids of a sequence as follows: GAAGGTGAC-CAAGTTCATGCTCCAAGCACCGTAGTAAGAGAGCA (SEQ ID NO:1, Micopu-Δ6D); GCTAAGAAGTGGGGACTCAACTACAA (SEQ ID NO:2, Micopu-Δ6D); GAAGGTGACCAAGTTCATGCT-GCTCTTGCTGGAACTCTTGG (SEQ ID NO:3, Pyrco-Δ5E); GGGTTAGCCACATTGTAGGTAACGTA (SEQ ID NO:4, Pyrco-Δ5E); GAAGGTGACCAAGTTCATGCT- TAAGAGACACCCTGGTGGAAAGA (SEQ ID NO:5, Pavsa-Δ5D); TAGCATCAGTTCCAACTTGGTAAGCAAT (SEQ ID NO:6, Pavsa-Δ5D); GAAGGTGACCAAGT-TCATGCTGAACACGTAAGCAGACCAAGCAG (SEQ ID NO:7, Picpa-w3D); CCCTCTTCTCCCTAACGAATTC-CTT (SEQ ID NO:8, Picpa-w3D); GAAGGTGACCAAGT-TCATGCTGAGGAACCTGTTGCTGCTGATGA (SEQ ID NO:9, Pavsa-Δ4D); GCGATCCTAGCACAAAGTT-GAAGGTA (SEQ ID NO:10, Pavsa-Δ4D); GAAGGTGAC-CAAGTTCATGCTGGATGGATCGCTTACCTCTTCGT (SEQ ID NO:11, Lack1-Δ12D); CAGGGTAAGGTTGTC-CTGTAACGTT (SEQ ID NO:12, Lack1-Δ12D); GAAGGTGACCAAGTTCATGCTCTATTG-GATGGGGACTCAAGC (SEQ ID NO:13, Pyrco-Δ6E); GGGAGATCCTTAGTAGCAGAAGAGAT (SEQ ID NO:14, Pyrco-Δ6E); GAAGGTGACCAAGTTCATGCTC-CTGAGAGGCGTCCTGTTGAAAT (SEQ ID NO:15, PAT); AACAGCAGCCATATCAGCAGCAGTA (SEQ ID NO:16, PAT); GAAGGTGACCAAGTTCATGCTTGT-TCTTGGGTGGGTCTGTCCTTC (SEQ ID NO:17, A05 Insert Junction 1); GAAGGTCGGAGTCAACGGATTGT-GTTCTTGGGTGGGTCTGTCCTTA (SEQ ID NO:18, A05 Insert Junction 1); ATCCACTAGCAGATTGTCGTTTCCC (SEQ ID NO:19, A05 Insert Junction 1); GTTG-GCTAAGGTCACGGTGGAG (SEQ ID NO:20, A05 Insert Junction 1); GAAGGTGACCAAGTTCATGCTCCGCCT-TCAGTTTAAACTATCAGTGTT (SEQ ID NO:21, A05 Insert Junction 1); GAAGGTCGGAGTCAACGGATTG-GTCACGGTGGAGGTCACCA (SEQ ID NO:22, A05 Insert Junction 1), GGTGTGTTCTTGGGTGGGTCTG (SEQ ID NO:23, A05 Insert Junction 1); GAAGGTGAC-CAAGTTCATGCTACTTTTTTTTCAACTGTTG-GCTAAGGTA (SEQ ID NO:24, A05 Insert Junction 2); GAAGGTCGGAGTCAACGGAT-TACTTTTTTTTCAACTGTTGGCTAAGGTC (SEQ ID NO:25, A05 Insert Junction 2), GTGTGTTCT-TGGGTGGGTCTG (SEQ ID NO:26, A05 Insert Junction 2); GTCGTTTCCCGCCTTCAGTTT (SEQ ID NO:27, A05 Insert Junction 2); GAAGGTGACCAAGTTCAT-GCTAAACTATCAGTGTTTGAACACCTCC (SEQ ID NO:28, A02 Insert Junction 1); GAAGGTCGGAGT-CAACGGATTACAACTTGTCGTGCTACACACCT (SEQ ID NO:29, A02 Insert Junction 1); GGTTGTGT-GAAAACGTGTGAGC (SEQ ID NO:30, A02 Insert Junction 1); GAAGGTGACCAAGTTCATGCTCTTT-TAGCTAAATAAGAGGTTCTGTATACT (SEQ ID NO:31, A02 Insert Junction 2); GAAGGTCGGAGTCAACGGAT-TCTTTTAGCTAAATAAGAGGTTCTGTATACA (SEQ ID NO:32, A02 Insert Junction 2); GATTGTGATTC-CGGGCAGT (SEQ ID NO:33, A02 Insert Junction 2); GTGTGAAAACGTGTGAGCAAT (SEQ ID NO:34, A02 Insert Junction 2); GAAGGTGACCAAGTTCATGCTTT-GTGATTCCGGGCAGTAG (SEQ ID NO:35, A02 Insert Junction 2), GAAGGTCGGAGTCAACGGATTTGTGAG-CAATTGTTGGAGGT (SEQ ID NO:36, A02 Insert Junction 2); TCTTATCAACATTAAGAACATAATCTTTTAG (SEQ ID NO:37, A02 Insert Junction 2); or complements thereof.

The present invention also provides methods for identifying an elite event NS-B50027-4 canola plant, comprising: (a) forming a mixture comprising a biological sample containing canola plant DNA and a first and second nucleic acid primer capable of amplifying an event-NS-B50027-4-specific nucleic acid molecule; (b) reacting the mixture under conditions that allow the first and second nucleic acid primers to amplify an event NS-B50027-4-specific nucleic acid molecule; and (c) detecting the presence of the amplified fragment nucleic acid molecule, wherein the presence of the canola elite event NS-B50027-4-specific nucleic acid molecule indicates that the canola plant is a NS-B50027-4 canola plant.

Another embodiment provides methods for detecting an elite event NS-B50027-4 nucleic acid molecule in a biological sample comprising: (a) forming a mixture comprising a biological sample containing DNA and a nucleic acid probe capable of hybridizing to an event NS-B50027-4-specific nucleic acid molecule; (b) reacting the mixture under conditions that allow the probe to hybridize to an event NS-B50027-4-specific nucleic acid molecule; and (c) detecting the presence of a hybridized nucleic acid molecule, wherein the presence of the event NS-B50027-4-specific nucleic acid molecule indicates that the sample contains event NS-B50027-4 nucleic acid molecule.

Yet another embodiment provides methods for detecting the presence of an event NS-B50027-4 nucleic acid molecule in a biological sample, comprising: (a) forming a mixture comprising a biological sample containing DNA and a first primer capable of annealing to a region of the event NS-B50027-4 insert nucleic acid molecule and a second primer capable of annealing to a flanking nucleic acid molecule in a host cell genome; (b) reacting the mixture under conditions that allow the first and second nucleic acid primers to produce an amplified nucleic acid molecule comprising a fragment of the event NS-B50027-4 insert nucleic acid molecule; and (c) detecting the presence of the amplified nucleic acid molecule, wherein the presence of the fragment of the event NS-B50027-4 insert nucleic acid molecule indicates that the sample contains event NS-B50027-4 insert DNA.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs, as well as technical superiority of the final cultivar. For seed-propagated cultivars, it must be feasible to produce seed easily and economically For example, a kit can include at least one set of primers sense (forward) and antisense (backward) primers specific for a Δ6-desaturase derived from the micro alga *Micromonas pusilla*, a Δ5-elongase derived from the micro alga *Pyramimonas cordata*, a Δ5-desaturase derived from the marine microalga *Pavlova salina*, a Δ15/ω3-desaturase derived from the yeast *Pichia pastoris*, a Δ4-desaturase derived from *Pavlova salina*, or a Δ12-desaturase derived from the yeast *Lachancea kluyveri* (see, e.g., Table 2); and at least one set of primers specific for the 5' junction between the insert and the native *Brassica* chromosome A02 DNA, such as a junction from nucleotides 2033 to 2132 of SEQ ID NO:40, a 100 bp region comprising 43 bp of the insert and 57 bp of *Brassica* chromosome A02 DNA, or at least one set of primers specific for the 3' junction between the insert and the native *Brassica* chromosome A02 DNA, such as a junction from nucleotides 14156 to 14255 of SEQ ID NO:40, a 100 bp region comprising 46 bp of the insert and 54 bp of *Brassica* chromosome A02 DNA; at least one set of primers specific for the 5' junction between the insert and the native *Brassica* chromosome A05 DNA, such as a junction from nucleotides 1110 to 1209 of SEQ ID NO:41, a 100 bp region comprising 50 bp of the insert and 50 bp of *Brassica* chromosome A05 DNA, or at least one set of primers specific for the 3' junction between the insert and the native *Brassica* chromosome A05 DNA, such as a junction from nucleotides 47724 to 47823 of SEQ ID NO:42, a 100 bp region comprising 50 bp of the insert and 50 bp of *Brassica* chromosome A05 DNA.

The amplification conditions for methods that use DNA primers to produce an amplicon diagnostic for NS-B50027-4 event are within the ordinary skill of the art. In addition, a control primer pair for amplification of an endogenous canola gene is included as an internal standard for the reaction conditions and produces an amplicon of approximately 100-5000 nucleotides. The analysis of NS-B50027-4 event plant tissue sample should include a positive tissue control from NS-B50027-4 event, a negative control from a canola plant that is not NS-B50027-4 event, and a negative control that contains no template canola DNA. Additional primers can be selected from the junctions shown in SEQ ID NO:47, NO:48, NO:49 and NO:50 by those skilled in the art of DNA amplification methods, and conditions optimized for the production of an amplicon that may be any that result in an amplicon diagnostic for NS-B50027-4. The use of these DNA primer sequences with modifications are within the scope of the embodiments described herein. The amplicon produced by the use of at least one primer sequence derived from SEQ ID NO:47, or at least one primer sequence derived from SEQ ID NO:48, or at least one primer sequence derived from SEQ ID NO:49, or at least one primer sequence derived from SEQ ID NO:50, that when used in a PCR method produces an amplicon diagnostic for NS-B50027-4 event can be used in the described methods and is an aspect of the present embodiments. The production of the NS-B50027-4 event amplicon can be performed by using a thermocycler or by methods and apparatus known to those skilled in the art.

The present invention also provides methods for identifying an elite event NS-B50027-4 canola plant, comprising: (a) forming a mixture comprising a biological sample containing canola plant DNA and a first and second nucleic acid primer capable of amplifying an event-NS-B50027-4-specific nucleic acid molecule; (b) reacting the mixture under conditions that allow the first and second nucleic acid primers to amplify an event NS-B50027-4-specific nucleic acid molecule; and (c) detecting the presence of the amplified fragment nucleic acid molecule, wherein the presence of the canola elite event NS-B50027-4-specific nucleic acid molecule indicates that the canola plant is a NS-B50027-4 canola plant.

Another embodiment provides methods for detecting an elite event NS-B50027-4 nucleic acid molecule in a biological sample comprising: (a) forming a mixture comprising a biological sample containing DNA and a nucleic acid probe capable of hybridizing to an event NS-B50027-4-specific nucleic acid molecule; (b) reacting the mixture under conditions that allow the probe to hybridize to an event NS-B50027-4-specific nucleic acid molecule; and (c) detecting the presence of a hybridized nucleic acid molecule, wherein the presence of the event NS-B50027-4-specific nucleic acid molecule indicates that the sample contains event NS-B50027-4 nucleic acid molecule.

Yet another embodiment provides methods for detecting the presence of an event NS-B50027-4 nucleic acid molecule in a biological sample, comprising: (a) forming a mixture comprising a biological sample containing DNA and a first primer capable of annealing to a region of the event NS-B50027-4 insert nucleic acid molecule and a second primer capable of annealing to a flanking nucleic acid molecule in a host cell genome; (b) reacting the mixture under conditions that allow the first and second nucleic acid primers to produce an amplified nucleic acid molecule comprising a fragment of the event NS-B50027-4 insert nucleic acid molecule; and (c) detecting the presence of the amplified nucleic acid molecule, wherein the presence of the fragment of the event NS-B50027-4 insert nucleic acid molecule indicates that the sample contains event NS-B50027-4 insert DNA.

Progeny

The line NS-B50027-4 described herein can also be used for breeding other lines. For example, the source materials can be self-pollinated, outcrossed, backcrossed, used to produce doubled haploids, used as source materials for genetic transformation, of be subjected to genetic transformation, further mutagenized, and used for other forms of breeding as is known to those skilled in the art. The methods and results of using the source material to breed other lines are also within the scope of these embodiments.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner Any DNA sequences, whether from a different species or from the same species, which are introduced into the genome using transformation or various breeding methods, are referred to herein collectively as "transgenes." Over the last fifteen to twenty years, several methods for producing transgenic plants have been developed, and the present invention, in particular embodiments, also relates to transformed versions of the claimed line.

Nucleic acids, oligonucleotides, or polynucleotides refer to RNA or DNA molecules that are linear or branched, single or double stranded, or hybrids thereof—including RNA/DNA hybrids. These terms also encompass 3' UTRs and 5' UTRs, typically at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

Plant transformation involves the construction of an expression vector that will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed canola plants using transformation methods as known in the art to incorporate transgenes into the genetic material of the canola plant(s), including NS-B50027-4 canola plants.

A genetic trait that has been engineered into a particular canola plant using transformation techniques could be moved into another line using traditional breeding techniques that are well known in the plant breeding arts. For example, plants harboring elite event NS-B50027-4 can, for example, be obtained from the seeds deposited at the ATCC. Such plants can be further propagated or used in a conventional breeding scheme to introduce elite event NS-B50027-4 into other cultivars of the same plant species. The deposited seeds belong to the species *Brassica napus*. Nevertheless, methods to introduce alleles or transgenes located on the A-genome or C-genome from *B. napus* to *B. juncea* are well known in the art and include repeated back-crossing. A backcrossing approach can be used to move a transgene from a transformed canola plant to an elite inbred line and the resulting progeny comprise the transgene. Also, if an inbred line is used for the transformation, then the transgenic plants can be crossed to a different line in order to produce a transgenic hybrid canola plant. As used herein, "crossing" can refer to a simple X by Y cross, or the process of backcrossing, depending on the context.

Various genetic elements can further be introduced into the plant genome using transformation. These elements include but are not limited to genes; coding sequences; inducible, constitutive, and tissue specific promoters; enhancing sequences; and signal and targeting sequences. The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner Any DNA molecules, whether from a different species or from the same species, inserted into the genome using transformation are referred to herein collectively as "transgenes". The process of "transforming" is the insertion of DNA into the genome. Several methods for producing transgenic plants have been developed, and the present invention, in particular embodiments, also relates to transformed versions of the claimed canola line NS-B50027-4.

Numerous methods for plant transformation have been developed, including biological and physical, plant transformation protocols. In addition, expression vectors and in vitro culture methods for plant cell or tissue transformation and regeneration of plants are available. See, e.g., Miki et al., *Procedures for introducing foreign DNA into plants*, in METH. PLANT MOLEC. BIOL. & BIOTECHNOL. at 63 (Glick & Thompson, eds., CRC Press, Boca Raton, 1993); Gruber et al., *Vectors for plant transformation*, id. at R 89; *Genetic transformation for the improvement of Canola*, PROC. WORLD CONF. BIOTECHNOL. FATS & OILS INDUS. at 43-46 (Am. Oil. Chem. Soc., Champaign, Ill., 1988).

The most prevalent types of plant transformation involve the construction of an expression vector. Such a vector comprises a DNA molecule that contains a coding region under the control of or operatively linked to a regulatory region, for example a promoter. The expression vector may contain one or more genes and one or more regulatory elements. At least one of the coding regions and their respective regulatory elements can be arranged in opposite orientation within the vector, providing a binary vector. In theory, arrangement of genes susceptible to gene silencing in binary fashion may minimize gene silencing. The vector(s) may be in the form of a plasmid, and can be used alone or in combination with other plasmids, to provide transformed canola plants using transformation methods as known in the art to incorporate transgenes into the genetic material of the NS-B50027-4 plant or NS-B50027-4-derived plant.

For example, an initial transformation cassette, pJP3416_GA7-modB, included seven genes capable of promoting the accumulation of omega-3 fatty acids in canola seed, and one selectable marker gene to facilitate the selection of putative transgenic plants in vitro. See WO 2013185184; U.S. Patent Publ'n No. 2015/0374654; Petrie et al., 6 Plant Meth. 8 (2010). The expressed genes are all synthetic—codon optimized and synthesized—hence the transgenic DNA molecules are not found in any natural organisms. The original sequences that were used as templates for codon optimization have been described. See Petrie et al., 12 Metab. Eng'g 233 (2010a); Petrie et al., 11 Plant Methods 6 (2010b); Petrie et al., 21 Transgenic Res. 139 (2012).

As is well-known in the art, functional gene promoters are regions of DNA that are important for gene transcription, but do not encode functional products such as peptides. For example, a common promoter for constitutive expression is derived from Cauliflower Mosaic Virus. Kay et al., 236 Sci. 1299 (1987); Coutu et al., 16 Transgenic Res. 771 (2007). Promoters under developmental control include promoters that preferentially initiate transcription in certain tissues, such as seeds, leaves, roots, fibers, xylem vessels, tracheids, or sclerenchyma. Promoters of particular relevance are "seed-preferred" promoters that initiate transcription primarily or only in seed. "Seed-preferred" promoters include both "seed-specific" promoters (those promoters active during seed development such as promoters of seed storage proteins) as well as "seed-germinating" promoters (those promoters active during seed germination). See Thompson et al., 10 BioEssays 108 (1989). Such seed-preferred promoters include, but are not limited to, Cim1 (cytokinin-induced message); cZ19B1 (maize 19 kDa zein); milps (myo-inositol-1-phosphate synthase) (see WO 2000/11177 and U.S. Pat. No. 6,225,529). For dicots, seed-specific promoters include, but are not limited to, bean β-phaseolin, napin, β-conglycinin, soybean lectin, cruciferin, conlinin, and the like. The seed-specific promoters used in GA7-modB have been described previously: *A. thaliana* FAE1 (Rossack et al., 46 Plant Molec. Biol. 717 (2001)); *L. usitatissimum* Cn11 and Cn12 (Chaudhary et al., WO 2001016340); and truncated *B. napus* napin promoter (Stalberg et al., 23 Plant Molec. Biol. 671 (1993)). See also WO 2013185184.

An "inducible" promoter is a promoter that is under environmental control. Examples of environmental conditions that may affect inducible promoters include chemical control (induced in the presence of certain chemicals), anaerobic conditions, or the presence of light. Tissue-specific, tissue-preferred, (e.g., seed-specific), and inducible promoters constitute the class of "non-constitutive" promoters. See Ward et al., 22 Plant Mol. Biol. 361 (1993); Meft et al., 90 PNAS 4567 (1993) (copper-inducible); Gatz et al., 243 Mol. Gen. Genet. 32 (1994) (induced by herbicide safeners); Gatz, et al., 227 Mol. Gen. Genet. 229 (1991) (tetracycline-inducible); Schena et al., 88 PNAS 10421 (1991) (glucocortico-steroid-inducible). See also WO 2001016340 and the promoters discussed therein.

A "constitutive" promoter is a promoter which is active under most environmental conditions. Exemplary constitutive promoters include the promoters from plant viruses such as the 35S promoter from Cauliflower Mosaic Virus (CMV) (Odell et al., 313 Nature 810 (1985)) and the promoters from such genes as rice actin (McElroy et al., 2 Plant Cell 163 (1990)); ubiquitin (Christensen et al., 12 Plant Mol. Biol. 619 (1989); Christensen et al., 18 Plant Mol. Biol. 6759 (1992)); pEMU (Last et al., 81 Theor. Appl. Genet. 581 (1991)); MAS (Velten et al., 3 EMBO J. 2723 (1984)) and maize H3 histone (Lepetit et al., 231 Mol. Gen. Genet. 276 (1992); Atanassova et al., 2 Plant J. 291 (1992)). The ALS promoter, Xbal/Ncol fragment 5' to the *Brassica napus* ALS3 structural gene (or a nucleotide sequence similarity to said Xbal/Ncol fragment), provides another constitutive promoter. See also WO 1996/30530 and promoters discussed therein. The CMV promoter is also associated with a useful enhancer region. See WO 1996/30530 and WO 2013185184 and promoters discussed therein.

Terminator regions, which include polyadenylation signals, are required for the production of complete and stable mRNA molecules. For example, the *A. tumefaciens* nopaline synthase terminator (NOS) terminator provides a useful terminator. Bevan, 12 Nucl. Acid Res. 8711 (1984); Rogers et al., in BIOTECHNOL. PLANT SCI. at 219 (Acad. Press, Inc., New York, N.Y., 1985); Sanders et al., 15 Nucl. Acids Res. 1543 (1987). A range of regulatory sequences were used in combination to drive and terminate transcription the various expression cassettes.

Transport of protein produced by transgenes to a subcellular compartment such as the chloroplast, vacuole, peroxisome, glyoxysome, cell wall, or mitochondrion, or for secretion into the apoplast, is accomplished by means of operably linking the nucleotide sequence encoding a signal sequence to the 5' or 3' region of a gene encoding the protein of interest. Targeting sequences at the 5' or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, e.g., Becker et al., 20 Plant Mol. Biol. 49 (1992); Knox et al., 9 Plant Mol. Biol. 3 (1987); Lerner et al., 91 Plant Physiol. 124 (1989); Fontes et al., 3 Plant Cell 483 (1991); Matsuoka et al., 88 PNAS 834 (1991); Creissen et al., 2 Plant J. 129 (1991); Kalderon et al., 39 Cell 499 (1984); Steifel et al., 2 Plant Cell 785 (1990).

Expression vectors typically include at least one genetic marker, operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. Positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., 80 PNAS 4803 (1983). Another commonly used selectable marker gene is the hygromycin phosphotransferase gene which confers resistance to the antibiotic hygromycin. Vanden Elzen et al., 5 Plant Mol. Biol. 299 (1985). Additional selectable marker genes of bacterial origin that confer resistance to antibiotics include gentamycin acetyl transferase, streptomycin phosphotransferase, aminoglycoside-3'-adenyl transferase, the bleomycin resistance determinant Hayford et al., 86 Plant Physiol. 1216 (1988); Jones et al., 210 Mol. Gen. Genet., 86 (1987); Svab et al., 14 Plant Mol. Biol. 197 (1990); Hille et al., 7 Plant Mol. Biol. 171 (1986). Other selectable marker genes confer resistance to herbicides such as glyphosate, glufosinate, or bromoxynil. Comai et al., 317 Nature 741 (1985); Gordon-Kamm et al., 2 Plant Cell 603 (1990); Stalker et al., 242 Sci. 419 (1988). Selectable marker genes for plant transformation that are not of bacterial origin include, for example, mouse dihydrofolate reductase, plant 5-enolpyruvylshikimate-3-phosphate synthase, and plant acetolactate synthase. Eichholtz et al., 13 Somatic Cell Mol. Genet. 67 (1987); Shah et al., 233 Sci. 478 (1986); Charest et al., 8 Plant Cell Rep. 643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include α-glucuronidase (GUS), α-galactosidase, luciferase and chloramphenicol, acetyltransferase. Jefferson, R. A., Plant Mol. Biol., 5:387 (1987); Teeri, et al., EMBO J., 8:343 (1989); Koncz, et al., PNAS, 84:131 (1987); and DeBlock, et al., EMBO J., 3:1681 (1984). Some in vivo methods for visualizing GUS activity do not require destruction of plant tissues. Molecular Probes, Publication 2908, IMAGENE GREEN, 1-4 (1993); Naleway et al., 115 J. Cell Biol. 151a (1991). In vivo methods for visualizing GUS activity have been problematic, however, exhibiting low sensitivity, high fluorescent backgrounds, and limitations associated with the use of luciferase genes as selectable markers. Green Fluorescent Protein (GFP) can be been utilized as a marker for gene expression in prokaryotic and eukaryotic cells. Chalfie et al., 263 Sci. 802 (1994). GFP and mutants of GFP may be used as screenable markers.

NS-B50027-4 and NS-B50027-4 progeny can further be transformed to confer disease or pest resistance. For example, a plant line can be transformed with a cloned resistance gene to engineer plants that are resistant to specific pathogen strains. See, e.g., Jones et al., 266 Sci. 789 (1994) (cloning of the tomato Cf-9 gene for resistance to *Cladosporium flavum*); Martin, et al., 262 Sci. 1432 (1993) (tomato Pto gene for resistance to *Pseudomonas syringae* pv. tomato, a protein kinase); Mindrinos et al., 78 Cell 1089 (1994) (*Arabidopsis* RSP2 gene for resistance to *P. syringae*); Geiser et al. 48 Gene 109 (1986) (*Bacillus thuringiensis* δ-endotoxin gene); Van Damme et al., 24 Plant Mol. Biol. 25 (1994), (*Clivia miniata* mannose-binding lectin); Sumitani et al., 57 Biosci. Biotech. Biochem. 1243 (1993) (amylase inhibitor); Abe et al., 262 J. Biol. Chem. 16793 (1987) (cysteine proteinase inhibitor); Huub et al., 21 Plant Mol. Biol. 985 (1993) (tobacco proteinase inhibitor I); Regan, 269 J. Biol. Chem. 9 (1994) (insect diuretic hormone receptor); Pratt et al., 163 Biochem. Biophys. Res. Comm 1243 (1989) (allostatin); Tomalski et al., U.S. Pat. No.

5,266,317 (insect-specific, paralytic neurotoxins); Scott et al., WO 1993/02197 (callase gene); Kramer et al., 23 Insect Biochem. Mol. Biol. 691 (1993) (tobacco hornworm chitinase); Kawalleck et al., 21 Plant Mol. Biol. 673 (1993) (parsley ubi4-2 polyubiquitin gene); WO 1995/16776 (derivatives of tachyplesin inhibit fungi); WO 1995/18855 (synthetic antimicrobial peptides); Jaynes et al., 89 Plant Sci. 43 (1993) (cecropin-β, lytic peptide renders transgenic tobacco plants resistant to Pseudomonas solanacearum); Botella et al., 24 Plant Mol. Biol., 24:757 (1994) (mung bean calmodulin); Griess, et al., 104 Plant Physiol. 1467 (1994) (maize calmodulin); Taylor, et al., Abstract #497, 7th Intl Symp. Molec. Plant-Microbe Interactions (Edinburgh, Scotland (1994) (enzymatic inactivation in tobacco via transgenic single-chain antibody); Tavladorakiet al., 366 Nature 469 (1993) (viral resistance via transgenic antibody); Lamb et al., 10 Bio technol. 1436 (1992) (fungal endo-α-1, 4-D-polygalacturonase fragments facilitate fungal colonization and plant nutrient released by solubilizing plant cell wall homo-α-1,4-D-galacturonase; Toubart et al., 2 Plant J. 367 (1992) (bean endopolygalacturonase-inhibiting protein); Logemann et al., 10 Bio/technology 305 (1992) (transgenic plants expressing barley ribosome-inactivating gene have increased resistance to fungal disease).

As noted, herbicide resistance is another useful trait that can be introduced by genetic modification. For example, resistance to herbicides that inhibit the growing point or meristem, such as an imidazolinone or a sulfonylurea, can be conferred by mutant ALS and AHAS enzymes. See, e.g., Lee et al., 7 EMBO J. 1241 (1988); Miki et al., 80 Theor. Appl. Genet. 449 (1990); glyphosate resistance is conferred by aroA and mutant 5-enolpyruvlshikimate-3-phosphate synthase (EPSPS)genes; glufosinate resistance is conferred by phosphinothricin-acetyl transferase genes; and resistance to pyridinoxy or phenoxy proprionic acids and cyclohexones is conferred by ACCase inhibitor-encoding genes. See, e.g., U.S. Pat. No. 4,940,835 (EPSPS confers glyphosate resistance); mutant aroA gene, ATCC Accession No. 39256, see Comai, U.S. Pat. No. 4,769,061; see also Umaballava-Mobapathie, 8 Transgenic Research 33 (1999) (*Lactuca sativa* resistant to glufosinate); Kumada et al., EP 0 333 033; Goodman et al., U.S. Pat. No. 4,975,374 (EPSPS confers resistance to herbicides such as L-phosphinothricin); Leemans et al., EP 0 242 246 (phosphinothricin-acetyl-transferase); DeGreef et al., 7 Bio/technol. 61 (1989) (chimeric bar genes encoding phosphinothricin acetyl transferase); Marshall et al., 83 Theor. Appl. Genet. 435 (1992) (Acc1-S1, Acc1-S2, and Acc1-S3 genes confer resistance to phenoxy propionic acids and cyclohexones, such as sethoxydim and haloxyfop); Przibilla et al., 3 Plant Cell 169 (1991) (PsbA and gs+ genes confer triazine resistance); Stalker, U.S. Pat. No. 4,810,648 (nitrilase genes confer benzonitrile resistance); Hayes et al., 285 Biochem. J. 173 (1992) (glutathione S-transferase); Hattori et al., 246 Mol. Gen. Genet. 419 (1995) (acetohydroxy acid synthase confers resistance to multiple herbicides); Shiota et al., 106 Plant Physiol. 17 (1994) (yeast NADPH-cytochrome P450 oxidoreductase); Aono et al., 36 Plant Cell Physiol. 1687 (1995) (glutathione reductase and superoxide dismutase); Datta, et al., 20 Plant Mol. Biol. 619 (1992) (various phosphotransferases); WO 2001/12825; U.S. Pat. Nos. 6,288,306; 6,282,837; 5,767, 373; (plants with altered protox activity are resistant to protox-targeting herbicides).

NS-B50027-4 and NS-B50027-4-derived progeny can further be modified to confer any number of value-added traits as are known in the art. See, e.g., Goto, et al., 521 Acta Horticulturae 101 (2000) (soybean ferritin gene); Curtis et al., 18 Plant Cell Rep. 889 (1999) (nitrate reductase); Knultzon et al., 89 PNAS 2625 (1992) (stearyl-ACP desaturase); Shiroza et al., 170 J. Bacteriol. 810 (1988) (nucleotide sequence of *Streptococcus mutans* fructosyl-transferase gene); Steinmetz et al., 20 Mol. Gen. Genet. 220 (1985) (*Bacillus subtilis* levan-sucrase gene); Pen et al., 10 Bio/technol. 292 (1992) (transgenic plants express *Bacillus licheni-formis* α-amylase); Elliot et al., 21 Plant Mol. Biol. 515 (1993) (tomato invertase genes); Søgaard et al., 268 J. Biol. Chem. 22480 (1993) (site-directed mutagenesis of barley α-amylase gene); Fisher et al., 102 Plant Physiol. 1045 (1993) (maize endosperm starch branching enzyme II).

Canola line NS-B50027-4 can also be manipulated to be male sterile by any of a number of methods known in the art, including by the use of mechanical methods, chemical methods, self-incompatibility (SI), cytoplasmic male sterility (CMS, either ogura or another system) or nuclear male sterility (NMS). The term "manipulated to be male sterile" refers to the use of any available techniques to produce a male sterile version of canola line NS-B50027-4. The male sterility may be either partial or complete male sterility. See, e.g., WO 2001/29237 (introduction of a deacetylase gene under the control of a tapetum-specific promoter and with the application of the chemical N—Ac—PPT); WO 1992/13956, WO 1992/13957 (stamen-specific promoters); Paul et al., 19 Plant Mol. Biol. 611 (1992) (introduction of barnase and the barstar genes); see also U.S. Pat. Nos. 5,859,341; 6,297,426; 5,478,369; 5,824,524; 5,850,014; 6,265,640; Hanson et. al., 16 Plant Cell S154 (2004).

Numerous methods for plant transformation have been developed, including biological and physical, plant transformation protocols. See, e.g., WO 2013185184; Miki et al., in METHS. PLANT MOLEC. BIOL. BIOTECHNOL. at 67-88 (Glick & Thompson, Eds., CRC Press, Inc., Boca Raton, Fla., 1993). In addition, expression vectors and in vitro culture methods for plant cell or tissue transformation and regeneration of plants are available. See, e.g., WO 2013185184; Gruber et al., METHS. PLANT MOLEC. BIOL. BIOTECHNOL. at 89-119 (Glick & Thompson, Eds., CRC Press, Inc., Boca Raton, Fla., 1993). One method for introducing an expression vector into plants uses the natural transformation system of *Agrobacterium*, see Horsch et al., 227 Sci. 1229 (1985); Curtis et al., 45 J. Exper. Botany 1441 (1994); Torres et al., 34 Plant Cell Tissue Organ Culture 279 (1993); Dinant et al., 3 Molec. Breeding 75 (1997); Kado, 10 Crit. Rev. Plant Sci. 1 (1991) (Ti and Ri plasmids of *A. tumefaciens* and *A. rhizogenes*, respectively, carry genes responsible for genetic transformation of plant); Gruber et al.; Miki et al.; Moloney et al., 8 Plant Cell Rep. 238 (1989) (*Agrobacterium* vector systems, methods for *Agrobacterium*-mediated gene transfer); U.S. Pat. No. 5,591,616.

Several methods of plant transformation collectively referred to as direct gene transfer have been developed as an alternative to *Agrobacterium*-mediated transformation. A generally applicable method of plant transformation is microprojectile-mediated transformation wherein DNA is carried on the surface of microprojectiles measuring 1 µm to 4 µm. The expression vector is introduced into plant tissues with a biolistic device that accelerates the microprojectiles to speeds of 300 m/s to 600 m/s which is sufficient to penetrate plant cell walls and membranes. Russell et al., 12 Plant Cell Rep. 165 (1993); Aragao et al., 20 Plant Mol. Biol. 357 (1992); Aragao et al., 12 Plant Cell Rep. 483 (1993); Aragao, 93 Theor. Appl. Genet. 142 (1996); Kim & Minamikawa 117 Plant Sci. 131 (1996); Sanford et al., 5 Part. Sci. Technol. 27 (1987); Sanford 6 Trends Biotech. 299 (1988);

Klein et al., 6 Bio/technol. 559 (1988); Sanford, 7 Physiol. Plant 206 (1990); Klein et al., 10 Bio/technol. 268 (1992).

Methods for physical delivery of DNA to plants are also known in the art. See, e.g., Zhang et al., 9 Bio/technol. 996 (1991) (sonication); Deshayes et al., 4 EMBO J., 2731 (1985) (liposomes); Christou et al., 84 PNAS 3962 (1987) (spheroplast NHW11915); Hain et al., 199 Mol. Gen. Genet. 161 (1985) ($CaCl_2$ precipitation); Draper et al., 23 Plant Cell Physiol. 451 (1982) (polyvinyl alcohol or poly-L-ornithine); Saker et al., 40 Biologia Plantarum, 507 (1997/98) (electroporation of protoplasts). Additional methods include, but are not limited to, expression vectors introduced into plant tissues using a direct gene transfer method, such as microprojectile-mediated delivery with a biolistic device, DNA injection, electroporation, and the like. Following transformation, expression of the above-described selectable marker genes may allow for preferential selection of transformed cells, tissues or plants, using regeneration and selection methods well-known in the art. See, e.g., WO 2013185184.

The foregoing methods for transformation would typically be used for producing a transgenic line. The transgenic line could then be crossed with another (non-transformed or transformed) line in order to produce a new transgenic canola line. Alternatively, a genetic trait engineered into a particular canola or Brassica, using well-known transformation techniques, could be introduced into another line using traditional backcrossing techniques that are also well-known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term "NS-B50027-4 plant" is used in the context of the present embodiments, this also includes any gene conversions of that line. The term "gene converted plant" refers to those NS-B50027-4 plants that are developed by backcrossing, genetic engineering, or mutation, wherein essentially all of the desired morphological and physiological characteristics of a variety are recovered in addition to the one or more genes transferred into the NS-B50027-4-derived line via the backcrossing technique, genetic engineering, or mutation. Backcrossing methods can be used with the present embodiments to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental Brassica plant that contributes the gene for the desired characteristic is termed the "nonrecurrent" or "donor parent." This terminology refers to the fact that the nonrecurrent parent is used one time in the backcross protocol and therefore does not recur. The parental Brassica plant to which the gene or genes from the nonrecurrent parent are transferred is known as the recurrent parent as it is used for several rounds in the backcrossing protocol. Poehlman & Sleper, 1994; Fehr, 1993. In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a canola plant is obtained wherein essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent cultivar is modified or substituted with the desired gene from the nonrecurrent parent, while retaining essentially all of the rest of the desired genetic, and therefore the desired physiological and morphological characteristics of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Gene traits may be identified that are not regularly selected in the development of a new line, but that can be improved by backcrossing techniques. Gene traits may or may not be transgenic. Examples of these traits include, but are not limited to, male sterility, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. See, e.g., U.S. Pat. Nos. 5,969,212; 7,164,059.

Further reproduction of the inbred line NS-B50027-4 can occur by tissue culture and regeneration. The term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. Tissue culture of various tissues of canola and regeneration of plants therefrom is well-known. See, e.g., Teng et al., 27 HortSci. 1030 (1992); Teng et al., 28 HortSci. 669 (1993); Zhang et al., 46 J. Genet. Breeding 287 (1992); Webb et al., 38 Plant Cell Tissue Organ Cult. 77 (1994); Curtis et al., 45 J. Exp. Bot. 1441 (1994); Nagata et al., 125 J. Am. Soc'y Hort. Sci. 669 (2000); Ibrahim, et al., 28 Plant Cell Tissue Organ Cult. 139 (1992); U.S. Pat. Nos. 5,959,185; 5,973,234; 5,977,445. Tissue culture as well as microspore culture for regeneration of canola plants can be accomplished successfully. See Chuong et al., 4 Plant Cell Rep. 4 (1985); Barsby et al., 5 Plant Cell Rep. 101 (1986); Kartha et al., 31 Physiol. Plant 217 (1974); Narasimhulu et al., 7 Plant Cell Rep. 104 (1988); Swanson, 6 Meth. Molec. Biol. 159 (1990); Cell Culture Tech. & Canola Improvement, 66 J. Am. Oil Chem. Soc. 455 (1989). It is clear from the literature that the state of the art is such that these methods of obtaining plants are used routinely with a high rate of success. Thus, another aspect of the present embodiments provides cells which upon growth and differentiation produce canola plants having the physiological and morphological characteristics of inbred transgenic line NS-B50027-4.

Generally, when the transgene is introduced into a plant through traditional crossing, its insertion site in the plant genome and its flanking regions are not changed. An "insertion region" refers to the region corresponding to a region of at least 40 base pairs, such as at least 100 base pairs, or up to more than 10,000 base pairs, encompassed by the upstream and the downstream flanking regions of a transgene in the (untransformed) plant genome and including the insertion site (and possible target site deletion). Taking into consideration minor differences due to mutations within a species, an insertion region may retain at least 85%, such as 90%, 95%, or 100% sequence identity with the upstream and downstream flanking regions of the foreign DNA in a given plant of that species. Insertion of the transgenic cassette into the plant genome can sometimes be associated, however, with deletion of plant DNA, referred to as "target site deletion." Nevertheless, additional transgenes or other genetic manipulations can be made in NS-B50027-4 without undue experimentation; and NS-B50027-4-derived plants can be identified as described herein.

The source material NS-B50027-4 can be used to produce lines for hybrid seed production if it is backcrossed onto a cytoplasmic male sterility source or some other source for sterilizing the inbred line as a female. Alternatively, the line can be used directly. For example, *B. napus* line NS-B50027-4 can be crossed with another canola plant to form a first generation population of F1 plants. The population of first generation F1 plants produced by this method is also an embodiment. This first-generation population of F1 plants comprises an essentially complete set of the alleles of canola line NS-B50027-4. Typically, an F1 hybrid is considered to have all the alleles of each parent. One of ordinary skill in the art can utilize either breeder books or molecular methods to identify a particular F1 plant produced using canola line NS-B50027-4, and any such individual plant is also encompassed by this invention. These embodiments also cover use of these methods with transgenic or single gene conversions of line NS-B50027-4.

Another embodiment of this invention is a method of using canola line NS-B50027-4 in breeding that involves the repeated backcrossing to canola line NS-B50027-4 any number of times. Using the transgenic methods described herein, backcrossing methods, or other breeding methods known to one of ordinary skill in the art, one can develop individual plants and populations of plants that retain at least 25%, 30%, 35%, 40%, 45%, 50%, 55%, 60%, 65%, 70%, 75%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% of the genetic profile of canola line NS-B50027-4. The percentage of the genetics retained in the progeny may be measured by either pedigree analysis or through the use of genetic techniques such as molecular markers or electrophoresis. In pedigree analysis, on average 50% of the starting germplasm would be passed to the progeny line after one cross to another line, 25% after another cross to a different line, and so on. Molecular markers could also be used to confirm and/or determine the pedigree of the progeny line.

A specific method for producing a line derived from canola line NS-B50027-4 is as follows. One of ordinary skill in the art crosses canola line NS-B50027-4 with another canola plant, such as an elite line. The F1 seed derived from this cross is grown to form a homogeneous population. The F1 seed contains 50% of the alleles from canola line NS-B50027-4 and 50% of the alleles of the other plant. The F1 seed is grown and allowed to self, thereby forming F2 seed. On average, the F2 seed has derived 50% of its alleles from line NS-B50027-4 and 50% from the other canola plant, but various individual plants from the population have a much greater percentage of their alleles derived from event NS-B50027-4. Wang et al., 40 Crop Sci. 659 (2000); Bernardo et al., 102 Theor. Appl. Genet. 986 (2001). As used in this context, the term population refers to a statistically representative sample. The F2 seed is grown and selection of plants made based on visual observation or measurement of traits. The traits used for selection may be the canola line NS-B50027-4 trait of high DHA production in seeds of the canola. The event NS-B50027-4-derived progeny that exhibits the desired NS-B50027-4-derived trait is selected and each plant is harvested separately. This F3 seed from each plant is grown in individual rows and allowed to self. Then, selected rows or plants from the rows are harvested and threshed individually. The selections are again based on visual observation of plant phenotype, or measurements for desirable traits of the plants, such as the desirable NS-B50027-4-derived trait. The process of growing and selection is repeated any number of times until an inbred NS-B50027-4-derived canola plant is obtained.

The NS-B50027-4-derived canola plant contains desirable traits derived from canola line NS-B50027-4, some of which may not have been expressed by the other canola plant to which canola line NS-B50027-4 was crossed and some of which may have been expressed by both canola lines but are now at a level equal to or greater than the level expressed in NS-B50027-4.

The NS-B50027-4-derived F1 canola or *Brassica* plants have, on average, 50% of their genes derived from NS-B50027-4, but various individual plants from the population have a much greater percentage of their alleles derived from NS-B50027-4. The breeding process, of crossing, self-pollination, and selection is repeated to produce another population of NS-B50027-4-derived canola plants with, on average, 25% of their genes derived from canola line NS-B50027-4, but various individual plants from the population have a much greater percentage of their alleles derived from NS-B50027-4. Another embodiment of the invention is an inbred NS-B50027-4-derived canola plant that has received the desirable NS-B50027-4-derived trait of high DHA.

The previous example can be modified in numerous ways, for instance selection may or may not occur at every self-pollinated generation, selection may occur before or after the actual self-pollination process occurs, or individual selections may be made by harvesting individual pods, plants, rows or plots at any point during the breeding process described. In addition, doubled-haploid breeding methods may be used at any step in the process. The population of plants produced at each and any generation of self-pollination is also an embodiment of the present embodiments, and each such population would consist of plants containing approximately 50% of its genes from canola line NS-B50027-4, 25% of its genes from canola line NS-B50027-4 in the second cycle of crossing and selection, 12.5% of its genes from canola line NS-B50027-4 in the third cycle of crossing and selection, and so on.

Another embodiment is the method of obtaining a homozygous NS-B50027-4-derived canola plant by crossing canola line NS-B50027-4 with another canola plant and applying doubled-haploid methods to the F1 seed or F1 plant or to any generation of canola line NS-B50027-4 obtained by the selfing of this cross. Pedigree breeding is used commonly for the improvement of self-pollinating crops or inbred lines of cross-pollinating crops. Two parents which possess favorable, complementary traits are crossed to produce an F1. An F2 population is produced by selfing one or several F1's or by intercrossing two F1's (sib mating).

Selection of the best individuals is usually begun in the F2 population. Then, beginning in the F3, the best individuals in the best families are selected. Replicated testing of families, or hybrid combinations involving individuals of these families, often follows in the F4 generation to improve the effectiveness of selection for traits with low heritability. At an advanced stage of inbreeding (i.e., F6 and F7), the best lines or mixtures of phenotypically similar lines are tested for potential release as new cultivars.

Still further, the present embodiments are directed to methods for producing NS-B50027-4-derived canola plants by crossing canola line NS-B50027-4 with a canola plant and growing the progeny seed, and repeating the crossing with the growing steps with the NS-B50027-4-derived canola plant from 1 to 2 times, 1 to 3 times, 1 to 4 times, or 1 to 5 times, and selfing any number of times after the first, second, third, fourth, or fifth cross. Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines with each generation due to failure of some seeds to germinate or some plants to produce at least one seed. As a result, not all of the F2 plants originally sampled in the population will be represented by a progeny when generation advance is completed.

A further embodiment provides a single-gene conversion of NS-B50027-4. A gene conversion occurs when DNA sequences are introduced through traditional (non-transformation) breeding techniques, such as backcrossing. DNA sequences, whether naturally occurring or transgenes, may be introduced using these traditional breeding techniques. Desired traits transferred through this process include, but are not limited to, fertility modification, fatty acid profile modification, other nutritional enhancements, industrial enhancements, disease resistance, insect resistance, herbicide resistance and yield enhancements. The trait of interest is transferred from the donor parent to the recurrent parent, in this case, the canola plant disclosed herein. Single gene traits may result from the transfer of either a dominant allele or a recessive allele. Selection of progeny containing the trait of interest is done by direct selection for a trait associated with a dominant allele. Selection of progeny for a trait that is transferred via a recessive allele requires growing and selfing the first backcross to determine which plants carry the recessive alleles. Recessive traits may require additional progeny testing in successive backcross generations to determine the presence of the gene of interest. Along with selection for the trait of interest, progeny are selected for the phenotype of the recurrent parent. It should be understood that occasionally additional polynucleotide sequences or genes are transferred along with the single gene conversion trait of interest. A progeny containing at least 90%, 95%, 96%, 97%, 98%, 99% or 99.5% of the genes from the recurrent parent, the canola plant disclosed herein, plus containing the gene-conversion trait, is considered to be a gene conversion of NS-B50027-4. When a trait is controlled by two genes (e.g., some disease resistance), selection is done simultaneously for two genes; and so on.

Mutation breeding is another method of introducing new traits into canola varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. See, e.g., Fehr, PRINCIPLES CULTIVAR DEVEL. (Macmillan Pub'l Co., 1993).

It should be understood that the canola line of the present embodiments can, through routine manipulation of cytoplasmic genes, nuclear genes, or other factors, be produced in a male-sterile form as described in the references discussed earlier. Such embodiments are also within the scope of the present claims. The present embodiments thus provide F1 hybrid seed and plants produced by the use of canola line NS-B50027-4.

There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs, also referred to as Microsatellites), and Single Nucleotide Polymorphisms (SNPs).

Isozyme Electrophoresis and RFLPs have been widely used to determine genetic composition. Shoemaker & Olsen (Molecular Linkage Map of Soybean (*Glycine max*), pp. 6.131-6.138 in S. J. O'Brien (ed.) Genetic Maps: Locus Maps of Complex Genomes, Cold Spring Harbor Laboratory Press, Cold Spring Harbor, N.Y. (1993)) developed a molecular genetic linkage map that consisted of 25 linkage groups with about 365 RFLP, 11 RAPD, three classical markers, and four isozyme loci. See also, Shoemaker, R. C., RFLP Map of Soybean, pp. 299-309, in Phillips, R. L. and Vasil, I. K. (eds.), DNA-Based Markers in Plants, Kluwer Academic Press, Dordrecht, the Netherlands (1994).

SSR technology is currently an efficient and practical marker technology; more marker loci can be routinely used and more alleles per marker locus can be found using SSRs in comparison to RFLPs. See, e.g., Diwan & Cregan, 95 Theor. Appl. Genet. 22 (1997). SNPs may also be used to identify the unique genetic composition of the invention and progeny varieties retaining that unique genetic composition. Various molecular marker techniques may be used in combination to enhance overall resolution. Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Thus, it is clear that the state of the art that these methods of obtaining plants are "conventional" in that they are used routinely and have a high rate of success. The utility of canola line NS-B50027-4 also extends to crosses with other species. Commonly, suitable species are of the family Brassicaceae. Accordingly, any and all methods using canola elite event NS-B50027-4 in breeding are encompassed by the present embodiments, including selfing, pedigree breeding, backcrosses, hybrid production and crosses to populations. All plants and populations of plants produced using canola line elite event NS-B50027-4 as a parent are within the scope of these embodiments, including those developed from varieties derived from canola line NS-B50027-4. Unique molecular marker profiles or breeding records can be used by those of ordinary skill in the art to identify the progeny lines or populations of progeny derived from canola line NS-B50027-4.

EXAMPLES

Example 1. Characterization and Selection of Line NS-B50027-4 in Field Trials

A difficult task in plant breeding is the identification of individual plants that are genetically superior, because for most traits the true genotypic value may be masked by other confounding plant traits or environmental factors. One method for identifying a superior plant is to observe its performance relative to other experimental plants and to one or more widely grown standard cultivars. If a single observation is inconclusive, replicated observations provide a better estimate of the genetic worth.

Plants initially identified as B0050-027-18 were selected based on a single-seed descent procedure by harvesting a sample of one seed per plant, and using the one-seed sample to plant the next generation. In general, the number of plants in a population declines each generation due to failure of some seeds to germinate or some plants to produce at least one seed. As a result, not all of the plants originally sampled in the population are represented by a progeny when generation advance is completed. Moreover, original transgenic events compound the complexity of inheritance, such that no prediction can be made regarding the genotype or phenotype of progeny. Thus, plants were self-pollinated and selected for type for successive generations until a particular line became homozygous, exhibited selected traits with excellent agronomic properties, and produced a uniform population of true-breeding progeny. More specifically, the test lines were selected following a breeding re-selection program at the Nuseed Innovation Centre (NIC), Horsham (Victoria, Australia). Selection and advancement of candidate lines was based on:
  (a) Copy number of the T-DNA insert;
  (b) Segregation pattern of DHA expression;
  (c) Homozygosity; (based on fatty acid phenotype and genotype);
  (d) Production of LC-ω3-DHA; and
  (e) Suitable agronomic traits for crop production, based on progeny testing at locations over winter and summer.

In Australia, canola is grown across the southern dryland cropping zone and mostly within winter-dominant rainfall environments. Australian production is mostly from spring type canola cultivars that have low vernalization requirements. In general, Australian cultivars typically retain some minor delay in the onset of flowering and have relatively high plant vigor or biomass production over winter months. The canola crop in Australia is typically sown from April to May after the first major rainfall event and harvested from October to December. Yield is influenced primarily by available water during the growing season and water use efficiency of the cultivar. Major pathotype gene resistance to blackleg disease, caused by *Leptosphaeria maculans*, can differentiate cultivars in terms of seedling survival and stem cankering, but Australian cultivars are considered generally to have high resistance when grown under recommended agronomic practices. Seed development follows a growing season of five to seven months, and occurs in late spring or early summer Apart from water availability, yield can be affected significantly by large temperature extremes (<0° C. to >35° C.) that may cause abortion of seed and seed pods.

As noted herein, transformation of canola germplasm was undertaken with an eight-gene construct that resulted in seed-specific accumulation of LC-ω3 fatty acids, in particular DHA. Broadly speaking, phenotype was characterized by product quality (PQ) (omega-3 fatty acids produced), although plants carried a marker gene (MG). Transformed material was reselected for locus homozygosity, expression of DHA in the seed, and agronomic traits and yield potential suitable for commercial production.

Three T2 generation-derived sibs from the transgenic event were compared with eight other canola cultivars (lines) for a range of important agronomic and seed traits across eight experimental locations (sites). In Victoria in 2015 the growing season rainfall was below long-term average and reduced the length of growing season. The eight Australian sites represented a wide range of environmental yield potentials as indicated by the range in site mean site yield (i.e., AV Garnet: 0.7 to 2.4 t/ha). Transgenic line B0050-027-18-X was represented by three transgenic lines: B0050-027-18-20 (T3), B0050-027-18-36-13 (T4), and B0050-027-18-105-13 (T4). Agronomic trait variation of the test lines was comparable to that of the commercial cultivars evaluated across all environments tested. This conclusion was supported by the finding that the grain yield of the highest yielding test line was statistically comparable, based on an across-site analysis (MET-REML), with the highest yielding commercial cultivars. Furthermore, for each site the highest yielding test line was significantly higher yielding than at least one cultivar, with the exception of one site where there were no significant differences. The test lines produced seed with slightly lower percent seed oil and with varied fatty acid composition; but this did not impact yield or agronomic performance. The expression of LC ω3 DHA fatty acid was highly stable across the tested environments.

Test lines were derived from transformed plantlets (var. AV Jade). Seed was bulked by allowing plants to self-pollinate in isolation (i.e., insect-proof tents).

The control cultivars (commercial breeding lines) used for comparison provided an agronomically diverse (e.g., plant habit, phenology) range of well-adapted (i.e., high but varying yield potential and oil content) cultivars grown widely in the cropping zone. These cultivars are all open-pollinated and described and extensively evaluated in, for example, the Australian National Variety Testing Program and Regional annual crop reports. See "nvtonline" website. Additionally, variation for plant disease resistance is well-described for blackleg in Australia. Van De Wouw et al., 67 Crop & Pasture Sci. 273 (2015). In Australia, blackleg disease can cause yield losses of up to 90%. Marcroft & Bluett, Agricul. Notes, AG1352, Victoria, Dept. Primary Indus. (2008). Genetic variation among commercial cultivars for specific seed fatty acid composition and seed oil content has been documented over time. See Seberry et al., *Quality of Australian canola* 2011 (Australian Oilseeds Fed., 2012). Plants from the cultivar AV Jade were transformed to produce the transgenic T0, and hence AV Jade can be considered a non-transformed isoline of the transgenic event described herein.

Phenotypic variation for test lines was characterized by plant emergence, plant vigor, flowering time, flowering duration, plant height, seed shattering, lodging resistance, blackleg severity, plant harvest count, grain yield, grain moisture, percent seed oil, and fatty acid content, particularly seed LC-ω3 polyunsaturated fatty acid (LC-PUFA), specifically concerning yield of EPA, DPA, and DHA. For all the traits measured, restricted estimated likelihood analysis was undertaken using ASREML in statistical software GenStat. Gilmour et al., ASREML user guide, release 3.0, Biometric Bulletin (3) (VSV Int'l, Waterhouse Stm Hemel Hempstead, U K, 2009). A linear mixed model statistical method was used to account for field spatial variation as extensively described and used for field plant breeding and genetics research. Cullis & Gleeson, 47 Biometrics 1449 (1991); Smith et al., 57 Biometrics 1138 (2001); Welham et al., *Analysis of linear mixed models by ASReml-R with Applications in Plant Breeding: Course Notes* (VSV Intl, Waterhouse Stm Hemel Hempstead, U K, 2013). A Meta-REML across-site analysis was further undertaken for grain yield (t/ha) to determine the across-site Best Linear Unbiased Prediction (BLUP) for lines tested.

Regarding plant emergence, this count was estimated by counting the number of emerged plants approximately twelve days post-sowing in two, one square meter (1 m$^2$) quadrants within each plot across all eight sites. The average of both quadrants was used to estimate the number of plants emerged per square meter and analyzed as a trait variate. A plant emergence score based on a visual estimate of average plant density per plot was recorded for each plot across all sites and analyzed as a trait variate (e.g., 1=Low=0-5 plants/m$^2$; 5=Moderate=25-30 plants/m$^2$; 9=High=Δ5-50 plants/m$^2$). Plant emergences based on number per square meter and plant emergence score varied significantly between line treatments for all eight sites. Statistically variation for plant emergence of the transgenic lines was significantly within the range expressed by the cultivars across all experiments. Plant vigor was predicted early in the growing season using an observation 1 to 9 score of vegetative biomass at plant cabbage stage (i.e., from six-leaf-stage) for each plot across all sites, and analyzed as a trait variate.

Flowering time was recorded as number of days from sowing to when 50% of plants in the plot had at least one open flower. This was recorded for each plot across all trials and analyzed as a trait variate. Start of flowering (number of days from sowing), based on 50% of plants flowering varied significantly between line treatments for all sites. The site mean flowering time varied from 99 to 110 days and is an indication of environmental differences across experimental sites for this trait. Statistically the variation for flowering time of the transgenic lines was significantly within the range expressed by the cultivars across all experiments.

Flowering duration was the calculated difference between flowering time and end flowering time (expressed as number of days). This was calculated for each plot across all trials and analyzed as a trait variate: Flowering duration=Flowering end day −Flowering time (50%). Start of flowering (number of days from sowing), based on 50% of plants flowering varied significantly between line treatments for all eight sites. The site mean flowering time varied from 99 to 110 days, reflecting environmental differences across experimental sites for this trait. Statistically, the variation for flowering time of the transgenic line was significantly within the range expressed by the cultivars across all experiments. Flowering end (number of days from sowing) based on 90% of plants having no flowers, varied significantly between lines for all eight sites. The site mean end of flowering time varied from 128 to 139 days, which reflected environmental differences across experimental sites for this trait. Statistically, the variation for end of flowering for the transgenic lines was significantly within the range expressed by the cultivars across all sites.

Plants at harvest based on plants per square meter varied significantly between lines for all eight sites. Statically, the variation for plant number at harvest time for the transgenic lines was significantly within the range expressed by the cultivars across all plantings and locations. The number of plants at emergence was significantly correlated to number of plants recorded at harvest. Some of the calculated survival percent exceeded 100%, which reflected slow seedling emergence in two cultivars (ATR Wahoo and AV Jade): not all seedlings had emerged at the time plant emergence counts were recorded.

Plant height at dry seed maturity stage was measured from base to growing tip in the center of the plot. The center of the plot was used to avoid confounding effects likely associated with inter-plot spatial area (edge effects). This trait was recorded for each plot across all trials and analyzed as a trait variate. Plant height at maturity (cm), varied significantly between line treatments for all sites. The site mean plant height varied from 63 cm to 105 cm, and indicated environmental differences across experimental sites for this trait. Statistically, the variation for height of maturity for the transgenic lines was significantly within the range expressed by the cultivars across all experiments.

Seed shattering (sometimes referred to as pod shattering) at maturity was analyzed using seed shattering count per ⅛th of a square meters recorded over a two-week period. This was undertaken by placing two trays between sown rows and beneath the canopy for each plot in all locations, and analyzed as a trait variate. A seed shattering score (based on a 1 (nil) to 9 scale (high: +40) scale) was also recorded at one site based on the number of seed observed on the ground just prior to harvest and analyzed as a trait variate. Seed shattering based on number of seeds on the ground at harvest varied significantly between line treatments for four of eight sites. The site mean seed shattering number varied from 3 to 15 (per ⅛th of a square meter), and indicated low levels of shattering across all sites. The seed shattering score at one of the sites also varied significantly between lines, and was closely correlated with the across-site mean seed shatter count. This indicates that shattering recorded as a score was a good predictor of seed shattering. Statistically, the variation for seed shattering based on seed counts and score for the transgenic lines was significantly within the range expressed by the cultivars across all experiments.

Lodging resistance was recorded as a 1 (resistant) to 9 (susceptible), scored on the basis of angle of plant lean from the base of the plant at maturity. There was no statistically significant variation for plant lodging. The lack of variation for this trait is likely to be associated with below average rainfall at late pod fill stage.

Blackleg leaf severity symptoms representative of *Leptosphaeria maculans* and *Leptosphaeria biglobosa* were recorded as a 1 (low<5%) to 9 (high>40%) score for one replicate across five sites. Not all plots were scored, due lack of observable variation. Symptoms associated with cankering and stem breakage were not observed. Blackleg disease leaf symptoms observed were at very low levels at all eight sites. One site was sown using bare seed (seed untreated with fungicide). There were no relative differences in plant emergence amongst lines tested between this site and other sites treated with seed fungicide. Leaf symptoms are not always predictive of the degree of stem cankering caused by *L. maculans* (the main cause of yield loss and basis for resistance rating in Australia, see Sosnowski et al., 33 Australian Plant Pathol. 401 (2004)). Several studies have evaluated blackleg resistance on the basis of pathogen infection on cotyledons, leaves, stem (canker) and plant survival under field conditions. Given the lack of cankering and stem breakage the canola lines can be considered resistant to the present disease pressure for the purposes described herein.

Plant harvest count was estimated by counting plants in two, one-square-meter quadrants within each plot in all eight sites. The average of both quadrants was then used to estimate the number of plants per square meter, and analyzed as a trait a variate. Plant survival (%) was calculated by expressing site means for plant count as a % of site means for plant emergence count: Plant survival %=(Plant harvest count×100)/Plant Emergence count.

Grain was harvested when seed was physiologically mature and dry (~7%) using a plot harvester. Harvest direction was kept consistent (i.e., front to back range for each row) for each trial to avoid harvest direction errors. Dry grain weight for each plot was determined and converted to units of t/ha based on plot area, and analyzed as a trait variate.

The grain moisture at harvest and in a lab sample was recorded and analyzed as a trait variate. A hand held moisture meter was used to analyze bulk samples directly at point of harvest in the field. Percent moisture was also determined using an oven drying method based on Australian Oilseed Federation (AOF) method 4-1.5. This method involved oven-drying a 5 gram sample in open tins at 130° C. for 1 hour. The samples were cooled in a desiccator for 40 minutes and weighed and percent moisture determined as a percent loss of mass. Grain moisture at harvest (%) varied significantly between line treatments for all eight sites. The site mean grain moisture at harvest varied from 9% to 12% which indicated that seeds were harvested at a similar grain stage. Statistically, the variation for grain moisture at harvest for the transgenic lines was significantly within the range expressed by the cultivars across all experiments. The grain moisture % at harvest was also correlated with flowering time, such that seed of later-flowering lines (i.e., ATR Wahoo and Monola515TT) had significantly higher grain moisture % at harvest time across all sites. Laboratory seed moistures varied significantly between lines across all sites. The differences between lines and across sites were very low, however, and averaged around 7%. This indicates no confounding effects of seed storage. The variation for seed moisture in the laboratory for the transgenic line was significantly ($P<0.05$) within the range expressed by non-transgenic lines.

The seed oil content (%) was analyzed using spinlock nuclear magnetic resonance (NMR) spectrometry on seed adjusted to 6% moisture. Briefly, samples of 5 grams to 10 grams of seed were weighed into an NMR tube and analyzed by the NMR spectrometer. Seed oil results were determined by a software calibration created originally using twenty reference samples of known percent oil content, as determined by gravimetric oil extraction. The seed oil content varied significantly ($P<0.05$) between lines across all eight sites. The site mean seed oil % varied from 37.0% to 41.5%, which was generally below the average for the planting locations, and was a likely consequence of below-average rainfall and higher-than-average temperatures experienced during the grain fill period. The relative line differences were very consistent across sites. The variation for seed oil content for the transgenic lines was slightly lower compared with the non-transgenic lines across all sites—on average by about 2%, which may offer a target for genetic improvement. The lower oil content may not be linked genetically to the transgenic event, but may be the result of transforming a lower oil content cultivar, i.e., AV Jade.

A summary of the characterization of the agronomic traits of event NS-B50027-4 compared with those of non-transgenic cultivars is shown in Table 4 (analysis REML; F pr<0.001 Sig for all traits).

TABLE 4

Across-site analysis of agronomic traits

| Trait: Line name Unit | Emergence Plant per m sq | Harvest Plant Count Plant per m sq | Emergence Score (1-9) | Plant Vigor Score (1-9) | Flowering Start Day | Flowering End Day | Flowering Duration Days | Height at Maturity cm | Shattered Seed No. | Yield t/ha | Grain Moisture at harvest % |
|---|---|---|---|---|---|---|---|---|---|---|---|
| ATR Bonito | 18.2 | 16.0 | 7.3 | 6.8 | 103.8 | 131.2 | 27.5 | 90.0 | 13.0 | 1.35 | 10.6 |
| ATR GEM | 17.9 | 16.6 | 7.1 | 6.7 | 105.3 | 133.6 | 28.2 | 91.0 | 10.9 | 1.21 | 13.0 |
| ATR Stingray | 17.6 | 17.3 | 7.1 | 5.9 | 100.9 | 129.7 | 28.8 | 82.7 | 14.4 | 1.34 | 8.2 |
| ATR WAHOO | 11.2 | 11.8 | 5.9 | 6.1 | 108.2 | 136.0 | 27.3 | 92.3 | 10.7 | 1.12 | 18.7 |
| AV GARNET | 18.6 | 16.3 | 7.4 | 7.2 | 104.4 | 132.8 | 28.6 | 102.1 | 15.0 | 1.31 | 10.2 |
| AV JADE | 7.8 | 12.5 | 5.0 | 4.8 | 106.7 | 134.8 | 28.3 | 89.9 | 9.8 | 0.96 | 9.9 |
| AV ZIRCON | 19.0 | 15.7 | 7.3 | 7.0 | 104.4 | 132.0 | 27.6 | 98.7 | 22.5 | 1.31 | 9.5 |
| Monola 515TT | 20.3 | 18.5 | 7.5 | 5.8 | 108.6 | 136.1 | 27.3 | 87.9 | 12.3 | 1.24 | 12.4 |
| NS-B50027-4 | 18.1 | 15.7 | 7.1 | 5.9 | 107.8 | 135.0 | 27.2 | 88.2 | 10.5 | 1.17 | 11.0 |
| B0050-027-18-36-13 | 22.5 | 20.3 | 7.2 | 5.9 | 106.6 | 134.4 | 27.9 | 76.4 | 10.3 | 0.95 | 10.8 |
| B0050-27-18-105-13 | 22.6 | 19.8 | 7.6 | 5.4 | 108.5 | 135.8 | 27.3 | 70.6 | 8.9 | 0.92 | 11.1 |
| Min Cultivar Value | 7.8 | 11.8 | 5.0 | 4.8 | 100.9 | 129.7 | 27.3 | 82.7 | 9.8 | 0.96 | 8.2 |
| NS-B50027-4 | 18.1 | 15.7 | 7.1 | 5.9 | 107.8 | 135.0 | 27.2 | 88.2 | 10.5 | 1.17 | 11.0 |
| Max Cultivar Value | 20.3 | 18.5 | 7.5 | 7.2 | 108.6 | 136.1 | 28.8 | 102.1 | 22.5 | 1.35 | 18.7 |
| Mean | 17.6 | 16.4 | 7.0 | 6.2 | 104.7 | 133.2 | 28.5 | 90.0 | 12.0 | 1.14 | 11.0 |
| VAR | 0.67 | 0.98 | 0.02 | 0.01 | 0.04 | 0.07 | 0.13 | 1.35 | 2.74 | 0.00 | 0.15 |
| SE | 0.81 | 0.98 | 0.14 | 0.11 | 0.21 | 0.27 | 0.35 | 1.15 | 1.65 | 0.06 | 0.39 |
| LSD | 1.62 | 1.95 | 0.28 | 0.21 | 0.41 | 0.54 | 0.71 | 2.30 | 3.30 | 0.11 | 0.78 |
| CV % | 4.6 | 6.0 | 2.0 | 1.7 | 0.2 | 0.2 | 1.3 | 1.3 | 13.8 | 5.0 | 3.6 |

Fatty Acids were determined using solvent extraction, followed by simultaneous saponification and methylation, and analysis by GC-FID. Briefly, this involved crushing the seed samples and extracting the oil into solvent from a crushed-seed subsample. The solvent was evaporated off under nitrogen, and an oil subsample was diluted in a new solvent. An aliquot was reacted with Meth Prep II (a saponification/methylation reagent). Samples were heated at 40° C. to speed the reaction, and then injected on GC-FID using a BPX-70 column for fatty acid determination. Fatty acids were calculated as % composition of the oil where the area of each fatty acid peak was determined as a percentage of the sum of all the fatty acid peaks in the chromatogram. These estimates were analyzed individually as a trait variate. The % of specific fatty was estimated for: palmitic acid; stearic acid; oleic & cis-vaccenic; linoleic; alpha linolenic acid (ALA); arachidic (also known as eicosanoic acid) and stearidonic (SDA); paullinic, gondoic, and gadoleic acid; erucic acid and eicosatetraenoic (ETA); eicosapentaenoic acid (EPA); docosapentaenoic acid (DPA); and docosahexaenoic acid (DHA). Table 5 presents an across-site analysis of seed fatty acid content (all values percent; analysis REML; Fpr<0.001 Sig for all traits):

TABLE 5

Across-site analysis of seed fatty acid content

| | Lab Seed Moisture | Seed Oil | Palmitic | Stearic | Oleic & Cis-vaccenic | Linoleic | ALA, Arachidic & SDA | Paullinic, Gondoic & Gadoleic | EPA | DPA | DHA | Sum of EPA DPA DHA |
|---|---|---|---|---|---|---|---|---|---|---|---|---|
| ATR Bonito | 6.7 | 41.9 | 3.9 | 1.7 | 60.5 | 20.9 | 10.1 | 1.1 | 0.0 | 0.0 | 0.0 | 0.0 |
| ATR GEM | 6.8 | 41.5 | 3.7 | 1.7 | 66.3 | 14.9 | 10.2 | 1.2 | 0.0 | 0.0 | 0.0 | 0.1 |
| ATR Stingray | 6.6 | 40.8 | 4.3 | 1.8 | 60.6 | 20.5 | 9.7 | 1.0 | 0.0 | 0.0 | 0.1 | 0.1 |
| ATR WAHOO | 6.8 | 41.7 | 3.7 | 1.6 | 60.7 | 20.4 | 10.4 | 1.2 | 0.0 | 0.0 | 0.1 | 0.1 |
| AV GARNET | 7.1 | 40.4 | 3.6 | 1.7 | 69.6 | 11.8 | 9.7 | 1.5 | 0.0 | 0.0 | 0.1 | 0.1 |
| AV JADE | 6.7 | 41.0 | 4.0 | 2.2 | 61.0 | 18.7 | 11.2 | 1.0 | 0.0 | 0.0 | 0.1 | 0.2 |
| AV ZIRCON | 6.8 | 41.0 | 3.8 | 1.6 | 69.3 | 11.8 | 10.4 | 1.3 | 0.0 | 0.0 | 0.0 | 0.0 |
| Monola 515TT | 6.9 | 40.9 | 3.6 | 2.1 | 73.3 | 12.2 | 5.2 | 1.4 | 0.0 | 0.0 | 0.1 | 0.2 |
| NS-B50027-4 | 6.9 | 37.0 | 4.1 | 2.1 | 45.9 | 8.2 | 20.7 | 3.4 | 0.4 | 1.0 | 8.6 | 9.9 |
| B0050-027-18-36-13 | 7.1 | 35.5 | 4.2 | 2.4 | 41.8 | 7.9 | 22.2 | 3.8 | 0.6 | 1.2 | 10.5 | 12.2 |
| B0050-27-18-105-13 | 7.2 | 35.3 | 4.1 | 2.4 | 42.0 | 7.7 | 22.1 | 3.9 | 0.5 | 1.2 | 10.3 | 12.0 |
| Min Cultivar Value | 6.6 | 40.4 | 3.6 | 1.6 | 60.5 | 11.8 | 5.2 | 1.0 | 0.0 | 0.0 | 0.0 | 0.0 |
| NS-B50027-4 | 6.9 | 37.0 | 4.1 | 2.1 | 45.9 | 8.2 | 20.7 | 3.4 | 0.4 | 1.0 | 8.6 | 9.9 |
| Max Cultivar Value | 7.1 | 41.9 | 4.3 | 2.2 | 73.3 | 20.9 | 11.2 | 1.5 | 0.0 | 0.0 | 0.1 | 0.2 |
| Mean | 6.8 | 39.6 | 3.9 | 2 | 55 | 14.8 | 15 | 2.3 | 0.1 | 0.6 | 3.1 | 3.8 |
| VAR | 0.002 | 0.05 | 0.0005 | 0.0003 | 0.1912 | 0.0385 | 0.0475 | 0.0032 | 0.0001 | 0.0005 | 0.0248 | 0.0345 |
| SE | 0.04 | 0.22 | 0.02 | 0.02 | 0.43 | 0.19 | 0.22 | 0.06 | 0.01 | 0.02 | 0.16 | 0.18 |
| LSD | 0.09 | 0.44 | 0.04 | 0.03 | 0.87 | 0.39 | 0.43 | 0.11 | 0.02 | 0.05 | 0.31 | 0.37 |
| CV % | 0.7 | 0.6 | 0.5 | 0.9 | 0.8 | 1.3 | 1.5 | 2.5 | 6.3 | 4.1 | 5.1 | 4.9 |

The percent of fatty acid in the seed present as stearic acid, as analyzed by GC-FID varied significantly between lines across all eight sites. The site-mean % stearic acid showed very little variation and ranged from 1.6% to 2.2%. Statistically, the variation for % stearic acid for the transgenic line was significantly within the range expressed by the non-transgenic lines across all sites.

The % of fatty acid in the seed as oleic and cis-vaccenic acid, as analyzed by GC-FID, varied significantly between lines across all eight sites. The site-mean % oleic and cis-vaccenic acid varied from 51% to 58%. Statistically, the variation for % oleic and cis-vaccenic acid for the transgenic line was significantly lower than the range expressed by the non-transgenic lines across all sites. This result is associated with the transgenic insert, and does not affect commercial agronomy or grain production.

The % of fatty acid in the seed present as linoleic acid, as analyzed using GC-FID, varied significantly between lines across all eight sites. The mean % linoleic acid per site ranged from 13.4% to 14.7%. The variation for % linoleic acid for the transgenic sib lines derived from one T2 event (plant B0050-027-18) was significantly ($P<0.05$) lower than the range expressed by the cultivars across all sites and sibs derived from other event sibs. The significant difference in % linoleic acid is likely associated with expression of transgenes. A reduction in the % linoleic acid is likely associated with the transgenic insert, but does not affect agronomy or grain production on the commercial scale.

The % of fatty acid present as ALA, arachidic, and SDA varied significantly between lines among all eight sites. The site mean for % ALA, arachidic, and SDA ranged from between 5% to 11%. The variation for the % ALA, arachidic, and SDA for the transgenic lines was significantly ($P<0.05$) higher than that expressed by the non-transgenic cultivars across all experiments. The significant differences seen for this trait at some sites was associated with expression of transgenes. This result is associated with the transgenic insert, and does not affect commercial agronomy or grain production. The specialty high oleic oil cultivar (Monola515 TT) produced significantly ($P<0.05$) lower % ALA compared to other cultivars, due to SNPs within the Fad genes.

The % of fatty acid present as paullinic, gondoic, and gadoleic acid varied significantly between lines across all eight sites. The site mean for % paullinic, gondoic, and gadoleic acid ranged from 2.0% to 2.5%. The variation for the % paullinic, gondoic, and gadoleic acid for the transgenic lines was significantly ($P<0.05$) higher than that expressed by the non-transgenic cultivars across all experiments. This result is associated with the transgenic insert and does not affect commercial agronomy or grain production.

The % of fatty acid present as erucic acid and ETA was recorded at five sites, and varied was generally close to 0%. The result associated with the transgenic insert does not commercially affect agronomy or grain production.

Seed LC-ω3 polyunsaturated fatty acid (LC-PUFA), specifically EPA, DPA, and DHA, was calculated as a percent for each plot sample and analyzed as a trait variate in which LC-PUFA=EPA %+DPA %+DHA %. Predicted DHA, as units of Kg/ha, was calculated for each plot and analyzed as a trait variate: DHA kg/ha=(Oil %×0.01)×(DHA %×0.01)× Grain yield (t/ha)×1000. Predicted LC-PUFA as units of Kg/ha was calculated for each plot as and analyzed as a trait variate: DHA kg/ha=(Oil %×0.01)×(LC-PUFA %×0.01)× Grain yield (t/ha)×1000.

The % of fatty acid as EPA varied significantly ($P<0.05$) among lines across all eight sites. The variation for the % for the transgenic lines was significantly ($P<0.05$) higher than that expressed by the non-transgenic cultivars. This result, associated with the transgenic insert, does not affect agronomy or grain production but indeed may make the grain more valuable.

The % of fatty acid as DPA varied significantly ($P<0.05$) between lines across all sites. The variation for the % for the transgenic lines was significantly ($P<0.05$) higher than that expressed by the non-transgenic cultivars across all sites. This result is associated with the transgenic insert and will not affect agronomy or grain production commercially.

The % of fatty acid as DHA varied significantly between lines across all eight sites. The variation for the % for the transgenic lines was significantly ($P<0.05$) higher than that expressed by the non-transgenic cultivars in all locations. This result is associated with the transgenic insert and does not affect commercial agronomy or grain production. Variance between transgenic sib lines was used as a basis for selection. DHA percent across sites and comparing elite event NS-B50027-4 with non-transgenic cultivars (as determined by GC-FID) is shown in Table 6 (analysis REML; F pr<0.001 Sig for all locations).

TABLE 6

| Site by cultivar/elite event mean seed % DHA (C22:6n3) | | | | | | | | | |
|---|---|---|---|---|---|---|---|---|---|
| Line name Site: | A | B | C | D | E | F | G | H | Across-site mean |
| ATR Bonito | 0.0 | 0.0 | 0.0 | 0.1 | 0.1 | 0.0 | 0.1 | 0.0 | 0.2 |
| ATR Gem | 0.0 | 0.0 | 0.0 | 0.1 | 0.1 | 0.1 | 0.1 | 0.0 | 0.1 |
| ATR Stingray | 0.0 | 0.1 | 0.2 | 0.3 | 0.0 | 0.1 | 0.1 | 0.0 | 0.3 |
| ATR Wahoo | 0.1 | 0.2 | 0.1 | 0.2 | 0.0 | 0.2 | 0.1 | 0.0 | 0.2 |
| AV Garnet | 0.0 | 0.0 | 0.0 | 0.2 | 0.1 | 0.2 | 0.2 | 0.0 | 0.2 |
| AV Jade | 0.0 | 0.3 | 0.5 | 0.0 | 0.2 | 0.1 | 0.3 | 0.0 | 0.3 |
| AV Zircon | 0.0 | 0.1 | 0.1 | 0.1 | 0.2 | 0.1 | 0.1 | 0.0 | 0.2 |
| Monola 515TT | 0.1 | 0.1 | 0.3 | 0.2 | 0.1 | 0.1 | 0.2 | 0.0 | 0.2 |
| NS-B50027-4 | 8.1 | 9.8 | 7.8 | 7.5 | 8.5 | 8.4 | 8.8 | 10.2 | 8.6 |
| B0050-027-18-36-13 | 10.0 | 12.2 | 9.5 | 9.7 | 10.1 | 10.4 | 10.8 | 13.3 | 10.8 |
| B0050-27-18-105-13 | 10.5 | 11.3 | 9.0 | 9.6 | 10.2 | 9.7 | 10.9 | 12.5 | 10.5 |
| Min Cultivar Value | 0.0 | 0.0 | 0.0 | 0.0 | 0.0 | 0.0 | 0.1 | 0.0 | 0.1 |
| NS-B50027-4 | 8.1 | 9.8 | 7.8 | 7.5 | 8.5 | 8.4 | 8.8 | 10.2 | 8.6 |
| Max Cultivar Value | 0.1 | 0.3 | 0.5 | 0.3 | 0.2 | 0.2 | 0.3 | 0.0 | 0.3 |
| Mean | 3.5 | 3.6 | 3 | 2.49 | 3.7 | 3.56 | 3.88 | 4.1 | |
| VAR | 0.15 | 0.07 | 0.079 | 0.29 | 0.14 | 0.14 | 0.11 | 0.18 | |
| SE | 0.39 | 0.27 | 0.281 | 0.53 | 0.37 | 0.37 | 0.33 | 0.42 | |
| LSD | 0.78 | 0.54 | 0.6 | 1.1 | 0.75 | 0.73 | 0.65 | 0.84 | |
| CV % | 11 | 7.5 | 9.4 | 21.5 | 10 | 10.6 | 8.4 | 10.4 | |

Predicted DHA expressed as Kg/ha, calculated on the basis of fatty acid profile, seed oil %, and grain yield, varied significantly (P<0.05) between lines across all sites. The variation for the % for the transgenic lines was significantly (P<0.05) higher than that expressed by the non-transgenic lines across all locations. This result is associated with the transgenic insert and does not affect commercial agronomy or grain production, except making the grain more valuable. Variance between transgenic sib lines was used as a basis for selection. There was high stability of DHA, in terms of units of production per area (Kg/ha), due to low across-site variation for seed oil and % DHA produced in the seed. Predicted yield of DHA (Kg/ha) across sites and comparing elite event NS-B50027-4 with non-transgenic cultivars is shown in Table 7 (analysis REML, F pr<0.001 Sig for all locations):

Regarding seed LC-PUFA omega 3-percent EPA, DPA, and DHA—the percent LC-PUFA varied significantly (P<0.05) among lines across all eight sites. The variation for the % for the transgenic lines was significantly (P<0.05) higher than that expressed by the cultivars across all experiments. This result is associated with the transgenic insert and does not affect agronomy or commercial grain production, except to increase the value of the grain. Variance between transgenic sib lines was used as a basis for selection. Trace levels of LC-PUFA observed in non-transgenic lines is likely to be associated with pollen flow, seed movement, or GC-FID error.

TABLE 7

Site by line mean seed predicted DHA (Kg/ha)

| Line name Site: | A | B | C | D | E | F | G | H | Across-site mean |
|---|---|---|---|---|---|---|---|---|---|
| ATR Bonito | 0 | 1 | 0 | 1 | 0 | 0 | 1 | 0 | 0 |
| ATR Gem | 0 | 0 | 0 | 0 | 2 | 2 | 2 | 1 | 1 |
| ATR Stingray | 0 | 0 | 0 | 1 | 0 | 0 | 0 | 0 | 0 |
| ATR Wahoo | 1 | 0 | 1 | 0 | 0 | 1 | 1 | 0 | 0 |
| AV Garnet | 0 | 1 | 2 | 1 | 1 | 4 | 1 | 2 | 1 |
| AV Jade | 0 | 0 | 1 | 0 | 1 | 0 | 0 | 0 | 0 |
| AV Zircon | 0 | 0 | 0 | 2 | 0 | 4 | 1 | 0 | 1 |
| Monola 515TT | 0 | 0 | 2 | 0 | 2 | 0 | 0 | 0 | 0 |
| NS-B50027-4 | 30 | 28 | 39 | 36 | 50 | 49 | 24 | 41 | 37 |
| B0050-027-18-36-13 | 25 | 27 | 41 | 41 | 52 | 53 | 24 | 36 | 37 |
| B0050-27-18-105-13 | 24 | 25 | 34 | 50 | 46 | 40 | 26 | 33 | 35 |
| Min Cultivar Value | 0.0 | 0.0 | 0.0 | 0.0 | 0.0 | 0.0 | 0.0 | 0.0 | 0.0 |
| NS-B50027-4 | 30.0 | 28.0 | 39.0 | 36.0 | 50.0 | 49.0 | 24.0 | 41.0 | 37.0 |
| Max Cultivar Value | 1.0 | 1.0 | 2.0 | 2.0 | 2.0 | 4.0 | 2.0 | 2.0 | 1.0 |
| Mean | 8 | 8 | 12 | 12 | 16 | 17 | 8 | 12 | |
| VAR | 3.93 | 3.08 | 14.60 | 38.66 | 10.77 | 24.55 | 7.60 | 6.94 | |
| SE | 1.98 | 1.75 | 3.81 | 6.20 | 3.28 | 4.79 | 2.75 | 2.63 | |
| LSD | 4.0 | 3.5 | 7.6 | 12.4 | 6.6 | 9.6 | 5.5 | 5.3 | |
| CV % | 23.6 | 22.5 | 33.1 | 53.4 | 20.3 | 29.8 | 34.2 | 22.7 | |

Table 8 shows the percent values as determined by GC-FID (analysis REML; F pr<0.001 Sig for all locations):

TABLE 8

Site by cultivar or transgenic line mean seed LC-PUFA (% sum of EPA + DPA + DHA)

| Line name Site: | A | B | C | D | E | F | G | H | Across-site mean |
|---|---|---|---|---|---|---|---|---|---|
| ATR Bonito | 0.0 | 0.0 | 0.0 | 0.1 | 0.1 | 0.0 | 0.2 | 0.2 | 0.3 |
| ATR Gem | 0.0 | 0.0 | 0.0 | 0.1 | 0.2 | 0.1 | 0.1 | 0.1 | 0.2 |
| ATR Stingray | 0.0 | 0.1 | 0.2 | 0.3 | 0.0 | 0.1 | 0.1 | 0.5 | 0.3 |
| ATR Wahoo | 0.1 | 0.2 | 0.1 | 0.2 | 0.0 | 0.2 | 0.1 | 0.2 | 0.2 |
| AV Garnet | 0.0 | 0.0 | 0.0 | 0.1 | 0.1 | 0.2 | 0.2 | 0.0 | 0.3 |
| AV Jade | 0.0 | 0.4 | 0.5 | 0.0 | 0.2 | 0.1 | 0.3 | 0.0 | 0.3 |
| AV Zircon | 0.0 | 0.2 | 0.1 | 0.1 | 0.2 | 0.1 | 0.1 | 0.3 | 0.2 |
| Monola 515TT | 0.1 | 0.1 | 0.3 | 0.2 | 0.2 | 0.1 | 0.2 | 0.0 | 0.3 |
| NS-B50027-4 | 9.5 | 11.4 | 9.1 | 8.9 | 9.8 | 9.8 | 10.3 | 11.8 | 10.1 |
| B0050-027-18-36-13 | 11.7 | 14.2 | 11.0 | 11.4 | 11.8 | 12.2 | 12.7 | 15.3 | 12.5 |
| B0050-27-18-105-13 | 12.2 | 13.2 | 10.5 | 11.3 | 11.9 | 11.3 | 12.7 | 14.5 | 12.3 |
| Min Cultivar Value | 0.0 | 0.0 | 0.0 | 0.0 | 0.0 | 0.0 | 0.1 | 0.0 | 0.2 |
| NS-B50027-4 | 9.5 | 11.4 | 9.1 | 8.9 | 9.8 | 9.8 | 10.3 | 11.8 | 10.1 |
| Max Cultivar Value | 0.1 | 0.4 | 0.5 | 0.3 | 0.2 | 0.2 | 0.3 | 0.5 | 0.3 |
| Mean | 4.3 | 4.4 | 3.6 | 3.05 | 4.5 | 4.34 | 4.75 | 4.9 | |
| VAR | 0.23 | 0.11 | 0.112 | 0.33 | 0.19 | 0.2 | 0.14 | 0.23 | |
| SE | 0.48 | 0.33 | 0.334 | 0.58 | 0.44 | 0.43 | 0.38 | 0.48 | |
| LSD | 0.95 | 0.66 | 0.7 | 1.2 | 0.87 | 0.87 | 0.76 | 0.96 | |
| CV % | 11 | 7.6 | 9.3 | 18.9 | 9.7 | 10.3 | 8 | 9.8 | |

Predicted LC-PUFA expressed as Kg/ha calculated on the basis of fatty acid profile, seed oil % and grain yield varied significantly between treatment lines across all sites. Statistically, the variation for the % for the transgenic lines was significantly higher than that expressed by the cultivars across all experiments. This result is associated with the transgenic insert and does not commercially affect agronomy or grain production. Variance between transgenic sib lines was used as a basis for selection. Trace levels in cultivar seed is likely to be associated with pollen flow, seed movement or GC-FID error. There is high stability of LC-PUFA in terms of units of production per area (Kg/ha) due to low across-site variation for seed oil and % DHA produced in the seed. Table 9 shows the predicted Kg/ha LC-PUFU (F pr<0.001 for all sites).

TABLE 9

Site by cultivar (line) mean seed predicted LC-PUFA (Kg/ha)

| Line name site: | A | B | C | D | E | F | G | H | Across-site mean |
|---|---|---|---|---|---|---|---|---|---|
| ATR Bonito | 0 | 1 | 0 | 1 | 0 | 0 | 1 | 0 | 0 |
| ATR Gem | 1 | 0 | 0 | 0 | 2 | 3 | 3 | 0 | 1 |
| ATR Stingray | 1 | 0 | 0 | 1 | 0 | 0 | 0 | 0 | 0 |
| ATR Wahoo | 0 | 0 | 2 | 0 | 0 | 1 | 1 | 0 | 1 |
| AV Garnet | 0 | 1 | 2 | 1 | 1 | 4 | 1 | 0 | 1 |
| AV Jade | 0 | 1 | 1 | 0 | 1 | 0 | 0 | 0 | 0 |
| AV Zircon | 0 | 0 | 0 | 2 | 0 | 4 | 2 | 0 | 1 |
| Monola 515TT | 0 | 0 | 2 | 0 | 2 | 0 | 0 | 0 | 1 |
| NS-B50027-4 | 35 | 33 | 46 | 43 | 58 | 58 | 28 | 46 | 43 |
| B0050-027-18-36-13 | 29 | 32 | 48 | 48 | 60 | 61 | 28 | 41 | 43 |
| B0050-27-18-105-13 | 28 | 29 | 40 | 58 | 53 | 46 | 30 | 40 | 41 |
| Mean | 10 | 10 | 14 | 14 | 20 | 20 | 10 | 14 | |
| VAR | 5.50 | 4.34 | 21.71 | 54.48 | 15.98 | 34.93 | 11.14 | 58.10 | |
| SE | 2.34 | 2.08 | 4.65 | 7.36 | 3.99 | 5.71 | 3.33 | 4.04 | |
| LSD | 4.7 | 4.2 | 9.3 | 14.7 | 8.0 | 11.4 | 6.7 | 8.1 | |
| CV % | 22.6 | 21.9 | 33.1 | 51.9 | 20.1 | 28.9 | 33.5 | 54.8 | |

Seed oil content, determined using NMR, was also tabulated for each of the cultivation sites, and is presented in Table 10 (units are percent; analysis REML; F pr<0.001 Sig for all sites):

TABLE 10

Site by cultivate seed oil mean oil %

| Line Site: | A | B | C | D | E | F | G | H | Across-site mean |
|---|---|---|---|---|---|---|---|---|---|
| ATR Bonito | 43.0 | 40.6 | 43.6 | 43.4 | 42.6 | 41.8 | 39.1 | 39.6 | 41.7 |
| ATR Gem | 43.7 | 40.7 | 43.9 | 42.7 | 42.3 | 40.5 | 37.8 | 39.5 | 41.3 |
| ATR Stingray | 41.4 | 39.7 | 42.6 | 42.8 | 41.1 | 39.1 | 38.9 | 39.9 | 40.6 |
| ATR Wahoo | 43.1 | 41.0 | 43.3 | 43.4 | 42.5 | 40.1 | 39.0 | 39.9 | 41.4 |
| AV Garnet | 43.9 | 39.9 | 43.4 | 41.8 | 41.5 | 39.1 | 36.5 | 36.4 | 40.2 |
| AV Jade | 41.7 | 40.2 | 42.6 | 42.2 | 42.5 | 38.6 | 37.5 | 39.4 | 40.6 |
| AV Zircon | 44.0 | 40.6 | 43.6 | 42.1 | 41.5 | 39.8 | 36.9 | 38.8 | 40.9 |
| Monola 515TT | 42.2 | 40.1 | 42.3 | 42.1 | 42.2 | 38.8 | 38.1 | 39.3 | 40.6 |
| NS-B50027-4 | 38.7 | 36.1 | 39.3 | 38.2 | 37.3 | 36.5 | 34.2 | 35.1 | 36.9 |
| B0050-027-18-36-13 | 36.7 | 34.3 | 37.2 | 37.9 | 36.8 | 34.3 | 33.4 | 33.2 | 35.5 |
| B0050-27-18-105-13 | 36.3 | 34.4 | 37.9 | 37.4 | 35.8 | 34.1 | 32.1 | 33.0 | 35.1 |
| Min Cultivar Value | 41.4 | 39.7 | 42.3 | 41.8 | 41.1 | 38.6 | 36.5 | 36.4 | 40.2 |
| NS-B50027-4 | 38.7 | 36.1 | 39.3 | 38.2 | 37.3 | 36.5 | 34.2 | 35.1 | 36.9 |
| Max Cultivar Value | 44.0 | 41.0 | 43.9 | 43.4 | 42.6 | 41.8 | 39.1 | 39.9 | 41.7 |
| Mean | 40.8 | 38.7 | 41.5 | 41.2 | 39.8 | 38.01 | 37 | 37.8 | |
| VAR | 0.13 | 0.09 | 0.23 | 0.13 | 0.13 | 0.19 | 0.18 | 0.1 | |
| SE | 0.36 | 0.3 | 0.477 | 0.36 | 0.36 | 0.42 | 0.43 | 0.31 | |
| LSD | 0.71 | 0.59 | 1 | 0.7 | 0.73 | 0.85 | 0.85 | 0.62 | |
| CV % | 1 | 0.8 | 1.2 | 0.9 | 0.9 | 1.1 | 1.2 | 0.8 | |

Additional analysis of the fatty acid content of NS-B50027-4 seed is presented in Table 11:

TABLE 11

Detailed fatty acid content data for NS-B50027-4
NS-B50027-4, Generation T7, Summer 2015-2016

| | C14:0 | C16:0 | C16:1n7c | C18:0 | C18:1n9c | C18:1n7c | C18:2n6c | GLA C18:3n6 | ALA C18:3n3 | C20:0 | SDA C18:4n3 | C20:1n9c |
|---|---|---|---|---|---|---|---|---|---|---|---|---|
| 1* | 0.05 | 4.33 | 0.24 | 2.16 | 38.83 | 4.26 | 7.81 | 0.58 | 21.54 | 0.64 | 2.20 | 1.31 |
| 2 | 0.05 | 4.28 | 0.23 | 2.19 | 38.32 | 4.17 | 7.76 | 0.59 | 21.58 | 0.65 | 2.21 | 1.31 |
| 3 | 0.05 | 4.20 | 0.22 | 2.19 | 38.77 | 4.06 | 7.81 | 0.60 | 21.73 | 0.66 | 2.22 | 1.28 |
| 4 | 0.05 | 4.19 | 0.21 | 2.16 | 38.69 | 4.09 | 7.79 | 0.61 | 21.66 | 0.63 | 2.25 | 1.34 |
| 5 | 0.05 | 4.26 | 0.21 | 2.18 | 38.35 | 4.22 | 7.81 | 0.59 | 21.78 | 0.64 | 2.25 | 1.29 |
| | 0.05 | 4.25 | 0.22 | 2.18 | 38.69 | 4.16 | 7.80 | 0.60 | 21.66 | 0.64 | 2.23 | 1.30 |

NS-B50027-4, Generation T6, Winter 2015

| | C14:0 | C16:0 | C16:1n7c | C18:0 | C18:1n9c | C18:1n7c | C18:2n6c | C18:3n6 | C18:3n3 | C20:0 | C18:4n3 | C20:1n9c |
|---|---|---|---|---|---|---|---|---|---|---|---|---|
| 1 | 0.0 | 4.60 | 0.21 | 2.22 | 41.95 | 3.10 | 6.35 | 0.47 | 21.06 | 0.69 | 2.27 | 1.14 |
| 2 | 0.0 | 5.00 | 0.25 | 2.01 | 36.02 | 3.50 | 6.70 | 0.66 | 21.46 | 0.66 | 3.21 | 1.10 |
| 3 | 0.09 | 4.67 | 0.24 | 2.32 | 34.45 | 3.41 | 6.33 | 0.60 | 22.53 | 0.71 | 3.35 | 1.01 |
| 4 | 0.0 | 4.57 | 0.20 | 2.01 | 34.27 | 3.08 | 6.47 | 0.59 | 23.14 | 0.65 | 3.24 | 1.08 |
| 5 | 0.0 | 5.08 | 0.30 | 2.22 | 36.51 | 3.99 | 6.55 | 0.57 | 21.59 | 0.72 | 3.41 | 1.06 |
| | 0.02 | 4.78 | 0.24 | 2.15 | 36.64 | 3.42 | 6.48 | 0.58 | 21.95 | 0.69 | 3.10 | 1.08 |

NS-B50027-4, Generation T5, Summer 2014-2015

| | | | | | | | | | | | | |
|---|---|---|---|---|---|---|---|---|---|---|---|---|
| 1 | 0.05 | 4.51 | 0.21 | 2.05 | 39.18 | 4.10 | 8.67 | 0.66 | 21.93 | 0.60 | 1.86 | 1.38 |

NS-B50027-4, Generation T4, Winter 2014

| | | | | | | | | | | | | |
|---|---|---|---|---|---|---|---|---|---|---|---|---|
| 1 | 0.17 | 3.93 | 0.16 | 2.14 | 44.54 | 2.65 | 7.02 | 0.45 | 19.4 | 0.64 | 2.21 | 1.26 |

*Sample number

| | C21:0 | DGLA C20:3n6 | ETE C20:3n3 | C22:0 | ETA C20:4n3 | C22:1n9c | EPA C20:5n3 | C24:0 | DPA6 C22:5n6 | C24:1n9c | DPA3 C22:5n3 | DHA C22:6n3 |
|---|---|---|---|---|---|---|---|---|---|---|---|---|
| 1* | 0 | 0 | 0.71 | 0.31 | 0 | 0 | 0.40 | 0.24 | | 0.10 | 0.85 | 9.69 |
| 2 | 0 | 0 | 0.70 | 0.32 | 0 | 0 | 0.39 | 0.23 | | 0.11 | 0.88 | 9.78 |
| 3 | 0 | 0 | 0.72 | 0.32 | 0 | 0 | 0.40 | 0.23 | | 0.09 | 0.89 | 9.83 |
| 4 | 0 | 0 | 0.71 | 0.33 | 0 | 0 | 0.41 | 0.23 | | 0.08 | 0.91 | 9.92 |
| 5 | 0 | 0 | 0.72 | 0.32 | 0 | 0.01 | 0.41 | 0.23 | | 0.10 | 0.89 | 9.80 |
| | 0 | 0 | 0.71 | 0.32 | 0 | 0 | 0.40 | 0.23 | | 0.10 | 0.88 | 9.80 |

NS-B50027-4, Generation T6, Winter 2015

| | | | | | | | | | | | | |
|---|---|---|---|---|---|---|---|---|---|---|---|---|
| 1 | 0 | 0 | 0.59 | 0.34 | 0 | 0 | 0.55 | 0 | 0.09 | 0 | 0.89 | 10.22 |
| 2 | 0 | 0 | 0.47 | 0.33 | 0 | 0 | 0.68 | 0 | 0.11 | 0.10 | 1.21 | 13.34 |
| 3 | 0 | 0 | 0.60 | 0.33 | 0 | 0 | 0.80 | 0 | 0 | 0.09 | 1.13 | 14.02 |
| 4 | 0 | 0 | 0.63 | 0.38 | 0 | 0 | 0.71 | 0.14 | 0.10 | 0.10 | 1.07 | 13.99 |
| 5 | 0 | 0 | 0.52 | 0.37 | 0 | 0 | 0.60 | 0.11 | 0 | 0.13 | 1.06 | 12.10 |
| | 0 | 0 | 0.56 | 0.35 | 0 | 0 | 0.67 | 0.05 | 0.06 | 0.08 | 1.07 | 12.73 |

NS-B50027-4, Generation T5, Summer 2014-2015

| | | | | | | | | | | | | |
|---|---|---|---|---|---|---|---|---|---|---|---|---|
| 1 | 0.14 | 0 | 0.83 | 0.33 | 0 | 0 | 0.32 | 0.8 | 0.16 | 0.13 | 0.71 | 8.43 |

NS-B50027-4, Generation T4, Winter 2014

| | | | | | | | | | | | | |
|---|---|---|---|---|---|---|---|---|---|---|---|---|
| 1 | | 0.07 | 0.46 | 0.26 | 1.09 | 0 | 0.41 | | | | 0.85 | 8.89 |

*Sample number

| | Oil NMR | Sum of EPA, DPA, DHA | Total Ω3 | Total Ω6 | Ω3/Ω6 | Total Saturated Fat | Total Monounsaturated Fat | Total PUFA |
|---|---|---|---|---|---|---|---|---|
| 1* | 39.3 | 10.94 | 35.39 | 8.39 | 4.22 | 7.74 | 44.74 | 43.78 |
| 2 | 38.8 | 11.04 | 35.54 | 8.36 | 4.25 | 7.41 | 44.62 | 43.89 |
| 3 | 39.2 | 11.12 | 35.79 | 8.41 | 4.26 | 7.64 | 44.41 | 44.20 |
| 4 | 39.5 | 11.23 | 35.85 | 8.40 | 4.27 | 7.59 | 44.41 | 44.25 |
| 5 | 39.4 | 11.10 | 35.85 | 8.40 | 4.27 | 7.68 | 44.19 | 44.25 |
| | | 11.09 | 35.68 | 8.39 | 4.25 | 7.67 | 44.48 | 44.07 |

TABLE 11-continued

Detailed fatty acid content data for NS-B50027-4
NS-B50027-4, Generation T7, Summer 2015-2016

NS-B50027-4, Generation T6, Winter 2015

| | | | | | | | |
|---|---|---|---|---|---|---|---|
| 1 | 11.66 | 35.58 | 6.91 | 5.15 | 7.85 | 46.40 | 42.48 |
| 2 | 15.23 | 40.37 | 7.47 | 5.41 | 7.99 | 40.96 | 47.84 |
| 3 | 15.95 | 42.42 | 6.93 | 6.12 | 8.11 | 39.19 | 49.35 |
| 4 | 15.76 | 42.78 | 7.17 | 5.97 | 7.75 | 38.73 | 59.94 |
| 5 | 13.75 | 39.27 | 7.12 | 5.52 | 8.49 | 41.98 | 46.38 |
| | 14.47 | 40.08 | 7.12 | 5.63 | 8.04 | 41.45 | 47.20 |

NS-B50027-4, Generation T5, Summer 2014-2015

| | Oil NMR | Sum of EPA, DPA, DHA | Total Ω3 | Total Ω6 | Ω3/Ω6 | Total Saturated Fat | Total Monounsaturated Fat | Total PUFA |
|---|---|---|---|---|---|---|---|---|
| 1 | | 9.46 | 34.09 | 9.49 | 3.59 | 7.76 | 45.00 | 43.58 |

*Sample number

The data in Table 11 confirm that in addition to LC-ω3 fatty acids, the seed of NS-B50027-4 also contains substantially more ALA than conventional canola varieties. See also Table 5. Although ALA is not a LC-PUFA, it is an ω3 fatty acid. The ratio of ω3:ω6 fatty acids in seed oil of NS-B50027-4 in Table 11 is about 3.59 to about 6.12; the ratio of ω3:ω6 fatty acids in conventional canola oil is about 0.5. Patterson et al., J. Nutr. Metab. (2012).

Table 12 presents data related to percent DHA and LC-PUFA in seed from sixteen generations of elite event NS-B50027-4 grown in experimental cultivations in Australia. An additional field trial in Australia generated bulk seed with 9.6% DHA and 10.1% LC-PUFA:

TABLE 12

Seed DHA % and LC-PUFA % from elite event NS-B50027-4 per generation

| | Generation | Seed sample | Environment | Growing Season | Year in Field | Location | Seed DHA % | Seed LC-PUFA% |
|---|---|---|---|---|---|---|---|---|
| 1 | T1 | Single plant | Glasshouse | Controlled Environment | | A | 5.7 | 6.0 |
| 2 | T2 | Single plant | Glasshouse | Controlled Environment | | A | 9.5 | 10.1 |
| 3 | T3 | Single plant | Glasshouse | Controlled Environment | | A | 12.6 | 13.1 |
| 4 | T3-x | Bulk | Isolation Tent | Winter/Spring | 2014 | B | 8.9 | 10.2 |
| 5 | T3-2x | Bulk | Open Field | Summer | 2014-15 | C | 8.4 | 9.5 |
| 6 | T3-3x | Bulk | Open Field | Winter/Spring | 2015 | D | 9.0 | 10.6 |
| 7 | T4 | Single plant | Glasshouse | Controlled Environment | | A | 11.9 | 13.2 |
| 8 | T5 | Single plant | Glasshouse | Controlled Environment | | A | 13.4 | 14.6 |
| 9 | T5-x | Bulk | Isolation Tent | Winter/Spring | 2015 | B | 12.7 | 14.5 |
| 10 | T5-2x | Bulk | Open Field | Summer | 2015-16 | C | 9.8 | 11.1 |
| 11 | T5-3x | Bulk | Open Field | Winter/Spring | 2016 | D | 9.6 | 10.6 |
| 12 | T6 | Single plant | Glasshouse | Controlled Environment | | A | 12.9 | 14.4 |
| 13 | T6-x | Bulk | Isolation Tent | Summer | 2015-16 | C | 17.3 | 18.8 |
| 14 | T6-2x | Bulk | Isolation Tent | Winter/Spring | 2016 | E | 10.1 | 12.1 |
| 15 | T7 | Single plant | Glasshouse | Controlled Environment | | A | 13.8 | 15.1 |
| 16 | T7-x | Bulk | Isolation Tent | Winter/Spring | 2016 | B | 12.5 | 14.1 |

Additionally, the ability of NS-B50027-4 to grow in Canada was tested under controlled experimental conditions at two different sites in 2016. Table 13 presents agronomic and yield data comparing NS-B50027-4 with several non-transgenic canola lines:

TABLE 13

Agronomic measurement data for non-transgenic canola cultivars and experimental transgenic test lines from two Canadian experimental cultivations in 2016

| Trait: Line Name | Emergence Plant per $m^2$ | Plant Height at Maturity cm | Start of Flowering Day | End of Flowering Day | Flowering Duration Days | Lodging at Maturity Score (1-9) | Shattered Seed No. | Harvest Plant Count per $m^2$ | Alternaria Symptoms (1-9) | Blackleg Resistance Score (1-9) | Plant Vigor Score (1-9) | Grain Moisture % | Grain % Garnet % | Grain Yield t/ha |
|---|---|---|---|---|---|---|---|---|---|---|---|---|---|---|
| ATR Bonito | 23 | 90 | 49 | 75 | 26 | 8 | 3 | 24 | 2 | 6 | 6 | 8 | 76 | 1.9 |
| ATR Gem | 22 | 98 | 48 | 76 | 27 | 7 | 2 | 23 | 3 | 6 | 6 | 8 | 79 | 2.0 |

TABLE 13-continued

Agronomic measurement data for non-transgenic canola cultivars and experimental transgenic test lines from two Canadian experimental cultivations in 2016

| Trait: Line Name | Emergence Plant per m² | Plant Height at Maturity cm | Start of Flowering Day | End of Flowering Day | Flowering Duration Days | Lodging at Maturity Score (1-9) | Shattered Seed No. | Harvest Plant Count per m² | Alternaria Symptoms Score (1-9) | Blackleg Resistance Score (1-9) | Plant Vigor Score (1-9) | Grain Moisture % | Grain % Garnet % | Grain Yield t/ha |
|---|---|---|---|---|---|---|---|---|---|---|---|---|---|---|
| ATR Stingray | 21 | 88 | 48 | 75 | 27 | 9 | 6 | 26 | 3 | 7 | 5 | 6 | 61 | 1.7 |
| ATR Wahoo | 22 | 98 | 48 | 75 | 27 | 7 | 4 | 26 | 2 | 7 | 6 | 10 | 87 | 2.2 |
| AV Garnet | 27 | 110 | 48 | 76 | 28 | 6 | 7 | 23 | 3 | 7 | 6 | 8 | 100 | 2.6 |
| AV Jade | 27 | 109 | 48 | 76 | 29 | 8 | 3 | 27 | 2 | 7 | 7 | 7 | 85 | 2.1 |
| AV Zircon | 14 | 125 | 50 | 76 | 26 | 8 | 9 | 18 | 1 | 7 | 5 | 8 | 101 | 2.6 |
| Monola 515TT | 26 | 79 | 47 | 73 | 27 | 8 | 13 | 25 | 2 | 6 | 6 | 6 | 60 | 1.6 |
| DK 7444 | 21 | 112 | 47 | 72 | 25 | 7 | 4 | 23 | 2 | 7 | 7 | 5 | 113 | 2.8 |
| LL 130 | 18 | 123 | 47 | 73 | 26 | 8 | 4 | 21 | 2 | 7 | 6 | 6 | 114 | 2.9 |
| NS-B50027-4 T3 | 11 | 109 | 49 | 77 | 28 | 8 | 4 | 16 | 2 | 8 | 4 | 8 | 80 | 2.1 |
| NS-B50027-4 T5 | 16 | 111 | 49 | 76 | 27 | 8 | 2 | 18 | 2 | 8 | 6 | 9 | 82 | 2.3 |
| Min Cultivar Value | 14 | 79 | 47 | 72 | 25 | 6 | 2 | 18 | 1 | 6 | 5 | 5 | 60 | 1.7 |
| NS-B50027-4 | 14 | 110 | 49 | 76 | 28 | 8 | 3 | 18 | 2 | 8 | 5 | 8 | 81 | 2.2 |
| Max Cultivar Value | 27 | 125 | 50 | 76 | 29 | 9 | 13 | 26 | 3 | 7 | 7 | 10 | 114 | 2.9 |

Because canola line NS-B50027-4 is substantially homogeneous, it can be reproduced by planting seeds of such line, growing the resulting canola plants under self-pollinating or sib-pollinating conditions with adequate isolation, and harvesting the resulting seed using conventional agronomic practices.

Example 2. Kompetitive Allele Specific PCR (KASP) Assays

The phenotypic expression of transgenes in canola is determined both by the structure of the transgene cassette itself and by its insert location in the plant genome: the presence of transgenes at particular locations in the plant genome may influence the expression of the transgene and the overall phenotype of the plant. The incorporation of a recombinant DNA molecule in the plant genome typically results from transformation of a cell or tissue (or from another genetic manipulation). The particular site(s) of incorporation may be a matter of chance or predetermined (if a process of targeted integration is used). The agronomically or industrially successful introduction of a commercially interesting trait in a plant by genetic manipulation can be a lengthy procedure dependent on different factors. The actual transformation and regeneration of genetically transformed plants are only the first in a series of selection steps, which include extensive genetic characterization, breeding, and evaluation in field trials, eventually leading to the selection of an elite event.

NS-B50027-4 was developed following extensive selection breeding and field trials, and provides a canola cultivar that produces at least about 7%-15% DHA. Genetic analysis indicated that NS-B50027-4 had a transgenic insert on chromosome A02, and another transgenic insert on chromosome A05. The insert on A05 comprises two complete T-DNA-bordered cassettes of eight genes (Micpu-Δ6D, Pyrco-Δ5E, Pavsa-Δ5D, Picpa-w3D, Pavsa-Δ4D, Lack1-Δ12D, Pyrco-Δ6E, and the PAT marker) aligned head-to-head (RB-LB:LB-RB). The insert on chromosome A02 comprises a set of four genes Micpu-Δ6D, Pyrco-Δ5E, Pavsa-Δ5D, and Picpa-w3D. Surprisingly, segregation crossing showed that the inserts on both chromosome A02 and chromosome A05 were required to achieve DHA production of about 11%.

About 1200 progeny from eight different BC and F₂ populations of DHA canola introgression breeding were used for DNA extraction based on LGC Octopure SOP developed in Nuseed Molecular Lab at Woodland. Briefly, two lyophilized leaf discs with diameter 0.25 inch were grounded in 300 μL, of DNA extraction buffer (100 mM Tris-HCl, PH 8.0; 25 mM EDTA, PH 8.0; 0.5% SDS, 1.5 M NaCl) at 1,400 rpm for 8 minutes with GenoGrinder. After incubation in 55° C. water bath for 45 minutes and centrifuge at 4,500 rpm for 30 minutes, 50 μL of supernatant were transferred to 100 μL of LGC binding buffer with magnetic sbeadex beads. After binding and washing, the DNA was eluted to 80 μL of LGC DNA elution buffer.

DNA concentration was measured with NanoDrop 8000 (Thermo Scientific), and was in the range of 5.0-20.0 ng/μL with an average of 10.0 ng/μL. The DNA samples were diluted 1×. For each reaction, 2.0 μL (~5.0 ng/μL) genomic DNA sample and 2 μL master mix with primers were dispensed to 384-well plate for KASP genotyping.

In addition to the progeny from DHA canola introgression populations, eight controls were included in genotyping. These included two non-GMO controls (Dwarf and AV Jade), two hemizygous controls (2.5 ng Av Jade or 2.5 ng Dwarf+2.5 ng B0050-027-18-20-12-19); two event positive controls (B0050-027-18-20-12-19), and four non-template controls (NTCs). The positive control (T5 plant B0050-027-18-20-12-19) was previously used for characterization of the DHA canola event through sequencing.

KASP assays were developed to provide simple, cost-effective, high throughput, and flexible ways to detect and monitor the eight transgenes and the four NS-B50027-4-specific junctions, and to further facilitate NS-B50027-4 introgression in breeding programs. The KASP™ genotyping chemistry, assay design, genotyping, and scoring were performed according to the standard protocol of manufacturer (LGC Ltd., Middlesex, UK) with modifications.

Sequence information was uploaded into LGC Kraken Workflow Manager, and KASP assays were designed using its assay design program Primer Picker. A typical KASP assay includes two allele-specific primers (Primer_Allele X for transgenic allele and Primer_Allele Y for non-transgenic, wildtype allele) and one common locus-specific primer (Primer_Common). Primer_Allele X is associated with fluorescent FAM, and Primer_Allele Y with fluorescent HEX.

Most of the assays targeting the junctions were this type of three-primer assays (Table 14). For detection of DHA canola, four-primer assays were also developed in addition to conventional three-primer assays mentioned above. The four-primer assays had transgenic allele-specific Primer_Allele X, wildtype allele-specific Primer_Allele Y, Omega 3 gene-specific Primer_Common and wildtype-specific Primer_Common 2 in the reaction. For detection of the eight genes in Omega 3 cassette, only two primers, Primer_Allele X and Primer_Common, were used in each assay (two-primer assay); both primers were Omega 3 gene-specific (Table 14):

TABLE 14

Primer sequences of 14 KASP assays for NS-B50027-4 detection and introgression

| KASP Assay ID | Target | Primer Name | Primer Sequence |
|---|---|---|---|
| NBN001 | Micpu-Δ6D | Primer_Allele X | GAAGGTGACCAAGTTCATGCTCCAAGCACCGTAGTAAGAGAGCA (SEQ ID NO: 1) |
| | | Primer_Common | GCTAAGAAGTGGGGACTCAACTACAA (SEQ ID NO: 2) |
| NBN002 | Pyrco-Δ5E | Primer_Allele X | GAAGGTGACCAAGTTCATGCTGCTCTTGCTGGAACTCTTGG (SEQ ID NO: 3) |
| | | Primer_Common | GGGTTAGCCACATTGTAGGTAACGTA (SEQ ID NO: 4) |
| NBN003 | Paysa-Δ5D | Primer_Allele X | GAAGGTGACCAAGTTCATGCTTAAGAGACACCCTGGTGGAAAGA (SEQ ID NO: 5) |
| | | Primer_Common | TAGCATCAGTTCCAACTTGGTAAGCAAT (SEQ ID NO: 6) |
| NBN004 | Picpa-ω3D | Primer_Allele X | GAAGGTGACCAAGTTCATGCTGAACACGTAAGCAGACCAAGCAG (SEQ ID NO: 7) |
| | | Primer_Common | CCCTCTTCTCCCTAACGAATTCCTT (SEQ ID NO: 8) |
| NBN005 | Paysa-Δ4D | Primer_Allele X | GAAGGTGACCAAGTTCATGCTGAGGAACCTGTTGCTGCTGATGA (SEQ ID NO: 9) |
| | | Primer_Common | GCGATCCTAGCACAAAGTTGAAGGTA (SEQ ID NO: 10) |
| NBN006 | Lack1-Δ12D | Primer_Allele X | GAAGGTGACCAAGTTCATGCTGGATGGATCGCTTACCTCTTCGT (SEQ ID NO: 11) |
| | | Primer_Common | CAGGGTAAGGTTGTCCTGTAACGTT (SEQ ID NO: 12) |
| NBN007 | Pyrco-Δ6E | Primer_Allele X | GAAGGTGACCAAGTTCATGCTCTATTGGATGGGGACTCAAGC (SEQ ID NO: 13) |
| | | Primer_Common | GGGAGATCCTTAGTAGCAGAAGAGAT (SEQ ID NO: 14) |
| NBN008 | PAT | Primer_Allele X | GAAGGTGACCAAGTTCATGCTCCTGAGAGGCGTCCTGTTGAAAT (SEQ ID NO: 15) |
| | | Primer_Common | AACAGCAGCCATATCAGCAGCAGTA (SEQ ID NO: 16) |
| NBN009 | A05 Insert Junction 1 | Primer_Allele X | GAAGGTGACCAAGTTCATGCTTGTTCTTGGGTGGGTCTGTCCTTC (SEQ ID NO: 17) |
| | | Primer_Allele Y | GAAGGTCGGAGTCAACGGATTGTGTTCTTGGGTGGGTCTGTCCTTA (SEQ ID NO: 18) |
| | | Primer_Common1 | ATCCACTAGCAGATTGTCGTTTCCC (SEQ ID NO: 19) |
| | | Primer_Common2 | GTTGGCTAAGGTCACGGTGGAG (SEQ ID NO: 20) |
| NBN010 | A05 Insert Junction 1 | Primer_Allele X | GAAGGTGACCAAGTTCATGCTCCGCCTTCAGTTTAAACTATCAGTGTT (SEQ ID NO: 21) |
| | | Primer_Allele Y | GAAGGTCGGAGTCAACGGATTGGTCACGGTGGAGGTCACCA (SEQ ID NO: 22) |
| | | Primer_Common | GGTGTGTTCTTGGGTGGGTCTG (SEQ ID NO: 23) |
| NBN011 | A05 Insert Junction 2 | Primer_Allele X | GAAGGTGACCAAGTTCATGCTACTTTTTTTTCAACTGTTGGCTAAGGTA (SEQ ID NO: 24) |
| | | Primer_Allele Y | GAAGGTCGGAGTCAACGGATTACTTTTTTTTCAACTGTTGGCTAAGGTC (SEQ ID NO: 25) |
| | | Primer_Common 1 | GTGTGTTCTTGGGTGGGTCTG (SEQ ID NO: 26) |
| | | Primer_Common 2 | GTCGTTTCCCGCCTTCAGTTT (SEQ ID NO: 27) |
| NBN014 | A02 Insert Junction 1 | Primer_Allele X | GAAGGTGACCAAGTTCATGCTAAACTATCAGTGTTTGAACACCTCC (SEQ ID NO: 28) |
| | | Primer_Allele Y | GAAGGTCGGAGTCAACGGATTACAACTTGTCGTGCTACACACCT (SEQ ID NO: 29) |
| | | Primer_Common | GGTTGTGTGAAAACGTGTGAGC (SEQ ID NO: 30) |
| NBN015 | A02 Insert Junction 2 | Primer_Allele X | GAAGGTGACCAAGTTCATGCTCTTTTAGCTAAATAAGAGGTTCTGTATACT (SEQ ID NO: 31) |
| | | Primer_Allele Y | GAAGGTCGGAGTCAACGGATTCTTTTAGCTAAATAAGAGGTTCTGTATACA (SEQ ID NO: 32) |
| | | Primer_Common 1 | GATTGTGATTCCGGGCAGT (SEQ ID NO: 33) |
| | | Primer_Common 2 | GTGTGAAAACGTGTGAGCAAT (SEQ ID NO: 34) |

TABLE 14-continued

Primer sequences of 14 KASP assays for NS-B50027-4 detection and introgression

| KASP Assay ID | Target | Primer Name | Primer Sequence |
|---|---|---|---|
| NBN016 | A02 Insert Junction 2 | Primer_Allele X | GAAGGTGACCAAGTTCATGCTTTGTGATTCCGGGCAGTAG (SEQ ID NO: 35) |
| | | Primer_Allele Y | GAAGGTCGGAGTCAACGGATTTGTGAGCAATTGTTGGAGG T (SEQ ID NO: 36) |
| | | Primer_Common | TCTTATCAACATTAAGAACATAATCTTTTAG (SEQ ID NO: 37) |

The KASP genotyping system requires two components: the assay mix and the master mix. The assay mix is a mixture of required primers, and the master mix contains all other required components, including PCR buffer, the universal fluorescent reporting system, and Taq polymerase.

The KASP reaction was run in the volume of 4.0 μL, consisting 2.0 μL (10.0 ng) of genomic DNA, 2.0 μL of 2×KASP master mix, and 0.06 μL of the assay (primer) mix. The assay (primer) mix is a combination of 12 μM of allele-specific Primer_Allele X and 12 μM of Primer_Common for two-primer assays, a combination of 12 μM of allele-specific Primer_Allele X, 12 μM of allele-specific Primer_Allele Y, and 30 μM of Primer_Common for three-primer assays, and a combination of 12 μM of allele-specific Primer_Allele X, 12 μM of allele-specific Primer_Allele Y, 12 μM of Primer_Common and 12 μM of Primer_Common2 for four-primer assays.

The reactions were run in 384-well plate in LGC Hydrocycler 16 with the following cycling parameters: 1 cycle of 94° C. for 15 min, followed by eight cycles of 94° C. for 30 sec and 64° C.-57° C. (drop 1.0° C. per cycle) for 60 sec, and followed by thirty cycles of 94° C. for 30 sec and 57° C. for 60 sec. If clear genotyping clusters have not been obtained, the plate was further thermally cycled by three extra cycles of 94° C. for 30 sec and 57° C. for 60 sec.

After the completion of KASP reactions, transgenic allele was labeled with FAM through Primer_Allele X, and non-transgenic, wildtype allele was label with HEX through Primer_Allele Y. The fluorescent signals were read in a PheraStar microplate reader with an excitation wavelength of 485 nm and an emission wavelength of 520 nm for FAM and 535 nm/556 nm for HEX. Data were analyzed using LGC Kraken database.

Gene-specific, dominant (NBN01-NBN08; one assay/gene) were developed for detection of eight genes in the construct cassette. Insert-specific, co-dominant KASP assays, which targeted the upstream (NBN57, NBN68, NBN58, NBN85 and NBN14) and downstream (NBN16, NBN62 and NBN64) junctions of the insert on A02, and the upstream (NBN52, NBN51, NBN09, NBN50, NBN48 and NBN10) and downstream (NBN83, NBN82, NBN84, NBN66, NBN41 and NBN43) junctions of insert on A05, were developed and validated with 1200 progeny from NS-B50027-4 introgression populations (Table 14). Over 10,000 samples have been genotyped with these markers.

Thirty Kompetitive Allele Specific PCR (KASP) assays were developed and validated, which target the eight genes and the four junctions of the two inserts of DHA canola event NS-B50027-4. These assays offered a simple, cost-effective, high throughput and flexible approach to detect and monitor NS-B50027-4 in a breeding program.

Example 3. Detailed Comparison of NS-B50027-4 and Non-Transgenic Canola

Data from canola seed production in experimental field plots from 2014-2016 were tabulated. The range of DHA and total EPA+DPA+DHA were based on several test field observations. Content of major fatty acids in both NS-B50027-4 and non-transgenic "Control" canola may vary by several percentage points depending on growing conditions. In the following Table 15, "0.0" may refer to a trace amount identified as below the amount needed to accurately determine the quantity of the component:

TABLE 15

Detailed comparison of fatty acid content of NS-B50027-4 with control

| Fatty acid | | NS-B50027-4 (%) | Control Canola (%) |
|---|---|---|---|
| Myristic | C14:0 | 0.1 | 0.1 |
| Palmitic | C16:0 | 4.3 | 3.9 |
| Palmitoleic | C16:1 | 0.2 | 0.2 |
| Stearic | C18:0 | 2.2 | 1.6 |
| Oleic | C18:1n9c | 38.7 | 63.6 |
| Cis-vaccenic | C18:1n7c | 4.2 | 3.5 |
| Linoleic | C18:2n6c | 7.8 | 13.1 |
| GLA | C18:3n6 | 0.6 | 0.0 |
| ALA | C18:3n3 | 21.7 | 10.3 |
| Arachidic | C20:0 | 0.6 | 0.6 |
| SDA | C18:4n3 | 2.2 | 0.0 |
| Gondoic | C20:1n9c | 1.3 | 1.5 |
| Heneicosanoic | C21:0 | 0.0 | 0.0 |
| DGLA | C20:3n6 | 0.0 | 0.0 |
| ETE | C20:3n3 | 0.7 | 0.0 |
| Behenic | C22:0 | 0.3 | 0.3 |
| ETA | C20:4n3 | 0.0 | 0.0 |
| Erucic | C22:1n9c | 0.0 | 0.0 |
| EPA | C20:5n3 | 0.4 | 0.0 |
| Lignoceric | C24:0 | 0.2 | 0.1 |
| DPA6 | C22:5n6 | 0.0 | 0.0 |
| Nervonic | C24:1n9c | 0.1 | 0.2 |
| DPA3 | C22:5n3 | 0.9 | 0.0 |
| DHA | C22:6n3 | 9.8 (8-10) | 0.0 |
| Other | | 3.8 | 1.3 |
| Sum: EPA + DPA + DHA | | 11.1 (10-12) | 0.0 |
| Total Omega 3 | | 35.7 | 10.4 |
| Total Omega 6 | | 8.4 | 11.3 |
| ω3/ω6 | | 4.3 | 0.9 |
| Total Saturated | | 7.7 | 6.7 |
| Total Monounsaturated | | 44.5 | 68.9 |
| Total Polyunsaturated | | 44.1 | 23.5 |

Seed harvested from experimental cultivation of NS-B50027-4 was crushed and oil obtained via cold-press. Seed harvested from the parental isogenic line, AV Jade, was similarly processed, and the content of each oil compared as shown in Table 16:

TABLE 16

NS-B50027-4 Oil Content

| Component (units) | NS-B50027-4 | AV Jade |
|---|---|---|
| Saturated TAG (%) | | |
| C4:0 Butyric | <0.1 | <0.1 |
| C6:0 Caproic | <0.1 | <0.1 |
| C8:0 Caprylic | <0.1 | <0.1 |
| C10:0 Capric | <0.1 | <0.1 |
| C12:0 Lauric | <0.1 | <0.1 |
| C14:0 Myristic | <0.1 | <0.1 |
| C15:0 Pentadecanoic | <0.1 | <0.1 |
| C16:0 Palmitic | 4.3 | 3.9 |
| C17:0 Margaric | <0.1 | <0.1 |
| C18:0 Stearic | 2.9 | 2.5 |
| C20:0 Arachidic | 0.8 | 0.5 |
| C22:0 Behenic | 0.4 | 0.2 |
| C24:0 Lignoceric | 0.1 | 0.1 |
| Total Saturated | 8.7 | 7.3 |
| Mono-unsaturated TAG (%) | | |
| C14:1 Myristoleic | <0.1 | <0.1 |
| C16:1 Palmitoleic | 0.2 | 0.1 |
| C17:1 Heptadecenoic | <0.1 | <0.1 |
| C18:1 Oleic | 44.9 | 58.8 |
| C20:1 Eicosenic | 1.3 | 1.0 |
| C22:1 Docosenoic | <0.1 | <0.1 |
| C24:1 Nervonic | <0.1 | <0.1 |
| PUFA TAG (%) | | |
| C18:2ω6 Linoleic | 7.6 | 18.9 |
| C18:3ω6 gamma-Linolenic | 0.5 | <0.1 |
| C18:3ω3 alpha-Linolenic | 20.9 | 10.5 |
| C20:2ω6 Eicosadienoic | <0.1 | <0.1 |
| C20:3ω6 Eicosatrienoic | <0.1 | <0.1 |
| C20:3ω3 Eicosatrienoic | 0.6 | <0.1 |
| C20:4ω6 Arachidonic | <0.1 | <0.1 |
| C20:5ω3 Eicosapentaenoic | 0.4 | <0.1 |
| C22:2ω6 Docosadienoic | <0.1 | <0.1 |
| C22:4ω6 Docosatetraenoic | <0.1 | <0.1 |
| C22:5ω3 Docosapentaenoic | 1.0 | <0.1 |
| C22:6ω3 Docosahexaenoic | 9.4 | 0.2 |
| Total PUFA (%) | 40.6 | 29.9 |
| Total Mono Trans Fatty Acids | 0.1 | 0.2 |
| Total Poly Trans Fatty Acids | 0.8 | 0.2 |
| P:M:S Ratio | 4.7:5.4:1 | 4.1:8.2:1 |
| PUFA (%) | | |
| Omega 3 Fatty Acids | 32.3 | 10.9 |
| Omega 6 Fatty Acids | 8.2 | 19.0 |
| ω3:ω6 | 3.94 | 0.57 |
| Vitamins | | |
| beta-Carotene (μg/100 g) | 110 | 82 |
| alpha-tocopherol (mg/100 g) | 19 | 15 |
| beta-tocopherol (mg/100 g) | <0.1 | <0.1 |
| delta-tocopherol (mg/100 g) | 0.6 | 0.8 |
| gamma-tocopherol (mg/100 g) | 43 | 42 |
| Astaxanthin (mg/kg) | <0.05 | <0.05 |
| Vitamin K1 (μg/100 g) | 17 | 15 |
| Phytosterols (mg/100 g) | | |
| Cholesterol | <5.0 | <5.0 |
| Brassicasterol | 29 | 67 |
| Campesterol | 250 | 170 |
| Campestanol | <5.0 | <5.0 |
| Stigmasterol | <5.0 | <5.0 |
| beta-Sitosterol | 370 | 320 |
| beta-Sitostanol | 34 | 27 |
| Total Phytosterol | 690 | 600 |

In accordance with the Budapest Treaty, Applicants have made a deposit of at least 2500 seeds of Canola NS-B50027-4 with the American Type Culture Collection (ATCC®) located at 10801 University Blvd., Manassas, Va., 20110-2209 U.S.A., Accession No. PTA-123186, and the viability of the seeds was confirmed by the ATCC®. During pendency of this application, access to the invention may be afforded to the Commissioner by request; all restrictions upon availability to the public are irrevocably revoked upon granting of the patent; the deposit of line NS-B50027-4 will be maintained in the ATCC depository, which is a public depository, for a period of 30 years, or 5 years after the most recent request, or for the effective life of the patent, whichever is longer; and will be replaced if it becomes nonviable during that period. The viability of the seeds was tested at the time of deposit. Applicants have satisfied all the requirements of 37 C.F.R. §§ 1.801-1.809. Applicants impose no restrictions on the availability of the deposited material from the ATCC; however, Applicant has no authority to waive any restrictions imposed by law on the transfer of biological material or its transportation in commerce. Applicant does not waive any infringement of its rights granted under this patent or under the Plant Variety Protection Act (7 U.S.C. § 2321 et seq.).

Although the foregoing embodiments have been described in some detail by way of illustration and example for purposes of clarity and understanding, it will be clear to one of skill in the art that certain changes and modifications, such as single gene modifications and mutations, somoclonal variants, variant individuals selected from large populations of the plants of the instant inbred line, and the like, may be practiced within the scope of the invention which is limited solely by the appended claims.

We claim:

1. Seed of inbred canola line NS-B50027-4, representative seed of said inbred canola line having been deposited under ATCC Accession No. PTA-123186.

2. A canola plant, or a part thereof, produced by growing the seed of claim 1.

3. The canola plant part of claim 2, wherein said part is at least one of seed, leaf, pollen, embryo, root, root tip, pod, flower, ovule, stalk, cell, protoplast, or tissue culture.

4. A method of producing canola oil, comprising obtaining seed of the plant of claim 2 and processing the seed to obtain canola oil.

5. A method of producing docosahexaenoic acid in the seed of the plant of claim 2, comprising cultivating the plant.

6. The seed of the plant cultivated as in claim 5.

7. The plant or plant part of claim 2, or a derivative or hybrid of said plant, comprising at least one pair of nucleic acid molecules selected from:
   (a) SEQ ID NO:43 (TGGAGGTGTTCAAACACT) and SEQ ID NO:44 (ATAGTATTAGTATACAGA), sequences at least 95% identical to either or both of these, or complements thereof;
   (b) SEQ ID NO:45 (GGCTAAGGTAACACTGAT) and SEQ ID NO:46 (CAGTGTTTGAAGGACAGA), sequences at least 95% identical to either or both of these, or complements thereof;
   (c) SEQ ID NO:47 and SEQ ID NO:48, sequences at least 95% identical to either or both these, or complements thereof; or
   (d) SEQ ID NO:49 and SEQ ID NO:50, sequences at least 95% identical to either or both these, or complements thereof;
   wherein the derivative or hybrid of said plant exhibits the derived trait of the seed of inbred canola line NS-B50027-4 of claim 1.

8. The plant of claim 2, wherein the plant comprises:
   (i) a first transgenic expression cassette consisting of the nucleic acid sequence indicated at positions 2090 to 14201 of SEQ ID NO:40; and
   (ii) a second transgenic expression cassette consisting of the nucleic acid sequence indicated at positions 1268 to 47773 of SEQ ID NO:41.

9. A collection of seed comprising at least 95% seed of the plant of claim 2, or a derivative or hybrid thereof, wherein said seed comprises about 5% to about 16% docosahexaenoic acid (DHA), inclusive (wt. % of total fatty acids in seed)), or about 5% to 17%, inclusive, long-chain polyunsaturated fatty acids (sum eicosapentaenoic acid, docosapentaenoic acid, and DHA as wt. % of total fatty acids in seed).

* * * * *